(12) United States Patent
Gordon et al.

(10) Patent No.: US 10,280,161 B2
(45) Date of Patent: May 7, 2019

(54) AZTREONAM DERIVATIVES AND USES THEREOF

(71) Applicant: ARIXA PHARMACEUTICALS, INC., Palo Alto, CA (US)

(72) Inventors: Eric M. Gordon, Palo Alto, CA (US); Matthew A. J. Duncton, Palo Alto, CA (US); John Freund, Atherton, CA (US)

(73) Assignee: ARIXA PHARMACEUTICALS, INC., Palo Alto, CA (US)

( * ) Notice: Subject to any disclaimer, the term of this patent is extended or adjusted under 35 U.S.C. 154(b) by 0 days.

(21) Appl. No.: 16/148,788

(22) Filed: Oct. 1, 2018

(65) Prior Publication Data

US 2019/0100516 A1 Apr. 4, 2019

Related U.S. Application Data

(60) Provisional application No. 62/566,909, filed on Oct. 2, 2017.

(51) Int. Cl.
| | |
|---|---|
| *A61K 31/427* | (2006.01) |
| *A61K 45/06* | (2006.01) |
| *C07D 417/12* | (2006.01) |
| *A61P 31/04* | (2006.01) |

(52) U.S. Cl.
CPC .......... *C07D 417/12* (2013.01); *A61K 31/427* (2013.01); *A61K 45/06* (2013.01); *A61P 31/04* (2018.01)

(58) Field of Classification Search
CPC .... C07D 417/12; A61K 31/427; A61K 45/06; A61P 31/04
See application file for complete search history.

(56) References Cited

U.S. PATENT DOCUMENTS 4,775,670 A * 10/1988 Sykes ................ C07D 205/085
514/210.15

OTHER PUBLICATIONS

International Search Report and Written Opinion for Application No. PCT/US2018/053778, dated Nov. 26, 2018, 11 pages.
Klinger-Strobel, Mareike, et al., "Aspects of Pulmonary Drug Delivery Strategies for Infections in Cystic Fibrosis—Where Do We Stand?", *Expert Opinion on Drug Delivery*, vol. 12, No. 8, Feb. 2, 2015, pp. 1351-1374, XP055524515, 25 pages.
Hutchinson, David, et al., "Inhaled Aztreonam Lysine: An Evidence-Based Review", *Expert Opinion on Pharmacotherapy*, vol. 14, No. 15, Aug. 31, 2013, pp. 2115-2124, XP055524539, 11 pages.

* cited by examiner

*Primary Examiner* — Rebecca L Anderson

(57) ABSTRACT

Disclosed herein are aztreonam derivatives, therapeutic methods of using the aztreonam derivatives, particularly in combination with β-lactamase inhibitors, and pharmaceutical compositions thereof. The aztreonam derivatives can be administered orally to provide orally bioavailable aztreonam.

27 Claims, 3 Drawing Sheets

AZTREONAM DERIVATIVES AND USES THEREOF

This application claims the benefit under 35 U.S.C. § 119(e) of U.S. Provisional Application No. 62/566,909 filed on Oct. 2, 2017, which is incorporated by reference in its entirety.

FIELD

The present disclosure relates to aztreonam derivatives and pharmaceutical compositions thereof and the use of the aztreonam derivatives to treat bacterial infections. The aztreonam derivatives can be administered orally to provide orally bioavailable aztreonam.

BACKGROUND

Aztreonam is a monobactam antibiotic used primarily to treat gram negative bacteria. Aztreonam has poor oral bioavailability and therefore is administered intravenously, intramuscularly or by inhalation.

SUMMARY

According to the present invention, compounds have the structure of Formula (1):

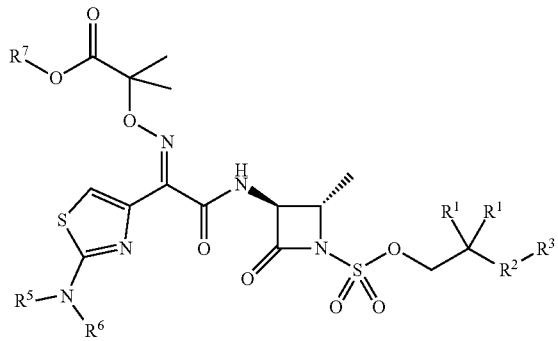

wherein, each $R^1$ is independently selected from $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

According to the present invention, pharmaceutical compositions comprise a compound according to the present invention and a pharmaceutically acceptable vehicle.

According to the present invention, methods of treating a bacterial infection in a patient comprise administering to a patient in need of such treatment a therapeutically effective amount of a compound according to the present invention.

According to the present invention, methods of treating a bacterial infection in a patient comprise administering to a patient in need of such treatment a therapeutically effective amount of a pharmaceutical composition according to the present invention.

According to the present invention, methods of synthesizing a derivative of aztreonam comprise: reacting 3-amino-2-tert-butoxycarbonylamino-butyric acid benzyl ester and a chlorosulfonyloxy ester in the presence of a base to provide the corresponding ((2R,3R)-4-(benzyloxy)-3-((tert-butoxycarbonyl)amino)-4-oxobutan-2-yl)sulfonyloxy ester; hydrogenating the ((2R,3R)-4-(benzyloxy)-3-((tert-butoxycarbonyl)amino)-4-oxobutan-2-yl)sulfonyloxy ester to provide the corresponding (2R,3R)-2-((tert-butoxycarbonyl)amino)-3-((sulfonyloxy)amino)butanoic acid ester; and cyclizing the (2R,3R)-2-((tert-butoxycarbonyl)amino)-3-((sulfonyloxy)amino)butanoic acid ester in the presence of a cyclization agent to provide the corresponding 3-lactam.

According to the present invention, methods of synthesizing a derivative of aztreonam comprise: reacting tert-butyl (2S,3R)-3-amino-2-(((benzyloxy)carbonyl)-amino)butanoate and a chlorosulfonyloxy ester in the presence of a base to provide the corresponding tert-butyl (2S,3R)-2-(((benzyloxy)carbonyl)amino)-3-((sulfonyloxy)amino)butanoate ester; and cyclizing the tert-butyl (2S,3R)-2-(((benzyloxy)carbonyl)amino)-3-((sulfonyloxy)amino)butanoate ester in the presence of a cyclization agent to provide the corresponding 3-lactam.

Reference is now made to certain compounds and methods. The disclosed embodiments are not intended to be limiting of the claims. To the contrary, the claims are intended to cover all alternatives, modifications, and equivalents.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
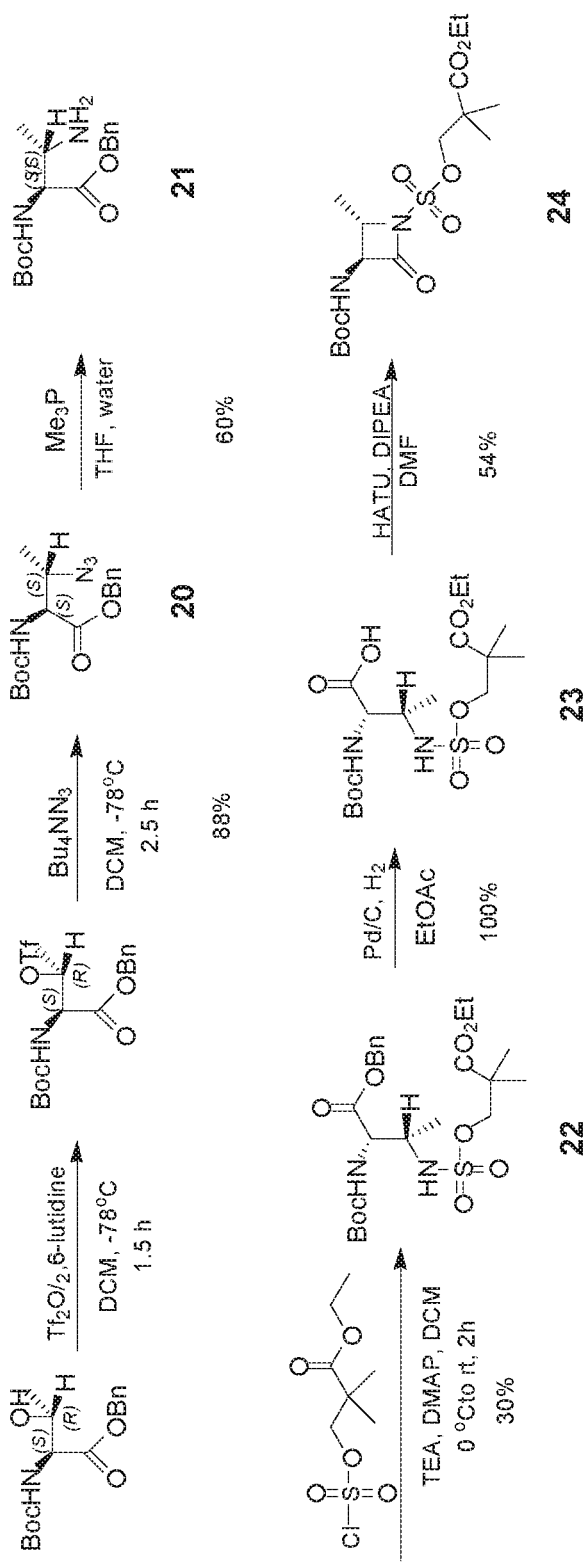
FIG. 1 shows certain steps in synthesizing aztreonam derivatives provided by the present disclosure. The steps correspond to those disclosed in Examples 20-24.

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by chemical structure and/or by chemical name. Compounds are named using the ChemBioDraw Ultra 14.0.0.117 (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing "Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, e.g., the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl, e.g., the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—$CH_2$-cyclo-$C_3H_5$), cyclopentylmethyl (—$CH_2$-cyclo-$C_5H_9$), or cyclohexylmethyl (—$CH_2$-cyclo-$C_6H_{11}$). A cycloalkylalkyl group can be cyclopropylethenyl (—CH═CH-cyclo-$C_3H_5$), cyclopentylethynyl (—C≡C-cyclo-$C_5H_9$), or the like.

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—$CH_3$)—, —SO—, and —$SO_2$—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ".

"Fluoroalkyl" refers to an alkyl group as defined herein in which one or more of the hydrogen atoms is replaced with a fluoro. A fluoroalkyl group can be $C_{1-6}$ fluoroalkyl, $C_{1-5}$ fluoroalkyl, $C_{1-4}$ fluoroalkyl, or $C_{1-3}$ fluoroalkyl. A fluoroalkyl group can be pentafluoroethyl (—$CF_2CF_3$), or trifluoromethyl (—$CF_3$).

"Fluoroalkoxy" refers to an alkoxy group as defined herein in which one or more of the hydrogen atoms is replaced with a fluoro. A fluoroalkoxy group can be $C_{1-6}$ fluoroalkoxy, $C_{1-5}$ fluoroalkoxy, $C_{1-4}$ fluoroalkoxy $C_{1-3}$, fluoroalkoxy, —$OCF_2CF_3$ or —$OCF_3$.

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR— where R is $C_{1-6}$ alkyl, —$SO_2$—, and —$SO_2$—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, ═N—N═, —N═N—, —N═N—NR—, —PR—, —P(O) OR—, —P(O)R—, —POR—, —SO—, —$SO_2$—, and —Sn (R)$_2$—, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, etc. In a heteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroaryl group can be selected from $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl or $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl groups can be derived, for example, from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, or $C_6$ heteroarylalkyl. In a heteroarylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-6}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Metabolic intermediate" refers to a compound that is formed in vivo by metabolism of a parent compound and that further undergoes reaction in vivo to release an active agent. Compounds of Formula (1) are protected sulfonate nucleophile prodrugs of aztreonam that are metabolized in vivo to provide the corresponding metabolic intermediates. Metabolic intermediates undergo nucleophilic cyclization to release aztreonam and one or more reaction products. It is desirable that the reaction products or metabolites thereof not be toxic.

"Neopentyl" refers to a radical in which a methylene carbon is bonded to a carbon atom, which is bonded to three non-hydrogen substituents. Examples of non-hydrogen substituents include carbon, oxygen, nitrogen, and sulfur. Each of the three non-hydrogen substituents can be carbon. Two of the three non-hydrogen substituents can be carbon, and the third non-hydrogen substituent can be selected from oxygen and nitrogen. A neopentyl group can have the structure:

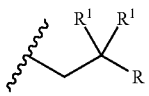

where each $R^1$ can be defined as for Formula (1).

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include arsindole, carbazole, 3-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and thiazolidine, oxazolidine.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug. For example, referring to compounds of Formula (1), promoieties bonded to the drug aztreonam, via the sulfate group aztreonam of Compounds of Formula (1) are prodrugs of aztreonam that can be metabolized within a patient's body to release aztreonam.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for a compound of Formula (1), a promoiety has the structure:

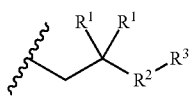

where $R^1$, $R^2$, and $R^3$ can be defined as for Formula (1).

"Single bond" as in the expression "$R^2$ is selected from a single bond" refers to a moiety in which $R^2$ and two of the bonds to $R^2$ correspond to a single bond. For example, in a moiety having the structure —C($R^1$)$_2$—$R^2$-$R^3$, where $R^2$ is a single bond, —$R^2$— corresponds to a single bond (—), and the moiety has the structure —C($R^1$)$_2$—$R^3$.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Solvates" refers to incorporation of solvents into to the crystal lattice of a compound described herein, in stoichiometric proportions, resulting in the formation of an adduct. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from deuterio, halogen, —NH$_2$, —OH, C$_{1-3}$ alkoxy, and C$_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, C$_{1-3}$ alkyl, =O, C$_{1-3}$ alkyl, C$_{1-3}$ alkoxy, and phenyl. Each substituent can be selected from deuterio, —OH, —NH$_2$, C$_{1-3}$ alkyl, and C$_{1-3}$ alkoxy.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Aztreonam is a monobactam antibiotic used to treat infections caused primarily by gram-negative bacteria. Aztreonam has poor oral bioavailability. Compounds provided by the present disclosure are N-sulfonate ester prodrugs of aztreonam. The aztreonam N-sulfonate ester prodrugs exhibit enhanced oral bioavailability compared to aztreonam. In the aztreonam prodrugs a nucleophilic moiety is positioned proximate the sulfonyl group. In vivo, the nucleophilic moiety reacts to release aztreonam in the systemic circulation. Aztreonam, (2-((((E)-1-(2-aminothiazol-4-yl)-2-(((2S,3S)-2-methyl-4-oxo-1-sulfoazetidin-3-yl)amino)-2-oxoethylidene)amino)oxy)-2-methylpropanoic acid), has the structure:

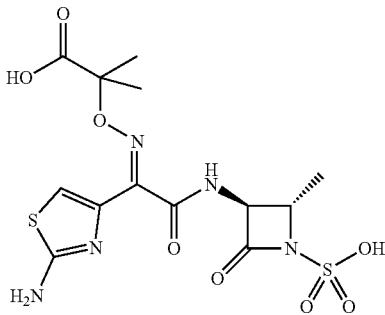 [SMILES: C[C@H]1[C@H](NC(=O)/C(=N/OC(C)(C)C(=O)O)c2csc(N)n2)C(=O)N1S(=O)(=O)O]

Compounds provided by the present disclosure include compounds of Formula (1):

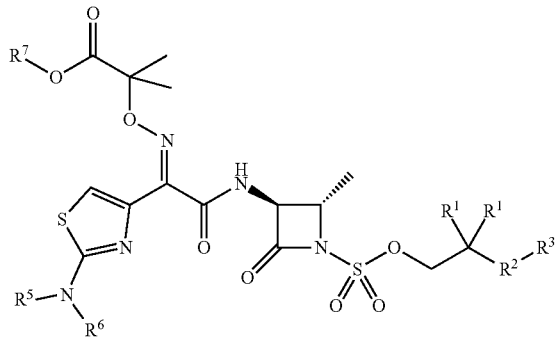

(1)

wherein,
each $R^1$ can be independently selected from $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ can be selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl, $R^3$ can be selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^7$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl In compounds of Formula (1), the compounds can have the structure of Formula (2):

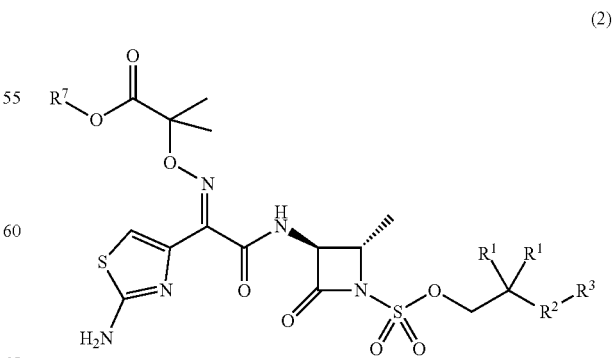

(2)

wherein each $R^1$, $R^2$, $R^3$, and $R^7$ are defined as for Formula (1).

In compounds of Formula (1), each substituent can independently be selected from deuterio, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R can be independently selected from hydrogen and C$_{1-6}$ alkyl, such has methyl, ethyl, n-propyl, isopropyl, n-butyl, tert-butyl, or iso-butyl.

In compounds of Formula (1), a substituent group can be a nucleophilic group. Nucleophilic groups are functional group having a reactive pair of electrons and having the ability of forming a chemical bond by donating electrons. Examples of suitable nucleophilic groups include esters, carboxylates, sulfonates, substituted or unsubstituted amines, alcohols (hydroxyl), thiols, sulfides, hydroxylamines, and imines. Other examples of suitable nucleophilic groups include —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each R$^4$ can be independently selected from hydrogen, C$_{1-6}$ alkyl, C$_{1-6}$ heteroalkyl, C$_{5-8}$ cycloalkyl, C$_{5-8}$ heterocycloalkyl, C$_{5-10}$ cycloalkylalkyl, C$_{5-10}$ heterocycloalkylalkyl, C$_{6-8}$ aryl, C$_{6-8}$ heteroaryl, C$_{5-10}$ arylalkyl, C$_{5-10}$ heteroarylalkyl, substituted C$_{1-6}$ alkyl, substituted C$_{1-6}$ heteroalkyl, substituted C$_{5-8}$ cycloalkyl, substituted C$_{5-8}$ heterocycloalkyl, substituted C$_{5-10}$ cycloalkylalkyl, substituted C$_{5-10}$ heterocycloalkylalkyl, substituted C$_{6-8}$ aryl, substituted C$_{6-8}$ heteroaryl, substituted C$_{5-10}$ arylalkyl, and substituted C$_{5-10}$ heteroarylalkyl.

In compounds of Formula (1), each substituent can independently be selected from —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), wherein each R$^4$ can be selected from hydrogen, C$_{1-8}$ alkyl, and C$_{1-8}$ heteroalkyl.

In compounds of Formula (1), R$^7$ can be hydrogen.
In compounds of Formula (1), R$^7$ can be C$_{1-3}$ alkyl, such as methyl, ethyl, n-propyl, or iso-propyl.
In compounds of Formula (1), each of R$^5$ and R$^6$ can be hydrogen.
In compounds of Formula (1), R$^7$ can be hydrogen; and R$^5$ and R$^6$ can be hydrogen.
In compounds of Formula (1), R$^7$ can be C$_{1-3}$ alkyl, such as methyl, ethyl, n-propyl, or iso-propyl; and each of R$^5$ and R$^6$ can be hydrogen.
In compounds of Formula (1) and (2), R$^7$ can be selected from hydrogen, C$_{1-6}$ alkyl, C$_{5-8}$ cycloalkyl, C$_{6-12}$ cycloalkylalkyl, C$_{2-6}$ heteroalkyl, C$_{5-8}$ heterocycloalkyl, C$_{6-12}$ heterocycloalkylalkyl.
In compounds of Formula (1) and (2), R$^7$ can be selected from hydrogen, C$_{1-6}$ alkyl, C$_{5-8}$ cycloalkyl, and C$_{6-12}$ cycloalkylalkyl.
In compounds of Formula (1) and (2), R$^7$ can be selected from hydrogen, ethyl, tert-butyl, hexyl, —(CH$_2$)$_2$—O—CH$_3$, and

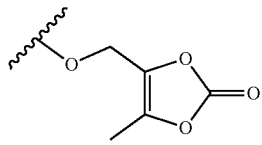 [SMILES: *OCc1oc(=O)oc1C]

(4-(yl-methyl)-5-methyl-1,3-dioxol-2-one).

In compounds of Formula (1) and (2), R$^7$ can be selected from hydrogen and C$_{1-6}$ alkyl.
In compounds of Formula (1), each of R$^5$, R$^6$, and R$^7$ can be hydrogen.
In compounds of Formula (1), the compounds can have the structure of Formula (3):

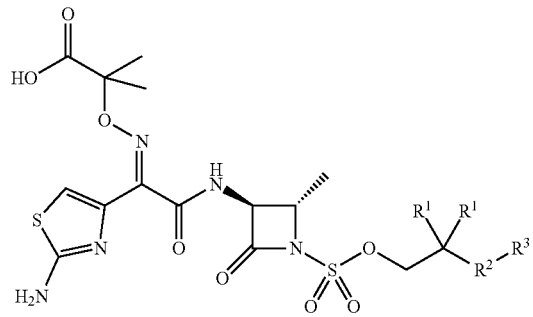

(3)

wherein each R$^1$, R$^2$, and R$^3$ are defined as for Formula (1).

In compounds of Formula (1), R$^5$ can be C$_{2-6}$ heteroalkyl comprising a terminal amine group, and R$^6$ can be hydrogen. For example, R$^5$ can be —O—(CH$_2$)$_2$—NH$_2$, —CH$_2$—O—CH$_2$—NH$_2$, or —(CH$_2$)$_2$—O—CH$_2$—NH$_2$, —CH$_2$—O—(CH$_2$)$_2$—NH$_2$.

In compounds of Formula (1) and (2), R$^7$ can be hydrogen, R$^5$ can be —O—(CH$_2$)$_2$—NH$_2$, and R$^6$ can be hydrogen.

In compounds of Formula (1) and (2), R$^5$ can be C$_{4-6}$ heterocycloalkyl comprising at least one —NH— moiety, and R$^6$ can be hydrogen. For example, R$^5$ can be 2-yl-piperidine, 3-yl-piperidine, or 4-yl-piperidine.

In compounds of Formula (1) and (2), R$^7$ can be hydrogen, R$^5$ can be 4-yl-piperidine, and R$^6$ can be hydrogen.

In compounds of Formula (1)-(3), each R$^1$ can independently be C$_{1-6}$ alkyl.
In compounds of Formula (1)-(3), each R$^1$ can independently be methyl, ethyl, or n-propyl.
In compounds of Formula (1)-(3), each R$^1$ can be the same and can be methyl, ethyl, or n-propyl.
In compounds of Formula (1)-(3), each R$^1$ can be methyl.
In compounds of Formula (1)-(3), each R$^1$ together with the geminal carbon atom to which each R$^1$ can be bonded can form a C$_{3-6}$ cycloalkyl ring or a substituted C$_{3-6}$ cycloalkyl ring.
In compounds of Formula (1)-(3), each R$^1$ together with the geminal carbon atom to which each R$^1$ is bonded can form a C$_{3-6}$ cycloalkyl ring. For example, each R$^1$ together with the geminal carbon atom to which each R$^1$ is bonded can form a cyclopropyl ring, a cyclobutyl ring, a cyclopentyl ring, or a cyclohexyl ring.
In compounds of Formula (1)-(3), each R$^1$ together with the geminal carbon atom to which each R$^1$ is bonded can form a C$_{3-6}$ heterocycloalkyl ring or a substituted C$_{3-6}$ heterocycloalkyl ring.
In compounds of Formula (1)-(3), R$^2$ can be selected from a single bond, C$_{1-2}$ alkanediyl, and substituted C$_{1-2}$ alkanediyl.
In compounds of Formula (1)-(3), R$^2$ can be a single bond.
In compounds of Formula (1)-(3), R$^2$ can be a single bond; and R$^3$ can be C$_{1-6}$ alkyl.
In compounds of Formula (1)-(3), R$^2$ can be selected from C$_{1-2}$ alkanediyl and substituted C$_{1-2}$ alkanediyl.

In compounds of Formula (1)-(3), $R^2$ can be methanediyl, ethanediyl, substituted methanediyl, or substituted ethanediyl.

In compounds of Formula (1)-(3), $R^2$ can be substituted $C_{1-2}$ alkanediyl where the substituent group can be selected from —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl.

In compounds of Formula (1)-(3), $R^2$ can be substituted $C_{1-2}$ alkanediyl where the substituent group can be a nucleophilic group. For example, $R^2$ can be substituted $C_{1-2}$ alkanediyl where the substituent group can be selected from —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each $R^4$ is defined as for Formula (1), or each $R^4$ can be selected from hydrogen and $C_{1-8}$ alkyl.

In compounds of Formula (1)-(3), $R^2$ can be substituted $C_{1-2}$ alkanediyl where the substituent group can be selected from —OH, —O—C(O)—R$^4$, —S—C(O)—R$^4$, —NH—C(O)—R$^4$, —C(O)—O—R$^4$, —C(O)—S—R$^4$, —C(O)—NH—R$^4$, —S—S—R$^4$, —S—R$^4$, —NH—R$^4$, —CH(—NH$_2$)(—R$^4$), substituted $C_{5-6}$ aryl, —NHR$^4$, and —CH(—NH$_2$)(—R$^4$), where $R^4$ is defined as for Formula (1), or each $R^4$ can be selected from hydrogen and $C_{1-8}$ alkyl.

In compounds of Formula (1)-(3), where $R^2$ can be substituted $C_{1-6}$ alkanediyl, substituted $C_{1-6}$ heteroalkanediyl, or substituted $C_{5-6}$ arenediyl, the stereochemistry of the carbon atom to which the substituent group is bonded can be of the (S) configuration.

In compounds of Formula (1)-(3), where $R^2$ can be substituted $C_{1-6}$ alkanediyl, substituted $C_{1-6}$ heteroalkanediyl, or substituted $C_{5-6}$ arenediyl, the stereochemistry of the carbon atom to which the substituent group is bonded can be of the (R) configuration.

In compounds of Formula (1)-(3), $R^2$ can be selected from $C_{5-6}$ cycloalkanediyl, $C_{5-6}$ heterocycloalkanediyl, $C_{5-6}$ arenediyl, and $C_{5-6}$ heterocycloalkanediyl.

In compounds of Formula (1)-(3), $R^2$ can be cyclopenta-1,3-diene-diyl, substituted cyclopenta-1,3-diene-diyl, benzene-diyl or substituted benzene-diyl. For example, $R^2$ can be 1,2-benzene-diyl or substituted 1,2-benzene-diyl.

In compounds of Formula (1)-(3), $R^3$ can be selected from —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, and —CH(—NH$_2$)(—R$^4$), where $R^4$ is defined as for Formula (1), or each $R^4$ can be selected from hydrogen and $C_{1-8}$ alkyl.

In compounds of Formula (1)-(3), $R^3$ can be selected from —O—C(O)—R$^4$, —C(O)—O—R$^4$, —S—C(O)—R$^4$, —C(O)—S—R$^4$, —S—S—R$^4$, —NH—R$^4$, and —CH(—NH$_2$)(—R$^4$); where $R^4$ is defined as for Formula (1), or each $R^4$ can be selected from hydrogen and $C_{1-8}$ alkyl.

In compounds of Formula (1)-(3), $R^3$ can be —C(O)—O—R$^4$, where $R^4$ is defined as for Formula (1), or each $R^4$ can be selected from hydrogen and $C_{1-8}$ alkyl.

In compounds of Formula (1)-(3), $R^4$ can be selected from hydrogen, $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1)-(3), $R^4$ can be selected from methyl, ethyl, phenyl, and benzyl.

In compounds of Formula (1)-(3), $R^4$ can be selected from hydrogen and $C_{1-8}$ alkyl.

In compounds of Formula (1)-(3), $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1)-(3), $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(3), $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(3), $R^3$ can be C(O)—O—R$^4$; and $R^4$ can be selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl, In compounds of Formula (1)-(3), $R^3$ can be C(O)—O—R$^4$; and $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1)-(3), $R^3$ can be C(O)—O—R$^4$; and $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(3), $R^3$ can be selected from —O—C(O)—CH$_3$, —O—C(O)—CH$_2$—CH$_3$, —O—C(O)-phenyl, —O—C(O)—CH$_2$-phenyl, —S—C(O)—CH$_3$, —S—C(O)—CH$_2$—CH$_3$, —S—C(O)— phenyl, —S—C(O)—CH$_2$-phenyl, —NH—C(O)—CH$_3$, —NH—C(O)—CH$_2$—CH$_3$, —NH—C(O)-phenyl, —NH—C(O)—CH$_2$-phenyl, —O—C(O)—O—CH$_3$, —O—C(O)—O—CH$_2$—CH$_3$, —O—C(O)—O-phenyl, —O—C(O)—O—CH$_2$-phenyl, —S—C(O)—O—CH$_3$, —S—C(O)—O—CH$_2$—CH$_3$, —S—C(O)—O-phenyl, —S—C(O)—O—CH$_2$-phenyl, —NH—C(O)—O—CH$_3$, —NH—C(O)—O—CH$_2$—CH$_3$, —NH—C(O)—O-phenyl, —NH—C(O)—O—CH$_2$-phenyl, —C(O)—O—CH$_3$, —C(O)—O—CH$_2$—CH$_3$, —C(O)—O-phenyl, —C(O)—O—CH$_2$-phenyl, —C(O)—S—CH$_3$, —C(O)—S—CH$_2$—CH$_3$, —C(O)—S-phenyl, —C(O)—S—CH$_2$-phenyl, —C(O)—NH—CH$_3$, —C(O)—NH—CH$_2$—CH$_3$, —C(O)—NH-phenyl, —C(O)—NH—CH$_2$-phenyl, —O—C(O)—O—CH$_3$, —O—C(O)—O—CH$_2$—CH$_3$, —O—C(O)—O-phenyl, —O—C(O)—O—CH$_2$-phenyl, —O—C(O)—S—CH$_3$, —O—C(O)—S—CH$_2$—CH$_3$, —O—C(O)—S-phenyl, —O—C(O)—S—CH$_2$-phenyl, —O—C(O)—NH—CH$_3$, —O—C(O)—NH—CH$_2$—CH$_3$, —O—C(O)—NH-phenyl, —O—C(O)—NH—CH$_2$-phenyl, —S—SH, —S—S—CH$_3$, —S—S—CH$_2$—CH$_3$, —S—S-phenyl, —S—S—CH$_2$-phenyl, —SH, —S—CH$_3$, —S—CH$_2$—CH$_3$, —S-phenyl, —S—CH$_2$-phenyl, —NH$_2$, —NH—CH$_3$, —NH—CH$_2$—CH$_3$, —NH-phenyl, —NH—CH$_2$-phenyl, —CH(—NH$_2$)(—CH$_3$), —CH(—NH$_2$)(—CH$_2$—CH$_3$), —CH(—NH$_2$)(-phenyl), and —CH(—NH$_2$)(—CH$_2$-phenyl).

In compounds of Formula (1)-(3), $R^3$ can be selected from $C_{5-6}$ cycloalkyl, $C_{5-6}$ heterocycloalkyl, $C_{5-6}$ aryl, $C_{5-6}$ heteroaryl, substituted $C_{5-6}$ cycloalkyl, substituted $C_{5-6}$ heterocycloalkyl, and substituted $C_{5-6}$ aryl, and substituted $C_{5-6}$ heteroaryl, comprising at least one nucleophilic group. For example, $R^3$ can have the structure of Formula (5a) or Formula (5b):

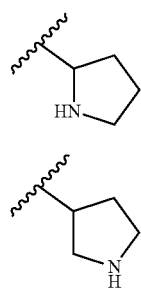

In compounds of Formula (1)-(3), $R^4$ can be selected from $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1)-(3), each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the at least one heteroatom.

In compounds of Formula (1)-(3), $R^2$ can be a single bond; $R^3$ can be $C_{1-3}$ alkyl; and each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In compounds of Formula (1)-(3), each $R^1$ together with the carbon atom to which they are bonded can from a $C_4$-, $C_5$-, or $C_6$-heterocycloalkyl group. The heterocycloalkyl group can have two adjacent sulfur atoms. In compounds of Formula (1)-(3) in each $R^1$ together with the carbon atom to which they are bonded can from a $C_4$-, $C_5$-, or $C_6$-heterocycloalkyl group, $R^2$ can be a single bond and $R^3$ can be $C_{1-6}$ alkyl, such as $C_{1-4}$ alkyl, such as methyl or ethyl:

In compounds of Formula (1)-(3), each $R^1$ together with the carbon atom to which they are bonded can from a substituted $C_4$-, substituted $C_5$-, or substituted $C_6$-heterocycloalkyl group. The substituted heterocycloalkyl group can have a sulfur atom and an adjacent carbonyl (=O) group. The substituted heterocycloalkyl group can have am oxygen atom and an adjacent carbonyl (=O) group.

In compounds of Formula (1)-(3), each $R^1$ together with the carbon atom to which they are bonded can from a substituted $C_4$-, substituted $C_5$-, or substituted $C_6$-heterocycloalkyl group, $R^3$ can be a single bond and $R^4$ can be $C_{1-6}$ alkyl, such as $C_{1-4}$ alkyl, such as methyl or ethyl:

In compounds of Formula (1)-(3), $R^2$ can be a single bond; $R^3$ can be $C_{1-3}$ alkyl; and each $R^1$ together with the carbon atom to which each $R^1$ is bonded can form a $C_{4-6}$ heterocycloalkyl ring or a substituted $C_{4-6}$ heterocycloalkyl ring.

In compounds of Formula (1)-(3), $R^2$ can be a single bond; $R^3$ can be $C_{1-3}$ alkyl; and each $R^1$ together with the carbon atom to which each $R^1$ is bonded can form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In compounds of Formula (1)-(3), $R^2$ can be a single bond; $R^3$ can be $C_{1-3}$ alkyl; and each $R^1$ together with the carbon atom to which each $R^1$ is bonded can form a 1,2-dithiolate ring, a 1,2-dithane ring, a thietan-2-one ring, a dihydrothiophen-2(3H)-one ring, a tetrahydro-2H-thipyran-2-one ring, an oxetan-2-one ring, a dihydrofuran-2(3H)-one ring, or a tetrahydro-2H-pyran-2-one ring.

In compounds of Formula (1)-(3),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1)-(3),
each $R^1$ and the geminal carbon to which each $R^1$ is bonded can form a $C_{3-6}$ cycloalkyl ring;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1)-(3),
$R^2$ can be a single bond;
$R^3$ be $C_{1-3}$ alkyl; and
each $R^1$ together with the carbon atom to which each $R^1$ is bonded can form a 1,2-dithiolate ring, a 1,2-dithane ring, a thietan-2-one ring, a dihydrothiophen-2(3H)-one ring, a tetrahydro-2H-thipyran-2-one ring, an oxetan-2-one ring, a dihydrofuran-2(3H)-one ring, or a tetrahydro-2H-pyran-2-one ring.

In compounds of Formula (1)-(3),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$); wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(3),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$; wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1)-(3),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$); wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(3),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$; wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1)-(3),
each $R^1$ can be methyl;
$R^2$ can be a single bond; and
$R^3$ can be —C(O)—O—$R^4$;
wherein $R^4$ can be selected from $C_{1-10}$ alkyl, $C_{1-10}$ heteroalkyl, $C_{7-10}$ alkylarene, and $C_{5-10}$ heteroalkylcycloalkyl.

In compounds of Formula (1)-(3),
each $R^1$ can be methyl;
$R^2$ can be a single bond;
$R^3$ can be —C(O)—O—$R^4$; wherein $R^4$ can be selected from $C_{1-10}$ alkyl, $C_{1-10}$ heteroalkyl, $C_{7-10}$ alkylarene, and $C_{5-10}$ heteroalkylcycloalkyl; and
each of $R^5$, $R^6$, and $R^7$ can be hydrogen.

In compounds of Formula (1)-(3), each of $R^5$, $R^6$, and $R^7$ can be hydrogen.

In compounds of Formula (1)-(3), each $R^1$ can be independently $C_{1-3}$ alkyl; each $R^2$ can be a single bond; and each of $R^5$, $R^6$, and $R^7$ can be hydrogen.

In compounds of Formula (1)-(3), each $R^1$ can be independently $C_{1-3}$ alkyl; and each $R^2$ can be a single bond.

In compounds of Formula (1)-(3),
each $R^1$ can be independently selected from $C_{1-3}$ alkyl, or each $R^1$ together with the geminal carbon atom to which they are bonded form a $C_{3-6}$ cycloalkyl ring, a substituted $C_{3-6}$ cycloalkyl ring, a $C_{3-6}$ heterocycloalkyl ring, or a substituted $C_{3-6}$ heterocycloalkyl ring;
$R^2$ can be a single bond;
$R^3$ can be —C(O)—O—$R^4$; and
$R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1)-(3),
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1)-(3),
each $R^1$ can be independently selected from $C_{1-3}$ alkyl, or each $R^1$ together with the carbon atom to which they are bonded form a $C_{3-6}$ cycloalkyl ring; and
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$arylalkyl, $C_{3-6}$ heterocycloalkyl, and substituted $C_{4-10}$ heterocycloalkylalkyl.

In compounds of Formula (1)-(3),
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1)-(3),
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

In compounds of Formula (1)-(3),
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond; and
$R^3$ can be $C_{1-3}$ alkyl.

In compounds of Formula (1)-(3),
each $R^1$ can be independently selected from $C_{1-3}$ alkyl;
$R^2$ can be selected from a single bond and methanediyl; and
$R^3$ can be selected from —O—C(O)—$R^4$ and —C(O)—O—$R^4$, wherein $R^4$ can be selected from $C_{1-10}$ alkyl and substituted phenyl.

In compounds of Formula (1)-(3),
each $R^1$ can be independently selected from $C_{1-3}$ alkyl;
$R^2$ can be a single bond;
$R^3$ can be —CH=C($R^4$)$_2$, wherein each $R^4$ can be —C(O)—O—$R^8$, or each $R^4$ together with the carbon atom to which they are bonded from a substituted heterocyclohexyl ring; and
each $R^8$ can be $C_{1-4}$ alkyl.

In compounds of Formula (1)-(3),
each $R^1$ can be independently selected from $C_{1-3}$ alkyl;
$R^2$ can be selected from a single bond and methanediyl; and
$R^3$ can be substituted phenyl, wherein the one or more substituents can be independently selected from —CH$_2$—O—C(O)—$R^4$ and —O—C(O)—$R^4$, wherein $R^4$ can be selected from $C_{1-10}$ alkyl and phenyl.

In compounds of Formula (1)-(3),
each $R^1$ can be independently selected from $C_{1-3}$ alkyl;
$R^2$ can be selected from —C($R^8$)$_2$— and —CH$_2$—C(R)$_2$—, wherein each $R^8$ can be independently selected from $C_{1-3}$ alkyl; and
$R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In compounds of Formula (1)-(3),
each $R^1$ together with the carbon atom to which they are bonded form a substituted $C_5$-heterocyclic ring;
$R^2$ can be a single bond; and
$R^3$ can be $C_{1-3}$ alkyl.

In compounds of Formula (1),
each of $R^5$ and $R^6$ can be hydrogen;
$R^7$ can be selected from hydrogen, $C_{1-6}$ alkyl, $C_{1-6}$ heteroalkyl, and 4-(yl-methyl)-5-methyl-1,3-dioxol-2-one;
$R^2$ is a single bond; and
$R^3$ is —C(O)—O—$R^4$, where $R^4$ is selected from $C_{1-6}$ alkyl.

A compound of Formula (1) can be a compound of sub-genus (1A), or a pharmaceutically acceptable salt thereof, wherein,
each of $R^5$ and $R^6$ can be hydrogen;
$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl, or each $R^1$ together with the carbon atom to which they are bonded form a $C_{3-6}$ cycloalkyl ring;

$R^2$ can be selected from single bond, methane-diyl, and ethane-diyl; and $R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1A), each of $R^5$, $R^6$, and $R^7$ can be hydrogen.

In compounds of subgenus (1A), each of $R^5$ and $R^6$ can be hydrogen; and $R^7$ can be selected from $C_{1-6}$ alkyl and $C_{1-6}$ heteroalkyl.

In compounds of subgenus (1A), each $R^1$ can be independently selected from $C_{1-3}$ alkyl.

In compounds of subgenus (1A), each $R^1$ together with the carbon atom to which they are bonded form a $C_{3-6}$ cycloalkyl ring.

In compounds of subgenus (1A), $R^2$ a single bond.

In compounds of subgenus (1A), $R^2$ can be methane-diyl.

In compounds of subgenus (1A), $R^2$ can be ethane-diyl.

In compounds of subgenus (1A), $R^3$ can be —C(O)—O—$R^4$.

In compounds of subgenus (1A), $R^3$ can be —S—C(O)—$R^4$.

In compounds of subgenus (1A), $R^4$ can be $C_{1-10}$ alkyl.

In compounds of subgenus (1A), $R^4$ can be $C_{1-10}$ heteroalkyl.

In compounds of subgenus (1A), $R^4$ can be $C_{5-10}$ arylalkyl.

In compounds of subgenus (1A), $R^4$ can be $C_{3-6}$ heterocycloalkyl.

In compounds of subgenus (1A), $R^4$ can be substituted $C_{4-10}$ heterocycloalkylalkyl.

A compound of Formula (1) can be a compound of sub-genus (1B), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl, or each $R^1$ together with the carbon atom to which they are bonded form a $C_{3-6}$ cycloalkyl ring;

$R^2$ can be a single bond; and $R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1B), each of $R^5$, $R^6$, and $R^7$ can be hydrogen.

In compounds of subgenus (1B), each of $R^5$ and $R^6$ can be hydrogen; and $R^7$ can be selected from $C_{1-6}$ alkyl and $C_{1-6}$ heteroalkyl.

In compounds of subgenus (1B), each $R^1$ can be independently selected from $C_{1-3}$ alkyl.

In compounds of subgenus (1B), each $R^1$ together with the carbon atom to which they are bonded form a $C_{3-6}$ cycloalkyl ring.

In compounds of subgenus (1B), $R^4$ can be selected from $C_{1-7}$ alkyl, $C_{1-10}$ heteroalkyl wherein the one or more heteroatoms can be oxygen, —$CH_2$—$C_{4-6}$ cycloalkyl, —$(CH_2)_2$—$C_{4-6}$ cycloalkyl, $C_3$-heterocycloalkyl wherein the one or more heteroatoms can be oxygen, and —$CH_2$—$C_{3-6}$ substituted heterocycloalkyl, and —$(CH_2)_2$—$C_{3-6}$ substituted heterocycloalkyl.

In compounds of subgenus (1B), in the substituted $C_{3-6}$ heterocycloalkyl the one or more heteroatoms can be oxygen, and the one or more substituents can be independently selected from $C_{1-3}$ alkyl and =O.

In compounds of subgenus (1B), each $R^1$ can be methyl, or each $R^1$ together with the carbon atom to which they are bonded form a cyclohexyl ring or a cyclopentyl ring.

In compounds of subgenus (1B), $R^4$ can be selected from methyl, ethyl, n-propyl, iso-propyl, n-butyl, n-hexyl, n-heptyl, —$CH_2$—$CH_2$—O—$CH_3$, benzyl, 3-oxetanyl, and methyl-5-methyl-1,3-dioxol-2-one.

In compounds of subgenus (1B), each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be methyl, or each $R^1$ together with the carbon atom to which they are bonded form a cyclohexyl ring or a cyclopentyl ring;

$R^2$ can be a single bond; and $R^3$ can be —C(O)—O—$R^4$, wherein $R^4$ can be selected from methyl, ethyl, n-propyl, iso-propyl, n-butyl, n-hexyl, n-heptyl, —$CH_2$—$CH_2$—O—$CH_3$, —$CH_2$-phenyl (benzyl), 3-oxetanyl, and methyl-5-methyl-1,3-dioxol-2-one.

A compound of Formula (1) can be a compound of sub-genus (1C), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl, or each $R^1$ together with the carbon atom to which they are bonded form a $C_{3-6}$ cycloalkyl ring;

$R^2$ can be —$(CH_2)_2$—; and $R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1C), each of $R^5$, $R^6$, and $R^7$ can be hydrogen.

In compounds of subgenus (1C), each of $R^5$ and $R^6$ can be hydrogen; and $R^7$ can be selected from $C_{1-6}$ alkyl and $C_{1-6}$ heteroalkyl.

In compounds of subgenus (1C), each $R^1$ can be independently selected from $C_{1-3}$ alkyl.

In compounds of subgenus (1C), each $R^1$ together with the carbon atom to which they are bonded form a $C_{3-6}$ cycloalkyl ring.

In compounds of subgenus (1C), $R^4$ can be selected from $C_{1-7}$ alkyl, $C_{1-10}$ heteroalkyl wherein the one or more heteroatoms can be oxygen, —$CH_2$—$C_{4-6}$ cycloalkyl, —$(CH_2)_2$—$C_{4-6}$ cycloalkyl, $C_3$-heterocycloalkyl wherein the one or more heteroatoms can be oxygen, —$CH_2$—$C_{3-6}$ substituted heterocycloalkyl, and —$(CH_2)_2$—$C_{3-6}$ substituted heterocycloalkyl.

In compounds of subgenus (1C), in the substituted $C_{3-6}$ heterocycloalkyl the one or more heteroatoms can be oxygen, and the one or more substituents can be independently selected from $C_{1-3}$ alkyl and =O.

In compounds of subgenus (1C), $R^4$ can be $C_{1-10}$ alkyl.

In compounds of subgenus (1C), each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be methyl;

$R^2$ can be —$(CH_2)_2$—; and $R^3$ can be —C(O)—O—$R^4$ wherein $R^4$ can be selected from n-hexyl and n-heptyl.

A compound of Formula (1) can be a compound of sub-genus (1D), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be selected from $C_{1-3}$ alkyl, or each $R^1$ together with the carbon atom to which they are bonded form a $C_{3-6}$ cycloalkyl ring;

$R^2$ can be —$CH_2$—; and $R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

In compounds of subgenus (1D), each of $R^5$, $R^6$, and $R^7$ can be hydrogen.

In compounds of subgenus (1D), each of $R^5$ and $R^6$ can be hydrogen; and $R^7$ can be selected from $C_{1-6}$ alkyl and $C_{1-6}$ heteroalkyl.

In compounds of subgenus (1D), each $R^1$ can be independently selected from $C_{1-3}$ alkyl.

In compounds of subgenus (1D), each $R^1$ together with the carbon atom to which they are bonded form a $C_{3-6}$ cycloalkyl ring.

In compounds of subgenus (1D), $R^4$ can be selected from $C_{1-7}$ alkyl, $C_{1-10}$ heteroalkyl wherein the one or more heteroatoms can be oxygen, —$CH_2$—$C_{4-6}$ cycloalkyl, —$(CH_2)_2$—$C_{4-6}$ cycloalkyl, $C_3$-heterocycloalkyl wherein the one or more heteroatoms can be oxygen, —$CH_2$—$C_{3-6}$ substituted heterocycloalkyl, —$(CH_2)_2$—$C_{3-6}$ substituted heterocycloalkyl.

In compounds of subgenus (1D), in the substituted $C_{3-6}$ heterocycloalkyl the one or more heteroatoms can be oxygen, and the one or more substituents can be independently selected from $C_{1-3}$ alkyl and =O.

In compounds of subgenus (1D), $R^4$ can be $C_{1-10}$ alkyl.

In compounds of subgenus (1D), each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be methyl;

$R^2$ can be —$CH_2$—; and $R^3$ can be —S—C(O)—$R^4$, wherein $R^4$ can be methyl.

A compound of Formula (1) can be a compound of sub-genus (1E), or a pharmaceutically acceptable salt thereof, wherein, each of $R^5$, $R^6$, and $R^7$ can be hydrogen;

each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;

$R^2$ can be a single bond; and $R^3$ can be $C_{1-3}$ alkyl.

In compounds of subgenus (1E), each of $R^5$, $R^6$, and $R^7$ can be hydrogen.

In compounds of subgenus (1E), each of $R^5$ and $R^6$ can be hydrogen; and $R^7$ can be selected from $C_{1-6}$ alkyl and $C_{1-6}$ heteroalkyl.

In compounds of subgenus (1E), each $R^1$ together with the carbon atom to which they are bonded form a $C_{3-6}$ heterocycloalkyl ring or a $C_{3-6}$ heterocycloalkyl ring;

In compounds of subgenus (1E), the one or more heteroatoms can be oxygen and the one or more substituents can be =O.

In compounds of subgenus (1E), each $R^1$ together with the carbon atom to which they are bonded form a dihydrofuran-2(3H)-one ring;

$R^2$ can be a single bond; and $R^3$ can be methyl.

A compound of Formula (1) can be a compound of sub-genus (1F), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from a single bond and methanediyl; and $R^3$ can be selected from —O—C(O)—$R^4$ and —C(O)—O—$R^4$, wherein $R^4$ can be selected from $C_{1-10}$ alkyl and substituted phenyl.

In compounds of subgenus (1F), each of $R^5$, $R^6$, and $R^7$ can be hydrogen.

In compounds of subgenus (1F), each of $R^5$ and $R^6$ can be hydrogen; and $R^7$ can be selected from $C_{1-6}$ alkyl and $C_{1-6}$ heteroalkyl.

In compounds of subgenus (1F), $R^2$ can be a single bond.

In compounds of subgenus (1F), $R^2$ can be methanediyl.

In compounds of subgenus (1F), $R^3$ can be —O—C(O)—$R^4$.

In compounds of subgenus (1F), $R^2$ can be methanediyl; and $R^3$ can be —O—C(O)—$R^4$.

In compounds of subgenus (1F), $R^3$ can be —C(O)—O—$R^4$.

In compounds of subgenus (1F), $R^2$ can be a single bond; and $R^3$ can be —C(O)—O—$R^4$.

In compounds of subgenus (1F), $R^2$ can be a single bond; $R^3$ can be —C(O)—O—$R^4$; and $R^4$ can be $C_{1-3}$ alkyl.

In compounds of subgenus (1F), $R^4$ can be $C_{1-10}$ alkyl.

In compounds of subgenus (1F), $R^4$ can be $C_{1-4}$ alkyl.

In compounds of subgenus (1F), $R^4$ can be substituted phenyl.

In compounds of subgenus (1F), $R^2$ can be methanediyl; $R^3$ can be —O—C(O)—$R^4$; and $R^4$ can be substituted phenyl.

In compounds of subgenus (1F), the one or more substituents can be independently selected from halogen, $C_{1-3}$ alkyl, and $C_{1-3}$ alkoxy.

In compounds of subgenus (1F), the substituted phenyl can be 2,6-substituted phenyl.

In compounds of subgenus (1F), each of the substituents can be selected from $C_{1-3}$ alkyl and Ca-3 alkoxy.

In compounds of subgenus (1F), the substituted phenyl can be 2,5,6-substituted phenyl.

In compounds of subgenus (1F), each of the substituents at the 2 and 6 positions can be independently selected from $C_{1-3}$ alkyl and $C_{1-3}$ alkoxy; and the substituent at the 5 position can be halogen.

A compound of Formula (1) can be a compound of sub-genus (1G), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be a single bond; and $R^3$ can be —CH=C($R^4$)$_2$, wherein each $R^4$ can be —C(O)—O—$R^8$, or each $R^4$ together with the carbon atom to which they are bonded from a substituted heterocyclohexyl ring; and each $R^8$ can be $C_{1-4}$ alkyl.

In compounds of subgenus (1G), each of $R^5$, $R^6$, and $R^7$ can be hydrogen.

In compounds of subgenus (1G), each of $R^5$ and $R^6$ can be hydrogen; and $R^7$ can be selected from $C_{1-6}$ alkyl and $C_{1-6}$ heteroalkyl.

In compounds of subgenus (1G), each $R^4$ can be —C(O)—O—$R^8$.

In compounds of subgenus (1G), each $R^4$ can be —C(O)—O—$R^8$, or each $R^4$ together with the carbon atom to which they are bonded from a substituted heterocyclohexyl ring.

In compounds of subgenus (1G), in the substituted heterocyclohexyl ring, the one or more heteroatoms can be oxygen.

In compounds of subgenus (1G), in the substituted heterocyclohexyl ring, the one or more substituents can be independently selected from $C_{1-3}$ alkyl and =O.

In compounds of subgenus (1G), the substituted heterocycloalkyl ring can be 2,2-dimethyl-5-yl-1,3-dioxane-4,6-dione.

A compound of Formula (1) can be a compound of sub-genus (1H), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each of $R^5$, $R^6$, and $R^7$ can be hydrogen;

each $R^1$ can be independently selected from $C_{1-3}$ alkyl;

$R^2$ can be selected from a single bond and methanediyl; and $R^3$ can be substituted phenyl, wherein the one or more substituents can be independently selected from —$CH_2$—O—C(O)—$R^4$ and —O—C(O)—$R^4$, wherein $R^4$ can be selected from $C_{1-10}$ alkyl and phenyl.

In compounds of subgenus (1H), each of $R^5$, $R^6$, and $R^7$ can be hydrogen.

In compounds of subgenus (1H), each of $R^5$ and $R^6$ can be hydrogen; and $R^7$ can be selected from $C_{1-6}$ alkyl, and $C_{1-6}$ heteroalkyl.

In compounds of subgenus (1H), $R^2$ can be a single bond.

In compounds of subgenus (1H), $R^2$ can be 2-substituted phenyl.

In compounds of subgenus (1H), the one or more substituents can be —$CH_2$—O—C(O)—$R^4$.

In compounds of subgenus (1H), the one or more substituents can be —O—C(O)—$R^4$.

In compounds of subgenus (1H), $R^4$ can be $C_{1-10}$ alkyl.

In compounds of subgenus (1H), $R^4$ can be selected from methyl, ethyl, iso-propyl, pivalolyl, and phenyl.

A compound of Formula (1) can be a compound of sub-genus (1I), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from —C($R^8$)$_2$— and —$CH_2$—C(R)$_2$—, wherein each $R^8$ can be independently selected from $C_{1-3}$ alkyl; and $R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In compounds of subgenus (1I), each of $R^5$, $R^6$, and $R^7$ can be hydrogen.

In compounds of subgenus (1I), each of $R^5$ and $R^6$ can be hydrogen; and $R^7$ can be selected from $C_{1-6}$ alkyl and $C_{1-6}$ heteroalkyl.

In compounds of subgenus (1I), each $R^1$ can be methyl.

In compounds of subgenus (1I), $R^2$ can be —C(R)$_2$—.

In compounds of subgenus (1I), $R^2$ can be —$CH_2$—C(R)$_2$—.

In compounds of subgenus (1I), each $R^8$ can be methyl.

In compounds of subgenus (1I), each $R^1$ can be methyl; and each $R^8$ can be methyl.

In compounds of subgenus (1I), $R^3$ can be —C(O)—O—$R^4$.

In compounds of subgenus (1I), $R^3$ can be —O—C(O)—$R^4$.

A compound of Formula (1) can be a compound of sub-genus (1J), or a pharmaceutically acceptable salt thereof, wherein, each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ together with the carbon atom to which they are bonded form a substituted $C_5$-heterocyclic ring;

$R^2$ can be a single bond; and $R^3$ can be $C_{1-3}$ alkyl.

In compounds of subgenus (1J), in the substituted $C_{5-6}$ heterocyclic ring, the one or more heteroatoms can be oxygen; and the one or more substituents can be independently selected from $C_{1-3}$ alkyl and =O.

In compounds of subgenus (1J), each $R^1$ together with the carbon atom to which they are bonded form a tetrahydro-2H-pyran-2-one ring.

In compounds of subgenus (1J), each of $R^5$ and $R^6$ can be hydrogen;

$R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from $C_{2-4}$ alkanediyl; and $R^3$ can be substituted $C_{5-6}$ heterocycloalkyl, wherein the one or more heteroatoms can be independently selected from N and O; and the one or more substituents can be independently selected from $C_{1-3}$ alkyl and =O.

In compounds of subgenus (1J), each of $R^5$, $R^6$, and $R^7$ can be hydrogen.

In compounds of subgenus (1J), each of $R^5$ and $R^6$ can be hydrogen; and $R^7$ can be selected from $C_{1-6}$ alkyl, and $C_{1-6}$ heteroalkyl.

In compounds of subgenus (1J), $R^3$ can have the structure of Formula (5):

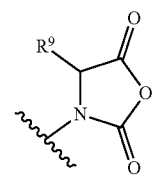

(5)

wherein $R^9$ can be selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

In compounds of subgenus (1J), $R^9$ can be selected from hydrogen and $C_{1-6}$ alkyl such as $C_{1-4}$ alkyl such as methyl or ethyl.

A compound of Formula (1) can have the structure of Formula (4):

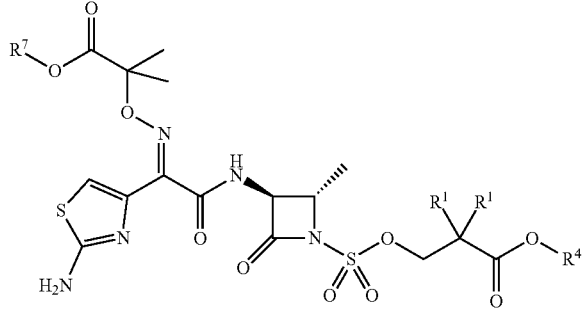

(4)

wherein each $R^1$, $R^4$, and $R^7$ is defined as for Formula (1).

In compound of Formula (4),
each $R^1$ can be selected from $C_{1-6}$ alkyl;
$R^4$ can be selected from $C_{1-6}$ alkyl, $C_{1-6}$ heteroalkyl, $C_{5-6}$ cycloalkyl, and $C_{5-6}$ heterocycloalkyl; and
$R^7$ can be selected from hydrogen, $C_{1-6}$ alkyl, $C_{1-6}$ heteroalkyl, and 4-(yl-methyl)-5-methyl-1,3-dioxol-2-one.

In compounds of Formula (4), each $R^1$ can be selected from $C_{1-3}$ alkyl; $R^4$ can be selected from $C_{1-6}$ alkyl and $C_{5-6}$ cycloalkyl; and $R^7$ can be selected from hydrogen and $C_{1-6}$ alkyl.

In compounds of Formula (1), the compound can be selected from:
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-3-oxo-3-propoxypropoxy)sulfonyl)-2-methyl-4-oxoazetidin-3-yl)amino)-2-oxoethylidene)amino)oxy)-2-methylpropanoic acid;
methyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
a pharmaceutically acceptable salt of any of the foregoing; and
a combination of any of the foregoing.

In compounds of Formula (1), the compound can be selected from:
2-((((E)-1-(2-aminothiazol-4-yl)-2-(((2S,3S)-1-((3-(benzoyloxy)-2,2-dimethylpropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-(benzoyloxy)-2,2-dimethylbutoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid;
6-(4-((((2S,3S)-3-((E)-2-(2-aminothiazol-4-yl)-2-(((2-carboxypropan-2-yl)oxy)imino)acetamido)-2-methyl-4-oxoazetidin-1-yl)sulfonyl)oxy)-3,3-dimethylbutoxy)-6-oxohexanoic acid;
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-isopropoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(hexyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(heptyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(tert-butoxy)-2,2-dimethyl-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-((3-(2-methoxyethoxy)-2,2-dimethyl-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-((2,2-dimethyl-3-(oxetan-3-yloxy)-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-(((1-(ethoxycarbonyl)cyclohexyl)methoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-(((1-(ethoxycarbonyl)cyclopentyl)methoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-(((1-(ethoxycarbonyl)cyclobutyl)methoxy)sulfonyl)-2-methyl-4-oxoazetidin-3-yl)amino)-2-oxoethylidene)amino)oxy)-2-methylpropanoic acid;

a pharmaceutically acceptable salt of any of the foregoing; and a combination of any of the foregoing.

A compound of Formula (1)-(4) can be a solvate, a pharmaceutically acceptable salt, or a combination thereof.

In compounds of Formula (1)-(4), a pharmaceutically acceptable salt can be the hydrochloride salt.

In compounds of Formula (1)-(4), a pharmaceutically acceptable salt can be the dihydrochloride salt.

A compound of Formula (1)-(4) can be a pharmaceutically acceptable salt of a compound of Formula (1)-(4), a hydrate thereof, or a solvate of any of the foregoing.

Compounds of Formula (1)-(4) can be synthesized using methods known in the art. The synthesis of aztreonam is described, for example, in Singh et al., *Organic Process Research & Development*, 2002, 6, 863-868. Formation of sulfate esters is also well-known in the art as disclosed, for example, in Simpson et al., *J. Am. Chem. Soc.* 2006, 128, 1605.

The general steps to synthesize a prodrug on an N-sulfonate group, such as the N-sulfate group of aztreonam is provided as follows.

Referring to FIG. 1, starting with Boc-O-benzyl threonine 1, treatment with triflate anhydride followed by reaction with tetrabutyl ammonium azide provides the corresponding azide intermediate 20. Trimethylphosphine reduction of the azide intermediate 20 produces the corresponding amino ester 21 in 60% yield. N-sulfonylation of the amino ester 22 with chlorosulfonate provides the corresponding sulfamate 25 with a 30% yield. Quantitative hydrogenolysis affords the sulfamate acid 23, which undergoes cyclization to the corresponding β-lactam 24 with a 54% yield. The steps are disclosed in Examples 20-24.

Figure 2:
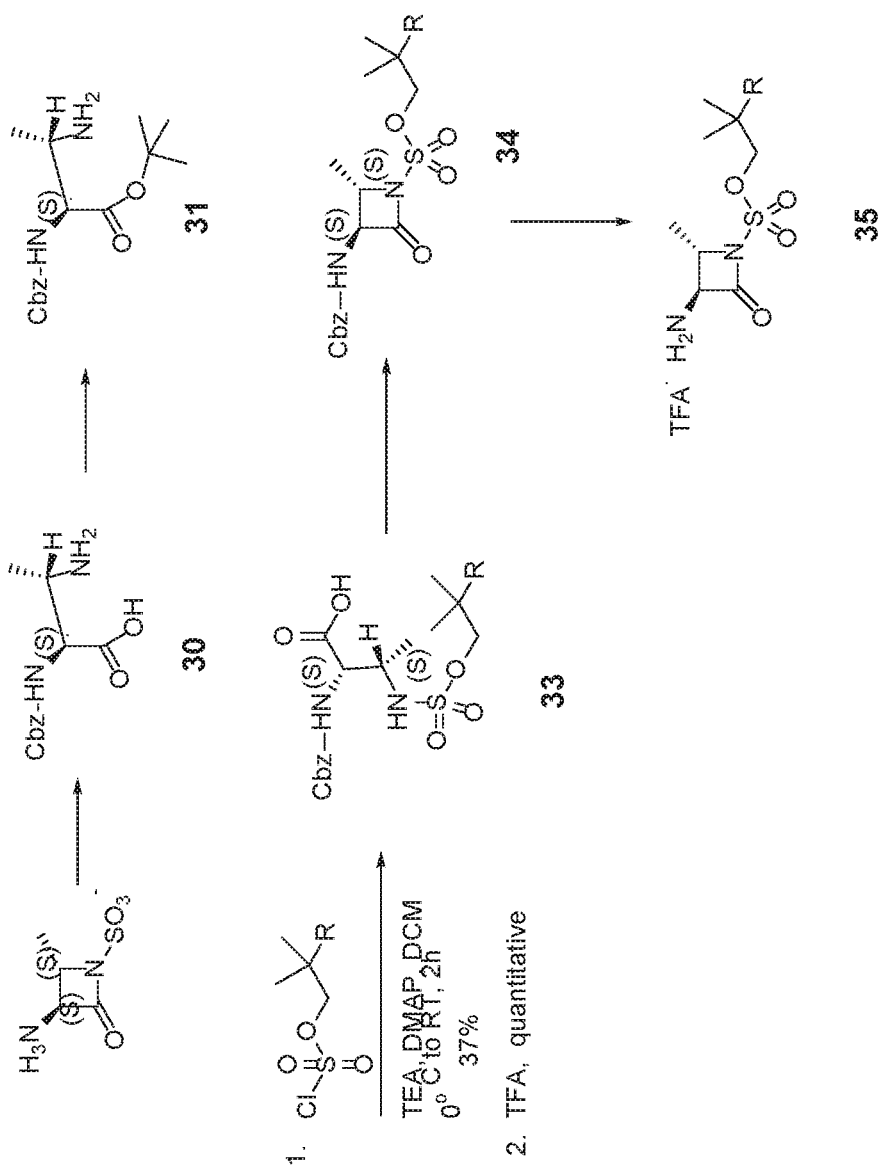
FIG. 2 shows certain steps in synthesizing aztreonam derivatives provided by the present disclosure. The steps correspond to those disclosed in Examples 30-34.

FIG. 2 shows an alternative route for synthesizing sulfonate ester prodrugs of aztreonam. Starting from the commercially available amino N-sulfonate, formation of the N-Cbz β-lactam followed by desulfation provides the corresponding oxazetidine 30. Treatment of the oxazetidine 9 with aqueous formic acid affords the crystalline amino acid 31. In this case the sulfonylation proceeds from acid 31 to the corresponding to tert-butyl ester. Treatment with a chlorosulfonate as shown in FIG. 1 provides acid N-sulfonate ester 33. Cyclization of the sulfonate ester 33 gives corresponding β-lactam 34 in a 21% yield. The amine group of the lactam 34 can be deprotected to provide the corresponding oxoazetidine N-sulfonate ester 35. The steps are provided in Examples 30-34.

Figure 3:
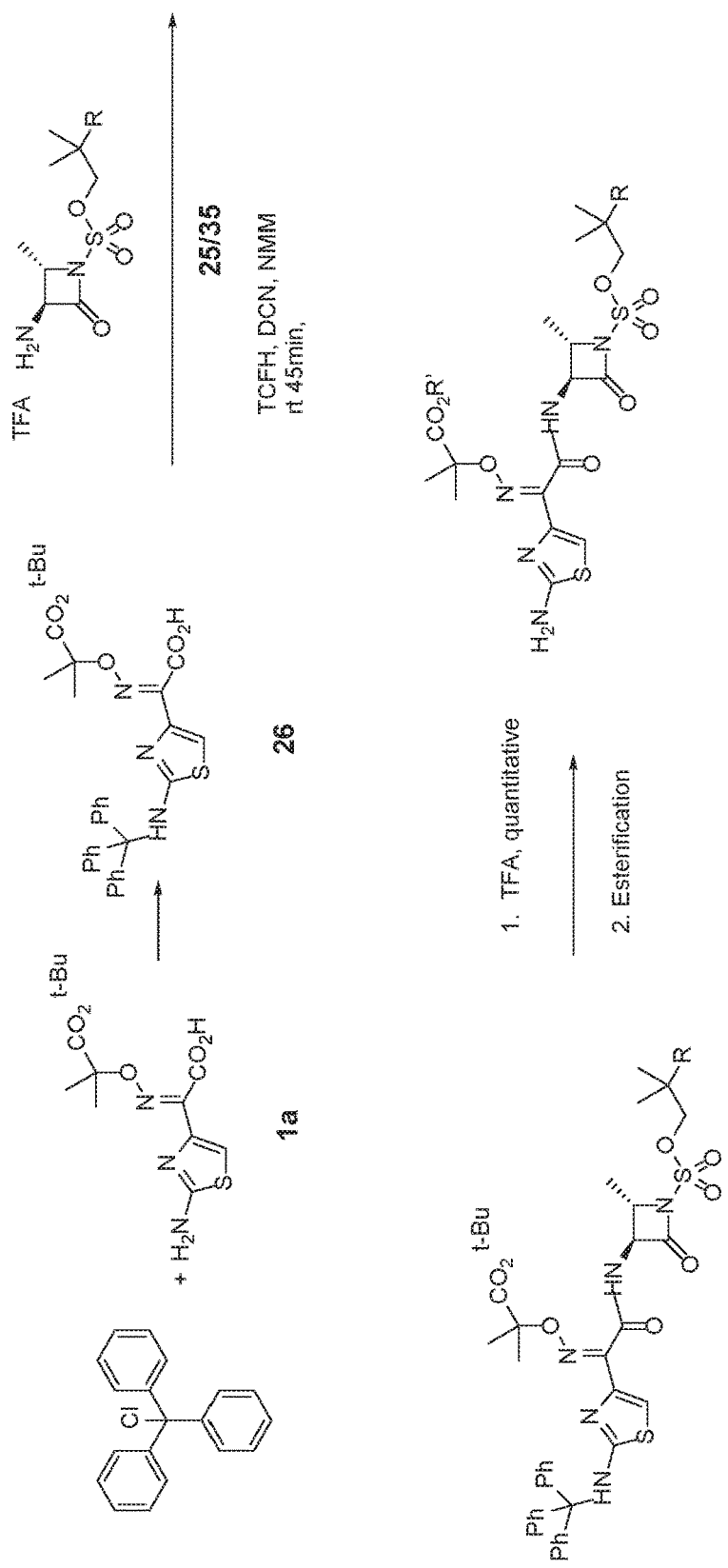
FIG. 3 shows certain steps in synthesizing aztreonam derivatives provided by the present disclosure. The steps correspond to those disclosed in Examples 2 and 27.

FIG. 3 shows a method for attaching a 2-((((2-aminothiazol-4-yl)(carboxy)methylene)amino)oxy)-2-methylpropanoic acid sidechain to the N-sulfonated oxazetidine ring. The steps are provided in Examples 26-27. (Z)-2-(2-Aminothiazol-4-yl)-2-(((1-(tert-butoxy)-2-methyl-1-oxopropan-2-yl)oxy)imino)acetic acid (1a) is reacted with tritylchloride in the presence of a base to provide the corresponding tritylamine 26. The tritylamine 26 is reacted with the N-sulfonate ester to provide the corresponding 3-((((2S,3S)-3-((E)-2-(((1-(tert-butoxy)-2-methyl-1-oxopropan-2-yl)oxy)imino)-2-(2-(tert-butylamino)thiazol-4-yl)acetamido)-2-methyl-4-oxoazetidin-1-yl)sulfonyl)oxy) ester 25/35 which can be deprotected and then esterified as appropriate to provide the corresponding aztreonam N-sulfonate ester prodrugs.

Compounds of Formula (1) or pharmaceutically acceptable salts thereof may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. Pharmaceutical compositions provided by the present disclosure can be provided as oral formulations. Oral formulations may be oral dosage forms.

Pharmaceutical compositions provided by the present disclosure may comprise a therapeutically-effective amount of a compound of Formula (1) or a pharmaceutically acceptable salt thereof together with a suitable amount of one or more pharmaceutically acceptable vehicles so as to provide a composition for proper administration to a patient. Suitable pharmaceutical vehicles and methods of preparing pharmaceutical compositions are described in the art. Examples of suitable pharmaceutical vehicles are described in the art.

Pharmaceutical compositions comprising a compound may be manufactured by means of conventional mixing, dissolving, granulating, levitating, emulsifying, encapsulating, entrapping or lyophilizing processes. Pharmaceutical compositions may be formulated in a suitable manner using one or more physiologically acceptable carriers, diluents; excipients or auxiliaries, which facilitate processing of compounds into preparations which can be used pharmaceutically. Suitable formulation is dependent upon the route of administration chosen.

A compound of Formula (1) may be incorporated into pharmaceutical compositions to be administered orally. Oral administration of such pharmaceutical compositions may result in uptake of the compound of Formula (1) throughout or in a portion of the gastrointestinal tract and entry into the systemic circulation. Such compositions may be prepared in a manner known in the pharmaceutical art and can comprise a compound of Formula (1) and at least one pharmaceutically acceptable vehicle. Pharmaceutical compositions may include a therapeutically effective amount of a compound of Formula (1) and a suitable amount of a pharmaceutically acceptable vehicle, so as to provide an appropriate form for administration to a patient.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, in tablet or pill forms, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions may include standard vehicles such as mannitol, lactose, starch, magnesium stearate, sodium saccharine, cellulose, magnesium carbonate, etc. Such vehicles may be of pharmaceutical grade.

For oral liquid preparations, such as suspensions, elixirs and solutions, can include suitable carriers, excipients, or diluents include water, saline, alkylene glycols (e.g., propylene glycol), polyalkylene glycols (e.g., polyethylene glycol) oils, alcohols, slightly acidic buffers from about pH 4 to about pH 6 (e.g., acetate, citrate, ascorbate from about 5 mM to about 50 mM), etc. Additionally, flavoring agents, preservatives, coloring agents, bile salts, acylcarnitines, and the like may be added.

Compositions comprising a compound of Formula (1) associated with at least one pharmaceutically acceptable vehicle including excipients, carriers, diluents and/or adjuvants. In forming the compositions, a compound of Formula (1) may be mixed with an excipient, diluted by a diluent or enclosed within a carrier, which can be in the form of a capsule, sachet, paper or other container. When an excipient serves as a diluent, it can be a solid, semi-solid, or liquid material, which can act as a vehicle, carrier, or medium for a compound of Formula (1). Thus, compositions may be in the form of tablets, pills, powders, lozenges, sachets, cachets, elixirs, suspensions, emulsions, solutions, and syrups containing, for example, up to 90 wt % of a compound of Formula (1) using, for example, soft and hard gelatin capsules, where wt % is based on the total weight of the dosage form.

In preparing a composition, it may be useful to mill a compound of Formula (1) to provide an appropriate particle size prior to combining with other ingredients. The milled particle size of a compound of Formula (1) may be adjusted depending on the aqueous solubility, and can be, for example, less than 200 mesh, less than 100 mesh, or less than 40 mesh. Examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. Compositions may additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions may be formulated so as to provide quick, sustained, or delayed release a compound of Formula (1) after oral administration to the patient by employing procedures known in the art.

A composition may be formulated in unit dosage form, each dosage form comprising an equivalent weight of a compound of Formula (1) within a range, for example, from 10 mg to 10 g. A unit dosage form refers to a physically discrete unit suitable as a unitary dosage for humans and other mammals, each unit containing a predetermined quantity of active material calculated to produce an intended therapeutic effect, in association with a suitable pharmaceutical excipient, diluent, carrier and/or adjuvant.

For preparing solid compositions such as tablets, a compound of Formula (1) may be mixed with a pharmaceutical excipient, diluent, carrier and/or adjuvant to form a solid pre-formulation composition containing a homogeneous mixture containing a compound of Formula (1). When referring to these pre-formulation compositions as homogeneous, it is meant that a compound of Formula (1) is dispersed evenly throughout the composition so that the composition can be readily subdivided into equally effective unit dosage forms such as tablets, pills, or capsules. This solid pre-formulation can then be subdivided into unit dosage forms of the type described herein comprising, for example, an equivalent weight of aztreonam ranging from about 10 mg to about 10 g.

Tablets or pills comprising a compound of Formula (1) may be coated or otherwise compounded to provide a dosage form affording the advantage of sustained release. For example, a tablet or pill may comprise an inner dosage and an outer dosage component, the latter being in the form of an envelope over and/or enclosing the former. The two components may be separated by an enteric layer. The enteric layer may serve to resist disintegration in the stomach and permit the inner component to pass intact into the duodenum, or to delay release. A variety of materials may be used for such enteric layers or coatings. For example, such materials include a number of polymeric acids and mixtures of polymeric acids with such materials as shellac, cetyl alcohol, or cellulose acetate.

Liquid dosage forms in which the compositions a compound of Formula (1) may be incorporated for oral administration can include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

An oral formulation comprising a compound of Formula (1) may be practiced with a number of different dosage forms, which can be adapted to provide sustained release of a compound of Formula (1) following oral administration.

A sustained release oral dosage form can comprise, for example, beads that on dissolution or diffusion release the prodrug over an extended period of hours, in certain embodiments, over a period of at least about 4 hours, in some embodiments, over a period of at least about 8 hours, over a period of at least about 12 hours, over a period of at least about 16 hours, over a period of at least about 20 hours, over a period of at least about 24 hours, and in certain embodiments, over a period of more than about 24 hours. Prodrug-releasing beads may have a central composition or core comprising a compound of Formula (1) and at least one pharmaceutically acceptable vehicle, and may include an optional lubricant, antioxidant, and/or buffer. Examples of suitable timed-release beads are known in the art.

Enteric-coated preparations may be used for oral sustained release administration. Coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

Drug-releasing lipid matrices or prodrug-releasing waxes may be used for oral sustained release administration.

Dosage forms may comprise a compound of Formula (1) coated on a polymer substrate. The polymer may be an erodible or a non-erodible polymer.

A dosage form may comprise a compound of Formula (1) loaded into a polymeric matrix that releases the prodrug by diffusion through a polymer, or by flux through pores or by rupture of a polymer matrix.

Osmotic delivery systems are used for oral sustained release administration

Regardless of the specific form of sustained release oral dosage form used, a compound of Formula (1) may be released from a dosage form such as an orally administered dosage form, over a sufficient period of time to provide prolonged therapeutic concentrations of a compound of Formula (1) in the blood of a patient enabling administration of the dosage form on only a once or twice per day basis. Following oral administration, dosage forms comprising a compound of Formula (1) can provide a therapeutic or prophylactic concentration of aztreonam in the plasma and/or blood of a patient for a time period of at least about 4 hours, for at least about 8 hours, for at least about 12 hours, for at least about 16 hours, for at least about 20 hours, or for at least about 24 hours following oral administration of the dosage form to the patient. A therapeutically or prophylactically effective concentration of aztreonam in the blood and/or plasma of a patient can depend on a number of factors including, for example, the disease being treated, the severity of the disease, the weight of the patient, the health of the patient, and so forth.

Pharmaceutical compositions provided by the present disclosure comprise a compound of Formula (1) together with a suitable amount of one or more pharmaceutically acceptable vehicles so as to provide a composition for proper administration to a patient. Examples of suitable pharmaceutical vehicles are known in the art.

Pharmaceutical compositions comprising a compound of Formula (1) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (1) or crystalline form thereof and one or more pharmaceutically acceptable vehicles into formulations that can be used pharmaceutically. Proper formulation is dependent upon the route of administration chosen. In certain embodiments, a pharmaceutical composition comprising a compound of Formula (1) or crystalline form thereof may be formulated for oral administration, and in certain embodiments for sustained release oral administration. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of at least one compound of Formula (1) calculated to produce an intended therapeutic effect. A unit dosage form may be for a single daily dose, for administration 2 times per day, or one of multiple daily doses, e.g., 3 or more times per day. When multiple daily doses are used, a unit dosage may be the same or different for each dose. One or more dosage forms may comprise a dose, which may be administered to a patient at a single point in time or during a time interval.

In certain embodiments, a compound of Formula (1) may be incorporated into pharmaceutical compositions to be administered orally. Oral administration of such pharmaceutical compositions may result in uptake of a compound of Formula (1) throughout the intestine and entry into the systemic circulation. Such oral compositions may be prepared in a manner known in the pharmaceutical art and comprise at least one compound of Formula (1) and at least one pharmaceutically acceptable vehicle. Oral pharmaceutical compositions may include a therapeutically effective amount of at least one compound of Formula (1) and a suitable amount of a pharmaceutically acceptable vehicle, so as to provide an appropriate form for administration to a patient.

Pharmaceutical compositions comprising at least one compound of Formula (1) may be formulated for immediate release for parenteral administration, oral administration, or for any other appropriate route of administration.

Controlled drug delivery systems may be designed to deliver a drug in such a way that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution-controlled systems, diffusion-controlled systems, ion exchange resins, osmotically controlled systems, erodable matrix systems, pH independent formulations, gastric retention systems, and the like.

An oral dosage form provided by the present disclosure may be a controlled release dosage form. Controlled delivery technologies can improve the absorption of a drug in a particular region or regions of the gastrointestinal tract.

The appropriate oral dosage form for a particular pharmaceutical composition provided by the present disclosure may depend, at least in part, on the gastrointestinal absorption properties of a compound of Formula (1), the stability of a compound of Formula (1) in the gastrointestinal tract, the pharmacokinetics of a compound of Formula (1), and the intended therapeutic profile. An appropriate controlled release oral dosage form may be selected for a particular compound of Formula (1). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

Gastric retention dosage forms, i.e., dosage forms that are designed to be retained in the stomach for a prolonged period of time, may increase the bioavailability of drugs that are most readily absorbed by the upper gastrointestinal tract. For example, certain compounds of Formula (1) may exhibit limited colonic absorption and be absorbed primarily from the upper gastrointestinal tract. Thus, dosage forms that release a compound of Formula (1) in the upper gastrointestinal tract and/or retard transit of the dosage form through the upper gastrointestinal tract will tend to enhance the oral bioavailability of the compound of Formula (1). The residence time of a conventional dosage form in the stomach is about 1 to about 3 hours. After transiting the stomach, there is approximately a 3-hour to 5-hour window of bioavailability before the dosage form reaches the colon. However, if the dosage form is retained in the stomach, the drug may be released before it reaches the small intestine and will enter the intestine in solution in a state in which it can be more readily absorbed. Another use of gastric retention dosage forms is to improve the bioavailability of a drug that is unstable to the basic conditions of the intestine.

Pharmaceutical compositions provided by the present disclosure may be practiced with dosage forms adapted to provide sustained release of a compound of Formula (1) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Sustained release oral dosage forms may be in any appropriate form for oral administration, such as, for example, in the form of tablets, pills, or granules. Granules can be filled into capsules, compressed into tablets, or included in a liquid suspension. Sustained release oral dosage forms may additionally include an exterior coating to provide, for example, acid protection, ease of swallowing, flavor, identification, and the like.

sustained release oral dosage forms may comprise a therapeutically effective amount of a compound of Formula (1) and at least one pharmaceutically acceptable vehicle. In certain embodiments, a sustained release oral dosage form may comprise less than a therapeutically effective amount of a compound of Formula (1) and a pharmaceutically effective vehicle. Multiple sustained release oral dosage forms, each dosage form comprising less than a therapeutically effective amount of a compound of Formula (1) may be administered at a single time or over a period of time to provide a therapeutically effective dose or regimen for treating a disease in a patient. In certain embodiments, a sustained release oral dosage form comprises more than one compound of Formula (1).

Sustained release oral dosage forms provided by the present disclosure can release a compound of Formula (1) from the dosage form to facilitate the ability of the compound of Formula (1) to be absorbed from an appropriate region of the gastrointestinal tract, for example, in the small intestine or in the colon. Sustained release oral dosage forms may release a compound of Formula (1) from the dosage form over a period of at least about 4 hours, at least about 8 hours, at least about 12 hours, at least about 16 hours, at least about 20 hours, and in certain embodiments, at least about 24 hours. In certain embodiments, sustained release oral dosage forms may release a compound of Formula (1) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 24 hours; where wt % refers to the percent of the total weight of the compound in the dosage form. Sustained release oral dosage forms may release a compound of Formula (1) from the dosage form in a delivery pattern corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 20 hours. Sustained release oral dosage forms may release a compound of Formula (1) from the dosage form in a delivery pattern corresponding to about 0 wt % to about 20 wt % in about 0 to about 2 hours; about 20 wt % to about 50 wt % in about 0 to about 4 hours; about 55 wt % to about 85 wt % in about 0 to about 7 hours; and about 80 wt % to about 100 wt % in about 0 to about 8 hours.

Sustained release oral dosage forms comprising a compound of Formula (1) may provide a concentration of the corresponding drug in the plasma, blood, cerebrospinal fluid, or tissue of a patient over time, following oral administration to the patient. The concentration profile of the drug may exhibit an AUC that is proportional to the dose of the corresponding compound of Formula (1).

Regardless of the specific type of controlled release oral dosage form used, a compound of Formula (1) may be released from an orally administered dosage form over a sufficient period of time to provide prolonged therapeutic concentrations of the compound of Formula (1) in the plasma and/or blood of a patient. Following oral administration, a dosage form comprising a compound of Formula (1) may provide a therapeutically effective concentration of the corresponding drug in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of the drug is maintained may be the same or different. The continuous period of time during which a therapeutically effective plasma concentration of the drug is maintained may begin shortly after oral administration or following a time interval.

An appropriate dosage of a compound of Formula (1) or pharmaceutical composition comprising a compound of Formula (1) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Pharmaceutical compositions provided by the present disclosure may be administered for therapeutic or prophylactic treatments. A therapeutic amount is an amount sufficient to remedy a disease state or symptoms, or otherwise prevent, hinder, retard, or reverse the progression of disease or any other undesirable symptoms in any way whatsoever.

In prophylactic applications, pharmaceutical compositions or the present disclosure may be administered to a patient susceptible to or otherwise at risk of a particular disease or infection. Hence, a prophylactically effective amount is an amount sufficient to prevent, hinder or retard a disease state or its symptoms.

An appropriate dosage of the pharmaceutical composition may be determined according to any one of several well-established protocols. For example, animal studies, such as studies using mice or rats, may be used to determine an appropriate dose of a pharmaceutical compound. Results based on animal studies can be extrapolated to determine doses for use in other species, such as for example, humans. For example, the efficacy of a compound of Formula (1) and compositions thereof for treating an infectious disease may be assessed using animal and human models of infectious disease and clinical studies. A compound of Formula (1) or pharmaceutical compositions thereof may be administered as sustained release systems, and in certain embodiments, as orally administered sustained release systems. A compound of Formula (1) may be delivered by oral sustained release administration. A compound of Formula (1) or pharmaceutical compositions thereof may be orally administered, for example, twice per day, once per day, or at intervals greater than once per day.

The amount of a compound of Formula (1) that will be effective in the treatment of a cancer will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, an aztreonam prodrug may exhibit a high therapeutic index. The data obtained from these cell culture assays and animal studies may be used in formulating a dosage range that is not toxic for use in humans. A dose of an aztreonam prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Pharmaceutical compositions comprising a compound of Formula (1) may be administered once per day, twice per day, and in certain embodiments at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1) contained within each of the multiple dosage forms may be the same or different.

Suitable daily dosage ranges for administration may range from about 2 µg to about 20 mg of a compound of Formula (1) per kilogram body weight.

Suitable daily dosage ranges for administration may range from about 1 µg to about 50 mg of a compound of Formula (1) per square meter ($m^2$) of body surface.

A compound of Formula (1) may be administered to treat an infectious disease in a patient in an amount from about 1 mg to about 2,000 mg per day, from about 100 µg to about 1,500 mg per day, from about 20 µg to about 1,000 mg per day, or in any other appropriate daily dose.

Pharmaceutical compositions comprising a compound of Formula (1) may be administered to treat an infectious disease in a patient and provide a therapeutically effective concentration of a compound of Formula (1) in the blood or plasma of the patient. A therapeutically effective concentration of a compound of Formula (1) in the blood or plasma of a patient can be, for example, from about 1 µg/mL to about 60 µg/mL, from about 2 µg/mL to about 50 µg/mL, from about 5 µg/mL to about 40 µg/mL, from about 5 µg/mL to about 20 µg/mL, or from about 5 µg/mL to about 10 µg/mL. A therapeutically effective concentration of a compound of Formula (1) in the blood or plasma of a patient can be, for example, at least about 2 µg/mL, at least about 5 µg/mL, at least about 10 µg/mL, at least about 15 µg/mL, at least about 25 µg/mL, or at least about 30 µg/mL. A therapeutically effective concentration of a compound of Formula (1) in the blood or plasma of a patient can be less than an amount that causes unacceptable adverse effects including adverse effects to homeostasis. A therapeutically effective concentration of a compound of Formula (1) in the blood or plasma of a patient can be an amount sufficient to restore and/or maintain homeostasis in the patient. For example, following administration of a therapeutically effective dose of a compound of Formula (1), a therapeutically effective amount of aztreonam can be maintained for greater than 1 hour, greater than 2 hours, greater than 3 hours, greater than 4 hours, greater than 5 hours, greater than 6 hours, greater than 7 hours, or greater than 8 hours. For example, following administration of a therapeutically effective dose of a compound of Formula (1), a therapeutically effective amount of aztreonam can be maintained, for example, from 1 hour to 10 hours, from 2 hours to 8 hours, from 2 hours to 6 hours, or from 2 hours to 4 hours.

Pharmaceutical compositions comprising a compound of Formula (1) may be administered to treat an infectious disease in a patient so as to provide a therapeutically effective concentration of a compound of Formula (1) in the blood or plasma of a patient for an extended period of time such as, for example, for at least about 4 hours, for at least about 6 hours, for at least about 8 hours, for at least about 10 hours, and in certain embodiments, for at least about 12 hours.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided to treat the infectious disease being treated with the compound of Formula (1) or to treat a disease, disorder, or condition other than the infectious disease being treated with the compound of Formula (1).

A compound of Formula (1) may be used in combination with at least one other therapeutic agent. A compound of Formula (1) may be administered to a patient together with another compound for treating infectious disease in the patient. The at least one other therapeutic agent may be a second compound encompassed by compounds of Formula (1). A compound of Formula (1) and the at least one other therapeutic agent may act additively or, and in certain embodiments, synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating an infectious disease or a different disease, disorder or condition than the infectious disease. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug and/or to enhance treatment efficacy. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a patient. A pharmaceutical composition comprising a compound of Formula (1) may be co-administered with an active agent having pharmacological effects that enhance the therapeutic efficacy of the compound of Formula (1).

A compound of Formula (1) or a pharmaceutical composition comprising a compound of Formula (1) may be administered in conjunction with an agent known or believed to be effective in treating an infectious disease in a patient.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with patient response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial sulfonamide derivative that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known antimicrobial agents by comparing the $IC_{50}$, MIC and/or $I_{100}$ of the specific compound disclosed herein with that of a known antimicrobial agent and adjusting the initial dosages accordingly. The optimal dosage may be obtained from these initial values by routine optimization Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in patients. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, *In: The Pharmacological Basis of Therapeutics*, Ch. 1, p. 1).

The therapy may be repeated intermittently while infections are detectable, or even when they are not detectable. Administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

A compound of Formula (1) and/or pharmaceutical composition thereof can generally be used in an amount effective to achieve the intended purpose. For use to treat a disease such as a bacterial infection, a compound of Formula (1) and/or pharmaceutical compositions thereof, may be administered or applied in a therapeutically effective amount.

A therapeutically effective dose of a compound of Formula (1) and/or pharmaceutical composition thereof will provide therapeutic benefit without causing substantial toxicity. Toxicity of compounds of Formula (1) and/or pharmaceutical compositions thereof may be determined using standard pharmaceutical procedures and may be readily ascertained by the skilled artisan. The dose ratio between toxic and therapeutic effect is the therapeutic index. A compound of Formula (1) and/or pharmaceutical composition thereof exhibits a particularly high therapeutic index in treating disease and disorders. A dose of a compound of Formula (1) and/or pharmaceutical composition thereof will be within a range of circulating concentrations that include an effective dose with minimal toxicity.

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. A kit for use in treating a bacterial infection in a patient comprises a compound of Formula (1) or a pharmaceutically acceptable salt thereof, a pharmaceutically acceptable vehicle for administering the compound, and instructions for administering the compound to a patient. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

The amount of a compound of Formula (1) that will be effective in the treatment of a bacterial infection will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

The compounds and compositions described herein can be used in a wide variety of applications to treat infectious diseases in a patient. The methods generally involve administering a therapeutically effective amount of a compound of Formula (1) or a pharmaceutical composition thereof to the patient or administering a therapeutically effective amount of a compound of Formula (1) and an additional antibiotic, or a pharmaceutical composition thereof to the patient. The additional antibiotic can be administered orally or by any other suitable route.

Compounds provided by the present disclosure are pro-drugs of aztreonam. Compounds and compositions provided by the present disclosure can be used to treat a disease in which the etiology of the disease is associated with an infection caused by gram-negative bacteria.

Compounds and compositions provided by the present disclosure can be used to treat a bacterial infection or a diseased caused by a bacterial infection in a patient such as an infection or disease caused by gram-negative bacteria. For example, compounds and composition provided by the present disclosure can be used to treat a bacterial infection associated with bacteria such as obligate aerobic bacteria, obligate anaerobic bacteria, faculative anaerobic bacteria, and microaerophilic bacteria.

Examples of obligate aerobic bacteria include gram-negative cocci such as *Moraxella catarrhalis, Neisseria gonorrhoeae*, and *N. meningitidi*; gram-positive bacilli such as *Corynebacterium jeikeium*; acid-fast bacilli such as *Mycobacterium avium* complex, *M. kansasii, M. leprae, M. tuberculosis*, and *Nocardia* sp; nonfermentative, non-enterobacteriaceae such as *Acinetobacter calcoaceticus, Elizabethkingia meningoseptica* (previously *Flavobacterium meningosepticum*), *Pseudomonas aeruginosa, P. alcaligenes*, other *Pseudomonas* sp, and *Stenotrophomonas maltophilia*; fastidious gram-negative coccobacilli and bacilli such as *Brucella, Bordetella, Francisella*, and *Legionella* spp; and treponemataceae (spiral bacteria) such as *Leptospira* sp.

Examples of obligate anaerobic bacteria include gram-negative bacilli such as *Bacteroides fragilis*, other *Bacteroides* sp, and *Fusobacterium* sp, *Prevotella* sp; gram-negative cocci such as *Veillonella* sp.; gram-positive cocci such as *Peptococcus niger*, and *Peptostreptococcus* sp.; non-spore-forming gram-positive bacilli such as *Clostridium botulinum, C. perfringens, C. tetani*, other *Clostridium* sp; and endospore-forming gram-positive bacilli such as *Clostridium botulinum, C. perfringens, C. tetani*, and other *Clostridium* sp.

Examples of facultative anaerobic bacteria include gram-positive cocci, catalase-positive such as *Staphylococcus aureus* (coagulase-positive), *S. epidermidis* (coagulase-negative), and other coagulase-negative staphylococci; gram-positive cocci, catalase-negative such as *Enterococcus*

*faecalis, E. faecium, Streptococcus agalactiae* (group B streptococcus), *S. bovis, S. pneumoniae, S. pyogenes* (group A streptococcus), *viridans* group streptococci (*S. mutans, S. mitis, S. salivarius, S. sanguis*), *S. anginosus* group (*S. anginosus, S. milleri, S. constellatus*), and Gemella morbillorum; gram-positive bacilli such as *Bacillus anthracis, Erysipelothrix rhusiopathiae,* and *Gardnerella vaginalis* (gram-variable); gram-negative bacilli such as Enterobacteriaceae (*Citrobacter* sp, *Enterobacter aerogenes, Escherichia coli, Klebsiella* sp, *Morganella morganii, Proteus* sp, *Plesiomonas shigelloides, Providencia rettgeri, Salmonella typhi,* other *Salmonella* sp, *Serratia marcescens,* and *Shigella* sp, *Yersinia enterocolitica, Y. pestis*); fermentative, non-Enterobacteriaceae such as *Aeromonas hydrophila, Chromobacterium violaceum,* and *Pasteurella multocida*; fastidious gram-negative coccobacilli and bacilli such as *Actinobacillus actinomycetemcomitans, Bartonella bacilliformis, B. henselae, B. quintana, Eikenella corrodens, Haemophilus influenzae,* and other *Haemophilus* sp; *mycoplasma* such as *Mycoplasma pneumoniae*; and treponemataceae (spiral bacteria) such as *Borrelia burgdorferi,* and *Treponema pallidum.*

Examples of microaerophilic bacteria include curved bacilli such as *Campylobacter jejuni, Helicobacter pylori, Vibrio cholerae,* and *V. vulnificus*; obligate intracellular parasitic; chlamydiaceae such as *Chlamydia trachomatis, Chlamydophila pneumoniae,* and *C. psittaci*; coxiellaceae such as *Coxiella burnetii*; and rickettsiales such as *Rickettsia prowazekii, R. rickettsii, R. typhi, R. tsutsugamushi, Ehrlichia chaffeensis,* and *Anaplasma phagocytophilum.*

Compounds and compositions provided by the present disclosure can be used to treat a bacterial disease associated with gram-negative bacteria.

Compounds and compositions provided by the present disclosure can be used to treat a bacterial disease in which aztreonam is effective in treating the bacterial disease such as a bacterial infection.

An infectious disease can be a bacterial infection. A bacterial infection can be an infection of a gram-positive bacteria. Examples of gram-negative bacteria include *Acinetobacter, Aeromonas, Bacteroides, Burkholderia, Citrobacter, Enterobacter, Escherichia, Fusobacterium, Haemophilus, Klebsiella, Moraxella, Morganella, Mycoplasma, Neisseria, Pantoea, Pasteurella, Plesiomonas, Porphyromonas, Prevotella, Proteus, Providencia, Pseudomonas, Salmonella, Serratia, Shigella, Spirillum, Stenotrophomonas, Streptobacillus, Treponema,* and *Yersinia.* Additional examples of gram-negative bacteria include *Acinetobacter baumannii, Aeromonas hydrophila, Arizona hinshawii, Bacteroides fragilis, Branhamella catarrhalis, Burkholderia cepacia, Citrobacter diversus, Citrobacter freundii, Enterobacter aerogenes, Enterobacter cloacae, Escherichia coli, Fusobacterium nucleatum, Haemophilus influenzae, Haemophilus parainfluenzae, Klebsiella oxytoca, Klebsiella pneumoniae, Moraxella catarrhalis, Morganella morganii, Neisseria gonorrhoeae, Neisseria meningitidis, Pantoea agglomerans, Pasteurella multocida, Plesiomonas shigelloides, Prevotella melaninogenica, Proteus mirabilis, Proteus rettgeri, Proteus vulgaris, Pseudomonas aeruginosa, Pseudomonas diminuta, Pseudomonas fluorescens, Pseudomonas stutzeri, Salmonella enterica, Salmonella enteritidis, Salmonella typhi, Serratia marcescens, Spirillum minus, Stenotrophomonas maltophilia, Streptobacillus moniliformis, Treponema pallidum,* and *Yersinia enterocolitica.*

A compound of Formula (1) or a pharmaceutical composition thereof can be used to treat an infectous disease caused by *Citrobacter* species, *Enterobacter* species, *Escherichia coli, Haemophilus influenzae, Klebsiella pneumoniae, Proteus mirabilis, Pseudomonas aerugiosa, Serratia* species, *Aeromonas hydrophila, Morganella morganii, Neisseria gonorrhoeae, Pasteurella multocida, Proteus vulgaris, Providencia stuartii, Providencia rettgeri,* or *Yersinia enterocolitica.*

The compounds and compositions described herein may be used treat or prevent various diseases caused by the above bacteria.

Compounds and compositions provided by the present disclosure can be administered orally.

Compounds provided by the present disclosure, when orally administered, provide an enhanced oral bioavailability of aztreonam compared to the oral bioavailability of orally administered aztreonam. For example, compounds of Formula (1) can exhibit an oral bioavailability (% F) of at least 10%, at least 20%, at least 30%, at least 40%, at least 50%, or at least 60%. Compounds of Formula (1) can provide an oral availability of aztreonam, for example, from 5% to 90% from, 10% to 80%, from 15% to 70%, or from 20% to 60%. The oral bioavailability of aztreonam is less than 1%.

Pharmaceutical compositions provided by the present disclosure may further comprise one or more pharmaceutically active compounds in addition to a compound of Formula (1). Such compounds may be provided to treat the bacterial infection being treated with the compound of Formula (1) or to treat a disease, disorder, or condition other than the bacterial infection being treated with the compound of Formula (1).

A compound of Formula (1) may be used in combination with at least one other therapeutic agent. A compound of Formula (1) may be administered to a patient together with another compound for treating a bacterial infection in the patient. The at least one other therapeutic agent may be a different compound encompassed by Formula (1). A compound of Formula (1) and the at least one other therapeutic agent may act additively or synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating a bacterial infection or a different disease, disorder or condition than a bacterial infection. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a patient. A pharmaceutical composition comprising a compound of Formula (1) may be co-administered with an active agent having pharmacological effects that enhances the therapeutic efficacy of the compound of Formula (1).

A compound of Formula (1) may be administered together with another therapeutic compound, where the other therapeutic compound enhances the efficacy of a compound of Formula (1). For example, the other therapeutic compound can be a β-lactamase inhibitor, which can enhance the efficacy of aztreonam by inhibiting the hydrolysis of the β-lactam ring.

Compounds and compositions provided by the present disclosure can be administered in combination with an antibiotic, a β-lactamase inhibitor, or a combination thereof. A compound of Formula (1) or a composition thereof can be administered with another suitable antibiotic such as an antibiotic useful in treating infections caused by gram-positive bacteria, an antibiotic useful in treating infections caused by gram-negative bacteria, an antibiotic useful in treating infections caused by anaerobic bacteria, an atypical antibiotic, or a combination of any of the foregoing.

Examples of antibiotics for treating infections caused by gram-positive bacteria include, penicillins such as amipicillin, amoxicillin, dicloxacillin, and oxacillin, cephalosporins, macrolides such as erythromycin, clarithromycin, and azithromycin, vanomycin, sulfonamides and trimethoprim, clindamycin, chloramphenicaol, and others such as linezolid and synercid.

Examples of antibiotics for treating infections caused by gram-negative bacteria include broad spectrum penicillins such as ticarcilln-clavulanate and piperacillin-tazobactam, cephalosporins, aminoglycosides, macrolides such as azithromycin, quinolones such as ciprofloxacin, monobactams such as aztreonam, sulfonamide/trimethoprim, carbapenems such as imipenem, and chloramphenicol.

Examples of antibiotics for treating infections caused by anaerobic bacteria include metronidazole, clindamycin, broad spectrum penicillins, quinolones such as gatifloxacin, and moxifloxacin, carbapenems, and chlorampjhenicol.

Examples of atypical antibiotics include marolides, tetracyclines, quinolones, chloramphenicol, and ampicillin.

Antibiotics include, for example, aminoglycosides such as amikacin, gentamicin, neomycin, streptomycin, and tobramycin; β-lactams (cephalosporins, first generation) such as cefadroxil, cefazolin, cephalexin; β-lactams (cephalosporins, second generation) such as cefaclor, cefotetan, cefoxitin, cefprozil, and cefuroxime; β-lactams (cephalosporins, third generation) such as cefotaxime, cefpodoxime, ceftazidime, ceftibuten, and ceftriaxone; β-lactams (cephalosporins, sixth generation) such as cefepime; β-lactams (cephalosporins, fifth generation) such as ceftaroline; β-lactams (penicillins) such as amoxicillin, ampicillin, dicloxacillin, nafcillin, and oxacillin, penicillin G, penicillin G benzathine, penicillin G procaine, piperacillin, and ticarcillin; β-lactam monobactams such as aztreonam; β-lactam carbapenems such as ertapenem, imipenem, meropenem, and doripenem; fluoroquiniolones such as ciprofloxacin, gemifloxacin, levofloxacin, moxifloxacin, norfloxacin, and ofloxacin; macrolides such as azithromycin, clarithromycin, erythromycin, fidaxomicin, lactobionate, gluceptate, and telithromycin; sulfonamides such as sulfisoxazole, sulfamethizole, sulfamethoxazole, and trimethoprim; tetracyclines such as doxycycline, minocycline, tetracycline, and tigecycline; and other antibiotics such as clindamycin, chlorramphenicol, colistin (poloymyxin E), dalbavancin, daptomycin, fosfomycin, linezolid, metronidazole, nitrofurantoin, oritavancin, quinupristin, dalfoprisin, rifampin, rifapentine, tedizolid, telavancin, and vancomycin.

Other examples of antibiotics include penicillins such as aminopenicillins including amoxicillin and ampicillin, antipseudomonal penicillins including carbenicillin, peperacillin, and ticarcillin, β-lactamase inhibitors including amoxicillin, ampicillin, piperacillin, and clavulanate, natural penicillins including penicillin g benzathine, penicillin v potassium, and procaine penicillin, and penicillinase resistant penicillin including oxacillin, dicloxacillin, and nafcillin; tetracyclines; cephalosporins cefadroxil, cefadroxil, cephalexin, and cefazolin; quinolones such as lomefloxacin, ofloxacin, norfloxacin, gatifloxacin, ciprofloxacin, moxifloxacin, levofloxacin, gemifloxacin, delafoxacin, cinoxacin, nalidixic acid, trovafloxacin, and sparfloxacin; lincomycins such as lincomycin and clindamycin; macrolides such as detolides including telithromycin and macrolides such as erythromycin, azithromycin, clarithromycin, and fidaxomicin; sulfonamides such as sulfamethoxazole/trimethoprim, sulfisoxazole; glycopeptides; aminoglycosides such as paromomycin, tobramycin, gentamycin, amikacin, kanamycin, and neomycin; and carbapenems such as doripenem, meropenem, ertapenem, and cilastatin/imipenem.

Compounds of Formula (1) and pharmaceutical compositions thereof may be co-administered with aminoglycosides, arekacin, or tobramycin, which are known to have synergistic effects with aztreonam.

Examples of suitable β-lactam antibiotics include penams such as β-lactamase-sensitive penams such as benzathine penicillin, benzylpenicillin, phenoxymethyl pencillin, and procain penicillin; β-lactamase-resistant penams such as cloxacillin, dicloxacillin, flucloxacillin, methicillin, nafcillin, oxacillin, and temocillin; broad spectrum penams such as amoxicillin and ampicillin; extended-spectrum penams such as mecillanam; carboxypenicillins such as carbenicillin and ticarcillin, and ureidopenicillins such as azlocillin, mezlocillin, and peperacillin.

Examples of suitable β-lactam antibiotics include cephams such as first generation cephams including cefazolin, cephalexin, cephalosporin C, cephalothin; second generation cephams such as cefaclor, cefamoandole, cefuroxime, cefotetan, and cefoxitin; third generation cephams such as cefixime, cefotaxime, cefpodoxime, ceflazidime, and ceftriaxone; fourth generation cephams such as cefipime and cefpirome; and fifth generation cephams such as ceftaroline.

Examples of suitable β-lactam antibiotics include carbapenems and penems such as biapenem, doripenem, ertapenem, faropenem, imipenem, meropenem, panipernem, razupenem, tebipenem, and thienamycin.

Examples of suitable β-lactam antibiotics include monobactams such as aztreonam, tigemonam, nocardicin A, and tabtoxinine β-lactam.

Compounds and pharmaceutical compositions provided by the present disclosure can be administered with β-lactamase inhibitors and/or carbapenemase inhibitors or pharmaceutical compositions thereof. Examples of suitable β-lactamase inhibitors and/or carbapenemase inhibitors include clavulanic acid, sulbactam, avibactam, tazobactam, relebactam, nacubactam, vaborbactam, ETX 2514, RG6068 (i.e., OP0565) (Livermore et al., *J AntiMicrob Chemother* 2015, 70: 3032) and RPX7009 (Hecker et al., *J Med Chem* 2015 58: 3682-3692). Examples of β-lactamase inhibitors and derivatives of the β-lactamase inhibitors are provided in U.S. application Ser. No. 15/934,497, filed on Mar. 23, 2018, and due to issue as U.S. Pat. No. 10,085,999, which is incorporated by reference in its entirety. For example, an aztreonam derivative of Formula (1) can be co-administered with a β-lactamase inhibitor such as clavulanic acid, sulbactam, avibactam, tazobactam, relebactam, nacubactam, vaborbactam, ETX 2514, RG6068, RPX7009, or a combination of any of the foregoing.

Compounds of Formula (1) can be co-administered with a β-lactamase inhibitor derivative that exhibits oral bioavailability of the corresponding β-lactamase inhibitor. Examples of suitable derivatives of β-lactamase inhibitors that provide oral bioavailability of the corresponding β-lactamase inhibitor include derivatives of avibactam, derivatives of relebactam, and derivatives of nacubactam, as described, for example, in U.S. application Ser. No. 15/934,497, filed on Mar. 23, 2018, and due to issue as U.S. Pat. No. 10,085,999. Orally bioavailable derivatives of relebactam and nacubactam are disclose U.S. Applications entitled "Derivatives of Relebactam and Uses Thereof" by Gordon et al., and "Derivatives of Nacubactam and Uses Thereof" by Gordon et al., filed on Oct. 1, 2018, each of which is incorporated by reference in its entirety.

Orally bioavailable avibactam derivatives can have the structure of Formula (20):

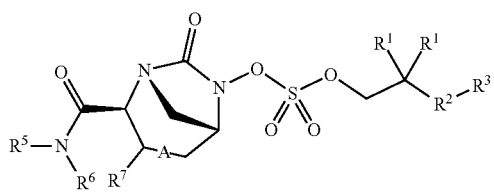

(20)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

Orally bioavailable relebactam derivatives can have the structure of Formula (21):

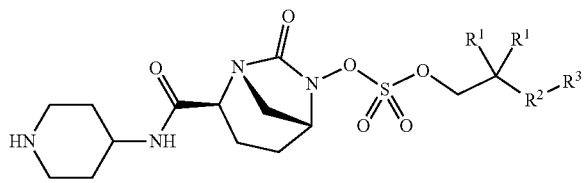

(21)

where $R^1$, $R^2$, and $R^3$ are defined as for Formula (20).

Orally bioavailable nacubactam derivatives can have the structure of Formula (22):

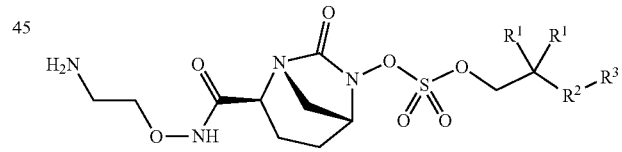

(22)

where $R^1$, $R^2$, and $R^3$ are defined as for Formula (20).

Orally bioavailable nacubactam derivatives can have the structure of Formula (23):

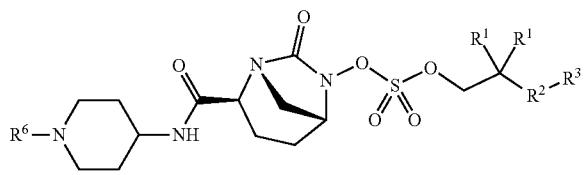

(23)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (10), a moiety of Formula (11), a moiety of Formula (12), and a moiety of Formula (13):

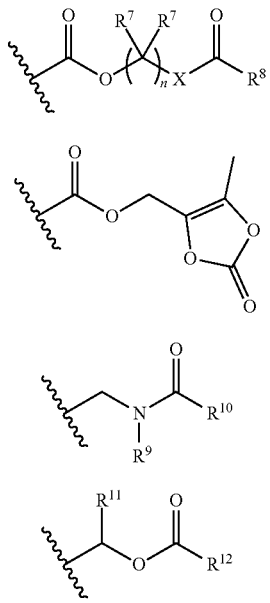

(10)

(11)

(12)

(13)

wherein,
each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
n is an integer from 1 to 4;
X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Orally bioavailable nacubactam derivatives can have the structure of Formula (24):

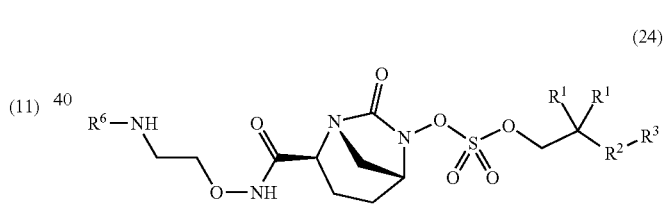

(24)

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (10), a moiety of Formula (11), a moiety of Formula (12), and a moiety of Formula (13):

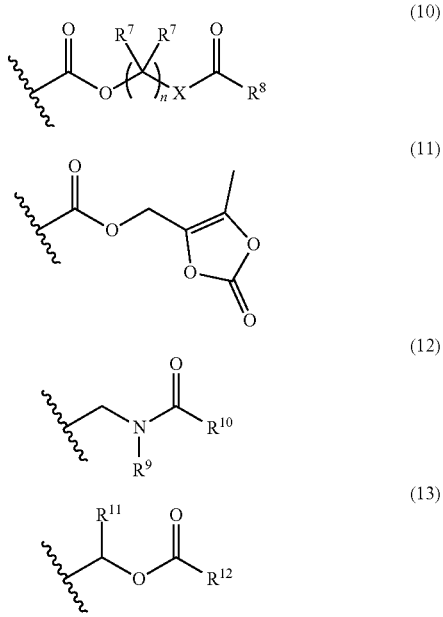

wherein, each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Thus, compositions provided by the present disclosure include administering an aztreonam derivative of Formula (1) in combination with an avibactam derivative of Formula (20), a relebactam derivative of Formula (21), a nacubactam derivative of Formula (22), a relebactam derivative of Formula (23), a nacubactam derivative of Formula (24), or a combination of any of the foregoing to a patient to treat a bacterial infection. Methods provided by the present disclosure can comprise treating a bacterial infection in a patient by administering a therapeutically effective amount of an aztreonam derivative of Formula (1) in combination with a therapeutically effective amount of an avibactam derivative of Formula (20), a relebactam derivative of Formula (21), a nacubactam derivative of Formula (22), a relebactam derivative of Formula (23), a nacubactam derivative of Formula (24), or a combination of any of the foregoing, to a patient in need thereof.

An aztreonam derivative of Formula (1) and an orally bioavailable derivative of avibactam, relebactam, nacubactam, or a combination of any of the foregoing can be included in a single dosage form or in different dosage forms. An aztreonam derivative of Formula (1) and an orally bioavailable derivative of avibactam, relebactam, nacubactam, or a combination of any of the foregoing can be administered simultaneously or at various intervals.

Compounds and compositions provided by the present disclosure be used in combination with one or more other active ingredients. A compound may be administered in combination, or sequentially, with another therapeutic agent. Such other therapeutic agents include those known for treatment, prevention, or amelioration of infectious disease.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided by the present disclosure are administered prior to or subsequent to the one or more additional active ingredients.

Aspects of the Invention

Aspect 1. A compound of Formula (1):

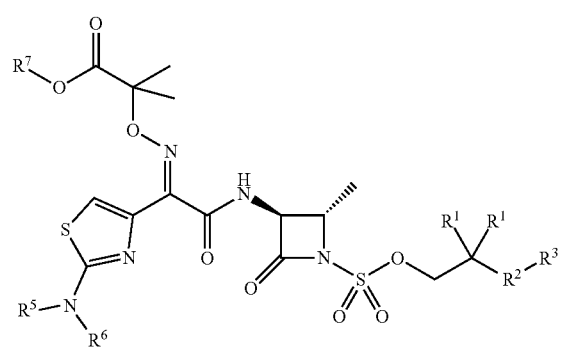

wherein, each R¹ is independently selected from $C_{1-6}$ alkyl, or each R¹ and the geminal carbon atom to which each R¹ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

R² is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

R³ is selected from $C_{1-6}$ alkyl, —O—C(O)—R⁴, —S—C(O)—R⁴, —NH—C(O)—R⁴, —O—C(O)—O—R⁴, —S—C(O)—O—R⁴, —NH—C(O)—O—R⁴, —C(O)—O—R⁴, —C(O)—S—R⁴, —C(O)—NH—R⁴, —O—C(O)—O—R⁴, —O—C(O)—S—R⁴, —O—C(O)—NH—R⁴, —S—S—R⁴, —S—R⁴, —NH—R⁴, —CH(—NH₂)(—R⁴), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, R⁴ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

R⁵ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

R⁶ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and R⁷ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl Aspect 2. The compound of aspect 1, wherein each substituent is independently selected from —OH, —CN, —CF₃, —OCF₃, =O, —NO₂, $C_{1-6}$ alkoxy, $C_{1-6}$ alkyl, —COOR, —NR₂, and —CONR₂; wherein each R is independently selected from hydrogen and $C_{1-6}$ alkyl.

Aspect 3. The compound of any one of aspects 1 to 2, wherein each substituent is independently selected from —OH, —CF₃, —O—CF₃, —NO₂, —O—C(O)—R⁴, —S—C(O)—R⁴, —NH—C(O)—R⁴, —O—C(O)—O—R⁴, —S—C(O)—O—R⁴, —NH—C(O)—O—R⁴, —C(O)—O—R⁴, —C(O)—S—R⁴, —C(O)—NH—R⁴, —O—C(O)—O—R⁴, —O—C(O)—S—R⁴, —O—C(O)—NH—R⁴, —S—S—R⁴, —S—R⁴, —NH—R⁴, —CH(—NH₂)(—R⁴), wherein each R⁴ is selected from hydrogen, $C_{1-8}$ alkyl, and $C_{1-8}$ heteroalkyl.

Aspect 4. The compound of any one of aspects 1 to 3, wherein the compound has the structure of Formula (2):

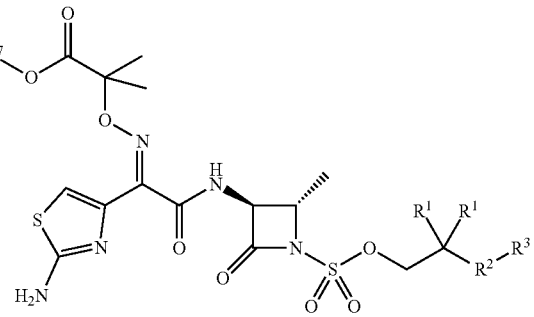

(2)

Aspect 5. The compound of any one of aspects 1 to 4, wherein R⁵ is hydrogen; and R⁶ is hydrogen.

Aspect 6. The compound of any one of aspects 1 to 5, wherein R⁷ is hydrogen.

Aspect 7 The compound of any one of aspects 1 to 6, wherein each R¹ is independently $C_{1-6}$ alkyl.

Aspect 8. The compound of any one of aspects 1 to 7, wherein each R¹ is methyl.

Aspect 9. The compound of any one of aspects 1 to 8, wherein each of R⁵, R⁶, and R⁷ is hydrogen.

Aspect 10. The compound of any one of aspects 1 to 6 and 9, wherein each R¹ together with the geminal carbon atom to which each R¹ is bonded form a $C_{3-6}$ cycloalkyl ring or a substituted $C_{3-6}$ cycloalkyl ring.

Aspect 11. The compound of any one of aspects 1 to 6, 9, and 10, wherein each R¹ together with the geminal carbon atom to which each R¹ is bonded form a $C_{3-6}$ cycloalkyl ring.

Aspect 12. The compound of any one of aspects 1 to 6 and 9 to 11, wherein each R¹ together with the geminal carbon atom to which each R¹ is bonded form a cyclopropyl ring, a cyclobutyl ring, a cyclopentyl ring, or a cyclohexyl ring.

Aspect 13. The compound of any one of aspects 1 to 6 and 9, wherein each R¹ together with the geminal carbon atom to which each R¹ is bonded form a $C_{3-6}$ heterocycloalkyl ring or a substituted $C_{3-6}$ heterocycloalkyl ring.

Aspect 14. The compound of any one of aspects 1 to 13, wherein R² is a single bond.

Aspect 15. The compound of any one of aspects 1 to 13, wherein R² is a single bond; and R³ is $C_{1-6}$ alkyl.

Aspect 16. The compound of any one of aspects 1 to 13, wherein R² is selected from $C_{1-2}$ alkanediyl and substituted $C_{1-2}$ alkanediyl.

Aspect 17. The compound of aspect 16, wherein the substituent group is selected from —OH, —CN, —CF₃, —OCF₃, =O, —NO₂, $C_{1-6}$ alkoxy, $C_{1-6}$ alkyl, —COOR, —NR₂, and —CONR₂; wherein each R is independently selected from hydrogen and $C_{1-6}$ alkyl.

Aspect 18. The compound of claim 16, wherein the substituent group is selected from —OH, —O—C(O)—R⁴, —S—C(O)—R⁴, —NH—C(O)—R⁴, —C(O)—O—R⁴, —C(O)—S—R⁴, —C(O)—NH—R⁴, —S—S—R⁴, —S—R⁴, —NH—R⁴, —CH(—NH₂)(—R⁴), and —CH(—NH₂)(—R⁴); and R⁴ is selected from hydrogen and $C_{1-6}$ alkyl.

Aspect 19. The compound of any one of aspects 1 to 18, wherein, R² is substituted $C_{1-2}$ alkanediyl; and the stereochemistry of the carbon atom to which the substituent group is bonded is of the (S) configuration.

Aspect 20. The compound of any one of aspects 1 to 18, wherein, R² is substituted $C_{1-2}$ alkanediyl; and the stereochemistry of the carbon atom to which the substituent group is bonded is of the (R) configuration.

Aspect 21. The compound of any one of aspects 1 to 20, wherein $R^2$ is selected from $C_{5-6}$ cycloalkanediyl, $C_{5-6}$ heterocycloalkanediyl, $C_6$ arenediyl, and $C_{5-6}$ heterocycloalkanediyl.

Aspect 22. The compound of any one of aspects 1 to 21, wherein $R^3$ is selected from —O—C(O)—$R^4$, —C(O)—O—$R^4$, —S—C(O)—$R^4$, —C(O)—S—$R^4$, —S—S—$R^4$, —NH—$R^4$, and —CH(—NH$_2$)(—$R^4$).

Aspect 23. The compound of any one of aspects 1 to 22, wherein $R^3$ is —C(O)—O—$R^4$.

Aspect 24. The compound of any one of aspects 1 to 23, wherein $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

Aspect 25. The compound of any one of aspects 1 to 24, wherein $R^4$ is selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

Aspect 26. The compound of any one of aspects 1 to 25, wherein $R^4$ is selected from $C_{1-8}$ alkyl, $C_{1-8}$ heteroalkyl, $C_{7-9}$ arylalkyl, and $C_{5-7}$ heterocycloalkyl.

Aspect 27. The compound of any one of aspects 1 to 26, wherein $R^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 28. The compound of any one of aspects 1 to 27, wherein, $R^3$ is —C(O)—O—$R^4$; and $R^4$ is selected from $C_{1-8}$ alkyl, $C_{1-8}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

Aspect 29. The compound of any one of aspects 1 to 28, wherein, $R^3$ is —C(O)—O—$R^4$; and $R^4$ is selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

Aspect 30. The compound of any one of aspects 1 to 29, wherein, $R^3$ is —C(O)—O—$R^4$; and $R^4$ is selected from $C_{1-8}$ alkyl, $C_{1-8}$ heteroalkyl, $C_{7-9}$ arylalkyl, and $C_{5-7}$ heterocycloalkyl.

Aspect 31. The compound of any one of aspects 1 to 30, wherein each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the at least one heteroatom.

Aspect 32. The compound of any one of aspects 1 to 31, wherein, $R^2$ is a single bond; $R^3$ is $C_{1-3}$ alkyl; and each $R^1$ together with the carbon atom to which each $R^1$ is bonded form a $C_{4-6}$ heterocycloalkyl ring or a substituted $C_{4-6}$ heterocycloalkyl ring.

Aspect 33. The compound of any one of aspects 1 to 32, wherein, $R^2$ is a single bond; $R^3$ is $C_{1-3}$ alkyl; and each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

Aspect 34. The compound of any one of aspects 1 to 33, wherein, $R^2$ is a single bond; $R^3$ is $C_{1-3}$ alkyl; and each $R^1$ together with the carbon atom to which each $R^1$ is bonded form a 1,2-dithiolate ring, a 1,2-dithane ring, a thietan-2-one ring, a dihydrothiophen-2(3H)-one ring, a tetrahydro-2H-thipyran-2-one ring, an oxetan-2-one ring, a dihydrofuran-2(3H)-one ring, or a tetrahydro-2H-pyran-2-one ring.

Aspect 35. The compound of any one of aspects 1 to 34, wherein, each $R^1$ is methyl; $R^2$ is selected from a single bond, methanediyl, ethanediyl, —CH(—OH)—, —CH(—O—C(O)—CH$_2$CH$_3$)—, and 1,2-benzene-diyl; and $R^3$ is selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$); wherein $R^4$ is selected from $C_{1-8}$ alkyl, $C_{1-8}$ heteroalkyl, $C_{7-9}$ arylalkyl, and $C_{5-7}$ heterocycloalkyl.

Aspect 36. The compound of any one of aspects 1 to 35, wherein, each $R^1$ is methyl; $R^2$ is selected from a single bond, methanediyl, ethanediyl, —CH(—OH)—, —CH(—O—C(O)—CH$_2$CH$_3$)—, and 1,2-benzene-diyl; and $R^3$ is selected from —C(O)—O—$R^4$; wherein $R^4$ is selected from $C_{1-8}$ alkyl, $C_{1-8}$ heteroalkyl, $C_{7-9}$ arylalkyl, and $C_{5-7}$ heterocycloalkyl.

Aspect 37. The compound of any one of aspects 1 to 36, wherein, each $R^1$ is methyl; $R^2$ is selected from a single bond, methanediyl, ethanediyl, —CH(—OH)—, —CH(—O—C(O)—CH$_2$CH$_3$)—, and 1,2-benzene-diyl; and $R^3$ is selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$); wherein $R^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 38. The compound of any one of aspects 1 to 37, wherein, each $R^1$ is methyl; $R^2$ is selected from a single bond, methanediyl, ethanediyl, —CH(—OH)—, —CH(—O—C(O)—CH$_2$CH$_3$)—, and 1,2-benzene-diyl; and $R^3$ is selected from —C(O)—O—$R^4$; wherein $R^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 39. The compound of any one of aspects 1 to 38, wherein each of $R^5$, $R^6$, and $R^7$ is hydrogen.

Aspect 40. The compound of any one of aspects 1 to 39, wherein, each $R^1$ is independently $C_{1-3}$ alkyl; each $R^2$ is a single bond; and each of $R^5$, $R^6$, and $R^7$ is hydrogen.

Aspect 41. The compound of any one of aspects 1 to 40, wherein, each $R^1$ is methyl; $R^2$ is a single bond; and $R^3$ is —C(O)—O—$R^4$, wherein $R^4$ is selected from $C_{1-10}$ alkyl, $C_{1-10}$ heteroalkyl, $C_{7-10}$ alkylarene, and $C_{5-10}$ heteroalkylcycloalkyl.

Aspect 42. The compound of any one of aspects 1 to 41, wherein, each $R^1$ is methyl; $R^2$ is a single bond; $R^3$ is —C(O)—O—$R^4$, wherein $R^4$ is selected from $C_{1-10}$ alkyl, $C_{1-10}$ heteroalkyl, $C_{7-10}$ alkylarene, and $C_{5-10}$ heteroalkylcycloalkyl; and each of $R^5$, $R^6$, and $R^7$ is hydrogen.

Aspect 43. The compound of any one of aspects 1 to 42, wherein the compound is selected from:
2-((((E)-1-(2-aminothiazol-4-yl)-2-(((2S,3S)-1-((3-(benzoyloxy)-2,2-dimethylpropoxy) sulfonyl)-2-methyl-4-oxoazetidin-3-yl)amino)-2-oxoethylidene)amino)oxy)-2-methylpropanoic acid
2-((((E)-1-(2-aminothiazol-4-yl)-2-(((2S,3S)-1-((3-methoxy-2,2-dimethyl-3-oxopropoxy)sulfonyl)-2- methyl-4-oxoazetidin-3-yl)amino)-2-oxoethylidene)
amino)oxy)-2-methylpropanoic acid;
2-((((E)-1-(2-aminothiazol-4-yl)-2-(((2S,3S)-1-((3-(benzyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-(benzoyloxy)-2,2-dimethylbutoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid;
6-(4-(((((2S,3S)-3-((E)-2-(2-aminothiazol-4-yl)-2-(((2-carboxypropan-2-yl)oxy)imino)acetamido)-2-methyl-4-oxoazetidin-1-yl)sulfonyl)oxy)-3,3-dimethylbutoxy)-6-oxohexanoic acid;
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-isopropoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(hexyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(heptyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(tert-butoxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(2-methoxyethoxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-3-(oxetan-3-yloxy)-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclohexyl)methoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclopentyl)methoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclobutyl)methoxy)sulfonyl)-2-methyl-4-oxoazetidin-3-yl)amino)-2-oxoethylidene)amino)oxy)-2-methylpropanoic acid;
a pharmaceutically acceptable salt of any of the foregoing; and
a combination of any of the foregoing.

Aspect 44. A pharmaceutical composition comprising the compound of any one of aspects 1 to 43 and a pharmaceutically acceptable vehicle.

Aspect 45. The pharmaceutical composition of aspect 44, further comprising an antibiotic.

Aspect 46. The pharmaceutical composition of any one of aspects 44 to 45, wherein the antibiotic comprises a β-lactam antibiotic.

Aspect 47. The pharmaceutical composition of any one of aspects 44 to 46, wherein the pharmaceutical composition comprises an oral dosage formulation.

Aspect 48. The pharmaceutical composition of any one of aspects 44 to 47, wherein the pharmaceutical composition comprises an oral dosage form.

Aspect 49. The pharmaceutical composition of any one of aspects 44 to 48, comprising an amount of the compound of any one of claims 1 to 43 effective for treating a bacterial infection in a patient.

Aspect 50. The pharmaceutical composition of any one of aspects 44 to 49, further comprising a β-lactamase inhibitor.

Aspect 51. A method of treating a bacterial infection in a patient comprising administering to a patient in need of such treatment a therapeutically effective amount of the compound of any one of claims 1 to 43.

Aspect 52. The method of aspect 51, wherein administering comprises orally administering.

Aspect 53. The method of any one of aspects 50 to 52, wherein administering comprises administering an oral dosage form.

Aspect 54. The method of any one of aspects 50 to 53, further comprising administering an antibiotic to the patient.

Aspect 55. The method of aspect 54, wherein the antibiotic comprises a β-lactam antibiotic.

Aspect 56. The method of any one of aspects 50 to 55, further comprising administering a β-lactamase inhibitor to the patient.

Aspect 57. A method of treating a bacterial infection in a patient comprising administering to a patient in need of such treatment a therapeutically effective amount of the pharmaceutical composition of any one of claims 44 to 50.

Aspect 58. The method of aspect 57, wherein administering comprises orally administering.

Aspect 59. The method of any one of aspects 50 to 58, wherein administering comprises administering an oral dosage form.

Aspect 60. The method of any one of aspects 50 to 59, further comprising administering an antibiotic to the patient.

Aspect 61. The method of aspect 60, wherein the antibiotic comprises a β-lactam antibiotic.

Aspect 62. The method of any one of aspect 50 to 61, wherein the bacterial infection comprises a gram negative bacterial infection.

Aspect 63. The method of any one of aspect 50 to 62, wherein the bacterial infection is capable of being treated with a therapeutically effective amount of aztreonam.

Aspect 64. The method of any one of aspect 50 to 63, wherein the bacterial infection is capable of being treated with a therapeutically effective amount of aztreonam when co-administered with a therapeutically effective amount of a β-lactamase inhibitor.

Aspect 65. A compound of Formula (1), or a pharmaceutically acceptable salt thereof, wherein,
each of $R^5$, $R^6$, and $R^7$ is hydrogen;
each $R^1$ is independently selected from $C_{1-3}$ alkyl, or each $R^1$ together with the carbon atom to which they are bonded form a $C_{3-6}$ cycloalkyl ring;

$R^2$ is selected from single bond, methane-diyl, and ethane-diyl; and $R^3$ is selected from —C(O)—O—$R^4$ and —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 66. The compound of aspect 65, wherein each $R^1$ is independently selected from $C_{1-3}$ alkyl.

Aspect 67. The compound of aspect 65, wherein each $R^1$ together with the carbon atom to which they are bonded form a $C_{3-6}$ cycloalkyl ring.

Aspect 68. The compound of aspect 65, wherein $R^2$ a single bond.

Aspect 69. The compound of any one of aspects 65 to 68, wherein $R^2$ is methane-diyl.

Aspect 70. The compound of any one of aspects 65 to 68, wherein $R^2$ is ethane-diyl.

Aspect 71. The compound of any one of aspects 65 to 71, wherein $R^3$ is —C(O)—O—$R^4$.

Aspect 72. The compound of any one of aspects 65 to 72, wherein $R^3$ is —S—C(O)—$R^4$.

Aspect 73. The compound of any one of aspects 65 to 72, wherein $R^4$ is $C_{1-10}$ alkyl.

Aspect 74. The compound of any one of aspects 65 to 72, wherein $R^4$ is $C_{1-10}$ heteroalkyl.

Aspect 75. The compound of any one of aspects 65 to 72, wherein $R^4$ is $C_{5-10}$ arylalkyl.

Aspect 76. The compound of any one of aspects 65 to 72, wherein $R^4$ is $C_{3-6}$ heterocycloalkyl.

Aspect 77. The compound of any one of aspects 65 to 72, wherein $R^4$ is substituted $C_{4-10}$ heterocycloalkylalkyl.

Aspect 78. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl, or each $R^1$ together with the carbon atom to which they are bonded form a $C_{3-6}$ cycloalkyl ring;
$R^2$ is a single bond; and
$R^3$ is —C(O)—O—$R^4$, where $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 79. The compound of aspect 78, wherein each $R^1$ is independently selected from $C_{1-3}$ alkyl.

Aspect 80. The compound of aspect 78, wherein each $R^1$ together with the carbon atom to which they are bonded form a $C_{3-6}$ cycloalkyl ring.

Aspect 81. The compound of any one of aspects 78 to 80, wherein $R^4$ is selected from $C_{1-7}$ alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, and —$CH_2$—$C_{3-6}$ substituted heterocycloalkyl, and —$(CH_2)_2$—$C_{3-6}$ substituted heterocycloalkyl.

Aspect 82. The compound of aspect 81, wherein in the substituted $C_{3-6}$ heterocycloalkyl the one or more heteroatoms is oxygen, and the one or more substituents is independently selected from $C_{1-3}$ alkyl and =O.

Aspect 83. The compound of any one of aspects 78 to 83, wherein each $R^1$ is methyl, or each $R^1$ together with the carbon atom to which they are bonded form a cyclohexyl ring or a cyclopentyl ring.

Aspect 84. The compound of any one of aspects 78 to 83, wherein $R^4$ is selected from methyl, ethyl, n-propyl, iso-propyl, n-butyl, n-hexyl, n-heptyl, —$CH_2$—$CH_2$—O—$CH_3$, benzyl, 3-oxetanyl, and methyl-5-methyl-1,3-dioxol-2-one.

Aspect 85. The compound of aspect 78, wherein
each of $R^5$, $R^6$, and $R^7$ is hydrogen;
each $R^1$ is methyl, or each $R^1$ together with the carbon atom to which they are bonded form a cyclohexyl ring or a cyclopentyl ring;
$R^2$ is a single bond; and
$R^3$ is —C(O)—O—$R^4$, wherein $R^4$ is selected from methyl, ethyl, n-propyl, iso-propyl, n-butyl, n-hexyl, n-heptyl, —$CH_2$—$CH_2$—O—$CH_3$, —$CH_2$-phenyl (benzyl), 3-oxetanyl, and methyl-5-methyl-1,3-dioxol-2-one.

Aspect 86. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl, or each $R^1$ together with the carbon atom to which they are bonded form a $C_{3-6}$ cycloalkyl ring;
$R^2$ is —$(CH_2)_2$—; and
$R^3$ is —C(O)—O—$R^4$ wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

Aspect 87. The compound of aspect 86, wherein each $R^1$ is independently selected from $C_{1-3}$ alkyl.

Aspect 88. The compound of aspect 86, wherein each $R^1$ together with the carbon atom to which they are bonded form a $C_{3-6}$ cycloalkyl ring.

Aspect 89. The compound of any one of aspects 86 to 88, wherein $R^4$ is selected from $C_{1-7}$ alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, —$CH_2$—$C_{3-6}$ substituted heterocycloalkyl, and —$(CH_2)_2$—$C_{3-6}$ substituted heterocycloalkyl.

Aspect 90. The compound of aspect 89, wherein in the substituted $C_{3-6}$ heterocycloalkyl the one or more heteroatoms is oxygen, and the one or more substituents is independently selected from $C_{1-3}$ alkyl and =O.

Aspect 91. The compound of any one of aspects 86 to 88, wherein $R^4$ is $C_{1-10}$ alkyl.

Aspect 92. The compound of aspect 86, wherein,
each of $R^5$, $R^6$, and $R^7$ is hydrogen;
each $R^1$ is methyl;
$R^2$ is —$(CH_2)_2$—; and
$R^3$ is —C(O)—O—$R^4$ where $R^4$ is selected from n-hexyl and n-heptyl.

Aspect 93. A compound of aspect 1 or a pharmaceutically acceptable salt thereof, wherein,
each of $R^5$, $R^6$, and $R^7$ is hydrogen;
each $R^1$ is selected from $C_{1-3}$ alkyl, or each $R^1$ together with the carbon atom to which they are bonded form a $C_{3-6}$ cycloalkyl ring;
$R^2$ is —$CH_2$—; and
$R^3$ is —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl.

Aspect 94. The compound of aspect 93, wherein each $R^1$ is independently selected from $C_{1-3}$ alkyl.

Aspect 95. The compound of aspect 93, wherein each $R^1$ together with the carbon atom to which they are bonded form a $C_{3-6}$ cycloalkyl ring.

Aspect 96. The compound of any one of aspects 93 to 95, wherein $R^4$ is selected from $C_{1-7}$ alkyl, $C_{1-10}$ heteroalkyl wherein the one or more heteroatoms is oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms is oxygen, —$CH_2$—$C_{3-6}$ substituted heterocycloalkyl, —$(CH_2)_2$—$C_{3-6}$ substituted heterocycloalkyl.

Aspect 97. The compound of aspect 96, wherein, in the substituted $C_{3-6}$ heterocycloalkyl the one or more heteroatoms is oxygen, and the one or more substituents is independently selected from $C_{1-3}$ alkyl and =O.

Aspect 98. The compound of any one of aspects 93 to 95, wherein $R^4$ is $C_{1-10}$ alkyl.

Aspect 99. The compound of aspect 93, wherein,
each of $R^5$, $R^6$, and $R^7$ is hydrogen;
each $R^1$ is methyl;
$R^2$ is —$CH_2$—; and
$R^3$ is —S—C(O)—$R^4$, wherein $R^4$ is methyl Aspect 100. A compound of aspect 1 or a pharmaceutically acceptable salt thereof, wherein,
each of $R^5$, $R^6$, and $R^7$ is hydrogen;
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ is a single bond; and
$R^3$ is $C_{1-3}$ alkyl.

Aspect 101. The compound of aspect 100 wherein each $R^1$ together with the carbon atom to which they are bonded form a $C_{3-6}$ heterocycloalkyl ring or a $C_{3-6}$ heterocycloalkyl ring;

Aspect 102. The compound of aspect 101, wherein the one or more heteroatoms is oxygen and the one or more substituents is =O.

Aspect 103. The compound of aspect 100, wherein,
each $R^1$ together with the carbon atom to which they are bonded form a dihydrofuran-2(3H)-one ring;
$R^2$ is a single bond; and
$R^3$ is methyl.

Aspect 104. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl;
$R^2$ is selected from a single bond and methanediyl; and
$R^3$ is selected from —O—C(O)—$R^4$ and —C(O)—O—$R^4$, wherein $R^4$ is selected from $C_{1-10}$ alkyl and substituted phenyl.

Aspect 105. The compound of aspect 104, wherein $R^2$ is a single bond.

Aspect 106. The compound of aspect 104, wherein $R^2$ is methanediyl.

Aspect 107. The compound of any one of aspects 104 to 106, wherein $R^3$ is —O—C(O)—$R^4$.

Aspect 108. The compound of any one of aspects 104 to 106, wherein $R^2$ is methanediyl; and $R^3$ is —O—C(O)—$R^4$.

Aspect 109. The compound of any one of aspects 104 to 106, wherein $R^3$ is —C(O)—O—$R^4$.

Aspect 110. The compound of any one of aspects 104 to 106, wherein $R^2$ is a single bond; and $R^3$ is —C(O)—O—$R^4$.

Aspect 111. The compound of aspect 104, wherein $R^2$ is a single bond; $R^3$ is —C(O)—O—$R^4$; and $R^4$ is $C_{1-3}$ alkyl.

Aspect 112. The compound of any one of aspects 104 to 111, wherein $R^4$ is $C_{1-10}$ alkyl.

Aspect 113. The compound of any one of aspects 104 to 111, wherein $R^4$ is $C_{1-4}$ alkyl.

Aspect 114. The compound of any one of aspects 104 to 111, wherein $R^4$ is substituted phenyl.

Aspect 115. The compound of aspect 104, wherein $R^2$ is methanediyl; $R^3$ is —O—C(O)—$R^4$; and $R^4$ is substituted phenyl.

Aspect 116. The compound of aspect 115, wherein the one or more substituents is independently selected from halogen, $C_{1-3}$ alkyl, and $C_{1-3}$ alkoxy.

Aspect 117. The compound of aspect 115, wherein the substituted phenyl is 2,6-substituted phenyl.

Aspect 118. The compound of aspect 117, wherein each of the substituents is selected from $C_{1-3}$ alkyl and $C_{1-3}$ alkoxy.

Aspect 119. The compound of aspect 115, wherein the substituted phenyl is 2,5,6-substituted phenyl.

Aspect 120. The compound of aspect 119, wherein each of the substituents at the 2 and 6 positions is independently selected from $C_{1-3}$ alkyl and $C_{1-3}$ alkoxy; and the substituent at the 5 position is halogen.

Aspect 121. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl;
$R^2$ is a single bond; and
$R^3$ is —CH=C($R^4$)$_2$, wherein each $R^4$ is —C(O)—O—$R^8$, or each $R^4$ together with the carbon atom to which they are bonded from a substituted heterocyclohexyl ring; and
each $R^8$ is $C_{1-4}$ alkyl.

Aspect 122. The compound of aspect 121, each $R^4$ is —C(O)—O—$R^8$.

Aspect 123. The compound of aspect 121, each $R^4$ is —C(O)—O—$R^8$, or each $R^4$ together with the carbon atom to which they are bonded from a substituted heterocyclohexyl ring.

Aspect 124. The compound of aspect 122, wherein in the substituted heterocyclohexyl ring, the one or more heteroatoms is oxygen.

Aspect 125. The compound of any one of aspects 123 to 124, wherein in the substituted heterocyclohexyl ring, the one or more substituents is independently selected from $C_{1-3}$ alkyl and =O.

Aspect 126. The compound of aspect 123, wherein the substituted heterocycloalkyl ring is 2,2-dimethyl-5-yl-1,3-dioxane-4,6-dione.

Aspect 127. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl;
$R^2$ is selected from a single bond and methanediyl; and
$R^3$ is substituted phenyl, wherein the one or more substituents is independently selected from —$CH_2$—O—C(O)—$R^4$ and —O—C(O)—$R^4$, wherein $R^4$ is selected from $C_{1-10}$ alkyl and phenyl.

Aspect 128. The compound of aspect 127, wherein $R^2$ is a single bond.

Aspect 129. The compound of aspect 127, wherein $R^2$ is methanediyl;

Aspect 130. The compound of aspect 127, wherein $R^2$ is 2-substituted phenyl.

Aspect 131. The compound of any one of aspects 127 to 130, wherein the one or more substituents is —$CH_2$—O—C(O)—$R^4$.

Aspect 132. The compound of any one of aspects 127 to 130, wherein the one or more substituents is —O—C(O)—$R^4$.

Aspect 133. The compound of any one of aspects 127 to 132, wherein $R^4$ is $C_{1-10}$ alkyl.

Aspect 134. The compound of any one of aspects 127 to 132, wherein $R^4$ is selected from methyl, ethyl, iso-propyl, pivalolyl, and phenyl.

Aspect 135. A compound of aspect 1 or a pharmaceutically acceptable salt thereof, wherein,
each of $R^5$, $R^6$, and $R^7$ is hydrogen;
each $R^1$ is independently selected from $C_{1-3}$ alkyl;
$R^2$ is selected from —C($R^8$)$_2$— and —$CH_2$—C(R)$_2$—, wherein each $R^8$ is independently selected from $C_{1-3}$ alkyl; and $R^3$ is selected from —C(O)—O—$R^4$ and —O—C(O)—$R^4$, wherein $R^4$ is selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

Aspect 136. The compound of aspect 135, wherein each $R^1$ is methyl.

Aspect 137. The compound of any one of aspects 135 to 136, wherein $R^2$ is —C($R^8$)$_2$—.

Aspect 138. The compound of any one of aspects 135 to 136, wherein $R^2$ is —CH$_2$—C($R^8$)$_2$—.

Aspect 139. The compound of any one of aspects 135 to 138, wherein each $R^8$ is methyl.

Aspect 140. The compound of any one of aspects 135 to 138, wherein each $R^1$ is methyl; and each $R^8$ is methyl.

Aspect 141. The compound of any one of aspects 135 to 140, wherein $R^3$ is —C(O)—O—$R^4$.

Aspect 142. The compound of any one of aspects 135 to 140, wherein $R^3$ is —O—C(O)—$R^4$.

Aspect 143. A compound of aspect 1 or a pharmaceutically acceptable salt thereof, wherein, each of $R^5$, $R^6$, and $R^7$ is hydrogen;

each $R^1$ together with the carbon atom to which they are bonded form a substituted $C_5$-heterocyclic ring;

$R^2$ is a single bond; and $R^3$ is $C_{1-3}$ alkyl.

Aspect 144. The compound of aspect 143, wherein in the substituted $C_{5-6}$ heterocyclic ring, the one or more heteroatoms is oxygen; and the one or more substituents is independently selected from $C_{1-3}$ alkyl and =O.

Aspect 145. The compound of aspect 143, wherein each $R^1$ together with the carbon atom to which they are bonded form a tetrahydro-2H-pyran-2-one ring.

Aspect 146. The compound of aspect 143, wherein, each of $R^5$, $R^6$, and $R^7$ is hydrogen;

each $R^1$ is independently selected from $C_{1-3}$ alkyl;

$R^2$ is selected from $C_{2-4}$ alkanediyl; and $R^3$ is substituted $C_{5-6}$ heterocycloalkyl, wherein the one or more heteroatoms is independently selected from N and O; and the one or more substituents is independently selected from $C_{1-3}$ alkyl and =O.

Aspect 147. The compound of aspect 146, wherein $R^4$ has the structure of Formula (6):

(6)

wherein $R^9$ is selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

Aspect 148. The compound of aspect 147, wherein $R^9$ is selected from hydrogen and $C_{1-6}$ alkyl.

Aspect 149. A compound having the structure of Formula (4):

(4)

wherein, each $R^1$ can be selected from $C_{1-6}$ alkyl;

$R^4$ can be selected from $C_{1-6}$ alkyl, $C_{1-6}$ heteroalkyl, $C_{5-6}$ cycloalkyl, and $C_{5-6}$ heterocycloalkyl; and $R^7$ can be selected from hydrogen, $C_{1-6}$ alkyl, $C_{1-6}$ heteroalkyl, and 4-(yl-methyl)-5-methyl-1,3-dioxol-2-one.

Aspect 150. The compound of aspect 149, wherein each $R^1$ can be selected from $C_{1-3}$ alkyl; $R^4$ can be selected from $C_{1-6}$ alkyl and $C_{5-6}$ cycloalkyl; and $R^7$ can be selected from hydrogen and $C_{1-6}$ alkyl.

Aspect 151. A compound selected from:

2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;

2-((((E)-1-(2-aminothiazol-4-yl)-2-(((2S,3S)-1-((2,2-dimethyl-3-oxo-3-propoxypropoxy)sulfonyl)-2-methyl-4-oxoazetidin-3-yl)amino)-2-oxoethylidene)amino)oxy)-2-methylpropanoic acid;

methyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

ethyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

propyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;

methyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

ethyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

propyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;

methyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

ethyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

propyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;

a pharmaceutically acceptable salt of any of the foregoing; and a combination of any of the foregoing.

Aspect 152. A pharmaceutical composition comprising the compound of any one of aspects 65 to 151 and a pharmaceutically acceptable vehicle.

Aspect 153. The pharmaceutical composition of aspect 152, further comprising an antibiotic.

Aspect 154. The pharmaceutical composition of any one of aspects 152 to 149, wherein the antibiotic comprises a β-lactam antibiotic.

Aspect 155. The pharmaceutical composition of any one of aspects 152 to 154, wherein the pharmaceutical composition comprises an oral dosage formulation.

Aspect 156. The pharmaceutical composition of any one of aspects 152 to 155, wherein the pharmaceutical composition comprises an oral dosage form.

Aspect 157. The pharmaceutical composition of any one of aspects 152 to 156, comprising an amount of the compound of any one of claims 65 to 151 effective for treating a bacterial infection in a patient.

Aspect 158. The pharmaceutical composition of any one of aspects 152 to 157, further comprising a β-lactamase inhibitor.

Aspect 159. The pharmaceutical composition of any one of aspect 56 and 158, wherein the β-lactamase inhibitor comprises an orally bioavailable β-lactamase inhibitor.

Aspect 160 The pharmaceutical composition of any one of aspects 158 to 159, wherein the β-lactamase inhibitor comprises a derivative of a β-lactamase inhibitor, which when orally administered to a patient provides the β-lactamase inhibitor in the systemic circulation of the patient.

Aspect 161. The pharmaceutical composition of aspect 160, wherein the derivative of a β-lactamase inhibitor has the structure of Formula (20):

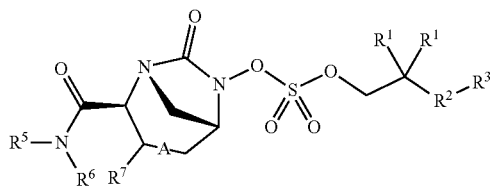

(20)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{5-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH═C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (═) and $R^7$ is $C_{1-3}$ alkyl.

Aspect 162. The pharmaceutical composition of any one of aspects 160 to 161, wherein the derivative of a β-lactamase inhibitor comprises a derivative of avibactam, a derivative of relebactam, a derivative of nacubactam, or a combination of any of the foregoing.

Aspect 163. The pharmaceutical composition of any one of aspects 160 to 162, wherein the derivative or avibactam has the structure of Formula (20a), the derivative of relebactam has the structure of Formula (21), and the derivative of nacubactam has the structure of Formula (22):

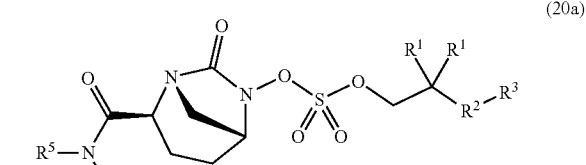

(20a)

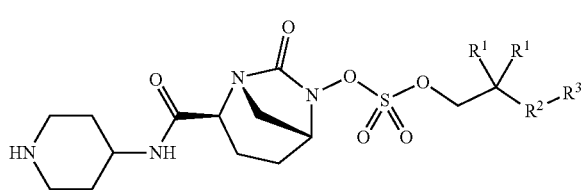

(21)

(22)

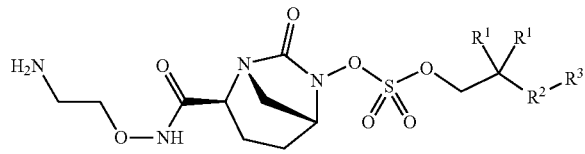

(24)

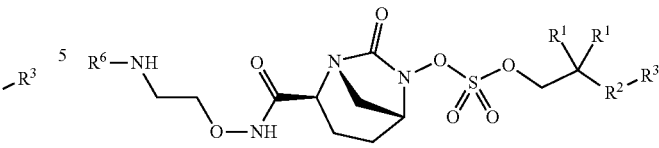

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH═C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

Aspect 164. The pharmaceutical composition of any one of aspects 160 to 162, wherein the derivative of relebactam has the structure of Formula (23) and the derivative of nacubactam has the structure of Formula (24):

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH═C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (10), a moiety of Formula (11), a moiety of Formula (12), and a moiety of Formula (13):

(10)

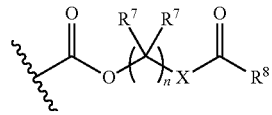

(11)

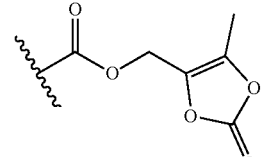

(12)

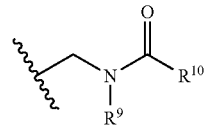

(23)

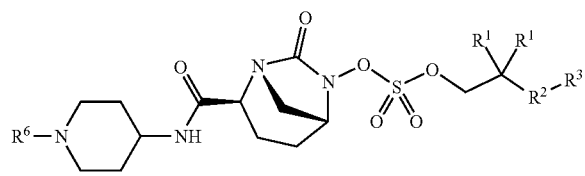

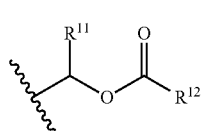

(13)

wherein, each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 165. The pharmaceutical composition of any one of aspects 160 to 162, wherein the derivative of avibactam has the structure of Formula (20a):

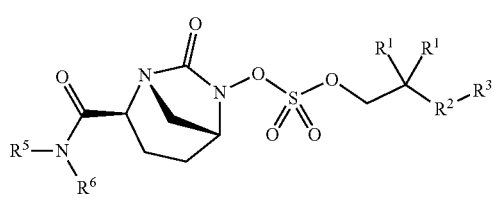

(20a)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

Aspect 166. A method of treating a bacterial infection in a patient comprising administering to a patient in need of such treatment a therapeutically effective amount of the compound of any one of claims 65 to 151.

Aspect 167. The method of aspect 166, wherein administering comprises orally administering.

Aspect 168. The method of any one of aspects 166 to 167, wherein administering comprises administering an oral dosage form.

Aspect 169. The method of any one of aspects 166 to 168, further comprising administering an antibiotic to the patient.

Aspect 170. The method of aspect 169, wherein the antibiotic comprises a β-lactam antibiotic.

Aspect 171. The method of any one of aspects 166 to 170, further comprising administering a β-lactamase inhibitor to the patient.

Aspect 172. The method of aspect 171, wherein administering a β-lactamase inhibitor comprises orally administering a β-lactamase inhibitor.

Aspect 173. The method of aspect 172, wherein administering a β-lactamase inhibitor comprises orally administering a compound that provides a therapeutically effective amount of a 3-lactamase inhibitor.

Aspect 174 The method of any one of aspects 171 to 174, wherein the β-lactamase inhibitor comprises a derivative of a β-lactamase inhibitor, which when orally administered to a patient provides the β-lactamase inhibitor in the systemic circulation of the patient.

Aspect 175. The pharmaceutical composition of aspect 174, wherein the derivative of a 3-lactamase inhibitor has the structure of Formula (20):

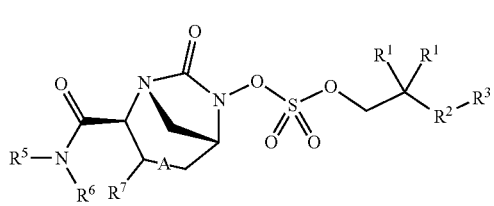

(20)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (=) and $R^7$ is $C_{1-3}$ alkyl.

Aspect 176. The pharmaceutical composition of aspect 174, wherein the derivative of a f-lactamase inhibitor comprises a derivative of avibactam, a derivative of relebactam, a derivative of nacubactam, or a combination of any of the foregoing.

Aspect 177. The pharmaceutical composition of aspect 176, wherein the derivative or avibactam has the structure of Formula (20a), the derivative of relebactam has the structure of Formula (21), and the derivative of nacubactam has the structure of Formula (22):

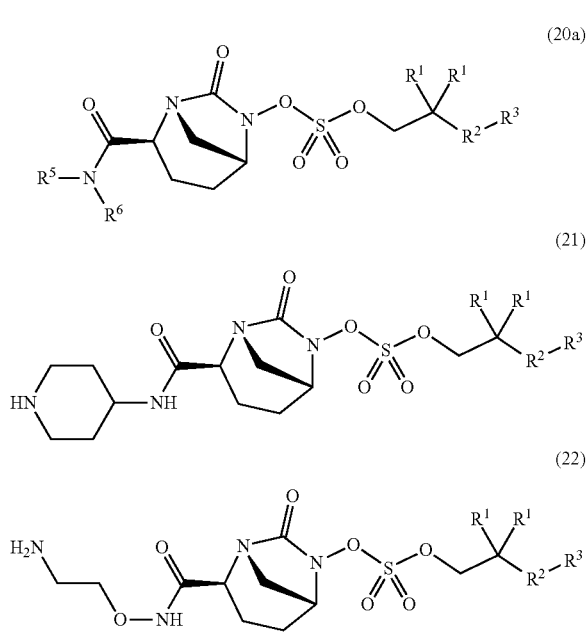

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

Aspect 178. The pharmaceutical composition of any one of aspects 176, wherein the derivative of relebactam has the structure of Formula (23) and the derivative of nacubactam has the structure of Formula (24):

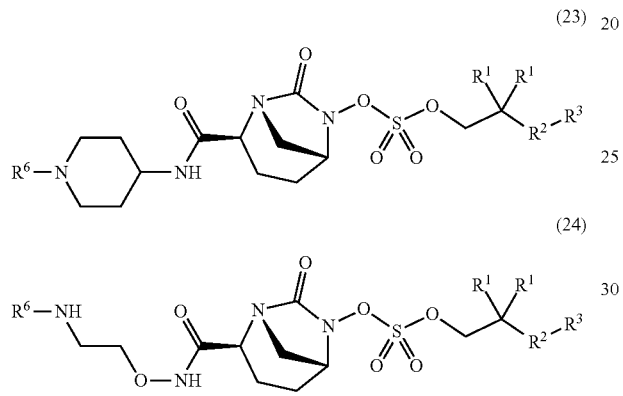

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH═C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (10), a moiety of Formula (11), a moiety of Formula (12), and a moiety of Formula (13):

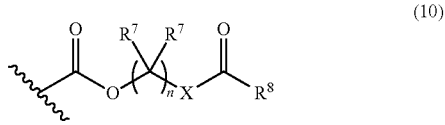

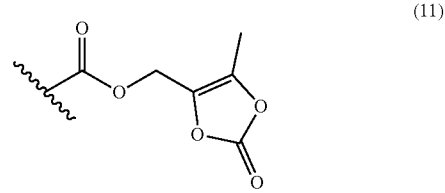

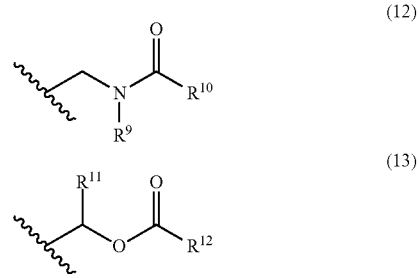

wherein, each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; $C_{1-6}$ alkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 179. The method f any one of aspects 166 to 178, wherein administering comprises orally administering.

Aspect 180. The method of any one of aspects 166 to 179, wherein administering comprises administering an oral dosage form.

Aspect 181. The method of any one of aspects 166 to 180, the bacterial infection comprises a gram negative bacterial infection.

Aspect 182. The method of any one of aspects 166 to 181, the bacterial infection is capable of being treated with a therapeutically effective amount of aztreonam.

Aspect 183. The method of any one of aspect 166 to 182, wherein the bacterial infection is capable of being treated with a therapeutically effective amount of aztreonam when co-administered with a therapeutically effective amount of a β-lactamase inhibitor.

Aspect 184. A method of synthesizing a derivative of aztreonam comprising:
reacting 3-amino-2-tert-butoxycarbonylamino-butyric acid benzyl ester and a chlorosulfonyloxy ester in the presence of a base to provide the corresponding ((2R,3R)-4-(benzyloxy)-3-((tert-butoxycarbonyl)amino)-4-oxobutan-2-yl)sulfonyloxy ester;
hydrogenating the ((2R,3R)-4-(benzyloxy)-3-((tert-butoxycarbonyl)amino)-4-oxobutan-2-yl)sulfonyloxy ester to provide the corresponding (2R,3R)-2-((tert-butoxycarbonyl)amino)-3-((sulfonyloxy)amino)butanoic acid ester; and
cyclizing the (2R,3R)-2-((tert-butoxycarbonyl)amino)-3-((sulfonyloxy)amino)butanoic acid ester in the presence of a cyclization agent to provide the corresponding β-lactam.

Aspect 185. A method of synthesizing a derivative of aztreonam comprising:
reacting tert-butyl (2S,3R)-3-amino-2-(((benzyloxy)carbonyl)-amino)butanoate and a chlorosulfonyloxy ester in the presence of a base to provide the corresponding tert-butyl (2S,3R)-2-(((benzyloxy)carbonyl)amino)-3-((sulfonyloxy)amino)butanoate ester; and
following removal of the tert-butyl ester, cyclizing the tert-butyl (2S,3R)-2-(((benzyloxy)carbonyl)amino)-3-((sulfonyloxy)amino)butanoate ester in the presence of a cyclization agent to provide the corresponding β-lactam.

EXAMPLES

The following examples describe in detail the synthesis of compounds of Formula (1), the characterization of compounds of Formula (1), and uses of compounds of Formula (1). It will be apparent to those skilled in the art that many modifications, both to materials and methods, may be practiced without departing from the scope of the disclosure.

General Procedures

All reagents were purchased from commercial suppliers and used without further purification. All solvents were reagent, or HPLC grade. Analytical TLC was performed on silica gel 60 F254 plates and visualized by UV, by staining with $KMnO_4$ dip, or by phosphomolybdic acid in EtOH dip. Flash chromatography was carried out using an automated system with pre-packed silica columns. Yields refer to isolated yields of pure compounds. $^{1}$H-NMR and $^{13}$C-NMR spectra were recorded on a 300 MHz spectrometer at 25° C. Chemical shifts are reported in parts per million (ppm) relative to deuterated solvent, or a TMS internal standard. Multiplicities are reported as follows: s=singlet; d=doublet; t=triplet; m=multiplet; br=broad. High resolution mass spectra were recorded using a time of flight mass spectrometer.

Example 1

2-((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1)

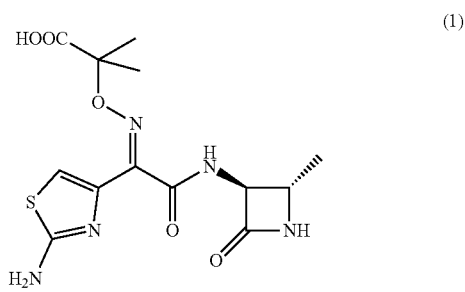 [SMILES: C[C@@H]1NC(=O)[C@H]1NC(=O)/C(=N/OC(C)(C)C(=O)O)c1csc(N)n1]

Step 1: Synthesis of (E)-2-((((2-aminothiazol-4-yl)(carboxy)methylene)amino)oxy)-2-methylpropanoic acid (1a)

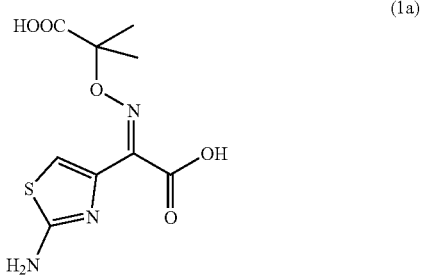 [SMILES: CC(C)(O/N=C(/C(=O)O)c1csc(N)n1)C(=O)O]

(E)-2-((((2-Aminothiazol-4-yl)(carboxy)methylene)amino)oxy)-2-methylpropanoic acid (1a) is synthesized according to the method described in Singh et al., *Organic Process Research & Development*, 2002, 8, 863-868.

Step 2: Synthesis of N-((2S,3S)-2-methyl-4-oxoazetidin-3-yl)-11-boranecarboxamide (1b)

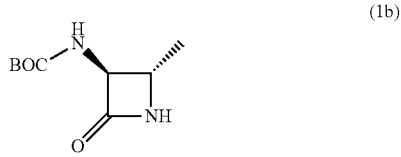

Tert-butyl ((2S,3S)-2-methyl-4-oxoazetidin-3-yl)carbamate (1b) is synthesized according to Miller et al., *Journal American Chemical Society*, 1980, 102, 7026.

Step 3: Synthesis of 2-((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1)

(E)-2-((((2-Aminothiazol-4-yl)(carboxy)methylene)amino)oxy)-2-methylpropanoic acid (1a) and tert-butyl ((2S,3S)-2-methyl-4-oxoazetidin-3-yl)carbamate (1b) are combined in the presence of a strong base such as TFA and a coupling agent to provide the title compound (1).

Example 2

Synthesis of 2-(((((E)-1-(2-aminothiazol-4-yl)-2-(((2S,3S)-1-((3-(benzoyloxy)-2,2-dimethylpropoxy)sulfonyl)-2-methyl-4-oxoazetidin-3-yl)amino)-2-oxoethylidene)amino)oxy)-2-methylpropanoic acid (2)

(2)

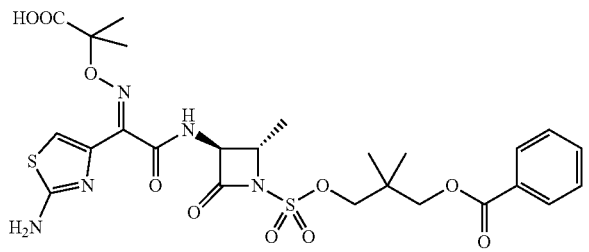

Step 1: Synthesis of 3-hydroxy-2,2-dimethylpropyl benzoate (2a)

(2a)

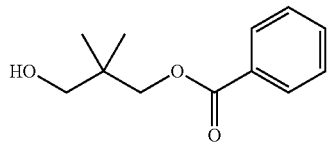

Benzoyl chloride (4.0 mL, 34.5 mmol) was added dropwise to a stirred solution of 2,2-dimethylpropane-1,3-diol (10.8 g, 103.4 mmol), pyridine (5.8 mL, 71.6 mmol) and N,N-4-dimethylaminopyridine (840 mg, 6.9 mmol) in dichloromethane (207 mL) at ca. 0° C. The mixture was stirred overnight with gradual warming to room temperature, quenched by addition of 1N HCl (100 mL) at 0° C. and extracted twice with dichloromethane. The combined organic extracts were washed with saturated aqueous NaHCO$_3$ (100 mL), brine (100 mL), dried (Na$_2$SO$_4$), filtered and the solvent concentrated under vacuum to leave a crude residue. The residue was split in to two batches and purified by column chromatography on silica gel using EtOAc/hexanes (0:1 to 1:4) as eluent to give the product (2a) (5.95 g, 99%) as a colorless oil (note: oil dried under vacuum for 2 days). LC-MS: m/z=209.0 [M+H]$^+$. $^1$H NMR (300 MHz, CDCl$_3$): 8.05 (m, 2H), 7.58 (m, 1H), 7.45 (m, 2H), 4.19 (s, 2H), 3.38 (d, J=6.3 Hz, 2H), 2.29 (t, J=6.3 Hz, 1H), 1.02 (s, 6H).

Step 2: Synthesis of 3-((chlorosulfonyl)oxy)-2,2-dimethylpropyl benzoate (2b)

(2b)

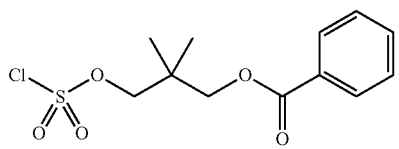

Reference is made to *J. Am. Chem. Soc.* 2006, 128, 1605-1610. A solution of distilled sulfuryl chloride (1.2 mL, 15.8 mmol) in Et$_2$O (15 mL) was cooled to −78° C. under an atmosphere of argon. A solution of 3-hydroxy-2,2-dimethylpropyl benzoate (2a) (3.0 g, 14.4 mmol) and pyridine (1.2 mL, 14.4 mmol) in Et$_2$O (3.0 mL) was then added dropwise over 1 h via a syringe. The syringe was rinsed with Et$_2$O (3×1 mL), each rinse being added to the reaction mixture. The acetone/CO$_2$ bath was removed, and the mixture allowed to warm to room temperature, then stirred at room temperature for 4 h. TLC analysis (EtOAc/hexanes; 3:7) did not indicate complete reaction, so re-cooled to −78° C. and added more SO$_2$Cl$_2$ (0.1 mL), then allowed to warm to room temperature, and stirred for an additional 2 h. The mixture was filtered and the filtrate was concentrated under vacuum to give the product (2b) (3.97 g, 89%) as an oil. $^1$H NMR (300 MHz, CDCl$_3$): 8.03 (m, 2H), 7.61-7.57 (m, 1H), 7.49-7.44 (m, 2H), 4.41 (s, 2H), 4.18 (s, 2H), 1.16 (s, 6H).

Step 3: Synthesis of 2-(((((E)-1-(2-aminothiazol-4-yl)-2-(((2S,3S)-1-((3-(benzoyloxy)-2,2-dimethylpropoxy)sulfonyl)-2-methyl-4-oxoazetidin-3-yl)amino)-2-oxoethylidene)amino)oxy)-2-methylpropanoic acid (2)

(2)

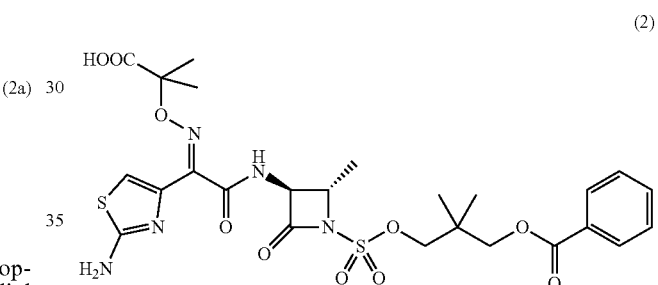

2-(((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1) is reacted with 3-((chlorosulfonyl)oxy)-2,2-dimethylpropyl benzoate (2b) in the presence of a base to provide the title compound.

Example 3

2-(((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid (3)

(3)

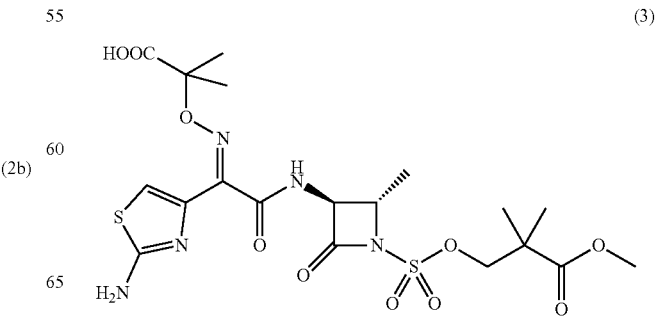

Step 1: Synthesis of ethyl 3-((chlorosulfonyl)oxy)-2,2-dimethylpropanoate (3a)

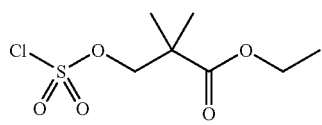

(3a)

A solution of distilled sulfuryl chloride (0.55 mL, 7.5 mmol) in Et$_2$O (10 mL) was cooled to −78° C. under an atmosphere of argon. A solution of ethyl 3-hydroxy-2,2-dimethylpropanoate (2a) (1.0 g, 6.8 mmol) and pyridine (0.55 mL, 6.8 mmol) in Et$_2$O (1.0 mL) was then added dropwise over 1 h via a syringe. The syringe was rinsed with Et$_2$O (3×1 mL), each rinse being added to the reaction mixture. The acetone/CO$_2$ bath was removed, and the mixture allowed to warm to room temperature, then stirred at room temperature for 4 h. TLC analysis (EtOAc/hexanes; 3:7) did not indicate complete reaction, so re-cooled to −78° C. and added more SO$_2$Cl$_2$ (0.11 mL), then allowed to warm to room temperature and stirred for an additional 2 h. The mixture was filtered and the filtrate was concentrated under vacuum to give the product (3a) (yield assumed quantitative). $^1$H NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Step 2: Synthesis of 2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid (3)

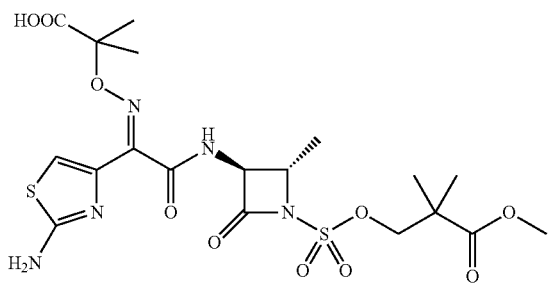

(3)

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with ethyl 3-((chlorosulfonyl)oxy)-2,2-dimethylpropanoate (3a) in the presence of a base to provide the title compound (3).

Example 4

Synthesis of 2-((((E)-1-(2-aminothiazol-4-yl)-2-(((2S,3S)-1-((3-(benzyloxy)-2,2-dimethyl-3-oxopropoxy)sulfonyl)-2-methyl-4-oxoazetidin-3-yl)amino)-2-oxoethylidene)amino)oxy)-2-methylpropanoic acid (4)

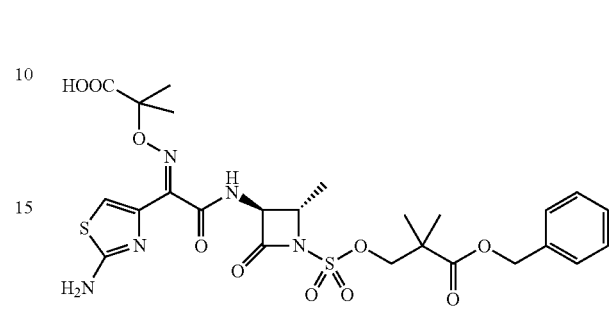

Step 1: Synthesis of benzyl 3-((chlorosulfonyl)oxy)-2,2-dimethylpropanoate (4a)

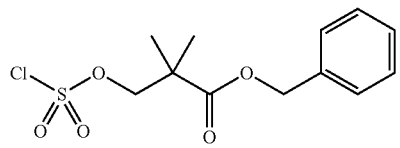 [SMILES: CC(C)(COS(=O)(=O)Cl)C(=O)OCc1ccccc1]

A solution of distilled sulfuryl chloride (0.77 mL, 10.6 mmol) in Et$_2$O (10 mL) was cooled to −78° C. under an atmosphere of argon. A solution of ethyl 3-hydroxy-2,2-dimethylpropanoate (Sigma-Aldrich; 2.0 g, 9.6 mmol) and pyridine (0.85 mL, 10.6 mmol) in Et$_2$O (2.0 mL) was then added dropwise over 1 h via a syringe. The syringe was rinsed with Et$_2$O with each rinse being added to the reaction mixture. The acetone/CO$_2$ bath was removed and the mixture allowed to warm to room temperature, then stirred at room temperature for 30 min. TLC analysis (EtOAc/hexanes; 3:7) did not indicate complete reaction, so re-cooled to −78° C. and added more SO$_2$Cl$_2$ (0.07 mL), then allowed to warm to room temperature and stirred for an additional 1 h. Et$_2$O (5 mL) was added and the mixture stirred for a few min, then filtered and the filtrate concentrated under vacuum to give the product (4a) (2.19 g, 75%). $^1$H-NMR (300 MHz, CDCl$_3$): δ 7.41-7.32 (m, 4H), 5.18 (s, 2H), 4.52 (s, 2H), 1.34 (s, 6H).

Step 2: Synthesis of 2-((((E)-1-(2-aminothiazol-4-yl)-2-(((2S,3S)-1-((3-(benzyloxy)-2,2-dimethyl-3-oxopropoxy)sulfonyl)-2-methyl-4-oxoazetidin-3-yl)amino)-2-oxoethylidene)amino)oxy)-2-methylpropanoic acid (4)

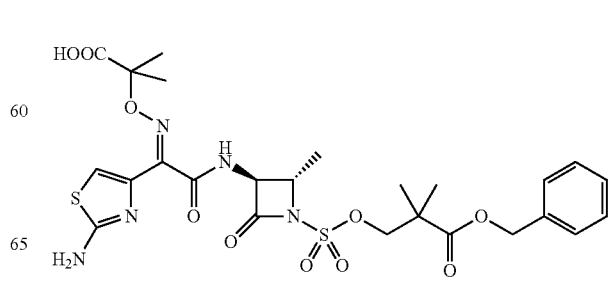

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with benzyl 3-((chlorosulfonyl)oxy)-2,2-dimethylpropanoate (4a) in the presence of a base to provide the title compound (4).

Example 5

Synthesis of 2-((((E)-1-(2-aminothiazol-4-yl)-2-(((2S,3S)-1-((4-(benzoyloxy)-2,2-dimethylbutoxy)sulfonyl)-2-methyl-4-oxoazetidin-3-yl)amino)-2-oxoethylidene)amino)oxy)-2-methylpropanoic acid (5)

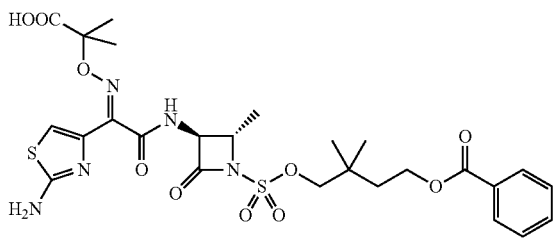 [SMILES: C[C@H]1[C@H](NC(=O)/C(=N/OC(C)(C)C(=O)O)c2csc(N)n2)C(=O)N1S(=O)(=O)OCC(C)(C)CCOC(=O)c1ccccc1]

Step 1: Synthesis of 2,2-dimethylbutane-1,4-diol (5a)

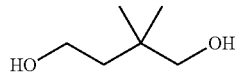

A solution of 2,2-dimethylsuccinic acid (10.0 g, 68.4 mmol) in THF (150 mL) was added dropwise to a suspension of lithium aluminum hydride (8.3 g, 219.0 mmol) in THF (80 mL) at 0° C. (ice bath). The mixture was warmed to room temperature over 20 min and then heated at reflux for 1.5 h. Upon completion (reaction monitored by TLC using MeOH/CH$_2$Cl$_2$ 5:95 as eluent) the reaction was quenched very carefully and dropwise by the addition of water (10 mL), 3 M NaOH (15 mL), and water (20 mL). The mixture was stirred at room temperature for 20 min, and the solids filtered over a pad of Celite®. The filter cake was rinsed thoroughly with THF. The filtrate was concentrated under vacuum giving a mixture of the title compound(5a) and unidentified by-products as a crude oil. The oil was purified by column chromatography on silica gel using MeOH/CH$_2$Cl$_2$ (0:1 to 1:9) as eluent to afford the product (4.649 g, 57%) as an oil. $^1$H-NMR (300 MHz, CDCl$_3$): δ 4.11 (s, 2H), 3.66 (t, J=5.9 Hz, 2H), 3.30 (s, 2H), 1.52 (t, J=5.6 Hz, 2H), 0.89 (s, 6H).

Step 2: Synthesis of 4-hydroxy-3,3-dimethylbutyl benzoate (5b)

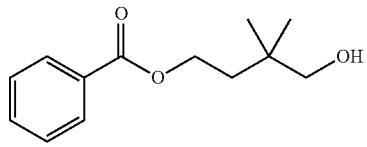 [SMILES: CC(C)(CO)CCOC(=O)c1ccccc1]

To a stirred solution of 2,2-dimethylbutane-1,4-diol (5a) (0.30 g, 2.5 mmol) in anhydrous dichloromethane (9 mL) was added benzoyl chloride (0.30 mL, 2.5 mmol), Et$_3$N (0.71 mL, 5.1 mmol), and a catalytic amount of N,N-4-dimethylaminopyridine at 0° C. (ice bath). The mixture was gradually warmed to room temperature and stirred overnight. After the starting material was completely consumed (reaction monitored by TLC using EtOAc/hexanes 2:8 as eluent), the reaction was quenched by the addition of 1 N HCl (20 mL) at 0° C. (ice bath), and the mixture was extracted twice with dichloromethane. The combined organic layers were washed with saturated aqueous NaHCO$_3$, brine, dried (Na$_2$SO$_4$), filtered and the solvent concentrated to yield a mixture, of at least two products, as a clear and colorless oil. The oil was purified by column chromatography on silica gel using EtOAc/hexanes (0:1 to 4:6) as eluent to give the product (5b) (0.29 g, 51%) as an oil (which was dried under high vacuum for 2 d). $^1$H-NMR (300 MHz, CDCl$_3$): δ 8.04-8.01 (m, 2H), 7.58-7.53 (m, 1H), 7.46-7.41 (m, 2H), 4.41 (t, J=7.4 Hz, 2H), 3.41 (s, 2H), 1.78 (t, J=7.4 Hz, 2H), 1.70 (s, 1H), 0.99 (s, 6H).

Step 3: Synthesis of 4-((chlorosulfonyl)oxy)-3,3-dimethylbutyl benzoate (5c)

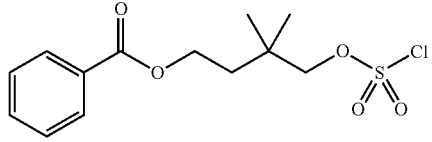 [SMILES: CC(C)(CCOC(=O)c1ccccc1)COS(=O)(=O)Cl]

A solution of freshly distilled sulfuryl chloride (0.11 mL, 1.5 mmol) in Et$_2$O (3 mL) was cooled to −78° C. under an atmosphere of Ar. A solution of 4-hydroxy-3,3-dimethylbutyl benzoate (5b) (0.28 g, 1.3 mmol) and pyridine (0.10 ml, 1.3 mmol) in Et$_2$O (2 mL) was added dropwise (over 1 h) to the cooled solution. The mixture was warmed to room temperature and stirred for 30 min (reaction was monitored by TLC using EtOAc/hexanes 2:8 as eluent). The mixture was re-cooled to −78° C. and sulfuryl chloride (0.02 mL) was added. The mixture was allowed to warm to room temperature and stirred for 30 min. Et$_2$O (5 mL) was added and the mixture stirred for a few minutes. The mixture was filtered and the filtrate concentrated under vacuum to give the product (5c) (0.305 g, 75%). $^1$H-NMR (300 MHz, CDCl$_3$): δ 8.03 (d, J=8.1 Hz, 2H), 7.60-7.54 (m, 1H), 7.47-7.42 (m, 2H), 4.44-4.38 (m, 2H), 4.29 (s, 2H), 1.89-1.85 (m, 2H), 1.13 (s, 6H).

Step 4: Synthesis of 2-((((E)-1-(2-aminothiazol-4-yl)-2-(((2S,3S)-1-((4-(benzoyloxy)-2,2-dimethylbutoxy)sulfonyl)-2-methyl-4-oxoazetidin-3-yl)amino)-2-oxoethylidene)amino)oxy)-2-methylpropanoic acid (5)

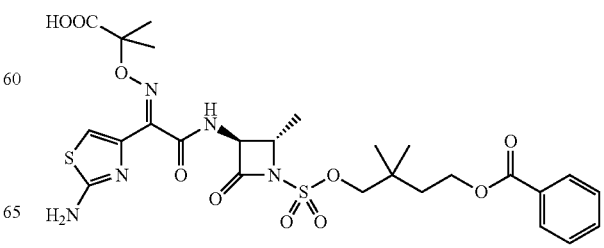

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with 4-((chlorosulfonyl)oxy)-3,3-dimethylbutyl benzoate (5c) in the presence of a base to provide the title compound (5).

Example 6

Synthesis of 2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid (6)

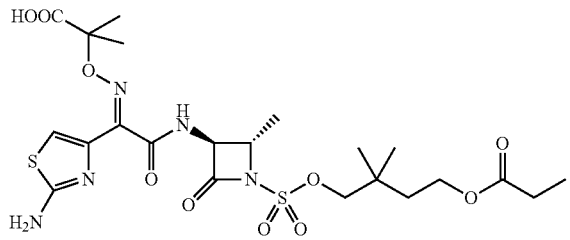

Step 1: Synthesis of 4-hydroxy-3,3-dimethylbutyl propionate (6a)

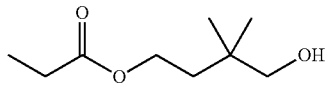

A solution of propionyl chloride (0.74 mL, 8.5 mmol) in anhydrous dichloromethane (5 mL) was added to a stirred solution of 2,2-dimethylbutane-1,4-diol (5a) (1.00 g, 8.5 mmol), Et₃N (2.4 mL, 16.9 mmol), and 4-N,N-dimethylaminopyridine (52 mg) in anhydrous dichloromethane (20 mL) at −78° C. under an atmosphere of argon. The mixture was stirred for 10 min and then allowed to warm to room temperature, stirred at room temperature for 1 h, then re-cooled to −78° C., and allowed to warm to room temperature slowly by allowing the mixture to stay in the cold bath and letting the dry ice sublime (recommended to allow warming to room temperature from −78° C. after addition of all the reagents). After the starting material was completely consumed (TLC 50% EtOAc/hexanes), the reaction was quenched by the addition of 0.5 N HCl (10 mL) at 0° C. The organic and aqueous layers were partitioned, and the aqueous layer was extracted with dichloromethane (2×20 mL). The combined organic layers were washed with saturated aqueous NaHCO₃ (20 mL), brine (20 mL), then dried (Na₂SO₄), filtered and the solvent concentrated under vacuum to leave a crude oil. The oil was purified by column chromatography on silica gel using EtOAc/hexanes (0:1 to 4:1) as eluent to give the product (6a) (463 mg, 22%) as an oil, contaminated with significant EtOAc solvent residues. ¹H-NMR (300 MHz, CDCl₃): δ 4.14 (t, J=7.4 Hz, 2H), 3.32 (s, 2H), 2.30 (q, J=7.6 Hz, 2H), 1.88 (s, 1H), 1.61 (t, J=7.7 Hz, 2H), 1.13 (t, J=7.5 Hz, 3H), 0.91 (fd, J=1.2 Hz, 6H).

Step 2: Synthesis of 4-((chlorosulfonyl)oxy)-3,3-dimethylbutyl propionate (6b)

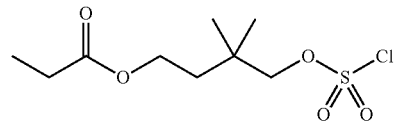 [SMILES: CCC(=O)OCCC(C)(C)COS(=O)(=O)Cl]

A solution of freshly distilled sulfuryl chloride (0.15 mL, 2.0 mmol) in Et₂O (3.5 mL) was cooled to −78° C. under an atmosphere of argon. A solution of 4-hydroxy-3,3-dimethylbutyl propionate (6a) (73% purity, the remainder being EtOAc; 441 mg, 1.8 mmol) and pyridine (0.15 mL, 1.8 mmol) in Et₂O (2.5 mL) was added dropwise over 1 h to the cooled solution. The mixture was allowed to warm to room temperature and was stirred for 30 min (monitored by TLC, 30% EtOAc/hexanes), re-cooled to −78° C. and sulfuryl chloride (0.03 mL) and pyridine (0.03 mL) was added, warmed to room temperature, and stirred for 30 min. Again, the mixture was re-cooled to −78° C. and another portion of sulfuryl chloride (0.15 mL) was added. The mixture was allowed to warm to room temperature, and stirred for 30 min. Et₂O (5 mL) was added and the mixture stirred for a few min. The mixture was filtered and the filtrate was concentrated under vacuum to give the product (6b) (401 mg, 79%). ¹H-NMR: (300 MHz, CDCl₃): 4.22 (s, 2H), 4.14 (t, J=6.8 Hz, 2H), 2.30 (q, J=7.6 Hz, 2H), 1.70 (t, J=6.8 Hz, 2H), 1.11 (t, J=7.7 Hz, 3H), 1.05 (s, 6H).

Step 3: Synthesis of 2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid (6)

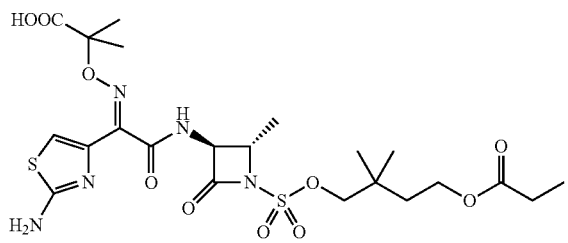 [SMILES: CCC(=O)OCCC(C)(C)COS(=O)(=O)N1C(=O)[C@@H](NC(=O)/C(=N/OC(C)(C)C(=O)O)c2csc(N)n2)[C@@H]1C]

2-((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1) is reacted with 4-((chlorosulfonyl)oxy)-3,3-dimethylbutyl propionate (6b) in the presence of a base to provide the title compound (6).

Example 7

Synthesis of 2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid (7)

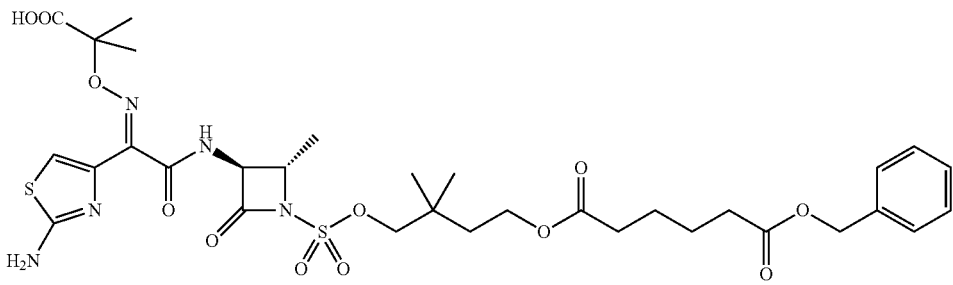 [SMILES: C[C@H]1[C@H](NC(=O)/C(=N/OC(C)(C)C(=O)O)c2csc(N)n2)C(=O)N1S(=O)(=O)OCC(C)(C)CCOC(=O)CCCCC(=O)OCc1ccccc1]

Step 1: Synthesis of Benzyl (Perfluorophenyl) Adipate (7a)

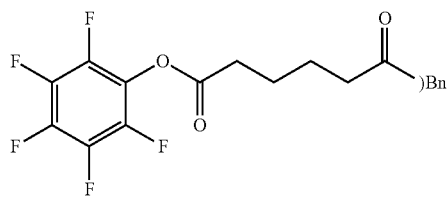

To a stirring solution of adipic acid monobenzyl ester (1.03 g, 4.3 mmol) and pentafluorophenol (0.87 g, 4.7 mmol) in EtOAc (18.7 mL) at 0° C. was added N,N'-dicyclohexylcarbodiimide (0.97 g, 4.7 mmol). The mixture was allowed to warm to room temperature and then stirred overnight. The resulting solid was removed by vacuum filtration through a pad of Celite®. The filter cake was washed with EtOAc. The filtrate was dry-loaded on to silica gel and purified by column chromatography on silica gel using EtOAc/hexanes (0:1 to 4:6) as eluent, to give the product (7a) (1.59 g, 93%) as a solid. $^1$H-NMR (300 MHz, CDCl$_3$): δ 7.37-7.35 (m, 5H), 5.13 (s, 2H), 2.68 (t, J=6.8 Hz, 2H), 2.44 (t, J=6.5 Hz, 2H), 1.82-1.78 (m, 4H).

Step 2: Synthesis of benzyl (4-hydroxy-3,3-dimethylbutyl) adipate (7b)

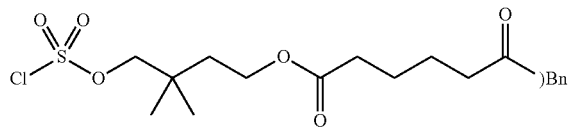

To a stirred solution of 2,2-dimethylbutane-1,4-diol (5a) (0.22 g, 1.8 mmol) in anhydrous dichloromethane (4 mL) at ca. 0° C. (ice bath), under an atmosphere of argon, was added benzyl (perfluorophenyl) adipate (7a) (0.36 g, 0.9 mmol), Et$_3$N (0.25 mL, 1.8 mmol), and a catalytic amount of 4-N,N-dimethylaminopyridine (small unweighed amount). The mixture was gradually warmed to room temperature, and then at room temperature overnight. The mixture was dry-loaded on to silica gel and purified by column chromatography on silica gel using EtOAc/hexanes (0:1 to 3:7) as eluent to give the product contaminated with regio-isomeric product. This mixture was re-purified by column chromatography on silica gel using EtOAc/hexanes (0:1 to 3:7) as eluent to give pure product (7b) (113 mg 38%). $^1$H-NMR (300 MHz, CDCl$_3$): 7.36-7.34 (m, 5H), 5.11 (s, 2H), 4.14 (t, J=7.2 Hz, 2H), 3.34 (d, J=5.7 Hz, 2H), 2.38-2.31 (m, 4H), 1.68-1.59 (m, 6H), 0.92 (s, 6H). The reaction could be repeated to give larger amounts of material.

Step 3: Synthesis of (4-((chlorosulfonyl)oxy)-3,3-dimethylbutyl) adipate (7c)

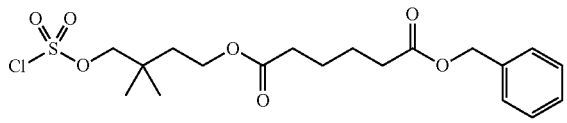 [SMILES: CC(C)(CCOC(=O)CCCCC(=O)OCc1ccccc1)COS(=O)(=O)Cl]

A solution of freshly distilled sulfuryl chloride (0.12 ml, 1.6 mmol) in Et$_2$O (5 mL) was cooled to −78° C. under an atmosphere of argon. A solution of benzyl (4-hydroxy-3,3-dimethylbutyl) adipate (7b) (446 mg, 1.3 mmol) and pyridine (0.11 mL, 1.3 mmol) in Et$_2$O (3.5 mL) was added dropwise over 1 h to the cooled solution. The mixture was allowed to warm to room temperature and was stirred for 30 min (monitored by TLC, 30% EA/hex). The reaction was not complete, so the mixture was recooled to −78° C., then sulfuryl chloride (0.05 mL) and pyridine (0.05 mL) were added. The mixture was allowed to warm to room temperature, and stirred for 30 min. Et$_2$O (5 mL) was added, and the mixture was stirred for a few mins. The mixture was filtered and the filtrate was concentrated under vacuum to give the product (7c) (446 mg, 77%). $^1$H-NMR (300 MHz, CDCl$_3$): δ 7.39-7.29 (m, 5H), 5.11 (s, 2H), 4.22 (s, 2H), 4.15 (t, J=6.8 Hz, 2H), 2.40-2.29 (m, 4H), 1.73-1.59 (m, 6H), 1.06 (s, 6H).

Step 4: Synthesis of 2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid (7)

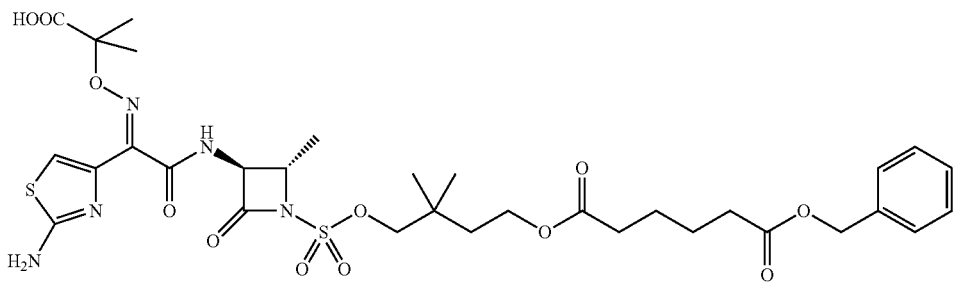 [SMILES: C[C@H]1[C@H](NC(=O)/C(=N/OC(C)(C)C(=O)O)c2csc(N)n2)C(=O)N1S(=O)(=O)OCC(C)(C)CCOC(=O)CCCCC(=O)OCc1ccccc1]

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with (4-((chlorosulfonyl)oxy)-3,3-dimethylbutyl) adipate (7c) in the presence of a base to provide the title compound (7).

Example 8

Synthesis of 6-(4-(((((2S,3S)-3-((E)-2-(2-aminothiazol-4-yl)-2-(((2-carboxypropan-2-yl)oxy)imino)acetamido)-2-methyl-4-oxoazetidin-1-yl)sulfonyl)oxy)-3,3-dimethylbutoxy)-6-oxohexanoic acid (8)

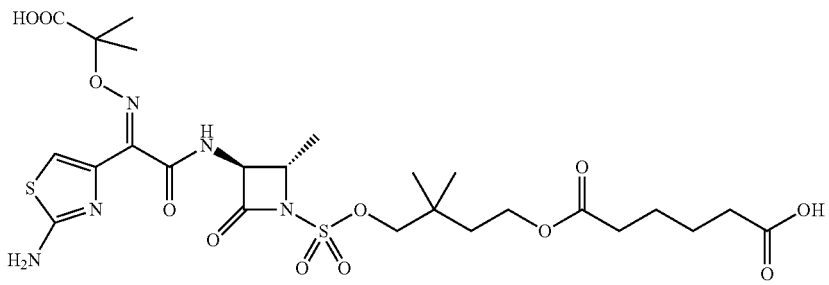 [SMILES: C[C@H]1[C@H](NC(=O)/C(=N/OC(C)(C)C(=O)O)c2csc(N)n2)C(=O)N1S(=O)(=O)OCC(C)(C)CCOC(=O)CCCCC(=O)O]

Palladium on carbon (10% by weight; 13 mg) is added to a Parr flask charged with 2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid (7) (93% purity; 50 mg, 0.1 mmol) in MeOH (14 mL). The mixture is hydrogenated at 1 atm of $H_2$ (balloon), at room temperature for 30 min. The mixture is filtered through a pad of Celite®, and the filter cake is rinsed with MeOH (ca. 20 mL). The filtrate is concentrated under vacuum, then purified by column chromatography on silica gel using MeOH/$CH_2Cl_2$ (0:1 to 4:96) as eluent, to give the title compound (8).

Example 9
Synthesis of 2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid (9)

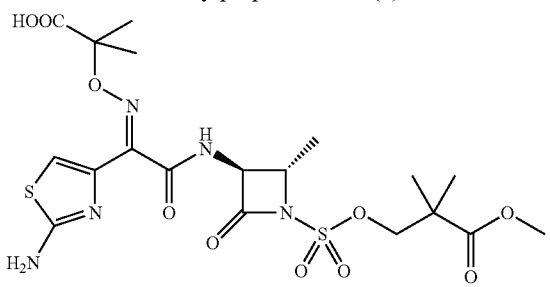

Step 1: Synthesis of methyl 3-((chlorosulfonyl)oxy)-2,2-dimethylpropanoate (9a)

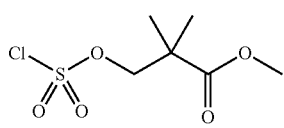

A solution of freshly distilled sulfuryl chloride (3.3 mL, 45.4 mmol) in Et$_2$O (45 mL) was cooled to −78° C. under an atmosphere of Ar. A solution of methyl 2,2-dimethyl-3-hydroxypropionate (3.0 g, 22.7 mmol) and pyridine (2.2 mL, 27.2 mmol) in Et$_2$O (20 mL) was added dropwise to the sulfuryl chloride solution over 30 min. The flask was rinsed with Et$_2$O (3×5 mL) and the rinse was added to the reaction mixture. The mixture was stirred at −78° C. until completion (monitored by TLC, 30% EA/hex, 30 min). The precipitate was filtered, and the filtrate was concentrated under vacuum to afford methyl 3-((chlorosulfonyl)oxy)-2,2-dimethylpropanoate(9a) (5.6 g, 70% yield). The mixture was stored at −78° C. and was used immediately for the next step without further purification. $^1$H-NMR (300 MHz, CDCl$_3$) δ 4.50 (s, 2H), 3.74 (s, 3H), 1.31 (s, 6H).

Step 2: Synthesis of 2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid (9)

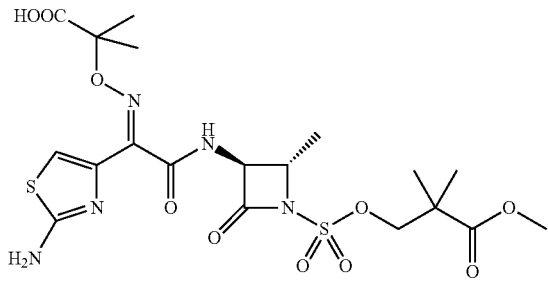 [SMILES: COC(=O)C(C)(C)COS(=O)(=O)N1C(=O)[C@@H](NC(=O)/C(=N/OC(C)(C)C(=O)O)c2csc(N)n2)[C@@H]1C]

2-((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1) is reacted with methyl 3-((chlorosulfonyl)oxy)-2,2-dimethylpropanoate (9a) in the presence of a base to provide the title compound (9).

Example 10

Synthesis of 2-((((E)-1-(2-aminothiazol-4-yl)-2-(((2S,3S)-1-((3-isopropoxy-2,2-dimethyl-3-oxopropoxy)sulfonyl)-2-methyl-4-oxoazetidin-3-yl)amino)-2-oxoethylidene)amino)oxy)-2-methylpropanoic acid (10)

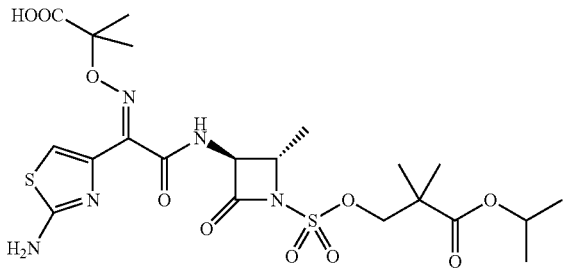 [SMILES: CC(C)OC(=O)C(C)(C)COS(=O)(=O)N1C(=O)[C@@H](NC(=O)/C(=N/OC(C)(C)C(=O)O)c2csc(N)n2)[C@@H]1C]

Step 1: Synthesis of isopropyl 3-hydroxy-2,2-dimethylpropanoate (10a)

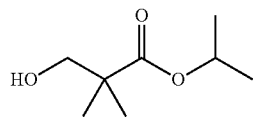

Reference is made to German Application Publication No. DE3045373. A mixture of 3-hydroxy-2,2-dimethylpropionic acid (4.7 g, 40 mmol), isopropanol (70 mL) and concentrated sulfuric acid (or fuming sulfuric acid; 1 mL) was heated to reflux and stirred overnight. After allowing to cool, the mixture was concentrated under vacuum and the residue partitioned between EtOAc (100 mL) and saturated aqueous NaHCO$_3$ (100 mL). The aqueous mixture was washed with H$_2$O (50 mL), saturated NaHCO$_3$ (50 mL) and brine (50 mL), then dried (Na$_2$SO$_4$), filtered and concentrated under vacuum to leave provide the product (10a) as an oil. The product was used directly in the next step without further purification. $^1$H-NMR (300 MHz, CDCl$_3$): δ 5.08-4.95 (m, 1H), 3.53 (fd, J=1.8 Hz, 2H), 2.49 (s, 1H), 1.25 (fd, J=2.4 Hz, 3H), 1.22 (fd, J=24 Hz, 3H), 1.17 (s, 3H), 1.16 (s, 3H).

Step 2: Synthesis of isopropyl 3-((chlorosulfonyl)oxy)-2,2-dimethylpropanoate (10b)

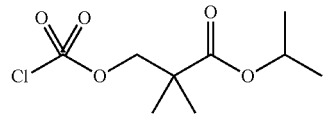

A solution of sulfuryl chloride (2.7 mL, 37.5 mmol) in Et$_2$O (45 mL) was cooled to −78° C. under an atmosphere of Ar. A solution of isopropyl 3-hydroxy-2,2-dimethylpropanoate (10a) (3.0 g, 18.7 mmol) and pyridine (1.82 mL, 22.5 mmol) in Et$_2$O (20 mL) was added dropwise to the sulfuryl chloride solution over the course of 30 min. The flask was rinsed with Et$_2$O (3×5 mL) and the rinse added to the reaction mixture. The mixture was stirred at −78° C. until completion by TLC (30 min; 30% EA/hex). The precipitate was filtered, and the filtrate was concentrated under vacuum to afford isopropyl 3-((chlorosulfonyl)oxy)-2,2-dimethylpropanoate (10b) (4.1 g, 85% yield). The mixture was stored at −78° C. and was used immediately for the next step without further purification. $^1$H-NMR (300 MHz, CDCl$_3$): δ 5.10-4.98 (m, 1H), 4.49 (s, 2H), 1.29 (s, 6H), 1.26 (s, 3H), 1.24 (s, 3H).

Step 3: Synthesis of 2-((((E)-1-(2-aminothiazol-4-yl)-2-(((2S,3S)-1-((3-isopropoxy-2,2-dimethyl-3-oxopropoxy)sulfonyl)-2-methyl-4-oxoazetidin-3-yl)amino)-2-oxoethylidene)amino)oxy)-2-methylpropanoic acid (10)

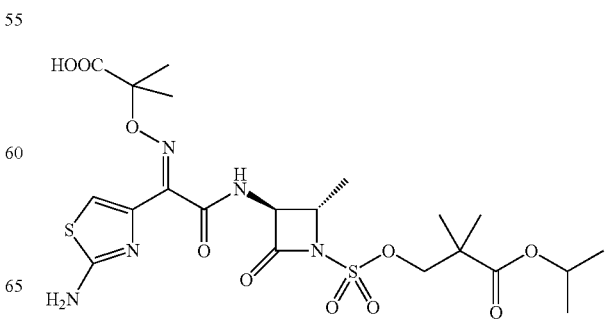

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with isopropyl 3-((chlorosulfonyl)oxy)-2,2-dimethylpropanoate (10b) in the presence of a base to provide the title compound (10).

Example 11

Synthesis of 2-((((E)-1-(2-aminothiazol-4-yl)-2-(((2S,3S)-1-((3-(hexyloxy)-2,2-dimethyl-3-oxopropoxy)sulfonyl)-2-methyl-4-oxoazetidin-3-yl)amino)-2-oxoethylidene)amino)oxy)-2-methylpropanoic acid (11)

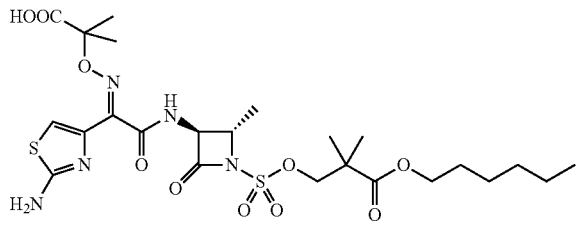 [SMILES: CCCCCCOC(=O)C(C)(C)COS(=O)(=O)N1C(=O)[C@@H](NC(=O)/C(=N/OC(C)(C)C(=O)O)c2csc(N)n2)[C@@H]1C]

Step 1: Synthesis of hexyl 3-hydroxy-2,2-dimethylpropanoate (11a)

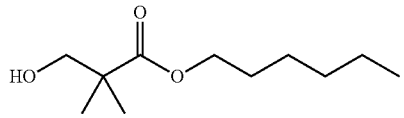

Reference is made to German Application Publication No. DE3045373. A mixture of 3-hydroxy-2,2-dimethylpropionic acid (4.7 g, 40 mmol), 1-hexanol (70 mL) and concentrated sulfuric acid (or fuming sulfuric acid; 1 mL) was heated to 80° C. and stirred overnight. After allowing to cool, the mixture was concentrated under vacuum (high vacuum pump required) and the residue partitioned between EtOAc (100 mL) and saturated aqueous NaHCO₃ (100 mL). The aqueous mixture was washed with H₂O (50 mL), saturated NaHCO₃ (50 mL) and brine (50 mL), then dried (Na₂SO₄), filtered and concentrated under vacuum to provide the product (11a) as an oil. The product was used directly in the next step without further purification. ¹H-NMR (300 MHz, CDCl₃): δ 4.04-3.98 (m, 2H), 3.47-3.45 (m, 2H), 2.26 (s, 1H), 1.58-1.32 (m, 2H), 1.32-1.23 (m, 6-1), 1.12 (s, 3H), 1.11 (s, 3H).

Step 2: Synthesis of hexyl 3-((chlorosulfonyl)oxy)-2,2-dimethylpropanoate (11b)

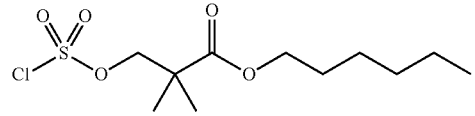 [SMILES: CCCCCCOC(=O)C(C)(C)COS(=O)(=O)Cl]

A solution of sulfuryl chloride (2.1 mL, 29.7 mmol) in Et₂O (40 mL) was cooled to −78° C. under an atmosphere of argon. A solution of hexyl 3-hydroxy-2,2-dimethylpropanoate (11a) (3.0 g, 14.8 mmol) and pyridine (1.4 mL, 17.8 mmol) in Et₂O (15 mL) was added dropwise to the sulfuryl chloride solution over the course of 30 min. The flask was rinsed with Et₂O (3×5 mL) and the rinse added to the reaction mixture. The mixture was stirred at −78° C. until completion by TLC (30 min; 30% EA/hex). The precipitate was filtered, and the filtrate was concentrated under vacuum to afford the product (11b) (3.7 g, 83% yield). The mixture was stored at −78° C. and was used immediately for the next step without further purification. ¹H-NMR (300 MHz, CDCl₃): 4.50 (s, 2H), 4.13 (t, J=6.8 Hz, 2H), 1.69-1.60 (m, 2H), 1.40-1.27 (m, 12H), 0.91-0.87 (m, 3H).

Step 3: Synthesis of 2-((((E)-1-(2-aminothiazol-4-yl)-2-(((2S,3S)-1-((3-(hexyloxy)-2,2-dimethyl-3-oxopropoxy)sulfonyl)-2-methyl-4-oxoazetidin-3-yl)amino)-2-oxoethylidene)amino)oxy)-2-methylpropanoic acid (11)

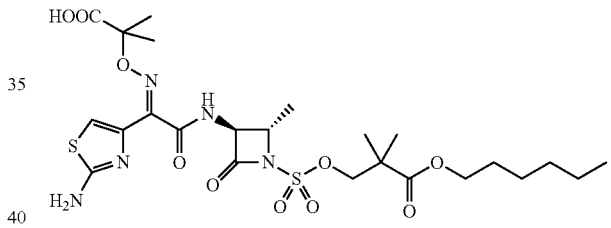

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with hexyl 3-((chlorosulfonyl)oxy)-2,2-dimethylpropanoate (11b) in the presence of a base to provide the title compound (11).

Example 12

Synthesis of 2-((((E)-1-(2-aminothiazol-4-yl)-2-(((2S,3S)-1-((3-(heptyloxy)-2,2-dimethyl-3-oxopropoxy)sulfonyl)-2-methyl-4-oxoazetidin-3-yl)amino)-2-oxoethylidene)amino)oxy)-2-methylpropanoic acid (12)

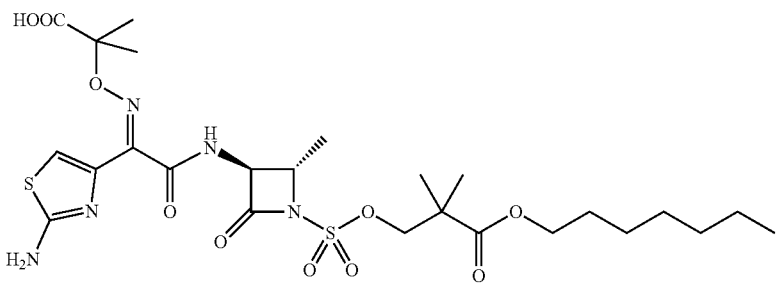 [SMILES: CCCCCCCOC(=O)C(C)(C)COS(=O)(=O)N1C(=O)[C@@H](NC(=O)/C(=N/OC(C)(C)C(=O)O)c2csc(N)n2)[C@@H]1C]

Step 1: Synthesis of heptyl 3-hydroxy-2,2-dimethylpropanoate (12a)

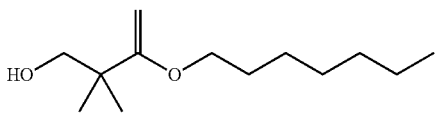

Reference is made to German Application Publication No. DE3045373. A mixture of 3-hydroxy-2,2-dimethylpropionic acid (4.7 g, 40 mmol), 1-heptanol (70 mL) and concentrated sulfuric acid (or fuming sulfuric acid; 1 mL) was heated to 80° C. and stirred overnight. After allowing the mixture to cool, the mixture was concentrated under vacuum (high vacuum pump required) and the residue partitioned between EtOAc (100 mL) and saturated aqueous NaHCO$_3$ (100 mL). The aqueous was washing with H$_2$O (50 mL), saturated NaHCO$_3$ (50 mL) and brine (50 mL), then dried (Na$_2$SO$_4$), filtered and concentrated under vacuum to provide the product (12a) as an oil. The product was used directly in the next step without further purification. $^1$H-NMR (300 MHz, CDCl$_3$): δ 4.31 (t, J=6.5 Hz, 2H), 3.77 (s, 2H), 1.87-1.81 (m, 2H), 1.53-1.50 (m, 8H), 1.41 (s, 6H), 1.12-1.08 (m, 3H).

Step 2: Synthesis of heptyl 3-((chlorosulfonyl)oxy)-2,2-dimethylpropanoate (12b)

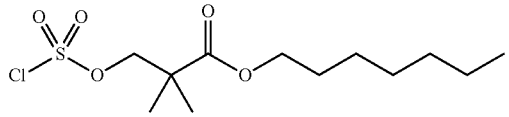 [SMILES: CCCCCCCOC(=O)C(C)(C)COS(=O)(=O)Cl]

A solution of sulfuryl chloride (2.0 mL, 27.7 mmol) in Et$_2$O (40 mL) was cooled to −78° C. under an atmosphere of argon. A solution of heptyl 3-hydroxy-2,2-dimethylpropanoate (12a) (3.0 g, 13.9 mmol) and pyridine (1.4 mL, 16.6 mmol) in Et$_2$O (15 mL) was added dropwise to the sulfuryl chloride solution over the course of 30 min. The flask was rinsed with Et$_2$O (3×5 mL) and the rinse added to the reaction mixture. The mixture was stirred at −78° C. until completion as monitored by TLC (30 min; 30% EA/hex). The precipitate was filtered, and the filtrate was concentrated under vacuum to afford heptyl 3-((chlorosulfonyl)oxy)-2,2-dimethylpropanoate (12b) (3.3 g, 75%). The mixture was stored at −78° C. and was used immediately for the next step without further purification. $^1$H-NMR (300 MHz, CDCl$_3$): δ 4.46 (s, 2H), 4.11-4.00 (m, 2H), 1.64-1.55 (m, 2H), 1.26-1.24 (m, 8H), 0.85-0.81 (m, 3H).

Step 3: Synthesis of 2-((((E)-1-(2-aminothiazol-4-yl)-2-(((2S,3S)-1-((3-(heptyloxy)-2,2-dimethyl-3-oxopropoxy)sulfonyl)-2-methyl-4-oxoazetidin-3-yl)amino)-2-oxoethylidene)amino)oxy)-2-methylpropanoic acid (12)

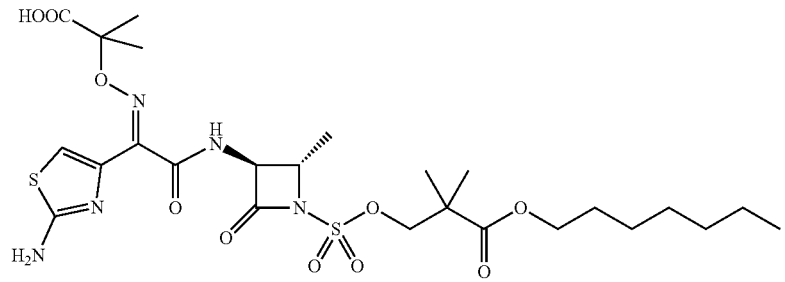 [SMILES: CCCCCCCOC(=O)C(C)(C)COS(=O)(=O)N1C(=O)[C@@H](NC(=O)/C(=N/OC(C)(C)C(=O)O)c2csc(N)n2)[C@@H]1C]

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with heptyl 3-((chlorosulfonyl)oxy)-2,2-dimethylpropanoate (12b). in the presence of a base to provide the title compound (12).

Example 13

Synthesis of 2-((((E)-1-(2-aminothiazol-4-yl)-2-(((2S,3S)-1-((3-(tert-butoxy)-2,2-dimethyl-3-oxopropoxy)sulfonyl)-2-methyl-4-oxoazetidin-3-yl)amino)-2-oxoethylidene)amino)oxy)-2-methylpropanoic acid (13)

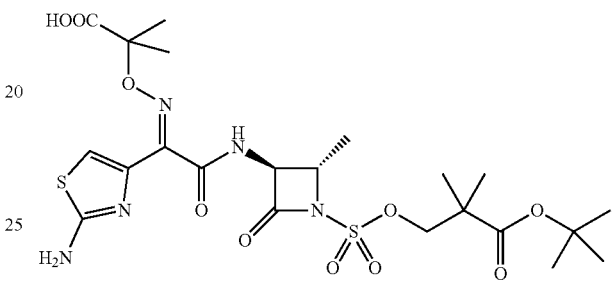

Step 1 and Step 2: Synthesis of tert-butyl 3-hydroxy-2,2-dimethylpropanoate (13a)

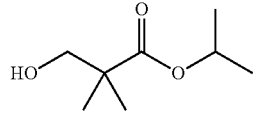

The compound was synthesized in accordance with PCT International Application Publication No. WO 2007116922. Sodium hydride (60% in mineral oil; 2.0 g) was added to a cooled solution of tert-butyl methyl malonate (4 g) in THF (100 mL) at 0° C. under an atmosphere of Ar. The mixture was stirred at 0° C. for 10 min. MeI (3.2 mL) was added to the mixture and the stirring was continued for 3 h (by this time the mixture was at room temperature). Brine and EtOAc were added to the mixture, and the organic layer was separated, dried (Na$_2$SO$_4$), filtered and concentrated under vacuum to give the product (ca. 4.5 g), which was used directly in the next step.

Solid lithium tri-tert-butoxy-aluminohydride (7.1 g, 28 mmol) was added portion-wise over 15 min to a solution of tert-butyl methyl 2,2-dimethyl-malonate (2.2 g) in THF (100 mL) under an atmosphere of Ar. The mixture was then heated to reflux and stirred overnight. After cooling to room temperature, a saturated solution of NH₄Cl and EtOAc were added, and the aqueous and organic layers were separated. The organic layer was washed with H₂O and brine, then dried (Na₂SO₄), filtered and concentrated under vacuum to provide a crude residue. The residue was purified by column chromatography on silica gel using EtOAc/hexanes (0:1 to 3:7) as eluent to give the product (13a) (900 mg) as an oil. $^1$H-NMR (300 MHz, CDCl₃): δ 3.50 (d, J=5.1 Hz, 2H), 2.53 (t, J=6.5 Hz, 1H), 1.45 (s, 9H), 1.14 (s, 6H)

Step 3: Synthesis of tert-butyl 3-((chlorosulfonyl)oxy)-2,2-dimethylpropanoate (13b)

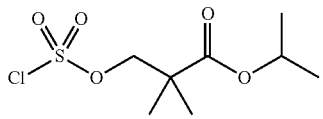

A solution of sulfuryl chloride (0.31 mL, 4.2 mmol) in Et₂O (6 mL) was cooled to −78° C. under an atmosphere of Ar. A solution of tert-butyl 3-hydroxy-2,2-dimethylpropanoate (13a) (0.49 g, 2.8 mmol) and pyridine (0.25 mL, 3.1 mmol) in Et₂O (6 mL) was added dropwise to the sulfuryl chloride solution over the course of 10 min. The mixture was stirred at −78° C. for 90 min and allowed to warm to 23° C. after TLC revealed that the reaction had not proceeded to completion (10% EtOAc/hexanes). The mixture was re-cooled to −78° C. and an additional 1-equivalent of sulfuryl chloride was added, stirred for 10 min, and the mixture allowed to warm to 23° C. (note: the mixture was allowed to stir for a total of 1 h after the addition and during the warming period). The precipitate was filtered, and the filtrate was concentrated under vacuum to give tert-butyl 3-((chlorosulfonyl)oxy)-2,2-dimethylpropanoate (13b) (961 mg, yield assumed quantitative) as a clear, oil. $^1$H-NMR (300 MHz, CDCl₃): δ 4.46 (fd, J=1.5 Hz, 2H), 1.47 (fd, J=1.2 Hz, 9H), 1.27 (s, 6H).

Step 4: Synthesis of 2-((((E)-1-(2-aminothiazol-4-yl)-2-(((2S,3S)-1-((3-(tert-butoxy)-2,2-dimethyl-3-oxopropoxy)sulfonyl)-2-methyl-4-oxoazetidin-3-yl)amino)-2-oxoethylidene)amino)oxy)-2-methylpropanoic acid (13)

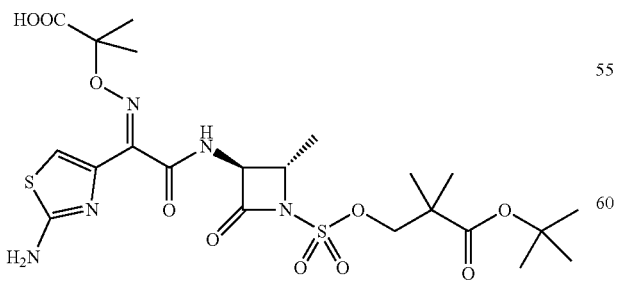

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with tert-butyl 3-((chlorosulfonyl)oxy)-2,2-dimethylpropanoate (13b) in the presence of a base to provide the title compound (13).

Example 14

Synthesis of 2-((((E)-1-(2-aminothiazol-4-yl)-2-(((2S,3S)-1-((3-(2-methoxyethoxy)-2,2-dimethyl-3-oxopropoxy)sulfonyl)-2-methyl-4-oxoazetidin-3-yl)amino)-2-oxoethylidene)amino)oxy)-2-methylpropanoic acid (14)

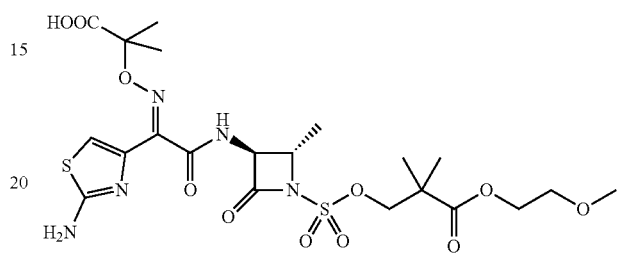

Step 1: Synthesis of 2-methoxyethyl 3-hydroxy-2,2-dimethylpropanoate (14a)

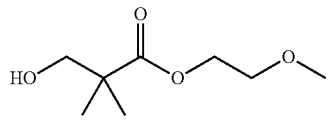

3-Hydroxy-2,2-dimethylpropanoic acid (1.2 g, 10.3 mmol) and Cs₂CO₃ (3.4 g, 10.4 mmol) were suspended in DMF (25 mL) at 23° C., then 2-bromoethyl methyl ether (1.0 mL, 10.4 mmol) was added. The resulting mixture was stirred at 70° C. overnight. After cooling, the mixture was filtered through a pad of Celite®. The filtrate was diluted with EtOAc (150 mL), and the mixture washed with water (3×100 mL) and brine, then dried (Na₂SO₄), filtered and concentrated to leave a crude residue. The residue was purified by column chromatography on silica gel using EtOAc/hexanes (1:4 to 4:1) as eluent to provide the product (14a) (1.3 g, crude weight) as an oil. $^1$H-NMR (300 MHz, CDCl₃): δ 4.28 (t, J=4.8 Hz, 2H), 3.62-3.55 (m, 4H), 3.38 (s, 3H), 2.65 (t, J=6.0 Hz, 1H), 1.21 (s, 6H).

Step 2: Synthesis of 2-methoxyethyl 3-((chlorosulfonyl)oxy)-2,2-dimethylpropanoate (14b)

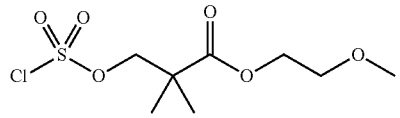 [SMILES: COCCOC(=O)C(C)(C)COS(=O)(=O)Cl]

A solution of freshly distilled sulfuryl chloride (0.2 mL, 2.8 mmol) in Et₂O (7.0 mL) was cooled to −78° C. under an atmosphere of Ar. A solution of 2-methoxyethyl 3-hydroxy-2,2-dimethylpropanoate (14a) (0.48 g, 2.7 mmol) and pyridine (0.24 mL, 3.0 mmol) in Et₂O (1 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (14b) (0.5 g, 67%) as an oil, which was used directly in the next step without further purification. Note: $^1$H-NMR indicated desired product with residue of pyridine and along with starting material.

Step 3: Synthesis of 2-((((E)-1-(2-aminothiazol-4-yl)-2-(((2S,3S)-1-((3-(2-methoxyethoxy)-2,2-dimethyl-3-oxopropoxy)sulfonyl)-2-methyl-4-oxoazetidin-3-yl)amino)-2-oxoethylidene)amino)oxy)-2-methylpropanoic acid (14)

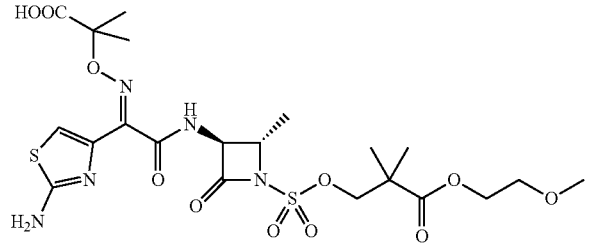 [SMILES: COCCOC(=O)C(C)(C)COS(=O)(=O)N1C(=O)[C@@H](NC(=O)/C(=N/OC(C)(C)C(=O)O)c2csc(N)n2)[C@@H]1C]

2-((((E)-1-(2-aminothiazol-4-yl)-2-(((2S,3S)-2-methyl-4-oxoazetidin-3-yl)amino)-2-oxoethylidene)amino)oxy)-2-methylpropanoic acid (1) is reacted with 2-methoxyethyl 3-((chlorosulfonyl)oxy)-2,2-dimethylpropanoate (14b) in the presence of a base to provide the title compound (14).

Example 15

Synthesis of 2-((((E)-1-(2-aminothiazol-4-yl)-2-(((2S,3S)-1-((2,2-dimethyl-3-(oxetan-3-yloxy)-3-oxopropoxy)sulfonyl)-2-methyl-4-oxoazetidin-3-yl)amino)-2-oxoethylidene)amino)oxy)-2-methylpropanoic acid (15)

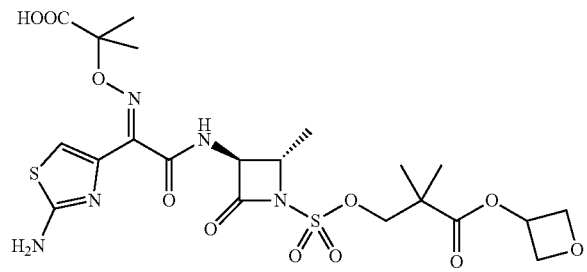 [SMILES: C[C@H]1[C@H](NC(=O)/C(=N/OC(C)(C)C(=O)O)c2csc(N)n2)C(=O)N1S(=O)(=O)OCC(C)(C)C(=O)OC1COC1]

Step 1: Synthesis of oxetan-3-yl 3-hydroxy-2,2-dimethylpropanoate (15a)

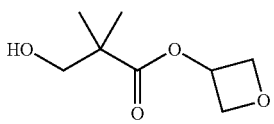

3-Hydroxy-2,2-dimethylpropanoic acid (4.7 g, 40 mmol) and Cs$_2$CO$_3$ (13.0 g, 40 mmol) were suspended in DMF (100 mL) at 23° C., then 3-iodooxetane (7.4 g, 40 mmol) was added. The resulting mixture was stirred at 70° C. overnight. After cooling, the mixture was diluted with EtOAc (150 mL), and the mixture washed with water (3×100 mL) and brine, then dried (Na$_2$SO$_4$), filtered and concentrated to provide a crude residue. The residue was purified by column chromatography on silica gel using EtOAc/hexanes as eluent to give the product (15a) (3.6 g, 51%) as an oil.

Step 2: Synthesis of oxetan-3-yl 3-((chlorosulfonyl)oxy)-2,2-dimethylpropanoate (15b)

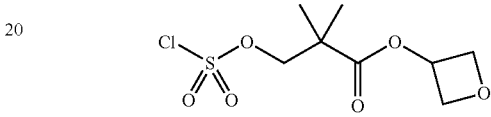

A solution of freshly distilled sulfuryl chloride (0.2 mL, 2.7 mmol) in Et$_2$O (3 mL) was cooled to −78° C. under an atmosphere of Ar. A solution of oxetan-3-yl 3-hydroxy-2,2-dimethylpropanoate (15a) (0.46 g, 2.6 mmol) and pyridine (0.2 mL, 2.7 mmol) in Et$_2$O (2 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (15b) (0.5 g, 69%) as an oil, which was used directly in the next step without further purification. $^1$H-NMR (300 MHz, CDCl$_3$): δ 5.50-5.46 (m, 1H), 4.94-4.89 (m, 2H), 4.65-4.60 (m, 2H), 4.52 (s, 2H), 1.72 (br. s, 1H), 1.36 (s, 6H).

Step 3: Synthesis of 2-((((E)-1-(2-aminothiazol-4-yl)-2-(((2S,3S)-1-((2,2-dimethyl-3-(oxetan-3-yloxy)-3-oxopropoxy)sulfonyl)-2-methyl-4-oxoazetidin-3-yl)amino)-2-oxoethylidene)amino)oxy)-2-methylpropanoic acid (15)

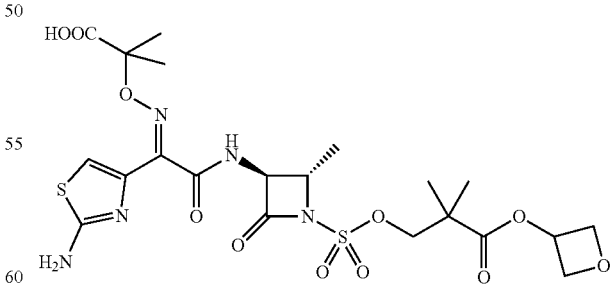

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with oxetan-3-yl 3-((chlorosulfonyl)oxy)-2,2-dimethylpropanoate (15b) in the presence of a base to provide the title compound (15).

Example 16

Synthesis of 2-((((E)-1-(2-aminothiazol-4-yl)-2-(((2S,3S)-1-(((1-(ethoxycarbonyl)cyclohexyl)methoxy)sulfonyl)-2-methyl-4-oxoazetidin-3-yl)amino)-2-oxoethylidene)amino)oxy)-2-methylpropanoic acid (16)

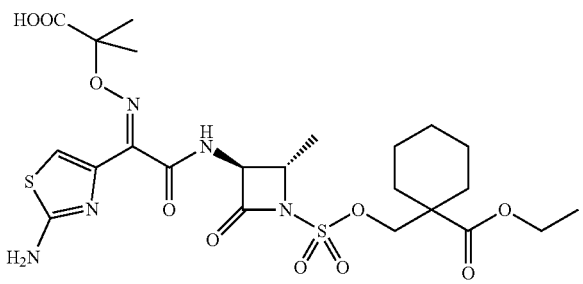 [SMILES: CCOC(=O)C1(COS(=O)(=O)N2C(=O)[C@@H](NC(=O)/C(=N/OC(C)(C)C(=O)O)c3csc(N)n3)[C@@H]2C)CCCCC1]

Step 1: Synthesis of ethyl 1-(((chlorosulfonyl)oxy)methyl)cyclohexanecarboxylate (16a)

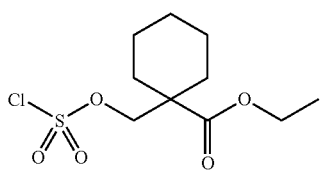 [SMILES: CCOC(=O)C1(COS(=O)(=O)Cl)CCCCC1]

A solution of freshly distilled sulfuryl chloride (77 µL, 1.1 mmol) in Et$_2$O (3 mL) was cooled to −78° C. under an atmosphere of Ar. A solution of ethyl 1-(hydroxymethyl)cyclohexanecarboxylate (0.2 g, 1.0 mmol) and pyridine (85 µL, 1.1 mmol) in Et$_2$O (2 mL) was added dropwise to the sulfuryl chloride solution over 11 min. The flask was rinsed with Et$_2$O (3×1 mL) and the rinse added to the reaction. The mixture was stirred at −78° C. until completion (ca. 30 min; monitored by TLC, 30% EtOAc/hex). The precipitate was filtered, and the filtrate was concentrated under vacuum to afford the title compound as an oil, which was used directly in the next step without purification. A second batch using 476 mg of the starting alcohol, afforded 600 mg of the product (16a) (approximately, 85% purity by $^1$H-NMR).

Step 2: Synthesis of 2-((((E)-1-(2-aminothiazol-4-yl)-2-(((2S,3S)-1-(((1-(ethoxycarbonyl)cyclohexyl)methoxy)sulfonyl)-2-methyl-4-oxoazetidin-3-yl)amino)-2-oxoethylidene)amino)oxy)-2-methylpropanoic acid (16)

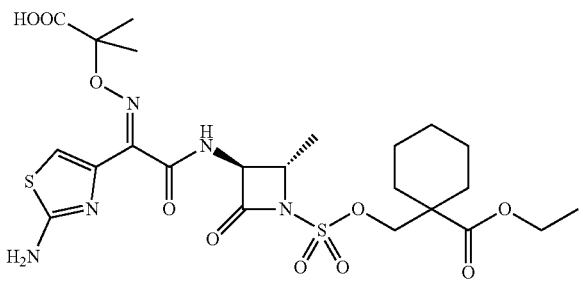 [SMILES: CCOC(=O)C1(COS(=O)(=O)N2C(=O)[C@@H](NC(=O)/C(=N/OC(C)(C)C(=O)O)c3csc(N)n3)[C@@H]2C)CCCCC1]

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with ethyl 1-(((chlorosulfonyl)oxy)methyl)cyclohexanecarboxylate (16a) in the presence of a base to provide the title compound (16).

Example 17

Synthesis of 2-((((E)-1-(2-aminothiazol-4-yl)-2-(((2S,3S)-1-(((1-(ethoxycarbonyl)cyclopentyl)methoxy)sulfonyl)-2-methyl-4-oxoazetidin-3-yl)amino)-2-oxoethylidene)amino)oxy)-2-methylpropanoic acid (17)

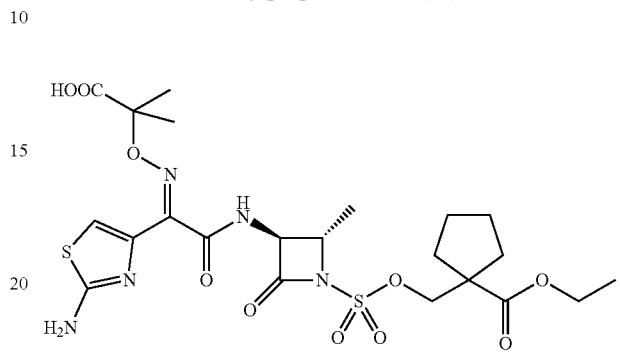

Step 1: Synthesis of ethyl 1-(((chlorosulfonyl)oxy)methyl)cyclopropanecarboxylate (17a)

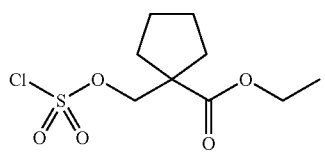 [SMILES: CCOC(=O)C1(COS(=O)(=O)Cl)CCCC1]

A solution of freshly distilled sulfuryl chloride (200 µL, 2.7 mmol) in Et$_2$O (3 mL) was cooled to −78° C. under an atmosphere of Ar. A solution of ethyl 1-(hydroxymethyl)cyclopentanecarboxylate (0.48 g, 2.7 mmol) and pyridine (222 µL, 2.7 mmol) in Et$_2$O (2 mL) was added dropwise to the sulfuryl chloride solution over 7 min. The flask was rinsed with Et$_2$O (2×1 mL) and both rinses were added to the reaction mixture. The mixture was stirred at −78° C. for 1.5 h. The precipitate was filtered, and the filter-cake washed with Et$_2$O (4 mL). The filtrate was concentrated under vacuum to afford the title compound (17a) as an oil, which was used directly in the next step without further purification.

Step 2: Synthesis of 2-((((E)-1-(2-aminothiazol-4-yl)-2-(((2S,3S)-1-(((1-(ethoxycarbonyl)cyclopentyl)methoxy)sulfonyl)-2-methyl-4-oxoazetidin-3-yl)amino)-2-oxoethylidene)amino)oxy)-2-methylpropanoic acid (17)

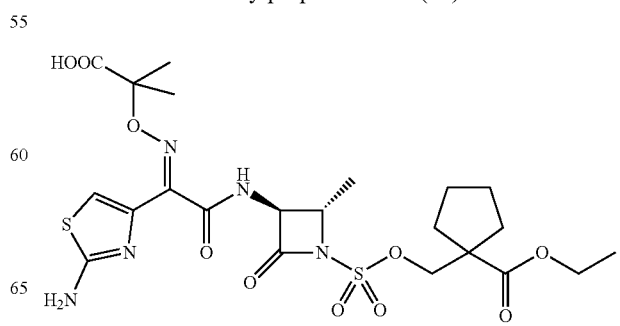

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with ethyl 1-(((chlorosulfonyl)oxy)methyl)cyclopropanecarboxylate (17a) in the presence of a base to provide the title compound (17).

Example 18

2-((((E)-1-(2-aminothiazol-4-yl)-2-(((2S,3S)-1-(((1-(ethoxycarbonyl)cyclobutyl)methoxy)sulfonyl)-2-methyl-4-oxoazetidin-3-yl)amino)-2-oxoethylidene)amino)oxy)-2-methylpropanoic acid (18)

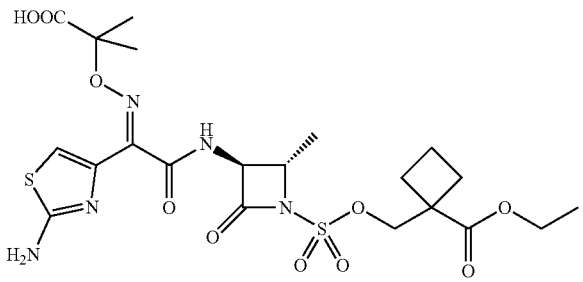 [SMILES: CCOC(=O)C1(COS(=O)(=O)N2C(=O)[C@@H](NC(=O)/C(=N/OC(C)(C)C(=O)O)c3csc(N)n3)[C@@H]2C)CCC1]

Step 1: Synthesis of ethyl 1-(((chlorosulfonyl)oxy)methyl)cyclobutanecarboxylate (18a)

A solution of freshly distilled sulfuryl chloride (451 μL, 6.2 mmol) in Et$_2$O (5 mL) was cooled to −78° C. under an atmosphere of Ar. A solution of ethyl 1-(hydroxymethyl)cyclobutanecarboxylate (1.0 g, 6.1 mmol) and pyridine (500 μL, 6.2 mmol) in Et$_2$O (10 mL) was added dropwise to the sulfuryl chloride solution over the course of 11 min. The flask was rinsed with Et$_2$O (3×1 mL), which was also added to the reaction mixture. The mixture was stirred at −78° C., which was allowed to warm to ambient temp. within 4 h. The precipitate was filtered, and the filtrate was concentrated under vacuum to afford the title compound (18a) (1.2 g, 76%) as an oil, which was used directly in the next step without further purification. Note: $^1$H-NMR indicated desired product, together with starting material.

Step 2: Synthesis of 2-((((E)-1-(2-aminothiazol-4-yl)-2-(((2S,3S)-1-(((1-(ethoxycarbonyl)cyclobutyl)methoxy)sulfonyl)-2-methyl-4-oxoazetidin-3-yl)amino)-2-oxoethylidene)amino)oxy)-2-methylpropanoic acid (18)

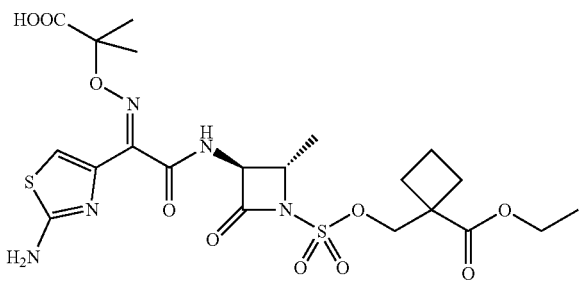 [SMILES: CCOC(=O)C1(COS(=O)(=O)N2C(=O)[C@@H](NC(=O)/C(=N/OC(C)(C)C(=O)O)c3csc(N)n3)[C@@H]2C)CCC1]

2-((((E)-1-(2-Aminothiazol-4-yl)-2-(((2S,3S)-2-methyl-4-oxoazetidin-3-yl)amino)-2-oxoethylidene)amino)oxy)-2-methylpropanoic acid (1) is reacted with ethyl 1-(((chlorosulfonyl)oxy)methyl)cyclobutanecarboxylate (18a) in the presence of a base to provide the title compound (18).

Example 19

Synthesis of (2S,3R)-benzyl 2-((tert-butoxycarbonyl)amino)-3-hydroxybutanoate (19)

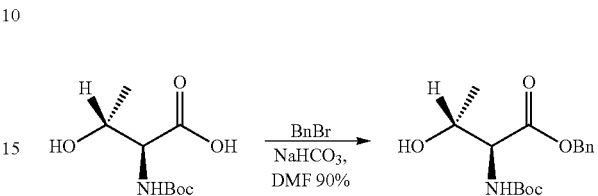

To a solution of Boc-L-threonine (15.0 g, 68.4 mmol) in DMF (465 mL) at 0° C., were added NaHCO$_3$ (16.0 g, 190.2 mmol) and benzyl bromide (40.6 mL, 342.1 mmol). After stirring overnight at 25° C., water was added and the mixture was extracted with EtOAc. The organic layers were washed with water and brine, and concentrated. The dried residue was purified with flash chromatography over silica gel (0-60%, EA/Hex) to obtain the benzyl ester product (19) (18.8 g, 89% yield) as a colorless oil. $^1$H-NMR (300 MHz, CDCl$_3$) δ 7.43-7.29 (m, 5H), 5.35 (d, J=9.2 Hz, 1H), 5.32-5.11 (m, 2H), 4.29 (d, J=9.4 Hz, 2H), 1.44 (s, 9H), 1.31-1.19 (m, 3H). LCMS (M+1)+: 310, calculated: 310.

Example 20

Synthesis of (2S,3S)-Benzyl 3-azido-2-((tert-butoxycarbonyl)amino)butanoate (20)

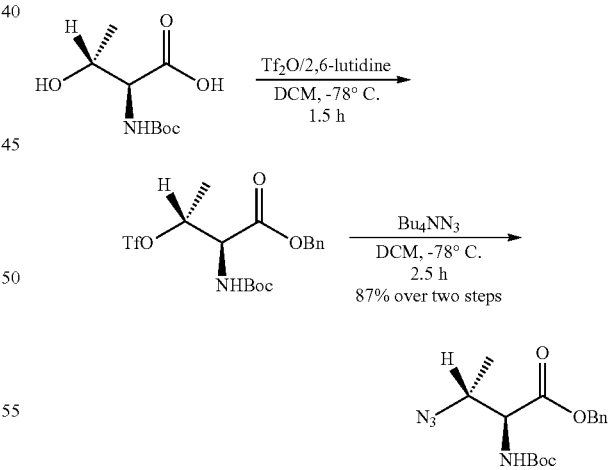

To a solution of the benzyl ester of Example 19 (16.08 g, 51.98 mmol) in anhydrous DCM (90 mL) at −78° C. were sequentially added Tf$_2$O (10.94 mL, 62.37 mmol) dropwise and 2,6-lutidine (7.87 mL, 67.57 mL) slowly. After stirring at the same temperature for 1.5 h and monitored with TLC (EtOAC/Hex 2:8), Bu$_4$NN$_3$ (36.38 g, 127.87 mmol) in anhydrous DCM (90 mL) was added slowly. After stirring for another 1 h at that temperature, the cooling bath was removed and the reaction was allowed to reach 25° C. for 1.5 h. A saturated aq. solution of NaHCO$_3$ was added, and the aqueous phase was extracted with EtOAc. The residue was purified with flash chromatography over silica gel (0-20%, EtOAc/Hex) to give the title compound (20) (15.24 g, 87% yield) as a colorless oil. $^1$H-NMR (300 MHz, CDCl$_3$) δ 7.61 (s, 1H), 7.36 (d, J=2.6 Hz, 4H), 5.29 (s, 1H), 5.29-5.11 (m, 2H), 4.46 (d, J=8.5 Hz, 1H), 3.84 (d, J=8.1 Hz, 1H), 1.45 (d, J=0.8 Hz, 9H), 1.34-1.16 (m, 3H). $^{13}$C NMR (75 MHz, cdcl3) δ: 169.5, 155.1, 134.9, 128.7, 128.6, 128.5, 80.5, 67.6, 58.8, 57.5, 28.3, 28.3, 15.4. LCMS (M+1)$^+$: 335, calculated: 335.

Example 21

Synthesis of (2S,3S)-Benzyl 3-amino-2-((tert-butoxycarbonyl)amino)butanoate (21)

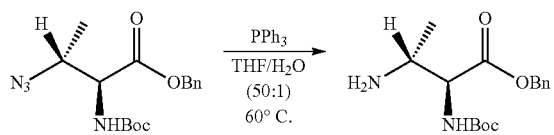 [SMILES: C[C@@H](N=[N+]=[N-])[C@H](NC(=O)OC(C)(C)C)C(=O)OCc1ccccc1 ; C[C@@H](N)[C@H](NC(=O)OC(C)(C)C)C(=O)OCc1ccccc1 ; "PPh3"]

To a solution of azido compound of Example 20 (2.11 g, 6.31 mmol) in THF (88 mL) was added Ph$_3$P (3.31 g, 12.62 mmol) and water (2.0 mL) and the reaction was heated to 60° C. overnight and monitored with TLC (in 50% EtOAc/Hex). When the reaction was completed, the solvent was removed in vacuo and the residue was purified with flash chromatography over silica gel (0-80% EtOAc/Hex) to give the title compound (21) (1.84 g, 94% yield) as a colorless oil. $^1$H-NMR (300 MHz, CDCl$_3$) δ 7.36 (t, J=1.5 Hz, 5H), 7.26 (s, 1H), 5.30 (m, 1H), 5.28-5.10 (m, 2H), 4.32 (s, 1H), 3.30 (s, 1H), 1.47 (s, 9H), 1.02 (d, J=6.7 Hz, 3H). LCMS (M+1)+: 309, calculated: 309.

Example 22

Synthesis of 2-tert-Butoxycarbonylamino-3-(2-ethoxycarbonyl-2-methyl-propoxysulfonylamino)-butyric acid benzyl ester (22)

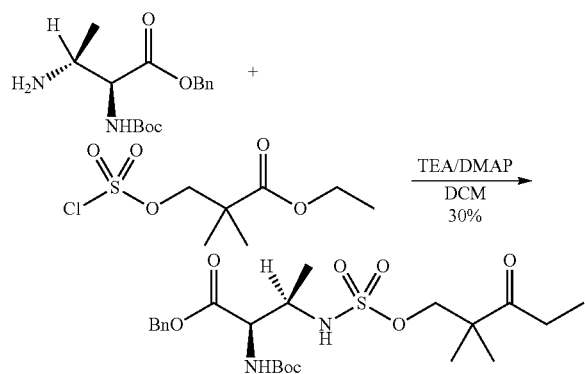

To a solution of 3-amino-2-tert-butoxycarbonylamino-butyric acid benzyl ester (21) (2.83 g, 9.18 mmol, 1.0 eq) and triethylamine (6.40 mL, 45.9 mmol, 5.0 eq) in dichloromethane (20 mL) was added dimethylaminepyridine (224 mg, 1.84 mmol, 0.20 eq) at 0° C. 3-Chlorosulfonyloxy-2,2-dimethyl-propionic acid ethyl ester (3a) (4.49 g, 18.4 mmol, 2.0 eq) in dichloromethane (5 mL) was added. The mixture was kept in the same temperature for 1.5 h and warmed to room temperature for 2 h. The reaction was concentrated to dryness. The residue was diluted with ethyl acetate and washed with 10% citric acid. The organic phase was separated, dried over sodium sulfate, and concentrated to dryness. The residue was purified by prep-HPLC to give the title compound (22) (1.44 g, 30%) as a solid $^1$H-NMR (300 MHz, CDCl$_3$) δ 7.37-7.27 (m, 5H), 6.03-5.96 (m, 1H), 5.52-5.46 (m, 1H), 5.18 (s, 2H), 4.57-4.52 (m, 1H), 4.18-4.07 (m, 4H), 4.01-3.95 (m, 1H), 1.42 (s, 9H), 1.33-1.22 (m, 9H), 1.16 (d, 3H). $^{13}$C NMR (75 MHz, CDCl$_3$) δ 174.8, 169.6, 134.7, 128.75, 128.70, 128.5, 81.0, 75.3, 67.9, 61.0, 57.7, 53.4, 52.8, 42.6, 28.2, 22.1, 16.6, 14.1. LCMS (M+1)$^+$: 517, calculated: 517.

Example 23

Synthesis of 2-tert-Butoxycarbonylamino-3-(2-ethoxycarbonyl-2-methyl-propoxysulfonylamino)-butyric acid (23)

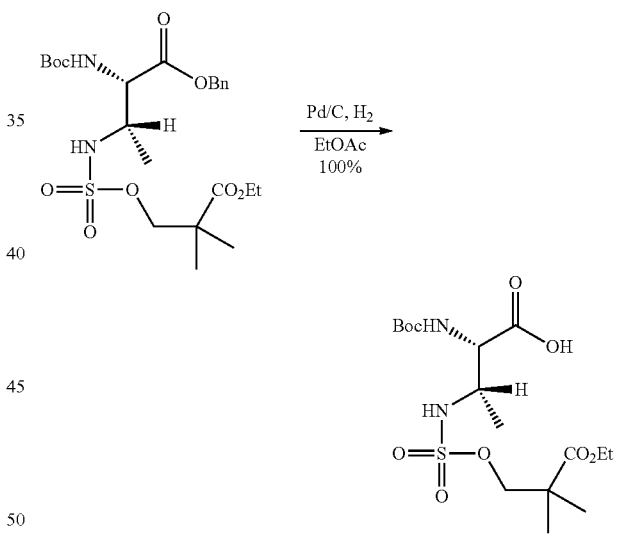

To a solution of 2-tert-butoxycarbonylamino-3-(2-ethoxycarbonyl-2-methyl-propoxysulfonylamino)-butyric acid benzyl ester (22) (1.32 g, 25.6 mmol, 1.0 eq) in ethyl acetate (20 mL) was added Pd/C (132 mg). The suspension was degassed 3 times and refilled with hydrogen. The mixture was stirred at room temperature for 2h. The reaction mixture was filtered though a pad of Celite. The filtrate was concentrated to dryness, affording the title compound (23) (1.08 g, 100%). $^1$H-NMR (300 MHz, CDCl$_3$) δ 6.23-1.18 (m, 1H), 5.68-5.63 (m, 1H), 4.45-4.40 (m, 1H), 4.19-4.05 (m, 4H), 3.97-3.89 (m, 1H), 1.50 (s, 9H), 1.39-1.22 (m, 12H). $^{13}$C NMR (75 MHz, d$_6$-acetone) δ 174.3, 170.8, 156.1, 79.1, 74.8, 60.5, 59.8, 57.8, 44.2, 27.7, 21.5, 21.4, 21.4, 16.1, 13.6, 13.6. LCMS (M+1)$^+$: 427, calculated: 427.

Example 24

Synthesis of ethyl 3-((((2S,3S)-3-((tert-butoxycarbonyl)amino)-2-methyl-4-oxoazetidin-1-yl)sulfonyl)oxy)-2,2-dimethylpropanoate (24)

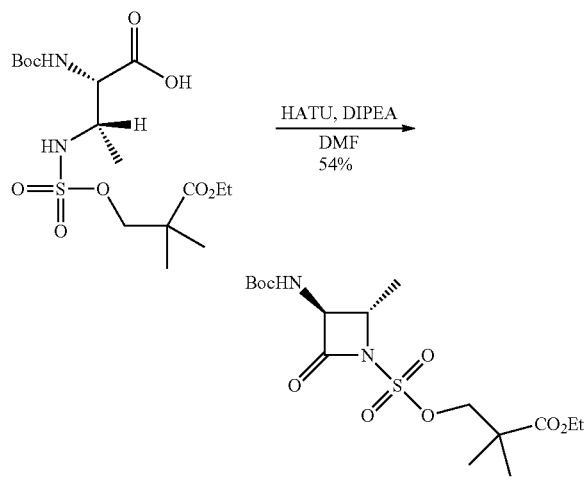

To a solution of 2-tert-butoxycarbonylamino-3-(2-ethoxycarbonyl-2-methyl-propoxysulfonylamino)-butyric acid (23) (198 mg, 0.465 mmol, 1.0 eq) in DMF (2 mL) HATU (212 mg, 0.558 mmol, 1.2 eq) and diisopropylethylamine (162 μL, 0.930 mmol, 2.0 eq) were added at 0° C. The reaction was stirred at 0° C. for 10 min and quenched with 10% citric acid. The mixture was purified by prep-HPLC to give the title compound (24) (104 mg, 55%). $^1$H-NMR (300 MHz, d$_6$-acetone) δ 7.05-6.97 (m, 1H), 4.56-4.51 (m, 1H), 4.49-4.40 (m, 3H), 4.17 (q, 2H), 1.55 (d, 3H), 1.42 (s, 9H), 1.33-1.22 (m, 9H). $^{13}$C NMR (75 MHz, d$_6$-acetone) δ 174.1, 164.1, 156.1, 79.9, 76.9, 64.6, 60.6, 59.1, 42.4, 27.5, 21.3, 21.1, 16.7, 13.5. LCMS (M+1)$^+$: 409, calculated: 409; (M-1)$^-$ 407.

Example 25

Synthesis of 3-(3-amino-2-methyl-4-oxo-azetidine-1-sulfonyloxy)-2,2-dimethyl-propionic acid ethyl ester (25)

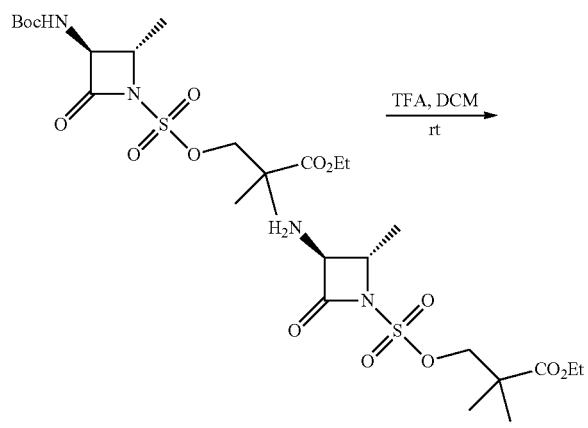

Ethyl 3-((((2S,3S)-3-((tert-butoxycarbonyl)amino)-2-methyl-4-oxoazetidin-1-yl)sulfonyl)oxy)-2,2-dimethylpropanoate (24) (12 mg) was treated with TFA/DCM (1:10, 1 mL) at 25° C. overnight. The reaction mixture was concentrated to dryness, affording the trifluoroacetate salt of the title compound (25). LCMS (2M+1)$^+$: 617, calculated: 617.

Example 26

Synthesis of ethyl 3-((((2S,3S)-3-((Z)-2-(((1-(tert-butoxy)-2-methyl-1-oxopropan-2-yl)oxy)imino)-2-(2-(tritylamino)thiazol-4-yl)acetamido)-2-methyl-4-oxoazetidin-1-yl) sulfonyl)oxy)-2,2-dimethylpropanoate (26)

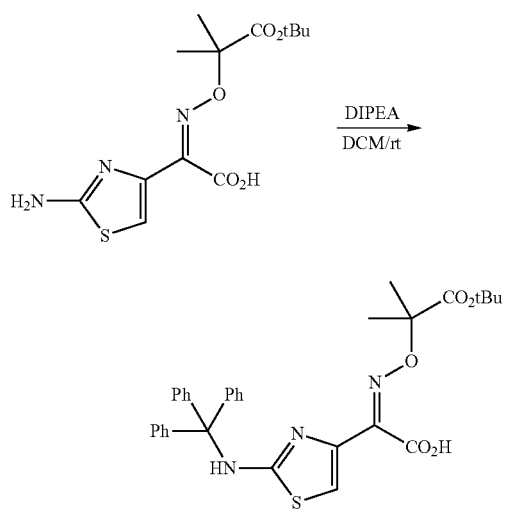

To the mixture of (Z)-2-(2-aminothiazol-4-yl)-2-(((1-(tert-butoxy)-2-methyl-1-oxopropan-2-yl)oxy)imino)acetic acid (tert-butyl 1a) (459 mg, 1.39 mmol) in DCM (7.0 mL) was added DIPEA (557 μL, 3.20 mmol) and tritylchloride (855 mg, 3.07 mmol) at 25° C. and the mixture was stirred for 3 h at 25° C. The solvent was removed under vacuum, and the residue was dissolved in EtOAc (20 mL) and washed with HCl (0.01N, 10 mL×3). The organic layer was then dried (Na$_2$SO$_4$), filtered and concentrated under vacuum. The residue was redissolved in Et$_2$O and the product precipitated out by addition of hexane. The product (26) was collected by filtration as an off-white solid. The filtrate was concentrated, dissolved in Et$_2$O, and precipitated with hexane to collect additional product (370 mg). LCMS: m/z=571 (M+H)$^+$

Example 27

Synthesis of ethyl 3-((((2S,3S)-3-((E)-2-(((1-(tert-butoxy)-2-methyl-1-oxopropan-2-yl)oxy)imino)-2-(2-(tert-butylamino)thiazol-4-yl)acetamido)-2-methyl-4-oxoazetidin-1-yl)sulfonyl)oxy)-2,2-dimethylpropanoate

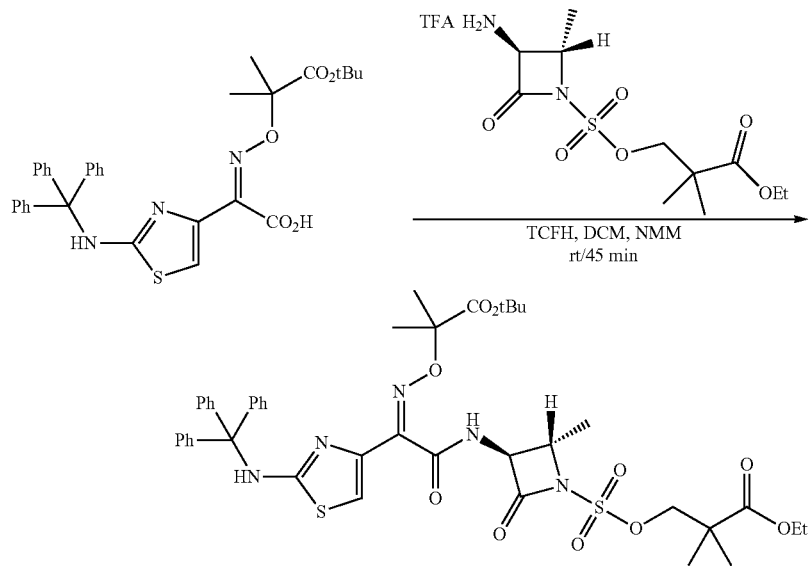

A solution of (Z)-2-(((1-(tert-butoxy)-2-methyl-1-oxopropan-2-yl)oxy)imino)-2-(2-(tritylamino)thiazol-4-yl)acetic acid (26) (17.2 mg, 0.030 mmol) in DCM (0.5 mL) was treated with TCFH (12.6 mg, 0.045 mmol) and NMM (3.0 µL, 0.027 mmol). A solution of 3-(3-amino-2-methyl-4-oxoazetidine-1-sulfonyloxy)-2,2-dimethyl-propionic acid ethyl ester (25) (12.2 mg, 0.030 mmol) in DCM (0.15 mL) was added to the reaction mixture at 25° C. and stirred for 2h. The reaction was monitored with LCMS. When the amine was consumed, the reaction was subjected to purification by column chromatography on silica gel using EtOAc/hexanes (0:1 to 4:1) as eluent (two column purifications required) to provide the title compound (27) (2.8 mg, 11%). LCMS m/z=862 (M+H)$^+$

Example 28

Synthesis of Tetrabutylammonium (2S,3S)-3-(((benzyloxy)carbonyl)amino)-2-methyl-4-oxoazetidine-1-sulfonate (28)

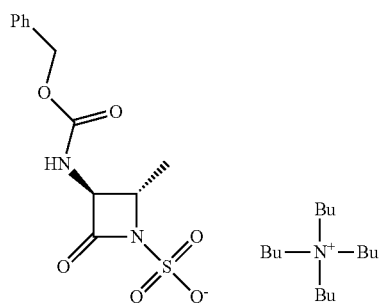

To a solution of (2S,3S)-3-amino-2-methyl-4-oxo-1-azetidinesulfonic acid (55.0 g, 305.2 mmol) in a mixture of EtOH (600 mL) and H$_2$O (300 mL) was added Et$_3$N (159.5 mL, 915.7 mmol) followed by benzyloxycarbonyl N-succinimide (83.7 g, 335.8 mmol). The reaction mixture was stirred at 25° C. for 16 h. Ethanol was removed under vacuum and the residue was diluted with H$_2$O (200 mL). The aqueous layer was extracted with EtOAc (2×100 mL). The EtOAc was discarded. Tetrabutyl ammonium hydroxide (207.9 g, 320.5 mmol) as 40% w/v in H$_2$O was added and the resulting aqueous layer was extracted with CHCl$_3$ (5×150 mL). The organic extract was dried (MgSO$_4$) and concentrated to give the title compound (28) (160 g, 94%) as a solid. $^1$H-NMR (300 MHz, CDCl$_3$): δ 7.38-7.31 (m, 5H), 4.31 (d, J=7.2 Hz, 1H), 6.01 (s, 2H) 5.50 (s, 1H), 5.12 (s, 2H), 4.31 (d, J=7.2 Hz, 1H), 3.28-3.22 (m, 8H), 1.62-1.59 (m, 8H), 1.46-1.39 (m, 11H), 1.01-0.96 (m, 12H); $^{13}$C-NMR (75 MHz, CDCl$_3$): δ 162.9, 155.7, 136.1, 135.7, 128.5, 128.3, 128.2, 128.0, 67.0, 62.7, 59.2, 58.5, 23.9, 19.6, 18.2, 13.7.

Example 29

Synthesis of Benzyl ((2S,3S)-2-methyl-4-oxoazetidin-3-yl)carbamate (29)

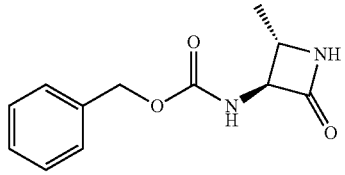 [SMILES: C[C@@H]1NC(=O)[C@H]1NC(=O)OCc1ccccc1]

(2S,3S)-3-(((Benzyloxy)carbonyl)amino)-2-methyl-4-oxoazetidine-1-sulfonate tetrabutylammonium salt (28) (131 g, 235.7 mmol) was dissolved in dry THF (2.8 L) and H₂O (12.8 mL, 710.5 mmol), and the resulting solution was cooled in an ice bath. Trifluoroacetic acid (280 mL) was added dropwise, and the mixture was stirred at 25° C. for 1.5 h. The reaction mixture was concentrated under vacuum, the residue was diluted with DCM (1.5 L), and then chilled with an ice bath. 10% Aqueous NaOH solution was added slowly until the mixture had a pH=8-9. The organic layer was washed with H₂O, dried (MgSO₄), and concentrated under vacuum. The residue was purified by column chromatography on silica gel using EtOAc/hexanes (1:9 to 1:0) to give the title compound (29) (30.1 g, 54%) as a solid. LC-MS: m/z=280.1 [M+HCO₂H]⁺; ¹H-NMR (300 MHz, CDCl₃): δ 7.38-7.31 (m, 5H), 6.01 (s, 1H) 5.50 (s, 1H), 5.12 (s, 2H), 4.31 (d, J=7.2 Hz, 1H), 3.74-3.71 (m, 1H), 1.42 (d, J=6 Hz, 3H); ¹³C-NMR (75 MHz, CDCl₃): δ 167.4, 155.9, 136.1, 67.2, 64.7, 54.0, 19.2.

Example 30

Synthesis of (2S,3R)-3-amino-2-(((benzyloxy)carbonyl)amino)butanoic acid HCl salt (30)

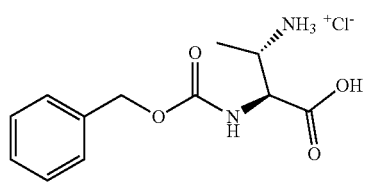

Benzyl (((2S,3S)-2-methyl-4-oxoazetidin-3-yl)carbamate (29) (6.0 g, 25.6 mmol) was dissolved in neat formic acid (50 mL). H₂O (50 mL) was added and the resulting mixture was stirred at 25° C. for 18 h. The mixture was concentrated under vacuum to give (2S,3R)-3-amino-2-(((benzyloxy)carbonyl)amino)butanoic formic acid salt as a solid. The formic acid salt was dissolved in MeCN (10 mL). 4N HCl in dioxane (15 mL) was added and the resulting solution was concentrated to dryness under vacuum. Another portion of 4N HCl in dioxane (15 mL) was added and the mixture was stirred for 1 h at 25° C. to provide a solid. Et₂O (50 mL) was added and the solid was collected by filtration to give the title compound (30) (6.8 g, 92%). LC-MS: m/z=253.3 [M+H]⁺; ¹H-NMR (300 MHz, CD₃OD): δ 7.59 (d, J=8.7 Hz, 1H), 7.41-7.30 (m, 5H), 5.15 (q, J=21 Hz, 2H), 4.68-4.64 (m, 1H), 3.88-3.84 (m, 1H), 1.25 (d, J=7.2 Hz, 3H); ¹³C-NMR (75 MHz, CD₃OD): δ 171.4, 159.1, 137.8, 129.5, 129.1, 129.0, 68.3, 56.9, 49.9, 14.1.

Example 31

Synthesis of tert-butyl (2S,3R)-3-amino-2-(((benzyloxy)carbonyl)-amino)butanoate (31)

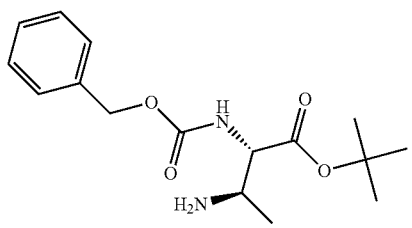 [SMILES: C[C@@H](N)[C@H](NC(=O)OCc1ccccc1)C(=O)OC(C)(C)C]

To a solution of (2S,3S)-3-amino-2-(((benzyloxy)carbonyl)amino)butanoic acid hydrochloride (30) (4.5 g, 15.5 mmol) in 1,4-dioxane (36 mL) at −10° C. was added dropwise concentrated H₂SO₄ (4.9 ml, 92.8 mmol). The reaction mixture was placed in a dry ice-acetone bath and iso-butylene (36 g, 622.5 mmol) was added. The reaction vessel was capped, and the reaction mixture was stirred at 25° C. for 48 h. Iso-butylene was removed by passing nitrogen through the solution, and the mixture was poured into a mixture of H₂O (150 mL) and saturated aqueous Na₂CO₃ (50 mL). The aqueous layer was extracted with EtOAc (3×100 mL), and the combined organic layers were washed with brine (50 mL), dried (MgSO₄), and concentrated under vacuum. The residue was purified by column chromatography on silica gel using DCM/MeOH (1:0 to 9:1) to the title compound (31) (2.83 g, 59%) as a clear oil. LC-MS: m/z=309.6 [M+H]⁺; ¹H-NMR (300 MHz, CDCl₃): δ 7.37-7.31 (m, 5H), 5.52 (d, J=6.9 Hz, 1H), 5.11 (s, 2H), 4.28-4.24 (m, 1H), 3.33-3.30 (m, 1H), 1.46 (s, 9H), 1.05 (d, J=6.9 Hz, 3H); ¹³C-NMR (75 MHz, CDCl₃): δ 170.0, 156.7, 136.3, 128.6, 128.3, 128.2, 82.5, 67.1, 60.5, 49.5, 28.1, 18.9.

Example 32

Synthesis of tert-butyl (2S,3R)-2-(((benzyloxy)carbonyl)amino)-3-(((3-ethoxy-2,2-dimethyl-3-oxopropoxy)sulfonyl)amino)butanoate (32)

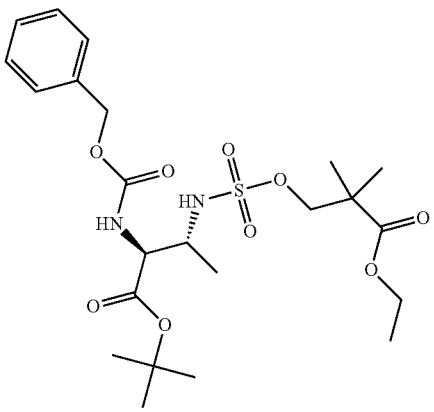 [SMILES: CCOC(=O)C(C)(C)COS(=O)(=O)N[C@H](C)[C@H](NC(=O)OCc1ccccc1)C(=O)OC(C)(C)C]

To a solution of tert-butyl (2S,3R)-3-amino-2-(((benzyloxy)carbonyl)-amino)butanoate (29) (2.55 g, 8.3 mmol) and N-methylmorpholine (2.73 mL, 24.8 mmol) in DCM (30 ml) at 0° C. was added dropwise ethyl 3-((chlorosulfonyl)oxy)-2,2-dimethylpropanoate (3a) (3.65 g, 14.5 mmol). The mixture was stirred at 40° C. for 6 h. The solvent was concentrated under vacuum and the residue was purified by column chromatography on silica gel using Et₂O/hexanes (1:9 to 1:0) to give the title compound (32) (2 g, 47%) as a clear oil. LC-MS: m/z=516.9 [M+H]⁺; ¹H-NMR (300 MHz, CDCl₃): δ 7.37-7.33 (m, 5H), 5.99 (d, J=7.8 Hz, 1H), 5.73 (d, J=5.7 Hz, 1H), 5.13 (s, 2H), 4.49 (dd, J=7.2 Hz, 3.0 Hz, 1H), 4.20-4.13 (m, 4H), 3.99-3.95 (m, 1H), 1.47 (s, 9H), 1.27-1.22 (m, 9H), 1.17 (d, J=6.6 Hz, 3H); ¹³C-NMR (75 MHz, CDCl₃): δ 174.9, 168.5, 135.9, 128.7, 128.5, 128.4, 84.0, 75.4, 67.7, 61.2, 58.6, 53.0, 42.8, 28.0, 22.2, 16.5, 14.2.

113

Alternative Synthesis of (2S,3R)-2-(((benzyloxy) carbonyl)amino)-3-(((3-ethoxy-2,2-dimethyl-3-oxo-propoxy)sulfonyl)amino)butanoic acid (32)

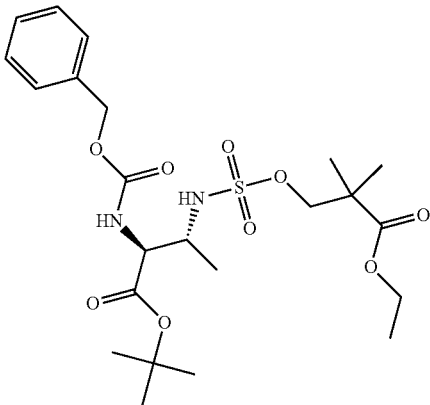 [SMILES: CCOC(=O)C(C)(C)COS(=O)(=O)N[C@H](C)[C@H](NC(=O)OCc1ccccc1)C(=O)OC(C)(C)C]

(2S,3S)-3-Amino-2-(((benzyloxy)carbonyl)amino)butanoic acid hydrochloride (30) (1.0 g, 3.5 mmol) and Et₃N (2.9 mL, 20.8 mmol) were suspended into CDCl₃ (30 mL). The mixture was cooled in an ice bath and neat ethyl 3-((chlorosulfonyl)oxy)-2,2-dimethylpropanoate (3a) (1.31 g, 5.2 mmol) was added to the cooled mixture. An aliquot was removed, and NMR analysis showed the absence of any benzyl protons. The reaction was stirred at 0° C. for 3 h and allowed to warm and stirred for 16 h. The solution was extracted with saturated aqueous NH₄Cl (3×15 mL), brine (2×15 mL), then dried (Na₂SO₄), filtered and concentrated. NMR analysis of the crude product was complex and LCMS showed the presence of desired m/z of 459 in negative mode. The crude material was dissolved into a mixture of MeCN/H₂O (3:1) filtered through a 0.45-μm PTFE cartridge and purified by preparative HPLC using MeCN/H₂O (1:9 to 9:1, no modifier) as eluent over a 20 min run time. Fractions were analyzed by LCMS and pure fractions were pooled and freeze-dried to give the title compound (32) (330 mg, 21%) as an oil. LC-MS: m/z=459 [M−H]⁺; ¹H-NMR (300 MHz, CDCl₃): δ 7.27-7.34 (m, 5H), 5.98-6.05 (m, 2H), 5.11 (s, 2H), 4.50-4.55 (m, 1H), 4.08-4.17 (m, 4H), 3.9-4.0 (m, 1H), 1.28 (d, J=7.2 Hz, 3H), 1.17-1.27 (m, 9H); ¹³C-NMR (75 MHz, CDCl₃): δ 175.5, 172.0, 157.0, 135.8, 128.7, 128.4, 128.2, 75.5, 67.8, 61.5, 58.2, 52.6, 42.8, 22.1, 17.5, 14.1.

Example 33

Synthesis of (2S,3S)-2-(((benzyloxy)carbonyl) amino)-3-(((3-ethoxy-2,2-dimethyl-3-oxopropoxy) sulfonyl)amino)butanoic acid (33)

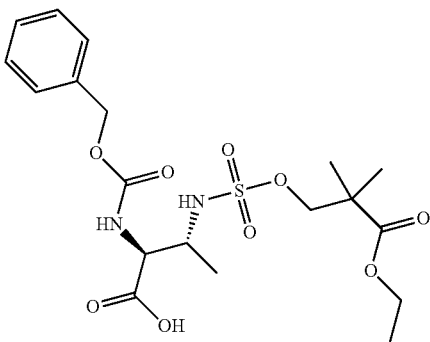 [SMILES: CCOC(=O)C(C)(C)COS(=O)(=O)N[C@H](C)[C@H](NC(=O)OCc1ccccc1)C(=O)O]

To a solution of tert-butyl (2S,3R)-2-(((benzyloxy)carbonyl)amino)-3-(((3-ethoxy-2,2-dimethyl-3-oxopropoxy)sul-fonyl)-amino)butanoate (32) (115 mg, 0.22 mmol) and neat formic acid (0.7 mL) was stirred at 25° C. for 5 h. The mixture was concentrated under vacuum, and the residue was dissolved in a mixture of EtOAc (2 mL) and hexanes (1 mL). The organic layer was washed with H₂O (3×1 mL), dried (MgSO₄), and concentrated. The material was dissolved in TFA for 30 min and evaporated to give the title compound (33) (97 mg, 96%) as a clear oil.

Example 34

Synthesis of ethyl 3-((((2S,3S)-3-(((benzyloxy)carbonyl)amino)-2-methyl-4-oxoazetidin-1-yl)sulfonyl) oxy)-2,2-dimethylpropanoate (34)

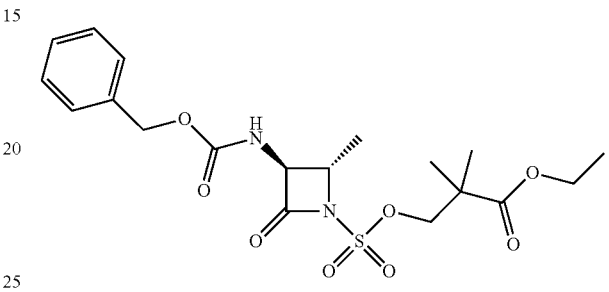

(2S,3R)-2-(((Benzyloxy)carbonyl)amino)-3-(((3-ethoxy-2,2-dimethyl-3-oxopropoxy)sulfonyl)amino)butanoic acid (33) (197 mg, 0.4 mmol) and N,N-diisopropylethylamine (447 μL, 2.6 mmol) were mixed with DMF (4.0 mL). The solution was cooled in an ice bath and 2-(7-aza-1H-benzotriazole-1-yl)-1,1,3,3-tetramethyluronium hexafluorophosphate (HATU) (253 mg, 0.7 mmol) was added in one portion. The mixture was stirred at 0° C. for 35 min and the crude mixture was directly purified by preparative-HPLC with MeCN/H₂O (1:9 to 9:1, no modifier) over a 30 min run-time. Note: the product eluted ~18 min. The fractions containing the product were freeze-dried and the resulting oil was analyzed by NMR to give a spectrum which conformed to the structure, as well as a small amount of DIPEA as an impurity. The impure solid was dissolved in DCM and adsorbed onto silica gel (1.5 g) and purified by column chromatography on silica gel (4 g cartridge) using EtOAc/hexanes (0:1 to 7:3) as eluent to give the title compound (34) (40 mg, 21%) as an oil. LC-MS: m/z=487 [M+HCO₂]⁺; 1H-NMR (300 MHz, CDCl₃): δ 7.27-7.40 (m, 5H), 6.22 (br. d, 1H), 5.14 (s, 2H), 4.63 (dd, J=8.4, 9.0 Hz, 1H), 4.56 (d, J=9.9 Hz, 1H), 4.10-4.20 (m, 4H), 1.62 (d, J=5.7 Hz, 1H), 1.22-1.33 (m, 9H); ¹³C-NMR (100 MHz, CDCl₃): δ 175.9, 164.7, 155.5, 135.9, 128.7, 128.5, 128.3, 77.3, 67.7, 64.6, 61.8, 61.0, 42.8, 22.2, 21.7, 18.0, 14.0.

Example 35

Synthesis of ethyl 3-((((2S,3S)-3-amino-2-methyl-4-oxoazetidin-1-yl)sulfonyl)oxy)-2,2-dimethylpropanoate TFA salt (35)

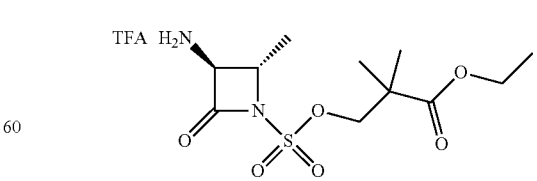

In an NMR tube, ethyl 3-((((2S,3S)-3-(((benzyloxy)carbonyl)amino)-2-methyl-4-oxoazetidin-1-yl)sulfonyl)oxy)-2,2-dimethylpropanoate (34) (5 mg) was dissolved into CD₃OD (0.65 mL) and the mixture was flushed with nitrogen. Palladium on carbon (1 mg) was added to the NMR tube and the tube sealed with a rubber septum. A balloon filled with hydrogen was used to flush the NMR tube while alternating between vortex mixing and sonication. After 30 minutes the sample was analyzed by NMR and found to have no starting material present. After adding 1 drop of TFA, the solution was filtered through a 0.2-μm PTFE frit, rinsed with methanol (3×0.6 mL), and concentrated to give a film of the title compound (35). $^1$H-NMR (300 MHz, acetone-$d_6$): δ 4.6 (d, J=6.0 Hz, 1H), 4.12-4.20 (m, 2H), 4.10 (s, 2H), 3.76-3.79 (m, 1H), 1.33 (d, J=6.9 Hz, 3H), 1.23-1.29 (m, 9H), 1.22-1.33 (m, 9H).

Example 36

Amide Coupling Reaction

The following diagrams illustrate reaction schemes for coupling a solution of (Z)-2-(((1-(tert-butoxy)-2-methyl-1-oxopropan-2-yl)oxy)imino)-2-(2-(tritylamino)thiazol-4-yl)acetic acid (26) with a 3-(3-amino-2-methyl-4-oxo-azetidine-1-sulfonyloxy)-2,2-dimethyl-propionic acid ester (25).

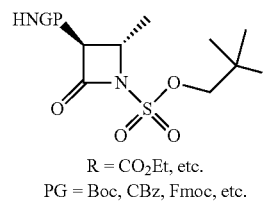
R = CO$_2$Et, etc.
PG = Boc, CBz, Fmoc, etc.

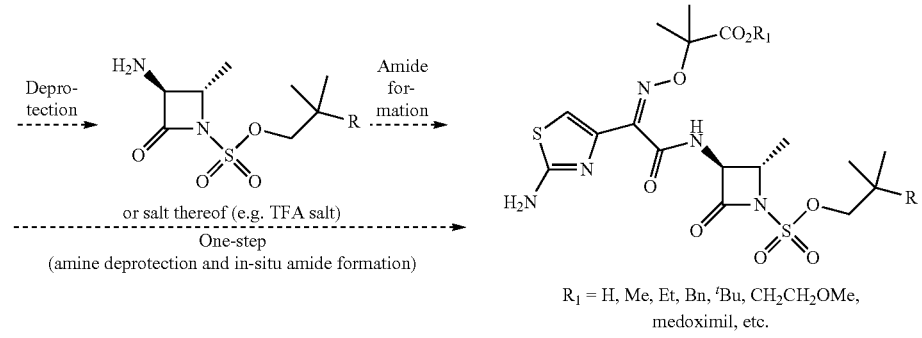
R$_1$ = H, Me, Et, Bn, $^t$Bu, CH$_2$CH$_2$OMe, medoximil, etc.
or salt thereof (e.g. TFA, HCl, etc.)

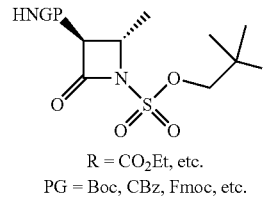
R = CO$_2$Et, etc.
PG = Boc, CBz, Fmoc, etc.

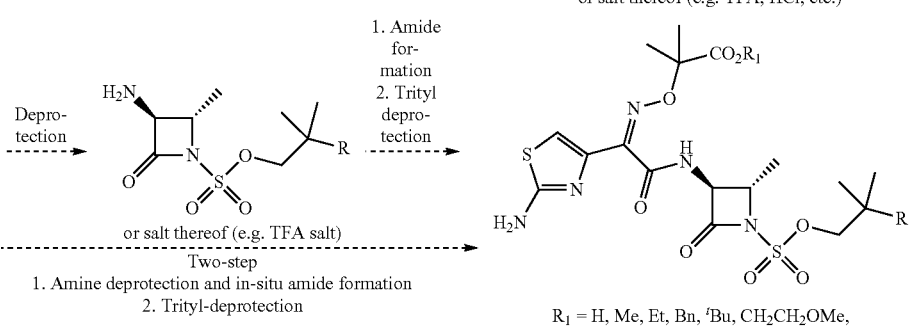
R$_1$ = H, Me, Et, Bn, $^t$Bu, CH$_2$CH$_2$OMe, medoximil, etc.
or salt thereof (e.g. TFA, HCl, etc.)

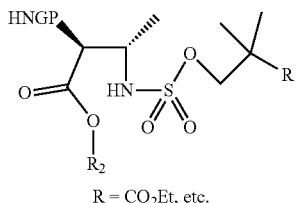
R = CO$_2$Et, etc.
R$_2$ = H, $^t$Bu, Bn, SEM, etc.
PG = Boc, CBz, Fmoc, etc.

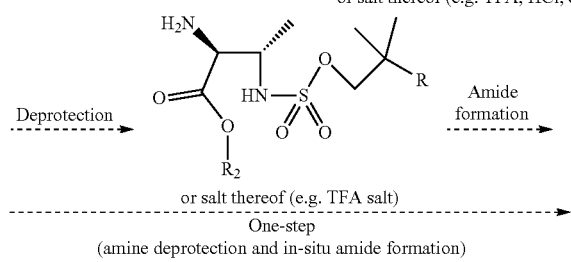

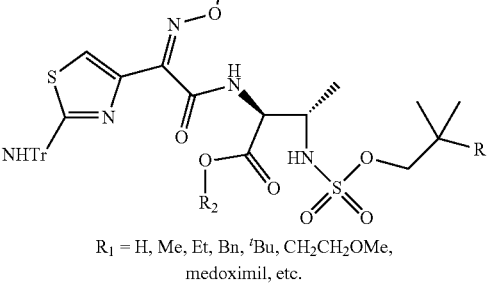
R$_1$ = H, Me, Et, Bn, $^t$Bu, CH$_2$CH$_2$OMe, medoximil, etc.

-continued

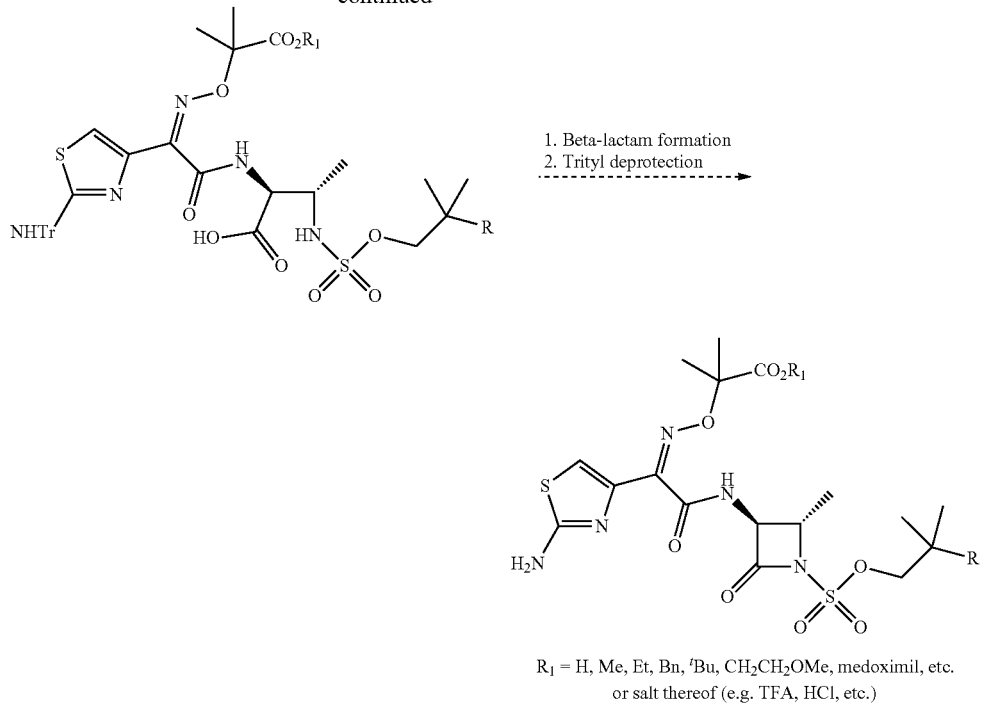

1. Beta-lactam formation
2. Trityl deprotection $R_1$ = H, Me, Et, Bn, $^tBu$, $CH_2CH_2OMe$, medoximil, etc.
or salt thereof (e.g. TFA, HCl, etc.)

Example 37

Synthesis of Aztreonam Derivatives

Other derivatives of aztreonam can be synthesized using the methods disclosed in Examples 29-33 and the chlorosulfonyls disclosed in Examples 38-98.

Example 38

Synthesis of 2-methoxyethyl 3-((chlorosulfonyl)oxy)-2,2-dimethylpropanoate (38)

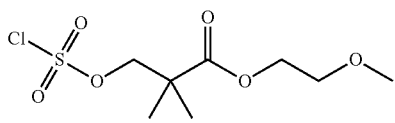 [SMILES: COCCOC(=O)C(C)(C)COS(=O)(=O)Cl]

A solution of distilled sulfuryl chloride (0.51 mL, 6.2 mmol) in $Et_2O$ (10 mL) was cooled to −78° C. under nitrogen. A solution of 2-methoxyethyl 3-hydroxy-2,2-dimethylpropanoate (15a) (1.0 g, 5.68 mmol) and pyridine (0.46 mL, 5.68 mmol) in $Et_2O$ (2.0 mL) was then added dropwise over 1 h via a syringe. The reaction was stirred at −78° C. for 1 h, and then the mixture was allowed to warm to room temperature and stirred for 2 h. After the mixture was filtered, the filtrate was concentrated under vacuum to give the product (38) as a colorless liquid (1.5 g, yield 96%). $^1$H-NMR (300 MHz, $CDCl_3$): δ 4.40 (s, 2H), 4.29 (t, 3H), 3.59 (t, 3H), 3.37 (s, 3H), 1.32 (s, 6H).

Example 39

Synthesis of hexyl 3-((chlorosulfonyl)oxy)-2,2-dimethylpropanoate (39)

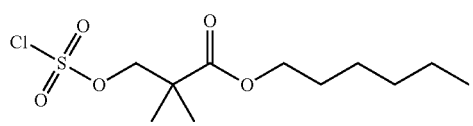 [SMILES: CCCCCCOC(=O)C(C)(C)COS(=O)(=O)Cl]

Step 1: Synthesis of hexyl 3-hydroxy-2,2-dimethylpropanoate (39a)

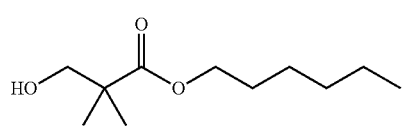

A mixture of 3-hydroxy-2,2-dimethylpropionic acid (4.7 g, 40 mmol), 1-hexanol (70 mL) and concentrated sulfuric acid (or fuming sulfuric acid, 1 mL) was heated to 80° C. and stirred overnight. After allowing to cool, the mixture was concentrated under vacuum (high vacuum pump required) and the residue was then partitioned between EtOAc (100 mL) and saturated aqueous $NaHCO_3$ (100 mL). The aqueous phase was washed with $H_2O$ (50 mL), saturated $NaHCO_3$ (50 mL) and brine (50 mL), and then dried over anhydrous $Na_2SO_4$, filtered and concentrated under vacuum to provide the product as an oil. The product was difficult to purify using silica gel chromatography; and therefore the product was distilled under high vacuum at 47° C. to provide 4.92 g of the pure ester product (39a) (yield 61%). $^1$H-NMR (300 MHz, CDCl$_3$) δ 4.10 (td, J=6.7, 1.3 Hz, 2H), 3.55 (d, J=5.1 Hz, 2H), 2.42 (s, 1H), 1.64 (s, 1H), 1.72-1.56 (m, 1H), 1.35 (s, 1H), 1.31 (s, 6H), 1.27-1.11 (m, 6H), 0.95-0.84 (m, 3H). MS (ESI) C$_{11}$H$_{22}$O$_3$=203 (M+1)$^+$.

Step 2: Synthesis of hexyl 3-((chlorosulfonyl)oxy)-2,2-dimethylpropanoate (39b)

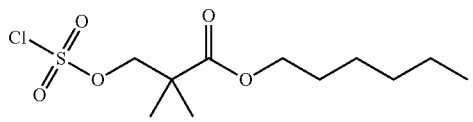 [SMILES: CCCCCCOC(=O)C(C)(C)COS(=O)(=O)Cl]

A solution of freshly distilled sulfuryl chloride (0.60 mL, 7.4 mmol) in Et$_2$O (10 mL) was cooled to −78° C. under an atmosphere of N$_2$. A solution of hexyl 3-hydroxy-2,2-dimethylpropanoate (39a) (1.0 g, 4.94 mmol) and pyridine (0.48 mL, 5.93 mmol) in Et$_2$O (5 mL) was added dropwise to the sulfuryl chloride solution over the course of 20 min. The flask was rinsed with Et$_2$O (3×1 mL) and the rinse added to the reaction mixture. The mixture was stirred at −78° C. until completion by TLC (30 min; 30% EA/hexane). The precipitate was filtered, and the filtrate was concentrated under vacuum to afford the crude product (39) as a solid foam and was used in the next step without further purification. $^1$H-NMR (300 MHz, CDCl$_3$): δ 4.50 (s, 2H), 4.13 (t, J=6.8 Hz, 2H), 1.69-1.60 (m, 2H), 1.40-1.27 (m, 12H), 0.91-0.87 (m, 3H).

Example 40

Synthesis of heptyl 3-((chlorosulfonyl)oxy)-2,2-dimethylpropanoate (40)

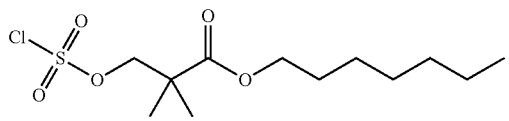 [SMILES: CCCCCCCOC(=O)C(C)(C)COS(=O)(=O)Cl]

Step 1: Synthesis of heptyl 3-hydroxy-2,2-dimethylpropanoate (40a)

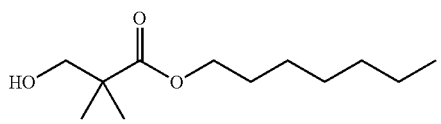

A mixture of 3-hydroxy-2,2-dimethylpropionic acid (4.7 g, 40 mmol), 1-heptanol (70 mL) and concentrated sulfuric acid (1 mL) was heated to 80° C. and stirred overnight. After allowing to cool, the mixture was concentrated under vacuum (high vacuum pump required) and the residue partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried (Na$_2$SO$_4$), filtered and concentrated under vacuum to provide the product as an oil. The product was distilled under high vacuum at 65° C. to provide the title compound (40a) as an oil (6.7 g, 77% yield). $^1$H-NMR (300 MHz, CDCl$_3$) δ 4.09 (td, J=6.7, 0.9 Hz, 2H), 3.55 (d, J=6.1 Hz, 2H), 2.43 (t, J=6.7 Hz, 1H), 1.60 (d, J=22.8 Hz, 4H), 1.3-1.58 (m, 6H), 1.27-1.14 (m, 6H), 0.92-0.83 (m, 3H).

Step 2: Synthesis of heptyl 3-((chlorosulfonyl)oxy)-2,2-dimethylpropanoate (40)

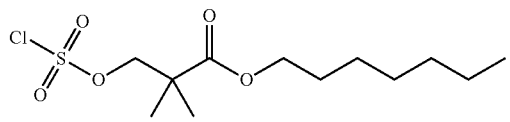 [SMILES: CCCCCCCOC(=O)C(C)(C)COS(=O)(=O)Cl]

A solution of sulfuryl chloride (0.6 mL, 7.4 mmol) in Et$_2$O (15 mL) was cooled to −78° C. under an atmosphere of N$_2$. A solution of heptyl 3-hydroxy-2,2-dimethylpropanoate (40a) (1.0 g, 4.94 mmol) and pyridine (479 μL, 5.93 mmol) in Et$_2$O (1 mL) was added dropwise to the sulfuryl chloride solution over the course of 30 min. The flask was rinsed with Et$_2$O (3×1 mL) and the rinse added to the reaction mixture. The mixture was stirred at −78° C. until completion as monitored by TLC (30 min; 30% EA/hexane). The precipitate was filtered, and the filtrate was concentrated under vacuum to afford heptyl 3-((chlorosulfonyl)oxy)-2,2-dimethylpropanoate (40b) (1.37 g, yield 92%). The mixture was stored at −78° C. and used in the next step without further purification. $^1$H-NMR (300 MHz, CDCl$_3$) δ 4.50 (s, 2H), 4.20-4.02 (m, 2H), 1.68 (m, 2H), 1.31 (d, J=3.1 Hz, 13H), 1.23 (s, 1H), 0.95-0.83 (m, 3H).

Example 41

Synthesis of ethyl 1-(((chlorosulfonyl)oxy)methyl)cyclohexanecarboxylate (41)

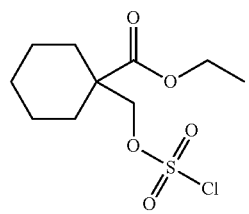 [SMILES: CCOC(=O)C1(COS(=O)(=O)Cl)CCCCC1]

Step 1: Synthesis of ethyl 1-(hydroxymethyl)cyclohexanecarboxylate (41a)

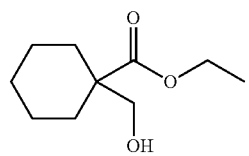

Diethyl cyclohexane-1,1-dicarboxylate (2.12 g, 9.29 mmol) was dissolved in THF (50 mL) and to which was added LiAl(OtBu)$_3$ (5.9 g, 23.2 mmol) in portions. The reaction mixture was stirred at reflux overnight. The reaction was cooled in an ice bath and treated carefully with 10% KHSO₄ aq. solution (30 mL) with stirring for 10 min. The precipitate formed was filtered out through a pad of Celite®. The filtrate was extracted with EtOAc (3×40 mL) and the organic phase was combined and washed with brine (50 mL), dried over NaSO₄, filtered and concentrated in vacuo. The residue was purified with CombiFlash (SiO₂) in 0-5% MeOH/DCM to obtain the desired product (41a) as an oil (1.23 g, 71% yield). ¹H-NMR (300 MHz, CDCl₃) δ 4.19 (qd, J=7.1, 0.8 Hz, 2H), 3.62 (d, J=6.4 Hz, 2H), 3.46 (s, 1H), 2.00 (dt, J=11.5, 6.4 Hz, 4H), 1.57-1.22 (m, 9H).

Step 2: Synthesis of ethyl 1-(((chlorosulfonyl)oxy) methyl)cyclohexanecarboxylate (41)

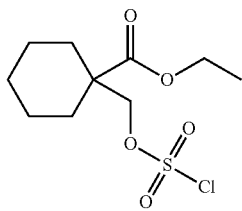 [SMILES: CCOC(=O)C1(COS(=O)(=O)Cl)CCCCC1]

A solution of freshly distilled sulfuryl chloride (294 µL, 3.63 mmol) in Et₂O (10 mL) was cooled to −78° C. under an atmosphere of nitrogen. A solution of ethyl 1-(hydroxymethyl)cyclohexanecarboxylate (41a) (0.615 g, 3.3 mmol) and pyridine (294 µL, 3.63 mmol) in Et₂O (6 mL) was added dropwise to the sulfuryl chloride solution during 15 min. The flask was rinsed with Et₂O (3×1 mL) and the rinse added to the reaction. The mixture was stirred at −78° C. until completion (ca. 30 min; monitored by TLC, 30% EtOAc/hexane). The precipitate was filtered, and the filtrate was concentrated under vacuum to afford the title compound (41) as an oil, 0.94 g in quantitative yield, which was used directly in the next step without purification. ¹H-NMR (300 MHz, CDCl₃): δ 4.52 (s, 2H), 4.21 (q, J=7.1 Hz, 2H), 2.04 (s, 2H), 1.53-1.39 (m, 8H), 1.39-1.21 (m, 3H).

Example 42

Synthesis of (5-methyl-2-oxo-1,3-dioxol-4-yl) methyl 3-((chlorosulfonyl)oxy)-2,2-dimethylpropanoate (42)

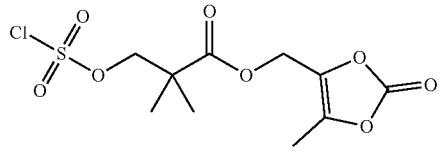 [SMILES: Cc1oc(=O)oc1COC(=O)C(C)(C)COS(=O)(=O)Cl]

Step 1: Synthesis of (5-methyl-2-oxo-1,3-dioxol-4-yl)methyl 3-hydroxy-2,2-dimethylpropanoate (42a)

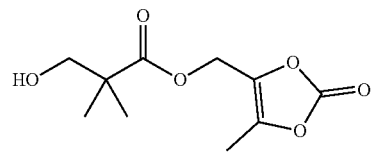 [SMILES: Cc1oc(=O)oc1COC(=O)C(C)(C)CO]

To a stirred solution of 3-hydroxy-2,2-dimethylpropanoic acid (4.0 g, 33.9 mmol) and potassium carbonate (4.68 g, 33.9 mmol) in DMF (45 mL) at 0° C. was added 4-(hydroxymethyl)-5-methyl-1,3-dioxol-2-one (5.03 g, 33.9 mmol) in DMF (5 mL) dropwise over 1 h. The reaction was stirred at room temperature overnight. The reaction mixture was diluted with EtOAc and washed with water and brine. The organic layer was dried with anhydrous Na₂SO₄, filtered, and concentrated under vacuum to give a crude residue. The residue was purified by silica gel column chromatography using EtOAc/hexane (1:4 to 2:3) as eluent to give the product (42a) as a yellow liquid (1.6 g, yield 21%). ¹H-NMR (300 MHz, CDCl₃): δ 4.86 (s, 2H), 3.58 (s, 2H), 2.18 (s, 3H), 1.20 (s, 6H).

Step 2: Synthesis of (5-methyl-2-oxo-1,3-dioxol-4-yl)methyl 3-((chlorosulfonyl)oxy)-2,2-dimethylpropanoate (42)

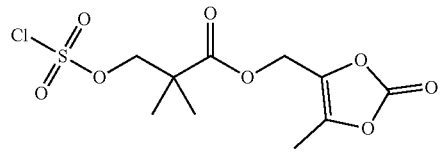 [SMILES: Cc1oc(=O)oc1COC(=O)C(C)(C)COS(=O)(=O)Cl]

A solution of distilled sulfuryl chloride (0.61 mL, 7.53 mmol) in Et₂O (15 mL) was cooled to −78° C. under nitrogen. A solution of (5-methyl-2-oxo-1,3-dioxol-4-yl) methyl 3-hydroxy-2,2-dimethylpropanoate (42a) (1.48 g, 6.43 mmol) in Et₂O (1 mL) was added. Subsequently, a solution of pyridine (0.55 mL, 6.86 mmol) in Et₂O (1 mL) was added over a period of 1 h. The reaction was stirred at −78° C. for 1 h. After the mixture was filtered, the filtrate was concentrated under vacuum to give the product (42) as a yellow oil (1.6 g, yield 76%). ¹H-NMR (300 MHz, CDCl₃): δ 4.90 (s, 2H), 4.49 (s, 2H), 2.19 (s, 3H), 1.33 (s, 6H).

Example 43

Synthesis of 3-((chlorosulfonyl)oxy)-2,2-dimethylpropyl benzoate (43)

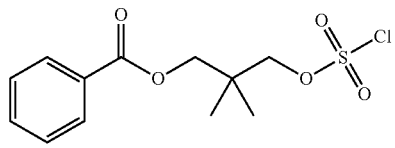 [SMILES: CC(C)(COC(=O)c1ccccc1)COS(=O)(=O)Cl]

Step 1: Synthesis of 3-hydroxy-2,2-dimethylpropyl benzoate (43a)

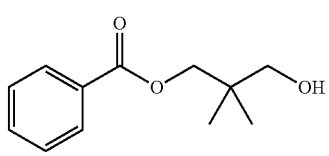

Benzoyl chloride (4.0 mL, 34.5 mmol) was added dropwise to a stirred solution of 2,2-dimethylpropane-1,3-diol (10.8 g, 103.4 mmol), pyridine (5.8 mL, 71.6 mmol) and N,N-4-dimethylaminopyridine (840 mg, 6.9 mmol) in dichloromethane (207 mL) at ca. 0° C. The mixture was stirred overnight with gradual warming to room temperature, quenched by addition of 1N HCl (100 mL) at 0° C. and extracted twice with dichloromethane. The combined organic extracts were washed with saturated aqueous NaHCO$_3$ (100 mL), brine (100 mL), dried (Na$_2$SO$_4$), filtered and the solvent concentrated under vacuum to leave a crude residue. The residue was split into two batches and purified by column chromatography on silica gel using EtOAc/hexanes (0:1 to 1:4) as eluent to give the product (43a) (5.95 g, 99%) as a colorless oil (note: oil dried under vacuum for 2 days). LC-MS: m/z=209.0 [M+H]$^+$. $^1$H-NMR (300 MHz, CDCl$_3$): 8.05 (m, 2H), 7.58 (m, 1H), 7.45 (m, 2H), 4.19 (s, 2H), 3.38 (d, J=6.3 Hz, 2H), 2.29 (t, J=6.3 Hz, 1H), 1.02 (s, 6H).

Step 2: Synthesis of 3-((chlorosulfonyl)oxy)-2,2-dimethylpropyl benzoate (43)

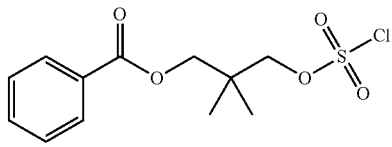 [SMILES: CC(C)(COC(=O)c1ccccc1)COS(=O)(=O)Cl]

Reference is made to *J. Am. Chem. Soc.* 2006, 128, 1605-1610. A solution of distilled sulfuryl chloride (1.2 mL, 15.8 mmol) in Et$_2$O (15 mL) was cooled to −78° C. under an atmosphere of argon. A solution of 3-hydroxy-2,2-dimethylpropyl benzoate (43a) (3.0 g, 14.4 mmol) and pyridine (1.2 mL, 14.4 mmol) in Et$_2$O (3.0 mL) was then added dropwise over 1 h via a syringe. The syringe was rinsed with Et$_2$O (3×1 mL), each rinse being added to the reaction mixture. The acetone/CO$_2$ bath was removed, and the mixture allowed to warm to room temperature, then stirred at room temperature for 4 h. TLC analysis (EtOAc/hexanes; 3:7) did not indicate complete reaction, so re-cooled to −78° C. and added more SO$_2$Cl$_2$ (0.1 mL), then allowed to warm to room temperature, and stirred for an additional 2 h. The mixture was filtered and the filtrate was concentrated under vacuum to give the product (43) (3.97 g, 89%) as an oil. $^1$H-NMR (300 MHz, CDCl$_3$): 8.03 (m, 2H), 7.61-7.57 (m, 1H), 7.49-7.44 (m, 2H), 4.41 (s, 2H), 4.18 (s, 2H), 1.16 (s, 6H).

Example 44

Synthesis of ethyl 3-((chlorosulfonyl)oxy)-2,2-dimethylpropanoate (44)

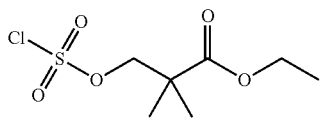

A solution of distilled sulfuryl chloride (0.55 mL, 7.5 mmol) in Et$_2$O (10 mL) was cooled to −78° C. under an atmosphere of argon. A solution of ethyl 3-hydroxy-2,2-dimethylpropanoate (1.0 g, 6.8 mmol) and pyridine (0.55 mL, 6.8 mmol) in Et$_2$O (1.0 mL) was then added dropwise over 1 h via a syringe. The syringe was rinsed with Et$_2$O (3×1 mL), each rinse being added to the reaction mixture. The acetone/CO$_2$ bath was removed, and the mixture was allowed to warm to room temperature, then stirred at room temperature for 4 h. TLC analysis (EtOAc/hexanes; 3:7) did not indicate that the reaction was complete. The mixture was re-cooled to −78° C. and more SO$_2$Cl$_2$ (0.11 mL) was added, and the mixture allowed to warm to room temperature and stirred for an additional 2 h. The mixture was filtered and the filtrate was concentrated under vacuum to give the product (44) (yield assumed quantitative). $^1$H-NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Example 45

Synthesis of benzyl 3-((chlorosulfonyl)oxy)-2,2-dimethylpropanoate (45)

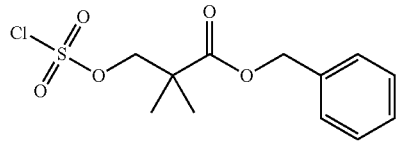 [SMILES: CC(C)(COS(=O)(=O)Cl)C(=O)OCc1ccccc1]

A solution of distilled sulfuryl chloride (0.77 mL, 10.6 mmol) in Et$_2$O (10 mL) was cooled to −78° C. under an atmosphere of argon. A solution of ethyl 3-hydroxy-2,2-dimethylpropanoate (Sigma-Aldrich; 2.0 g, 9.6 mmol) and pyridine (0.85 mL, 10.6 mmol) in Et$_2$O (2.0 mL) was then added dropwise over 1 h via a syringe. The syringe was rinsed with Et$_2$O with each rinse being added to the reaction mixture. The acetone/CO$_2$ bath was removed and the mixture allowed to warm to room temperature, then stirred at room temperature for 30 min. TLC analysis (EtOAc/hexanes; 3:7) did not indicate complete reaction, so re-cooled to −78° C. and added more SO$_2$Cl$_2$ (0.07 mL), then allowed to warm to room temperature and stirred for an additional 1 h. Et$_2$O (5 mL) was added and the mixture stirred for a few min, then filtered and the filtrate concentrated under vacuum to give the product (45) (2.19 g, 75%). $^1$H-NMR (300 MHz, CDCl$_3$): δ 7.41-7.32 (m, 4H), 5.18 (s, 2H), 4.52 (s, 2H), 1.34 (s, 6H).

Example 46

Synthesis of Phenyl Sulfochloridate (46)

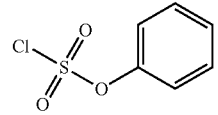 [SMILES: O=S(=O)(Cl)Oc1ccccc1]

Reference is made to *J. Am. Chem. Soc.* 2013, 135, 10638-10641. A solution of distilled sulfuryl chloride (2.6 mL, 35.1 mmol) in Et$_2$O (30 mL) was cooled to −78° C. under an atmosphere of argon. A solution of phenol (3.0 g, 31.9 mmol) in Et$_2$O (3.0 mL) and pyridine (2.6 mL, 31.9 mmol) were then added concurrently, but from different syringes, dropwise over 1 h. The syringes were each rinsed with Et$_2$O and each rinse was added to the reaction mixture. The mixture was allowed to warm to room temperature slowly and stirred at room temperature overnight. The mixture was filtered, and the filtrate concentrated under vacuum to give the product (4.65 g), contaminated with other products and phenol starting material. The phenyl sulfochloridate product (46) was not purified further and was used directly in the next step.

Example 47

Synthesis of 4-((chlorosulfonyl)oxy)-3,3-dimethylbutyl benzoate (47)

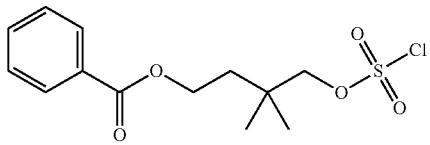 [SMILES: CC(C)(CCOC(=O)c1ccccc1)COS(=O)(=O)Cl]

Step 1: Synthesis of 2,2-dimethylbutane-1,4-diol (47a)

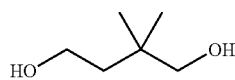

A solution of 2,2-dimethylsuccinic acid (10.0 g, 68.4 mmol) in THF (150 mL) was added dropwise to a suspension of lithium aluminum hydride (8.3 g, 219.0 mmol) in THF (80 mL) at 0° C. (ice bath). The mixture was warmed to room temperature over 20 min and then heated at reflux for 1.5 h. Upon completion (reaction monitored by TLC using MeOH/CH$_2$Cl$_2$ 5:95 as eluent) the reaction was quenched very carefully and dropwise by the addition of water (10 mL), 3 M NaOH (15 mL), and water (20 mL). The mixture was stirred at room temperature for 20 min, and the solids filtered over a pad of Celite®. The filter cake was rinsed thoroughly with THF. The filtrate was concentrated under vacuum giving a mixture of the title compound and unidentified by-products as a crude oil. The oil was purified by column chromatography on silica gel using MeOH/CH$_2$Cl$_2$ (0:1 to 1:9) as eluent to afford the product (47a) (4.649 g, 57%) as an oil. $^1$H-NMR (300 MHz, CDCl$_3$): δ 4.11 (s, 2H), 3.66 (t, J=5.9 Hz, 2H), 3.30 (s, 2H), 1.52 (t, J=5.6 Hz, 2H), 0.89 (s, 6H).

Step 2: Synthesis of 4-hydroxy-3,3-dimethylbutyl benzoate (47b)

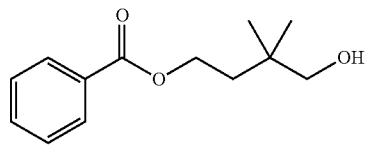 [SMILES: CC(C)(CO)CCOC(=O)c1ccccc1]

To a stirred solution of 2,2-dimethylbutane-1,4-diol (47a) (0.30 g, 2.5 mmol) in anhydrous dichloromethane (9 mL) was added benzoyl chloride (0.30 mL, 2.5 mmol), Et$_3$N (0.71 mL, 5.1 mmol), and a catalytic amount of N,N-4-dimethylaminopyridine at 0° C. (ice bath). The mixture was gradually warmed to room temperature and stirred overnight. After the starting material was completely consumed (reaction monitored by TLC using EtOAc/hexanes 2:8 as eluent), the reaction was quenched by the addition of 1N HCl (20 mL) at 0° C. (ice bath), and the mixture was extracted twice with dichloromethane. The combined organic layers were washed with saturated aqueous NaHCO$_3$, brine, dried (Na$_2$SO$_4$), filtered and the solvent concentrated to yield a mixture, of at least two products, as a clear and colorless oil. The oil was purified by column chromatography on silica gel using EtOAc/hexanes (0:1 to 4:6) as eluent to give the product (47b) (0.29 g, 51%) as an oil (which was dried under high vacuum for 2 d). $^1$H-NMR (300 MHz, CDCl$_3$): δ 8.04-8.01 (m, 2H), 7.58-7.53 (m, 1H), 7.46-7.41 (m, 2H), 4.41 (t, J=7.4 Hz, 2H), 3.41 (s, 2H), 1.78 (t, J=7.4 Hz, 2H), 1.70 (s, 1H), 0.99 (s, 6H).

Step 3: Synthesis of 4-((chlorosulfonyl)oxy)-3,3-dimethylbutyl benzoate (47)

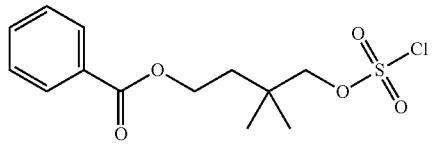 [SMILES: CC(C)(CCOC(=O)c1ccccc1)COS(=O)(=O)Cl]

A solution of freshly distilled sulfuryl chloride (0.11 mL, 1.5 mmol) in Et$_2$O (3 mL) was cooled to −78° C. under an atmosphere of Ar. A solution of 4-hydroxy-3,3-dimethylbutyl benzoate (47b) (0.28 g, 1.3 mmol) and pyridine (0.10 ml, 1.3 mmol) in Et$_2$O (2 mL) was added dropwise (over 1 h) to the cooled solution. The mixture was warmed to room temperature and stirred for 30 min (reaction was monitored by TLC using EtOAc/hexanes 2:8 as eluent). The mixture was re-cooled to −78° C. and sulfuryl chloride (0.02 mL) was added. The mixture was allowed to warm to room temperature, and stirred for 30 min. Et$_2$O (5 mL) was added and the mixture stirred for a few minutes. The mixture was filtered and the filtrate concentrated under vacuum to give the product (47) (0.305 g, 75%). $^1$H-NMR (300 MHz, CDCl$_3$): δ 8.03 (d, J=8.1 Hz, 2H), 7.60-7.54 (m, 1H), 7.47-7.42 (m, 2H), 4.44-4.38 (m, 2H), 4.29 (s, 2H), 1.89-1.85 (m, 2H), 1.13 (s, 6H).

Example 48

Synthesis of 4-((chlorosulfonyl)oxy)-3,3-dimethylbutyl propionate (48)

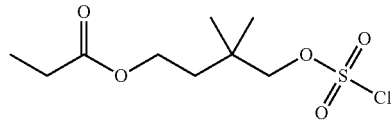 [SMILES: CCC(=O)OCCC(C)(C)COS(=O)(=O)Cl]

Step 1: Synthesis of 4-hydroxy-3,3-dimethylbutyl propionate (48a)

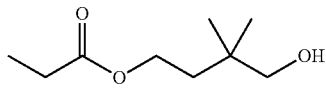

A solution of propionyl chloride (0.74 mL, 8.5 mmol) in anhydrous dichloromethane (5 mL) was added to a stirred solution of 2,2-dimethylbutane-1,4-diol (47a) (1.00 g, 8.5 mmol), Et$_3$N (2.4 mL, 16.9 mmol), and 4-N,N-dimethylaminopyridine (52 mg) in anhydrous dichloromethane (20 mL) at −78° C. under an atmosphere of argon. The mixture was stirred for 10 min and then allowed to warm to room temperature, stirred at room temperature for 1 h, then re-cooled to −78° C., and allowed to warm to room temperature slowly by allowing the mixture to stay in the cold bath and letting the dry ice sublime (recommended to allow warming to room temperature from −78° C. after addition of all the reagents). After the starting material was completely consumed (TLC 50% EtOAc/hexanes), the reaction was quenched by the addition of 0.5 N HCl (10 mL) at 0° C. The organic and aqueous layers were partitioned, and the aqueous layer was extracted with dichloromethane (2×20 mL). The combined organic layers were washed with saturated aqueous NaHCO$_3$ (20 mL), brine (20 mL), then dried (Na$_2$SO$_4$), filtered and the solvent concentrated under vacuum to leave a crude oil. The oil was purified by column chromatography on silica gel using EtOAc/hexanes (0:1 to 4:1) as eluent to give the product (48a) (463 mg, 22%) as an oil, contaminated with significant EtOAc solvent residues. $^1$H-NMR (300 MHz, CDCl$_3$): δ 4.14 (t, J=7.4 Hz, 2H), 3.32 (s, 2H), 2.30 (q, J=7.6 Hz, 2H), 1.88 (s, 1H), 1.61 (t, J=7.7 Hz, 2H), 1.13 (t, J=7.5 Hz, 3H), 0.91 (fd, J=1.2 Hz, 6H).

Step 2: Synthesis of 4-((chlorosulfonyl)oxy)-3,3-dimethylbutyl propionate (48)

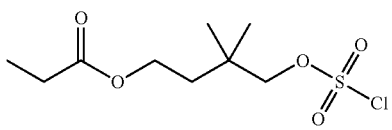 [SMILES: CCC(=O)OCCC(C)(C)COS(=O)(=O)Cl]

A solution of freshly distilled sulfuryl chloride (0.15 mL, 2.0 mmol) in Et$_2$O (3.5 mL) was cooled to −78° C. under an atmosphere of argon. A solution of 4-hydroxy-3,3-dimethylbutyl propionate (48a) (73% purity, the remainder being EtOAc; 441 mg, 1.8 mmol) and pyridine (0.15 mL, 1.8 mmol) in Et$_2$O (2.5 mL) was added dropwise over 1 h to the cooled solution. The mixture was allowed to warm to room temperature and was stirred for 30 min (monitored by TLC, 30% EtOAc/hexanes), re-cooled to −78° C. and sulfuryl chloride (0.03 mL) and pyridine (0.03 mL) was added, warmed to room temperature, and stirred for 30 min. Again, the mixture was re-cooled to −78° C. and another portion of sulfuryl chloride (0.15 mL) was added. The mixture was allowed to warm to room temperature, and stirred for 30 min. Et$_2$O (5 mL) was added and the mixture stirred for a few min. The mixture was filtered and the filtrate was concentrated under vacuum to give the product (48) (401 mg, 79%). $^1$H-NMR: (300 MHz, CDCl$_3$): 4.22 (s, 2H), 4.14 (t, J=6.8 Hz, 2H), 2.30 (q, J=7.6 Hz, 2H), 1.70 (t, J=6.8 Hz, 2H), 1.11 (t, J=7.7 Hz, 3H), 1.05 (s, 6H).

Example 49

Synthesis of benzyl (4-((chlorosulfonyl)oxy)-3,3-dimethylbutyl) adipate (49)

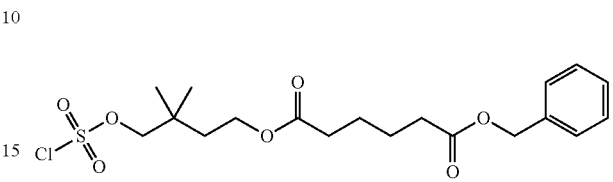

Step 1: Synthesis of benzyl (perfluorophenyl) adipate (49a)

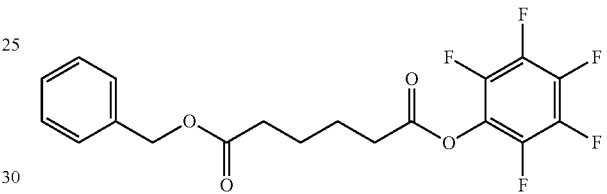

To a stirring solution of adipic acid monobenzyl ester (1.03 g, 4.3 mmol) and pentafluorophenol (0.87 g, 4.7 mmol) in EtOAc (18.7 mL) at 0° C. was added N,N'-dicyclohexylcarbodiimide (0.97 g, 4.7 mmol). The mixture was allowed to warm to room temperature and then stirred overnight. The resulting solid was removed by vacuum filtration through a pad of Celite®. The filter cake was washed with EtOAc. The filtrate was dry-loaded on to silica gel and purified by column chromatography on silica gel using EtOAc/hexanes (0:1 to 4:6) as eluent, to give the product (49a) (1.59 g, 93%) as a solid. $^1$H-NMR (300 MHz, CDCl$_3$): δ 7.37-7.35 (m, 5H), 5.13 (s, 2H), 2.68 (t, J=6.8 Hz, 2H), 2.44 (t, J=6.5 Hz, 2H), 1.82-1.78 (m, 4H).

Step 2: Synthesis of benzyl (4-hydroxy-3,3-dimethylbutyl) adipate (49b)

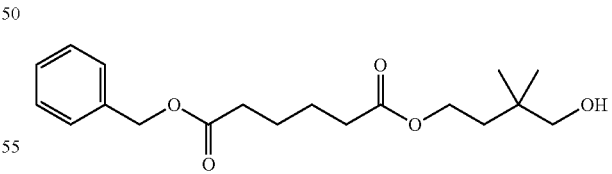

To a stirred solution of 2,2-dimethylbutane-1,4-diol (47a) (0.22 g, 1.8 mmol) in anhydrous dichloromethane (4 mL) at ca. 0° C. (ice bath), under an atmosphere of argon, was added benzyl (perfluorophenyl) adipate (49a) (0.36 g, 0.9 mmol), Et$_3$N (0.25 mL, 1.8 mmol), and a catalytic amount of 4-N,N-dimethylaminopyridine (small unweighed amount). The mixture was gradually warmed to room temperature, and then at room temperature overnight. The mixture was dry-loaded on to silica gel and purified by column chromatography on silica gel using EtOAc/hexanes (0:1 to 3:7) as eluent to give the product contaminated with regio-isomeric product. This mixture was re-purified by column chromatography on silica gel using EtOAc/hexanes (0:1 to 3:7) as eluent to give pure product (49b) (113 mg 38%). ¹H-NMR (300 MHz, CDCl₃): 7.36-7.34 (m, 5H), 5.11 (s, 2H), 4.14 (t, J=7.2 Hz, 2H), 3.34 (d, J=5.7 Hz, 2H), 2.38-2.31 (m, 4H), 1.68-1.59 (m, 6H), 0.92 (s, 6H). The reaction could be repeated to give larger amounts of material.

Step 3: Synthesis of benzyl (4-((chlorosulfonyl)oxy)-3,3-dimethylbutyl) adipate (49)

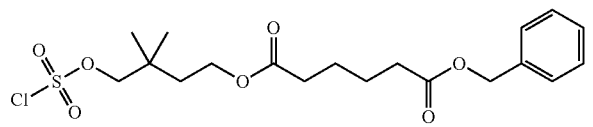 [SMILES: CC(C)(CCOC(=O)CCCCC(=O)OCc1ccccc1)COS(=O)(=O)Cl]

A solution of freshly distilled sulfuryl chloride (0.12 ml, 1.6 mmol) in Et₂O (5 mL) was cooled to −78° C. under an atmosphere of argon. A solution of benzyl (4-hydroxy-3,3-dimethylbutyl) adipate (49b) (446 mg, 1.3 mmol) and pyridine (0.11 mL, 1.3 mmol) in Et₂O (3.5 mL) was added dropwise over 1 h to the cooled solution. The mixture was allowed to warm to room temperature and was stirred for 30 min (monitored by TLC, 30% EA/hex). The reaction was not complete, so the mixture was recooled to −78° C., then sulfuryl chloride (0.05 mL) and pyridine (0.05 mL) were added. The mixture was allowed to warm to room temperature, and stirred for 30 min. Et₂O (5 mL) was added, and the mixture was stirred for a few mins. The mixture was filtered and the filtrate was concentrated under vacuum to give the product (49) (446 mg, 77%). ¹H-NMR (300 MHz, CDCl₃): δ 7.39-7.29 (m, 5H), 5.11 (s, 2H), 4.22 (s, 2H), 4.15 (t, J=6.8 Hz, 2H), 2.40-2.29 (m, 4H), 1.73-1.59 (m, 6H), 1.06 (s, 6H).

Example 50

Synthesis of methyl 3-((chlorosulfonyl)oxy)-2,2-dimethylpropanoate (50)

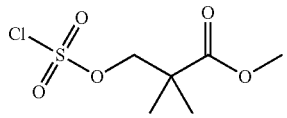

A solution of freshly distilled sulfuryl chloride (3.3 mL, 45.4 mmol) in Et₂O (45 mL) was cooled to −78° C. under an atmosphere of Ar. A solution of methyl 2,2-dimethyl-3-hydroxypropionate (3.0 g, 22.7 mmol) and pyridine (2.2 mL, 27.2 mmol) in Et₂O (20 mL) was added dropwise to the sulfuryl chloride solution over 30 min. The flask was rinsed with Et₂O (3×5 mL) and the rinse was added to the reaction mixture. The mixture was stirred at −78° C. until completion (monitored by TLC, 30% EA/hex, 30 min). The precipitate was filtered, and the filtrate was concentrated under vacuum to afford methyl 3-((chlorosulfonyl)oxy)-2,2-dimethylpropanoate (50) (5.6 g, 70% yield). The mixture was stored at −78° C. and was used immediately for the next step without further purification. ¹H-NMR (300 MHz, CDCl₃) δ 4.50 (s, 2H), 3.74 (s, 3H), 1.31 (s, 6H).

Example 51

Synthesis of isopropyl 3-((chlorosulfonyl)oxy)-2,2-dimethylpropanoate (48)

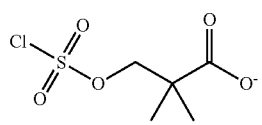

Step 1: Synthesis of isopropyl 3-hydroxy-2,2-dimethylpropanoate (51a)

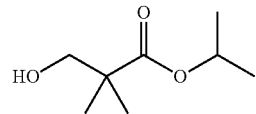

Reference is made to German Application Publication No. DE3045373. A mixture of 3-hydroxy-2,2-dimethylpropionic acid (4.7 g, 40 mmol), isopropanol (70 mL) and concentrated sulfuric acid (or fuming sulfuric acid; 1 mL) was heated to reflux and stirred overnight. After allowing to cool, the mixture was concentrated under vacuum and the residue partitioned between EtOAc (100 mL) and saturated aqueous NaHCO₃ (100 mL). The aqueous mixture was washed with H₂O (50 mL), saturated NaHCO₃ (50 mL) and brine (50 mL), then dried (Na₂SO₄), filtered and concentrated under vacuum to leave provide the product as an oil. The product (51a) was used directly in the next step without further purification. ¹H-NMR (300 MHz, CDCl₃): δ 5.08-4.95 (m, 1H), 3.53 (fd, J=1.8 Hz, 2H), 2.49 (s, 1H), 1.25 (fd, J=2.4 Hz, 3H), 1.22 (fd, J=2.4 Hz, 3H), 1.17 (s, 3H), 1.16 (s, 3H).

Step 2: Synthesis of isopropyl 3-((chlorosulfonyl)oxy)-2,2-dimethylpropanoate (51)

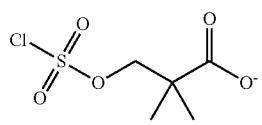

A solution of sulfuryl chloride (2.7 mL, 37.5 mmol) in Et₂O (45 mL) was cooled to −78° C. under an atmosphere of Ar. A solution of isopropyl 3-hydroxy-2,2-dimethylpropanoate (51a) (3.0 g, 18.7 mmol) and pyridine (1.82 mL, 22.5 mmol) in Et₂O (20 mL) was added dropwise to the sulfuryl chloride solution over the course of 30 min. The flask was rinsed with Et₂O (3×5 mL) and the rinse added to the reaction mixture. The mixture was stirred at −78° C. until completion by TLC (30 min; 30% EA/hex). The precipitate was filtered, and the filtrate was concentrated under vacuum to afford isopropyl 3-((chlorosulfonyl)oxy)-2,2-dimethylpropanoate (51) (4.1 g, 85% yield). The mixture was stored at −78° C. and was used immediately for the next step without further purification. ¹H-NMR (300 MHz, CDCl₃): δ 5.10-4.98 (m, 1H), 4.49 (s, 2H), 1.29 (s, 6H), 1.26 (s, 3H), 1.24 (s, 3H).

Example 52

Synthesis of hexyl 3-((chlorosulfonyl)oxy)-2,2-dimethylpropanoate (52)

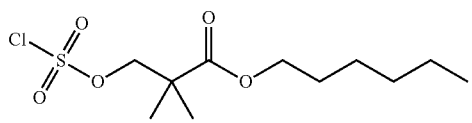 [SMILES: CCCCCCOC(=O)C(C)(C)COS(=O)(=O)Cl]

Step 1: Synthesis of hexyl 3-hydroxy-2,2-dimethylpropanoate (52a)

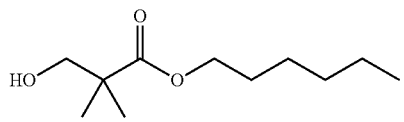

Reference is made to German Application Publication No. DE3045373. A mixture of 3-hydroxy-2,2-dimethylpropionic acid (4.7 g, 40 mmol), 1-hexanol (70 mL) and concentrated sulfuric acid (or fuming sulfuric acid; 1 mL) was heated to 80° C. and stirred overnight. After allowing to cool, the mixture was concentrated under vacuum (high vacuum pump required) and the residue partitioned between EtOAc (100 mL) and saturated aqueous NaHCO₃ (100 mL). The aqueous mixture was washed with H₂O (50 mL), saturated NaHCO₃ (50 mL) and brine (50 mL), then dried (Na₂SO₄), filtered and concentrated under vacuum to provide the product (52a) as an oil. The product (49a) was used directly in the next step without further purification. ¹H-NMR (300 MHz, CDCl₃): δ 4.04-3.98 (m, 2H), 3.47-3.45 (m. 2H). 2.26 (s, 1H), 1.58-1.32 (min, 2H), 1.32-1.23 (m, 6H). 1.12 (s, 3H), 1.11 (s. 3H).

Step 2: Synthesis of hexyl 3-((chlorosulfonyl)oxy)-2,2-dimethylpropanoate (52)

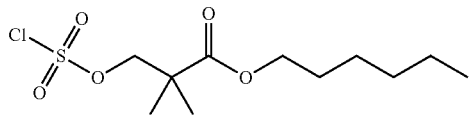 [SMILES: CCCCCCOC(=O)C(C)(C)COS(=O)(=O)Cl]

A solution of sulfuryl chloride (2.1 mL, 29.7 mmol) in Et₂O (40 mL) was cooled to −78° C. under an atmosphere of argon. A solution of hexyl 3-hydroxy-2,2-dimethylpropanoate (52a) (3.0 g, 14.8 mmol) and pyridine (1.4 mL, 17.8 mmol) in Et₂O (15 mL) was added dropwise to the sulfuryl chloride solution over the course of 30 min. The flask was rinsed with Et₂O (3×5 mL) and the rinse added to the reaction mixture. The mixture was stirred at −78° C. until completion by TLC (30 min; 30% EA/hex). The precipitate was filtered, and the filtrate was concentrated under vacuum to afford the product (52) (3.7 g, 83% yield). The mixture was stored at −78° C. and was used immediately for the next step without further purification. ¹H-NMR (300 MHz, CDCl₃): 4.50 (s, 2H), 4.13 (t, J=6.8 Hz, 2H), 1.69-1.60 (m, 2H), 1.40-1.27 (m, 12H), 0.91-0.87 (m, 3H).

Example 53

Synthesis of heptyl 3-((chlorosulfonyl)oxy)-2,2-dimethylpropanoate (53)

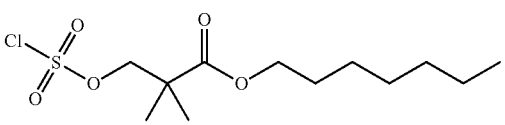 [SMILES: CCCCCCCOC(=O)C(C)(C)COS(=O)(=O)Cl]

Step 1: Synthesis of heptyl 3-hydroxy-2,2-dimethylpropanoate (53a)

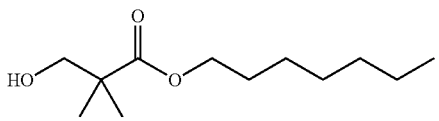

Reference is made to German Application Publication No. DE3045373. A mixture of 3-hydroxy-2,2-dimethylpropionic acid (4.7 g, 40 mmol), 1-heptanol (70 mL) and concentrated sulfuric acid (or fuming sulfuric acid; 1 mL) was heated to 80° C. and stirred overnight. After allowing the mixture to cool, the mixture was concentrated under vacuum (high vacuum pump required) and the residue partitioned between EtOAc (100 mL) and saturated aqueous NaHCO₃ (100 mL). The aqueous was washing with H₂O (50 mL), saturated NaHCO₃ (50 mL) and brine (50 mL), then dried (Na₂SO₄), filtered and concentrated under vacuum to provide the product (53a) as an oil. The product was used directly in the next step without further purification. ¹H-NMR (300 MHz, CDCl₃): δ 4.31 (t, J=6.5 Hz, 2H), 3.77 (s, 2H), 1.87-1.81 (m, 2H), 1.53-1.50 (m, 8H), 1.41 (s, 6H), 1.12-1.08 (m, 3H).

Step 2: Synthesis of heptyl 3-((chlorosulfonyl)oxy)-2,2-dimethylpropanoate (53)

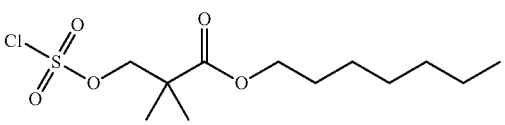 [SMILES: CCCCCCCOC(=O)C(C)(C)COS(=O)(=O)Cl]

A solution of sulfuryl chloride (2.0 mL, 27.7 mmol) in Et₂O (40 mL) was cooled to −78° C. under an atmosphere of argon. A solution of heptyl 3-hydroxy-2,2-dimethylpropanoate (53a) (3.0 g, 13.9 mmol) and pyridine (1.4 mL, 16.6 mmol) in Et$_2$O (15 mL) was added dropwise to the sulfuryl chloride solution over the course of 30 min. The flask was rinsed with Et$_2$O (3×5 mL) and the rinse added to the reaction mixture. The mixture was stirred at −78° C. until completion as monitored by TLC (30 min; 30% EA/hex). The precipitate was filtered, and the filtrate was concentrated under vacuum to afford heptyl 3-((chlorosulfonyl)oxy)-2,2-dimethylpropanoate (53) (3.3 g, 75%). The mixture was stored at −78° C. and was used immediately for the next step without further purification. $^1$H-NMR (300 MHz, CDCl$_3$): δ 4.46 (s, 2H), 4.11-4.00 (m, 2H), 1.64-1.55 (m, 2H), 1.26-1.24 (m, 8H), 0.85-0.81 (m, 3H).

Example 54

Synthesis of tert-butyl 3-((chlorosulfonyl)oxy)-2,2-dimethylpropanoate (54)

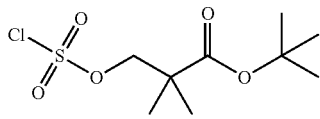 [SMILES: CC(C)(C)OC(=O)C(C)(C)COS(=O)(=O)Cl]

Step 1 and Step 2: Synthesis of tert-butyl 3-hydroxy-2,2-dimethylpropanoate (54a)

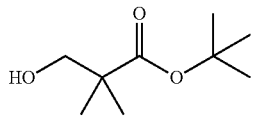

The compound was synthesized in accordance with PCT International Application Publication No. WO 2007116922. Sodium hydride (60% in mineral oil; 2.0 g) was added to a cooled solution of tert-butyl methyl malonate (4 g) in THF (100 mL) at 0° C. under an atmosphere of Ar. The mixture was stirred at 0° C. for 10 min. MeI (3.2 mL) was added to the mixture and the stirring was continued for 3 h (by this time the mixture was at room temperature). Brine and EtOAc were added to the mixture, and the organic layer was separated, dried (Na$_2$SO$_4$), filtered and concentrated under vacuum to give the product (ca. 4.5 g), which was used directly in the next step.

Solid lithium tri-tert-butoxy-aluminohydride (7.1 g, 28 mmol) was added portion-wise over 15 min to a solution of tert-butyl methyl 2,2-dimethyl-malonate (2.2 g) in THF (100 mL) under an atmosphere of Ar. The mixture was then heated to reflux and stirred overnight. After cooling to room temperature, a saturated solution of NH$_4$Cl and EtOAc were added, and the aqueous and organic layers were separated. The organic layer was washed with H$_2$O and brine, then dried (Na$_2$SO$_4$), filtered and concentrated under vacuum to provide a crude residue. The residue was purified by column chromatography on silica gel using EtOAc/hexanes (0:1 to 3:7) as eluent to give the product (54a) (900 mg) as an oil. $^1$H-NMR (300 MHz, CDCl$_3$): δ 3.50 (d, J=5.1 Hz, 2H), 2.53 (t, J=6.5 Hz, 1H), 1.45 (s, 9H), 1.14 (s, 6H)

Step 3: Synthesis of tert-butyl 3-((chlorosulfonyl)oxy)-2,2-dimethylpropanoate (54)

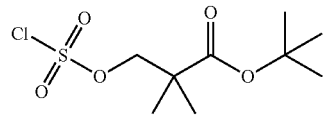 [SMILES: CC(C)(C)OC(=O)C(C)(C)COS(=O)(=O)Cl]

A solution of sulfuryl chloride (0.31 mL, 4.2 mmol) in Et$_2$O (6 mL) was cooled to −78° C. under an atmosphere of Ar. A solution of tert-butyl 3-hydroxy-2,2-dimethylpropanoate (54a) (0.49 g, 2.8 mmol) and pyridine (0.25 ml, 3.1 mmol) in Et$_2$O (6 mL) was added dropwise to the sulfuryl chloride solution over the course of 10 min. The mixture was stirred at −78° C. for 90 min and allowed to warm to 23° C. after TLC revealed that the reaction had not proceeded to completion (10% EtOAc/hexanes). The mixture was re-cooled to −78° C. and an additional 1 equivalent of sulfuryl chloride was added, stirred for 10 min, and the mixture allowed to warm to 23° C. (note: the mixture was allowed to stir for a total of 1 h after the addition and during the warming period). The precipitate was filtered, and the filtrate was concentrated under vacuum to give tert-butyl 3-((chlorosulfonyl)oxy)-2,2-dimethylpropanoate (54) (961 mg, yield assumed quantitative) as a clear, oil. $^1$H-NMR (300 MHz, CDCl$_3$): δ 4.46 (fd, J=1.5 Hz, 2H), 1.47 (fd, J=1.2 Hz, 9H), 1.27 (s, 6H).

Example 55

Synthesis of 2-methoxyethyl 3-((chlorosulfonyl)oxy)-2,2-dimethylpropanoate (55)

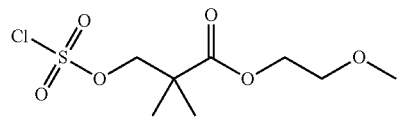 [SMILES: COCCOC(=O)C(C)(C)COS(=O)(=O)Cl]

Step 1: Synthesis of 2-methoxyethyl 3-hydroxy-2,2-dimethylpropanoate (55a)

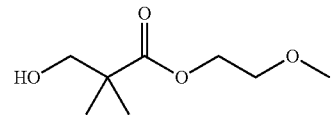

3-Hydroxy-2,2-dimethylpropanoic acid (1.2 g, 10.3 mmol) and Cs$_2$CO$_3$ (3.4 g, 10.4 mmol) were suspended in DMF (25 mL) at 23° C., then 2-bromoethyl methyl ether (1.0 mL, 10.4 mmol) was added. The resulting mixture was stirred at 70° C. overnight. After cooling, the mixture was filtered through a pad of Celite®. The filtrate was diluted with EtOAc (150 mL), and the mixture washed with water (3×100 mL) and brine, then dried (Na$_2$SO$_4$), filtered and concentrated to leave a crude residue. The residue was purified by column chromatography on silica gel using EtOAc/hexanes (1:4 to 4:1) as eluent to provide the product (55a) (1.3 g, crude weight) as an oil. ¹H-NMR (300 MHz, CDCl₃): δ 4.28 (t, J=4.8 Hz, 2H), 3.62-3.55 (m, 4H), 3.38 (s, 3H), 2.65 (t, J=6.0 Hz, 1H), 1.21 (s, 6H).

Step 2: Synthesis of 2-methoxyethyl 3-((chlorosulfonyl)oxy)-2,2-dimethylpropanoate (55)

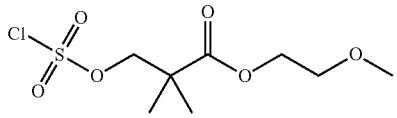 [SMILES: COCCOC(=O)C(C)(C)COS(=O)(=O)Cl]

A solution of freshly distilled sulfuryl chloride (0.2 mL, 2.8 mmol) in Et₂O (7.0 mL) was cooled to −78° C. under an atmosphere of Ar. A solution of 2-methoxyethyl 3-hydroxy-2,2-dimethylpropanoate (55a) (0.48 g, 2.7 mmol) and pyridine (0.24 mL, 3.0 mmol) in Et₂O (1 mL) was added dropwise to the sulfuryl chloride solution over the course of 11 min. The flask was rinsed with Et₂O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (55) (0.5 g, 67%) as an oil, which was used directly in the next step without further purification. Note: ¹H-NMR indicated desired product with residue of pyridine and along with starting material.

Example 56

Synthesis of oxetan-3-yl 3-((chlorosulfonyl)oxy)-2,2-dimethylpropanoate (56)

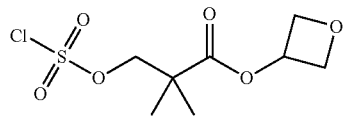 [SMILES: CC(C)(COS(=O)(=O)Cl)C(=O)OC1COC1]

Step 1: Synthesis of oxetan-3-yl 3-hydroxy-2,2-dimethylpropanoate (56a)

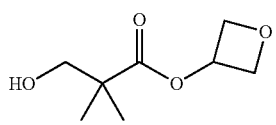

3-Hydroxy-2,2-dimethylpropanoic acid (4.7 g, 40 mmol) and Cs₂CO₃ (13.0 g, 40 mmol) were suspended in DMF (100 mL) at 23° C., then 3-iodooxetane (7.4 g, 40 mmol) was added. The resulting mixture was stirred at 70° C. overnight. After cooling, the mixture was diluted with EtOAc (150 mL), and the mixture washed with water (3×100 mL) and brine, then dried (Na₂SO₄), filtered and concentrated to provide a crude residue. The residue was purified by column chromatography on silica gel using EtOAc/hexanes as eluent to give the product (56a) (3.6 g, 51%) as an oil.

Step 2: Synthesis of oxetan-3-yl 3-((chlorosulfonyl)oxy)-2,2-dimethylpropanoate (56)

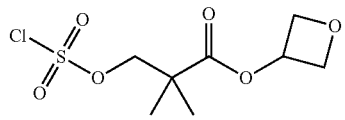 [SMILES: CC(C)(COS(=O)(=O)Cl)C(=O)OC1COC1]

A solution of freshly distilled sulfuryl chloride (0.2 mL, 2.7 mmol) in Et₂O (3 mL) was cooled to −78° C. under an atmosphere of Ar. A solution of oxetan-3-yl 3-hydroxy-2,2-dimethylpropanoate (56a) (0.46 g, 2.6 mmol) and pyridine (0.2 mL, 2.7 mmol) in Et₂O (2 mL) was added dropwise to the sulfuryl chloride solution over the course of 11 min. The flask was rinsed with Et₂O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (56) (0.5 g, 69%) as an oil, which was used directly in the next step without further purification. ¹H-NMR (300 MHz, CDCl₃): δ 5.50-5.46 (m, 1H), 4.94-4.89 (m, 2H), 4.65-4.60 (m, 2H), 4.52 (s, 2H), 1.72 (br. s, 1H), 1.36 (s, 6H).

Example 57

Synthesis of ethyl 1-(((chlorosulfonyl)oxy)methyl)cyclohexanecarboxylate (57)

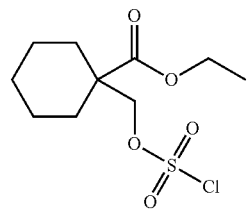 [SMILES: CCOC(=O)C1(COS(=O)(=O)Cl)CCCCC1]

A solution of freshly distilled sulfuryl chloride (77 µL, 1.1 mmol) in Et₂O (3 mL) was cooled to −78° C. under an atmosphere of Ar. A solution of ethyl 1-(hydroxymethyl)cyclohexanecarboxylate (0.2 g, 1.0 mmol) and pyridine (85 µL, 1.1 mmol) in Et₂O (2 mL) was added dropwise to the sulfuryl chloride solution over 11 min. The flask was rinsed with Et₂O (3×1 mL) and the rinse added to the reaction. The mixture was stirred at −78° C. until completion (ca. 30 min; monitored by TLC, 30% EtOAc/hex). The precipitate was filtered, and the filtrate was concentrated under vacuum to afford the title compound (57) as an oil, which was used directly in the next step without purification. A second batch using 476 mg of the starting alcohol, afforded 600 mg of the product (57) (approximately, 85% purity by ¹H-NMR).

Example 58

Step 1: Synthesis of ethyl 1-(((chlorosulfonyl)oxy)methyl)cyclopentane-1-carboxylate (58)

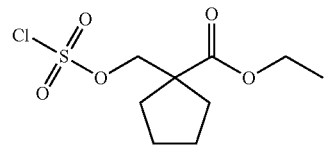 [SMILES: CCOC(=O)C1(COS(=O)(=O)Cl)CCCC1]

A solution of freshly distilled sulfuryl chloride (200 µL, 2.7 mmol) in Et$_2$O (3 mL) was cooled to −78° C. under an atmosphere of Ar. A solution of ethyl 1-(hydroxymethyl) cyclopentanecarboxylate (0.48 g, 2.7 mmol) and pyridine (222 µL, 2.7 mmol) in Et$_2$O (2 mL) was added dropwise to the sulfuryl chloride solution over 7 min. The flask was rinsed with Et$_2$O (2×1 mL) and both rinses were added to the reaction mixture. The mixture was stirred at −78° C. for 1.5 h. The precipitate was filtered, and the filter-cake washed with Et$_2$O (4 mL). The filtrate was concentrated under vacuum to afford the title compound (58) as an oil, which was used directly in the next step without further purification.

Example 59

Synthesis of ethyl 1-(((chlorosulfonyl)oxy)methyl) cyclobutanecarboxylate (59)

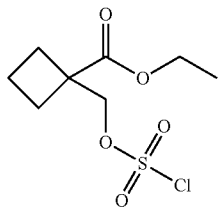

A solution of freshly distilled sulfuryl chloride (451 µL, 6.2 mmol) in Et$_2$O (5 mL) was cooled to −78° C. under an atmosphere of Ar. A solution of ethyl 1-(hydroxymethyl) cyclobutanecarboxylate (1.0 g, 6.1 mmol) and pyridine (500 µL, 6.2 mmol) in Et$_2$O (10 mL) was added dropwise to the sulfuryl chloride solution over the course of 11 min. The flask was rinsed with Et$_2$O (3×1 mL), which was also added to the reaction mixture. The mixture was stirred at −78° C., which was allowed to warm to ambient temp. within 4 h. The precipitate was filtered, and the filtrate was concentrated under vacuum to afford the title compound (59) (1.2 g, 76%) as an oil, which was used directly in the next step without further purification. Note: $^1$H-NMR indicated desired product (19a), together with starting material.

Example 60

Synthesis of ethyl 5-((chlorosulfonyl)oxy)-4,4-dimethylpentanoate (60)

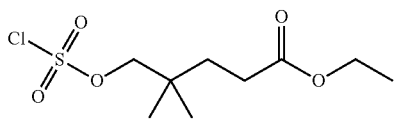 [SMILES: CCOC(=O)CCC(C)(C)COS(=O)(=O)Cl]

Step 1: Synthesis of ethyl 5-hydroxy-4,4-dimethylpentanoate (60a)

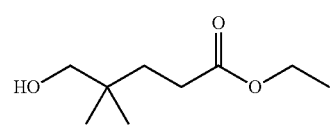

To a suspension of sodium 5-ethoxy-2,2-dimethyl-5-oxopentanoate (3.77 g, 17.9 mmol) in a mixture of tetrahydrofuran (39 mL) and DMF (13 mL) was added a solution of isopropyl chloroformate, 1.0M in toluene (27.0 mL, 27.0 mmol) at 0° C. The mixture was stirred at 0° C. for 10 min, and then allowed to warm to room temperature, and stirred for 2 h. The solution was cooled to 0° C. and sodium borohydride (1.21 g, 35.9 mmol) was added. The mixture was stirred for 20 min then methanol (6.5 mL) was added to the solution. After 10 min of stirring, ethyl acetate (25 mL) modified with a few drops of triethylamine and a saturated aqueous solution of NH$_4$Cl (25 mL) were added. The layers were separated, and the aqueous layer was extracted with EtOAc (2×40 mL). The combined organic layers were washed with brine, dried (MgSO$_4$), filtered and the filtrate was concentrated under vacuum. The residue was purified by column chromatography on silica gel using EtOAc/hexanes modified with 0.1% TEA (5:95 to 4:6) to give the product (60a) (2.01 g, 64% crude) as a colorless oil. One drop of triethylamine was added to the product to suppress lactonization.

Step 2: Synthesis of ethyl 5-((chlorosulfonyl)oxy)-4,4-dimethylpentanoate (60)

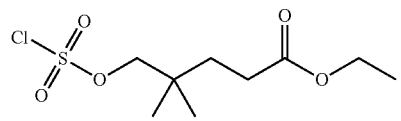 [SMILES: CCOC(=O)CCC(C)(C)COS(=O)(=O)Cl]

A solution of sulfuryl chloride (0.64 mL, 8.7 mmol) in Et$_2$O (10 mL) was cooled to −78° C. under an atmosphere of nitrogen. A solution of ethyl 5-hydroxy-4,4-dimethylpentanoate (60a) (0.76 g, 4.4 mmol) and pyridine (0.39 mL, 4.8 mmol) in Et$_2$O (10 mL) was added dropwise to the sulfuryl chloride solution over the course of 10 min. The syringe was rinsed with Et$_2$O (3×1 mL) and this was also added to the mixture. The mixture was stirred at −78° C. for 1.5 h, additional pyridine (0.9 equiv.) was added, and the mixture was filtered through a pad of Celite®. The filtrate was concentrated under vacuum to give the product (60) (0.897 g) as a colorless oil. This was used in the next step without further purification.

Example 61

Synthesis of hexyl 5-((chlorosulfonyl)oxy)-4,4-dimethylpentanoate (61)

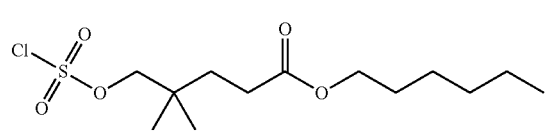 [SMILES: CCCCCCOC(=O)CCC(C)(C)COS(=O)(=O)Cl]

Step 1: Synthesis of sodium-5-(hexyloxy)-2,2-dimethyl-5-oxopentanoate (61a)

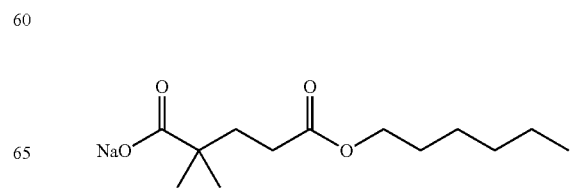

To a solution of 2,2-dimethylglutaric anhydride (5.0 g, 35.2 mmol) in 1-hexanol (50 mL) was added a solution of sodium hexan-1-olate (5.4 g, 43.5 mmol) in 1-hexanol. After 20 h of stirring, the solvent was evaporated and the resulting solid was suspended in diethyl ether (80 mL). The mixture was filtered and the solid was washed with diethyl ether (2×40 mL). The solid was dried under high vacuum to afford the product (61a) (3.84 g, 41%) as a solid. $^1$H-NMR (300 MHz, D$_2$O): δ 4.14 (t, J=6.5 Hz, 2H), 2.38-2.33 (m, 2H), 1.82-1.77 (m, 2H), 1.75-1.63 (m, 2H), 1.43-1.28 (m, 6H), 1.12 (s, 6H), 0.92-0.88 (m, 3H). The spectrum revealed that the product was contaminated with a small amount of an unidentified substance.

Step 2: Synthesis of hexyl 5-hydroxy-4,4-dimethylpentanoate (61b)

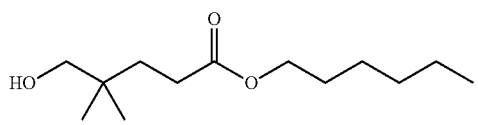 [SMILES: CCCCCCOC(=O)CCC(C)(C)CO]

To a suspension of sodium 5-(hexyloxy)-2,2-dimethyl-5-oxopentanoate (61a) (3.84 g, 14.4 mmol) in a mixture of THF (31 mL) and DMF (10 mL) was added isopropyl chloroformate, 1.0M in toluene (21.6 mL, 21.6 mmol) at 0° C. and the mixture was stirred for 10 min. After 3.3 h of stirring at room temperature, the solution was cooled to 0° C. and sodium borohydride (0.98 g, 28.8 mmol) was added. The mixture was stirred for 20 min and MeOH (5.2 mL) was added to the solution (reaction monitored by TLC using 2:8 ethyl acetate/hexanes as eluent). After 15 min, a few drops of triethylamine were added. After another 15 min of stirring, ethyl acetate (25 mL) and a solution of saturated aqueous NH$_4$Cl was added (25 mL). The organic and aqueous layers were separated, and the aqueous layer was extracted with EtOAc (2×40 mL). The combined organic layers were washed with brine, dried (MgSO$_4$), and filtered, and the filtrate was concentrated in vacuo. The residue was purified by column chromatography on silica gel using EtOAc/hexanes modified with 0.1% Et$_3$N (5:95 to 3:7) to give the product (61b) (2.16 g, 65%) as a colorless oil. One drop of Et$_3$N was added to suppress lactonization.

Step 3: Synthesis of hexyl 5-((chlorosulfonyl)oxy)-4,4-dimethylpentanoate (61)

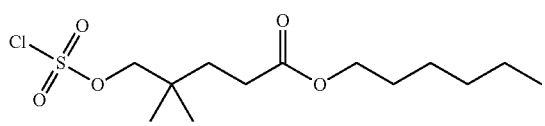 [SMILES: CCCCCCOC(=O)CCC(C)(C)COS(=O)(=O)Cl]

A solution of sulfuryl chloride (0.38 mL, 5.2 mmol) in Et$_2$O (8.5 mL) was cooled to −78° C. under a nitrogen atmosphere. A solution of hexyl 5-hydroxy-4,4-dimethylpentanoate (61b) (0.60 g, 2.6 mmol) and pyridine (0.42 mL, 5.2 mmol) in Et$_2$O (8.5 mL) was added dropwise to the sulfuryl chloride solution over the course of 10 min. The syringe was rinsed with Et$_2$O (3×1 mL) and the rinse was also added to the mixture. The mixture was stirred for 4.5 h (reaction monitored by TLC using 2:8 EtOAc/hexanes as eluent). The solids were filtered off and the solvent was concentrated in vacuo to give the product (61) as a colorless oil with a quantitative yield. To this was added 3 mL of THF and the solution was stored at −78° C. This was used in the next step without further purification.

Example 62

Synthesis of heptyl 5-((chlorosulfonyl)oxy)-4,4-dimethylpentanoate (62)

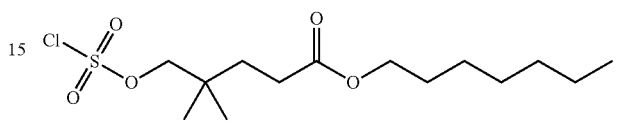

Step 1: Synthesis of sodium 5-(heptyloxy)-2,2-dimethyl-5-oxopentanoate (62a)

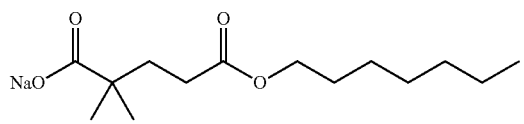

To a solution of 2,2-dimethylglutaric anhydride (5.0 g, 35.2 mmol) in 1-heptanol (40 mL) was added a solution of sodium heptan-1-olate (6.01 g, 43.5 mmol) in 1-heptanol (30 mL). After stirring overnight the solvent was evaporated and the resulting solid was suspended in Et$_2$O (80 mL). The mixture was filtered and the solid was washed with Et$_2$O (2×40 mL). The solid was dried under high vacuum to afford the product (62a) (7.89 g, 80%) as a solid. $^1$H-NMR (300 MHz, D$_2$O): δ 4.14 (t, J=6.5 Hz, 2H), 2.36-2.32 (m, 2H), 1.82-1.77 (m, 2H), 1.74-1.63 (m, 2H), 1.40-1.31 (m, 8H), 1.11 (s, 6H), 0.92-0.87 (m, 3H). The spectrum revealed that the product was contaminated with a small amount of an unidentified substance.

Step 2: Synthesis of heptyl 5-hydroxy-4,4-dimethylpentanoate (62b)

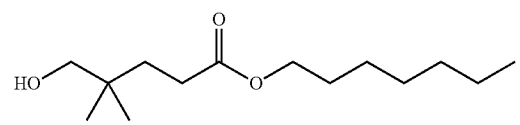 [SMILES: CCCCCCCOC(=O)CCC(C)(C)CO]

To a suspension of sodium 5-(heptyloxy)-2,2-dimethyl-5-oxopentanoate (62a) (7.89 g, 28.1 mmol) in a mixture of THF (61 mL) and DMF (20 mL) was added isopropyl chloroformate, 1.0M in toluene (42.2 mL, 42.2 mmol) at 0° C. and the mixture was stirred for 10 min. After 4 h of stirring at room temperature, the suspension was cooled to 0° C. and sodium borohydride (1.9 g, 56.3 mmol) was added. The mixture was stirred for 20 min and then MeOH (10 mL) was added to the solution (reaction monitored by TLC using 2:8 ethyl acetate/hexanes). After 30 min of stirring, EtOAc (50 mL), a few drops of Et$_3$N, and a saturated aqueous solution of NH$_4$Cl were added (50 mL).

The aqueous and organic layers were separated, and the aqueous layer was extracted with EtOAc (2×80 mL). The combined organic layers were washed with brine (80 mL), and the filtrate was concentrated in vacuo. The residual solution was washed with H$_2$O (3×100 mL), brine (100 mL), and dried (Na$_2$SO$_4$), and concentrated. During all extractions, several drops of Et$_3$N were added to the organic layer to suppress lactonization. The residue was purified by column chromatography on silica gel using EtOAc/hexanes modified with 0.1% Et$_3$N (0:1 to 3:7) as eluent to give the product (62a) (3.35 g, 49% crude) as a colorless oil.

Step 3: Synthesis of heptyl 5-((chlorosulfonyl)oxy)-4,4-dimethylpentanoate (62)

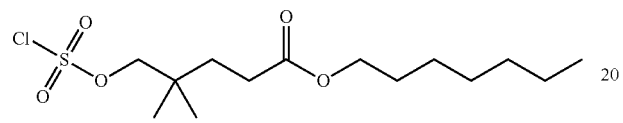

A solution of sulfuryl chloride (0.60 mL, 8.2 mmol) in Et$_2$O (13 mL) was cooled to −78° C. under a nitrogen atmosphere. A solution of heptyl 5-hydroxy-4,4-dimethylpentanoate (62a) (1.0 g, 4.1 mmol) and pyridine (0.66 mL, 8.2 mmol) in Et$_2$O (13 mL) was added dropwise to the sulfuryl chloride solution over the course of 10 min. The syringe was rinsed with diethyl ether (3×1 mL) and this was also added to the mixture. The mixture was stirred for 4.5 h (reaction monitored by TLC using 2:8 ethyl acetate/hexanes as eluent). The solids were filtered-off, and the filtrate concentrated in vacuo to give the product (62) (1.13 g) as a colorless oil. To this was added 3 mL of THF and the solution stored at −78° C. This was used in the next step without further purification.

Example 63

Synthesis of 2-methoxyethyl 5-((chlorosulfonyl)oxy)-4,4-dimethylpentanoate (63)

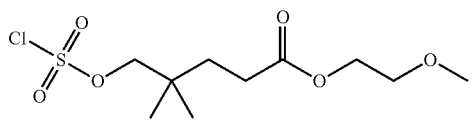 [SMILES: COCCOC(=O)CCC(C)(C)COS(=O)(=O)Cl]

Step 1: Synthesis of sodium 5-(2-methoxyethoxy)-2,2-dimethyl-5-oxopentanoate (63a)

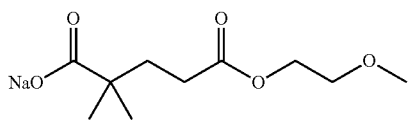

To a solution of 2,2-dimethylglutaric anhydride (5.0 g, 35.2 mmol) in 2-methoxyethanol (30 mL) was added a solution sodium 2-methoxyethanolate (4.27 g, 43.5 mmol) in 2-methoxyethanol (30 mL). After 20 h of stirring, the solvent was evaporated and the resulting solid was suspended in Et$_2$O (80 mL). The mixture was filtered and the solid was washed with Et$_2$O (2×40 mL). The solid was dried under high vacuum to afford the product (63a) (6.44 g, 76%) as a solid. $^1$H-NMR (300 MHz, D$_2$O): δ 4.30-4.27 (m, 2H), 3.75-3.72 (m, 2H), 3.42 (s, 3H), 2.41-2.36 (m, 2H), 1.83-1.78 (m, 2H), 1.12 (s, 6H). The spectrum revealed that the product was contaminated with a small amount of an unidentified substance.

Step 2: Synthesis of 2-methoxyethyl 5-hydroxy-4,4-dimethylpentanoate (63b)

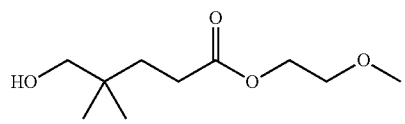

To a suspension of sodium 5-(2-methoxyethoxy)-2,2-dimethyl-5-oxopentanoate (63a) (6.44 g, 26.8 mmol) in a mixture of THF (58 mL) and DMF (19 mL) was added isopropyl chloroformate, 1.0M in toluene (40.2 mL, 40.2 mmol) at 0° C. and stirred for 10 min. After 4 h of stirring at room temperature, the mixture was stored at −78° C. overnight. The suspension was cooled to 0° C. and sodium borohydride (1.81 g, 53.6 mmol) was added. The mixture was stirred for 20 min and then MeOH (9.6 mL) was added to the solution (reaction monitored by TLC using 3:7 EtOAc/hexanes as eluent). After 30 min of stirring, EtOAc (50 mL) with a few drops of Et$_3$N followed by a saturated aqueous solution of NH$_4$Cl (50 mL) were added. The layers were separated and the aqueous layer was extracted with EtOAc (2×80 mL). The combined organic layers were washed with brine, dried (MgSO$_4$), filtered, and the filtrate was concentrated in vacuo. The residue was purified by column chromatography on silica gel to give the product (63b) (2.54 g, 46% crude).

Step 3: Synthesis of 2-methoxyethyl 5-((chlorosulfonyl)oxy)-4,4-dimethylpentanoate (63)

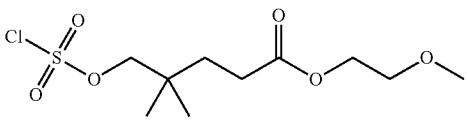 [SMILES: COCCOC(=O)CCC(C)(C)COS(=O)(=O)Cl]

A solution of sulfuryl chloride (0.36 mL, 4.9 mmol) in Et$_2$O (8 mL) was cooled to −78° C. under a nitrogen atmosphere. A solution of 2-methoxyethyl 5-hydroxy-4,4-dimethylpentanoate (63b) (0.50 g, 2.4 mmol) and pyridine (0.40 mL, 4.9 mmol) in Et$_2$O (8 mL) was added dropwise to the sulfuryl chloride solution over the course of 10 min. The syringe was rinsed with Et$_2$O (3×1 mL) and the rinse was also added to the mixture. The mixture was stirred for 4.5 h (reaction monitored by TLC using 2:8 EtOAc/hexanes as eluent). The solids were filtered-off and the filtrate concentrated in vacuo to give the product (63) (0.60 g, 2.0 mmol) as a colorless oil. To this was added 3 mL of THF and the solution was stored at −78° C. This was used in the next step without further purification.

Example 64

Synthesis of 5-((chlorosulfonyl)oxy)-2,2,4,4-tetramethylpentyl propionate (64)

Step 1: Synthesis of 5,5-dimethyltetrahydro-2H-pyran-2-one (64a)

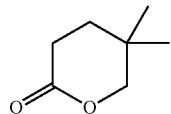

To a solution of ethyl 5-hydroxy-4,4-dimethylpentanoate (57a) (26.5 g, 152.1 mmol) in dichloromethane (683 mL) was added trifluoroacetic acid (1.75 mL, 22.8 mmol). The mixture was stirred at room temperature for 3 d. The reaction was quenched with a saturated aqueous sodium bicarbonate solution (150 mL), stirred rapidly for 30 min, and the layers were separated. The organic layer was washed with brine (150 mL), dried ($Na_2SO_4$), and concentrated under vacuum. The residue was purified by column chromatography on silica gel flash using EtOAc/hexanes (0:1 to 45:55) as eluent to give the product (64a) (8.79 g, 45%) as a colorless oil. The product was used in the next step without further purification and was contaminated with small amounts of unidentified byproducts. $^1$H-NMR (300 MHz, $CDCl_3$): δ 3.97 (s, 2H), 2.56 (t, J=7.4 Hz, 2H), 1.69 (t, J=7.4 Hz, 2H), 1.05 (s, 6H).

Step 2: Synthesis of 3,3,5,5-tetramethyltetrahydro-2H-pyran-2-one (64b)

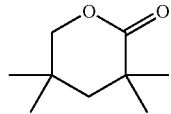

5,5-Dimethyltetrahydro-2H-pyran-2-one (64a) (8.79 g, 68.6 mmol) was dissolved in anhydrous DMF (150 mL) and the resulting solution was cooled to 0° C. under an inert atmosphere of argon. Sodium hydride, 60% in mineral oil (8.23 g, 205.7 mmol) was added in one portion and the mixture stirred for 20 min. This was followed by the drop-wise addition of MeI (17.1 mL, 274.3 mmol). The resulting solution was stirred at 0° C. for 20 min and then at room temperature for 3 d. The mixture was diluted with EtOAc (350 mL) and then quenched at 0° C. via the careful dropwise addition of a saturated aqueous solution of $NH_4Cl$ (100 mL). The aqueous and organic layers were separated, and the aqueous layer was extracted with EtOAc (350 mL). The combined organic layers were washed with $H_2O$ (6×300 mL), brine (300 mL), dried ($Na_2SO_4$), and concentrated under vacuum. The residue was purified by column chromatography on silica using EtOAc/hexanes (1:9) as eluent to give the product (64b) (3.42 g, 32%). The product was used in the next step without further purification and was contaminated with small amounts of various unidentified byproducts. $^1$H-NMR (300 MHz, $CDCl_3$): δ 4.01 (s, 2H), 1.62 (s, 2H), 1.30 (s, 6H), 1.02 (s, 6H).

Step 3: Synthesis of 2,2,4,4-tetramethylpentane-1,5-diol (64c)

A necked round bottom flask containing a stirring slurry of 95% $LiAlH_4$ (0.87 g, 21.6 mmol) in $Et_2O$ (126 mL) was cooled to 0° C. under an atmosphere of argon. To this slurry was added a solution of 3,3,5,5-tetramethyltetrahydro-2H-pyran-2-one (64b) (2.94 g, 18.8 mmol) in $Et_2O$ (50 mL) under an inert atmosphere of argon. This was warmed to room temperature and stirred overnight. The mixture was cautiously quenched with $H_2O$ (80 mL) then 3 M NaOH (120 mL) and stirred for 30 min. The mixture was filtered through a pad of Celite®, and the pad was rinsed thoroughly with $Et_2O$. The aqueous and organic layers were separated, and the aqueous layer was extracted with $Et_2O$ (3×100 mL). The combined organic layers were concentrated under vacuum and the residue was purified by column chromatography on silica gel using EtOAc/hexanes (2:8 to 6:4) as eluent to give the product (64c) (2.59 g, 86%) as a solid. $^1$H-NMR (300 MHz, $CDCl_3$): δ 3.41 (s, 4H), 2.55 (s, 2H), 1.34 (s, 2H), 0.95 (s, 12H)

Step 4: Synthesis of 5-hydroxy-2,2,4,4-tetramethylpentyl propionate (64d)

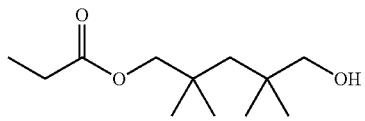

To a stirring solution of 2,2,4,4-tetramethylpentane-1,5-diol (64c) (0.48 g, 3.0 mmol) and pyridine (0.24 mL, 3.0 mmol) in DCM (20 mL) was added propionyl chloride (0.26 mL, 3.0 mmol) dropwise over the course of 30 min at ca. 0° C. (ice bath). The reaction mixture was stirred overnight at room temperature. The mixture was diluted with $H_2O$ (20 mL), and the layers were separated. The aqueous layer was extracted with DCM (2×20 mL), and the combined organic layers were washed with brine (20 mL), dried ($Na_2SO_4$), and concentrated under vacuum. The residue was purified by column chromatography on silica gel EtOAc/hexanes (5:95 to 6:4) as eluent to give the product (64d) (411 mg, 63%). $^1$H-NMR (300 MHz, $CDCl_3$): δ 3.85 (s, 2H), 3.32 (s, 2H), 2.37 (q, J=7.7 Hz, 2H), 1.50 (s, 1H), 1.36 (s, 2H), 1.16 (t, J=7.5 Hz, 3H), 1.03 (s, 6H), 0.99 (s 6H).

Step 5: Synthesis of 5-((chlorosulfonyl)oxy)-2,2,4,4-tetramethylpentyl propionate (64)

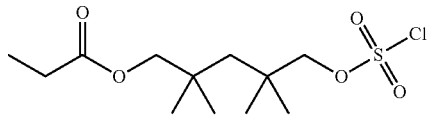 [SMILES: CCC(=O)OCC(C)(C)CC(C)(C)COS(=O)(=O)Cl]

A solution of sulfuryl chloride (0.136 mL, 1.9 mmol) in Et$_2$O (6.4 mL) was cooled to −78° C. under an atmosphere of argon. A solution of 5-hydroxy-2,2,4,4-tetramethylpentyl propionate (39d) (404 mg, 1.9 mmol) and pyridine (0.15 mL, 1.9 mmol) in Et$_2$O (6.4 mL) was added dropwise to the sulfuryl chloride solution over the course of 10 min. The mixture was warmed to room temperature and stirred for 70 min. The solids were filtered to give a solution of the product (64) in Et$_2$O as the filtrate. The yield was assumed quantitative, and the mixture was used in the next step without further purification.

Example 65

Synthesis of 5-((chlorosulfonyl)oxy)-2,2,4,4-tetramethylpentyl benzoate (65)

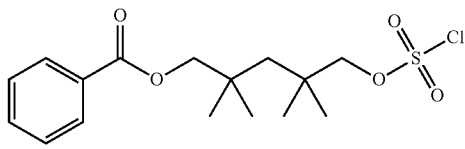 [SMILES: CC(C)(COC(=O)c1ccccc1)CC(C)(C)COS(=O)(=O)Cl]

Step 1: Synthesis of 5-hydroxy-2,2,4,4-tetramethylpentyl benzoate (65a)

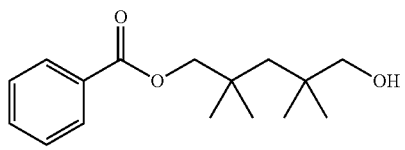 [SMILES: CC(C)(CO)CC(C)(C)COC(=O)c1ccccc1]

To a stirred solution of 2,2,4,4-tetramethylpentane-1,5-diol (64c) (0.48 g, 3.0 mmol) and pyridine (0.24 mL, 3.0 mmol) in DCM (20 mL) was added benzoyl chloride (0.37 mL, 3.0 mmol) dropwise over the course of 30 min at ca. 0° C. (ice bath) under an atmosphere of argon. The reaction mixture was stirred overnight at room temperature. The mixture was diluted with H$_2$O (20 mL), and the layers were separated. The aqueous layer was extracted with DCM (2×20 mL), and the combined organic layers were washed with brine (20 mL), dried (Na$_2$SO$_4$), and concentrated under vacuum. The residue was purified by column chromatography on silica gel using EtOAc/hexanes (5:95 to 1:1) as eluent to give the product (65a) (548 mg, 69%) as an oil. $^1$H-NMR (300 MHz, CDCl$_3$): δ 8.06 (d, J=8.4 Hz, 2H), 7.59-7.55 (m, 1H), 7.48-7.43 (m, 2H), 4.09 (s, 2H), 3.35 (s, 2H), 1.48 (s, 2H), 1.13 (s, 6H), 1.02 (s, 6H).

Step 2: Synthesis of 5-((chlorosulfonyl)oxy)-2,2,4,4-tetramethylpentyl benzoate (65)

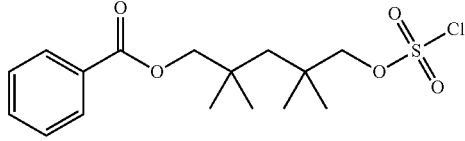 [SMILES: CC(C)(COC(=O)c1ccccc1)CC(C)(C)COS(=O)(=O)Cl]

A solution of sulfuryl chloride (0.15 mL, 2.0 mmol) in Et$_2$O (8.5 mL) was cooled to −78° C. under an atmosphere of argon. A solution of 5-hydroxy-2,2,4,4-tetramethylpentyl benzoate (65a) (541 mg, 2.0 mmol) and pyridine (0.17 mL, 2.0 mmol) in Et$_2$O (8.5 mL) was added dropwise to the sulfuryl chloride solution over the course of 10 min. The mixture was stirred at 0° C. for 20 min, then at room temperature for 90 min. The mixture was filtered and the filtrate used to provide a solution of the product (65) in Et$_2$O (ca. 20 mL). The yield was assumed quantitative and the product was used in the next step without further purification.

Example 66

Synthesis of 5-((chlorosulfonyl)oxy)-2,2,4,4-tetramethylpentyl 2,6-dimethylbenzoate (66)

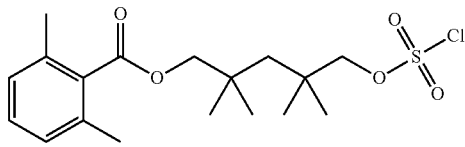 [SMILES: Cc1cccc(C)c1C(=O)OCC(C)(C)CC(C)(C)COS(=O)(=O)Cl]

Step 1: Synthesis of 5-hydroxy-2,2,4,4-tetramethylpentyl 2,6-dimethylbenzoate (66a)

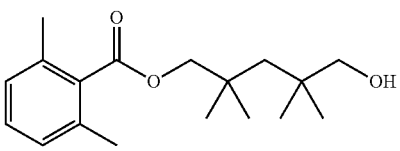 [SMILES: Cc1cccc(C)c1C(=O)OCC(C)(C)CC(C)(C)CO]

To a stirred solution of 2,2,4,4-tetramethylpentane-1,5-diol (61c) (0.48 g, 3.0 mmol) and pyridine (0.24 mL, 3.0 mmol) in DCM (20 mL) was added 2,6-dimethylbenzoyl chloride (0.45 mL, 3.0 mmol) dropwise over the course of 30 min at 0° C. (ice bath) under an atmosphere of argon. The reaction mixture was stirred overnight at room temperature. The mixture was diluted with H$_2$O (20 mL), and the layers were separated. The aqueous layer was extracted with DCM (2×20 mL), and the combined organic layers were washed with brine (20 mL), dried (Na$_2$SO$_4$), and concentrated under vacuum. The residue was purified by column chromatography on silica gel using EtOAc/hexanes (5:95 to 1:1) as eluent to give the product (66a) (462 mg, 53%) as an oil. $^1$H-NMR (300 MHz, CDCl$_3$): δ 7.22-7.17 (m, 1H), 7.04 (d, J=7.5 Hz, 2H), 4.10 (s, 2H), 3.32 (s, 2H), 2.33 (s, 6H), 1.41 (s, 2H), 1.10 (s, 6H), 1.00 (s, 6H).

Step 2: Synthesis of 5-((chlorosulfonyl)oxy)-2,2,4,4-tetramethylpentyl 2,6-dimethylbenzoate (66)

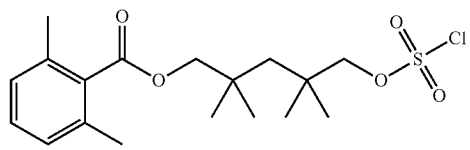 [SMILES: Cc1cccc(C)c1C(=O)OCC(C)(C)CC(C)(C)COS(=O)(=O)Cl]

A solution of sulfuryl chloride (0.11 mL, 1.5 mmol) in Et$_2$O (7 mL) was cooled to −78° C. under an atmosphere of argon. A solution of 5-hydroxy-2,2,4,4-tetramethylpentyl 2,6-dimethylbenzoate (66a) (453 mg, 1.5 mmol) and pyridine (0.13 mL, 1.5 mmol) in Et$_2$O (7 mL) was added dropwise to the sulfuryl chloride solution over the course of 10 min. The mixture was stirred in an ice bath for 20 min, then at room temperature for 90 min. The mixture was filtered and the filtrate stored to give a solution of the product (66) in Et$_2$O (ca. 20 mL). The yield assumed quantitative. This mixture was used in the next step without further purification (a small quantity was concentrated under vacuum and the NMR taken of the residue). $^1$H-NMR (300 MHz, CDCl$_3$): δ 7.21 (t, J=7.7 Hz, 1H), 7.05 (d, J=7.2 Hz, 2H), 4.20 (s, 2H), 4.07 (s, 2H), 2.32 (s, 6H), 1.50 (s, 2H), 1.14 (s, 6H), 1.12 (s, 6H).

Example 67

Synthesis of (3-methyl-2-oxotetrahydrofuran-3-yl)methyl sulfochloridate (67)

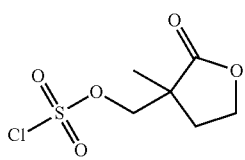

Pyridine (0.28 mL, 3.5 mmol) was added to a stirred mixture of 3-(hydroxymethyl)-3-methyldihydrofuran-2 (3H)-one (prepared according to *Synlett* 2010, 2625-2627) (0.30 g, 2.3 mmol) and Et$_2$O (8 mL) under an atmosphere of argon. The solution was cooled to −78° C. and sulfuryl chloride (0.28 mL, 3.5 mmol) in Et$_2$O (3 mL) was slowly added at −78° C. The mixture was stirred at −78° C. for 1 h and then warmed to room temperature and stirred for 1 h. The reaction mixture was filtered to remove the pyridine salt, and the filtrate was concentrated under vacuum to give the product (67) as an oil, that was used directly in the next step without further purification (yield assumed quantitative).

Example 68

Synthesis of 3-((chlorosulfonyl)oxy)-2,2-dimethylpropyl pivalate (68)

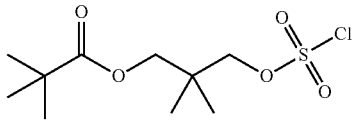 [SMILES: CC(C)(COC(=O)C(C)(C)C)COS(=O)(=O)Cl]

Step 1: Synthesis of 3-hydroxy-2,2-dimethylpropyl pivalate (68a)

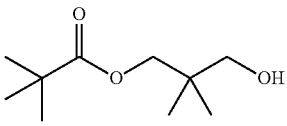

To a stirred solution of 2,2-dimethylpropane-1,3-diol (5.07 g, 48.7 mmol) in DCM (50 mL) at 0° C. under an atmosphere of argon was added trimethylacetyl chloride (2.0 mL, 16.2 mmol), pyridine (2.63 mL, 32.5 mmol) and N,N-4-dimethylaminopyridine (0.4 g, 3.2 mmol). The mixture was allowed to warm to room temperature and stirred at room temperature overnight. The mixture was cooled to 0° C. and the reaction was quenched with the addition of 1N HCl (50 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 1:5) as eluent to give the product (68a) as an oil. $^1$H-NMR (300 MHz, CDCl$_3$): δ 3.92 (s, 2H), 3.27 (s, 2H), 1.22 (s, 9H), 0.92 (s, 6H).

Step 2: Synthesis of 3-((chlorosulfonyl)oxy)-2,2-dimethylpropyl pivalate (68)

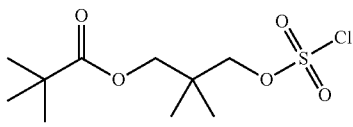 [SMILES: CC(C)(COC(=O)C(C)(C)C)COS(=O)(=O)Cl]

Pyridine (0.75 mL, 9.3 mmol) was added to a stirred mixture of 3-hydroxy-2,2-dimethylpropyl pivalate (68a) (1.17 g, 6.2 mmol) and Et$_2$O (20 mL) under an atmosphere of argon. The solution was cooled to −78° C. and sulfuryl chloride (0.75 mL, 9.3 mmol) in Et$_2$O (8 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (68) as an oil, that was used directly in the next step without further purification (yield assumed quantitative).

Example 69

Synthesis of 3-((chlorosulfonyl)oxy)-2,2-dimethylpropyl 3-chloro-2,6-dimethoxybenzoate (69)

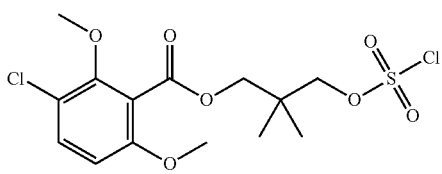 [SMILES: COc1ccc(Cl)c(OC)c1C(=O)OCC(C)(C)COS(=O)(=O)Cl]

Step 1: Synthesis of 3-hydroxy-2,2-dimethylpropyl 2,6-dimethoxybenzoate (69a)

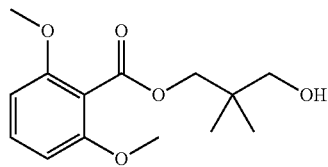 [SMILES: COc1cccc(OC)c1C(=O)OCC(C)(C)CO]

To a stirred solution of 2,2-dimethylpropane-1,3-diol (3.89 g, 37.4 mmol) in DCM (40 mL) at 0° C. under an atmosphere of argon was added 2,6-dimethoxybenzoyl chloride (80% purity; 3.13 g, 12.5 mmol), pyridine (2.02 mL, 24.9 mmol), and N,N-4-dimethylaminopyridine (0.3 g, 2.5 mmol). The mixture was allowed to warm to room temperature and stirred at room temperature overnight. The mixture was cooled to 0° C. and the reaction was quenched by the addition of 1N HCl (50 mL), then extracted with DCM (twice). The combined organic layers were washed with sat. sodium bicarbonate and brine, then dried ($Na_2SO_4$), and concentrated under vacuum. The residue was purified by column chromatography on silica gel using EtOAc/hexanes (0:1 to 1:5) as eluent to give the product (69a) as an oil. $^1$H-NMR (300 MHz, $CDCl_3$): δ 7.19 (t, J=5.0 Hz, 1H), 6.48 (d, J=8.1 Hz, 2H), 4.09 (s, 2H), 3.71 (s, 6H), 3.33 (s, 2H), 0.89 (s, 6H).

Step 2: Synthesis of 3-((chlorosulfonyl)oxy)-2,2-dimethylpropyl 3-chloro-2,6-dimethoxybenzoate (69)

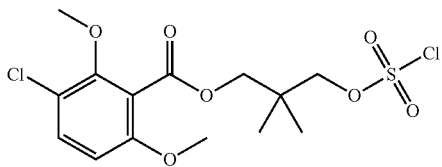 [SMILES: COc1ccc(Cl)c(OC)c1C(=O)OCC(C)(C)COS(=O)(=O)Cl]

Pyridine (0.16 mL, 2.0 mmol) was added to a stirred mixture of 3-hydroxy-2,2-dimethylpropyl 2,6-dimethoxybenzoate (69a) (0.35 g, 1.3 mmol) and $Et_2O$ (10 mL) under an atmosphere of argon. The solution was cooled to −78° C. and sulfuryl chloride (0.16 mL, 2.0 mmol) in $Et_2O$ (8 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (69) as an oil, that was used directly in the next step without further purification (yield assumed quantitative). $^1$H-NMR (300 MHz, $CDCl_3$): δ 7.36 (d, J=8.7 Hz, 1H), 6.66 (d, J=8.7 Hz, 1H), 4.35 (s, 2H), 4.21 (s, 2H), 3.89 (s, 3H), 3.81 (s, 3H), 1.13 (s, 6H).

Example 70

Synthesis of 4-hydroxy-2,2,3,3-tetramethylbutyl 2,6-dimethylbenzoate (70)

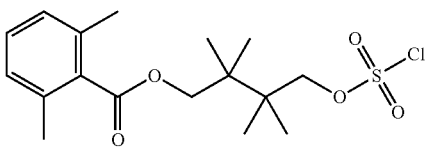 [SMILES: Cc1cccc(C)c1C(=O)OCC(C)(C)C(C)(C)COS(=O)(=O)Cl]

Step 1: Synthesis of 2,2,3,3-tetramethylbutane-1,4-diol (70a)

A solution of 3,3,4,4-tetramethyldihydrofuran-2(3H)-one (prepared according to U.S. Pat. No. 3,658,849) (1.0 g, 7.0 mmol) in $Et_2O$ (28 mL) was added to a stirring slurry of $LiAlH_4$ (95%; 0.32 g, 8.1 mmol) in $Et_2O$ (28 mL) at 0° C. under an atmosphere of argon. The mixture was warmed to room temperature and stirred overnight. Sodium sulfate decahydrate was slowly added until effervescence in the flask ceased. The solid was filtered through a pad of Celite®, and the pad was washed with EtOAc. The filtrate was concentrated under vacuum, and the residue was purified by column chromatography on silica gel using EtOAc/hexanes (0:1 to 7:3) as eluent to give the product (70a) (0.7 g) as a solid. $^1$H-NMR (300 MHz, $CDCl_3$): δ 3.41 (s, 4H), 0.88 (s, 12H).

Step 2: Synthesis of 4-hydroxy-2,2,3,3-tetramethylbutyl 2,6-dimethylbenzoate (70b)

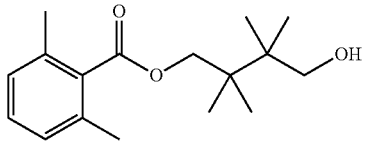 [SMILES: Cc1cccc(C)c1C(=O)OCC(C)(C)C(C)(C)CO]

To a stirred solution of 2,2,3,3-tetramethylbutane-1,4-diol (70a) (0.71 g, 4.9 mmol) in DCM (15 mL) at 0° C. under an atmosphere of argon was added 2,6-dimethylbenzoyl chloride (0.2 mL, 1.6 mmol), pyridine (0.26 mL, 3.2 mmol) and N,N-4-dimethylaminopyridine (0.04 g, 0.3 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (70b) as an oil (266 mg). $^1$H-NMR (300 MHz, CDCl$_3$): δ 7.18 (t, J=8.4 Hz, 1H), 7.02 (d, J=6.9 Hz, 2H), 4.25 (s, 2H), 3.51 (s, 2H), 2.31 (s, 6H), 0.98 (s, 6H), 0.93 (s, 6H).

Step 3: Synthesis of 4-((chlorosulfonyl)oxy)-2,2,3,3-tetramethylbutyl 2,6-dimethylbenzoate (70)

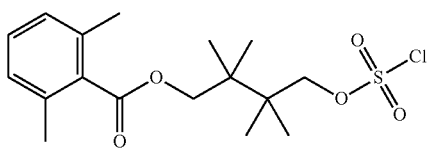 [SMILES: Cc1cccc(C)c1C(=O)OCC(C)(C)C(C)(C)COS(=O)(=O)Cl]

Pyridine (0.11 mL, 1.3 mmol) was added to a stirred mixture of 4-hydroxy-2,2,3,3-tetramethylbutyl 2,6-dimethylbenzoate (70b) (0.26 g, 0.9 mmol) and Et$_2$O (10 mL) under an atmosphere of argon. The solution was cooled to −78° C. and sulfuryl chloride (0.11 mL, 1.3 mmol) in Et$_2$O (3 mL) was slowly added at −78° C. The mixture was stirred at −78° C. for 1 h and then warmed to room temperature and stirred for 1 h. The reaction mixture was filtered to remove the pyridine salt, and the filtrate was concentrated under vacuum to give the product (70) as an oil, that was used directly in the next step without further purification (yield assumed quantitative).

Example 71

Synthesis of 4-((chlorosulfonyl)oxy)-2,2,3,3-tetramethylbutyl benzoate (71)

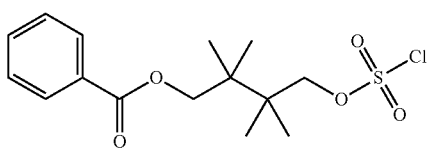 [SMILES: CC(C)(COC(=O)c1ccccc1)C(C)(C)COS(=O)(=O)Cl]

Step 1: Synthesis of 4-hydroxy-2,2,3,3-tetramethylbutyl benzoate (71a)

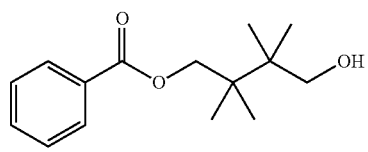 [SMILES: CC(C)(CO)C(C)(C)COC(=O)c1ccccc1]

To a stirred solution of 2,2,3,3-tetramethylbutane-1,4-diol (67a) (0.74 g, 5.0 mmol) in DCM (15 mL) at 0° C. under an atmosphere of argon was added benzoyl chloride (0.25 mL, 2.0 mmol), pyridine (0.33 mL, 4.0 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (71a) as an oil. $^1$H-NMR (300 MHz, CDCl$_3$): δ 8.05 (d, J=7.2 Hz, 2H), 7.58 (t, J=7.4 Hz, 1H), 7.46 (t, J=7.4 Hz, 2H), 4.27 (s, 2H), 3.59 (s, 2H), 1.05 (s, 6H), 0.99 (s, 6H).

Step 2: Synthesis of 4-((chlorosulfonyl)oxy)-2,2,3,3-tetramethylbutyl benzoate (71)

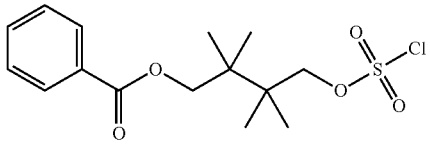 [SMILES: CC(C)(COC(=O)c1ccccc1)C(C)(C)COS(=O)(=O)Cl]

Pyridine (0.29 mL, 3.6 mmol) was added to a stirred mixture of 4-hydroxy-2,2,3,3-tetramethylbutyl benzoate (71a) (0.70 g, 2.8 mmol) and Et$_2$O (10 mL) under an atmosphere of argon. The solution was cooled to −78° C. and sulfuryl chloride (0.29 mL, 3.6 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (71) as an oil, that was used directly in the next step without further purification (yield assumed quantitative).

Example 72

Synthesis of 4-((chlorosulfonyl)oxy)-2,2,3,3-tetramethylbutyl propionate (72)

Step 1: Synthesis of 4-hydroxy-2,2,3,3-tetramethylbutyl propionate (72a)

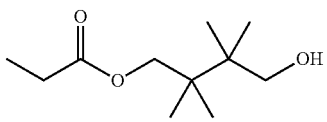

To a stirred solution of 2,2,3,3-tetramethylbutane-1,4-diol (70a) (0.59 g, 4.0 mmol) in DCM (15 mL) at 0° C. under an atmosphere of argon was added propionyl chloride (0.25 mL, 3.1 mmol), pyridine (0.33 mL, 4.0 mmol) and N,N-4- dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give di-acylated material, followed by the product (72a) (300 mg) as an oil. $^1$H-NMR (300 MHz, CDCl$_3$): δ 3.99 (s, 2H), 3.49 (s, 2H), 2.38-2.31 (q, 2H), 1.15 (t, J=7.8 Hz, 3H), 0.91 (d, J=4.8 Hz, 12H).

Step 2: Synthesis of 4-((chlorosulfonyl)oxy)-2,2,3,3-tetramethylbutyl propionate (72)

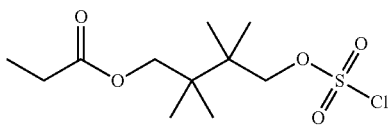 [SMILES: CCC(=O)OCC(C)(C)C(C)(C)COS(=O)(=O)Cl]

Pyridine (0.16 mL, 1.9 mmol) was added to a stirred mixture of 4-hydroxy-2,2,3,3-tetramethylbutyl propionate (72a) (0.30 g, 1.5 mmol) and Et$_2$O (10 mL) under an atmosphere of argon. The solution was cooled to −78° C. and sulfuryl chloride (0.16 mL, 1.9 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (72) as an oil, that was used directly in the next step without further purification (yield assumed quantitative).

Example 73

Synthesis of (3-methyl-2-oxotetrahydro-2H-pyran-3-yl)methyl sulfochloridate (73)

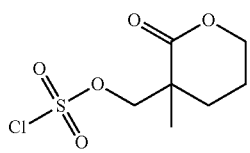

Step 1: Synthesis of 3-((benzyloxy)methyl)-3-methyltetrahydro-2H-pyran-2-one (73a)

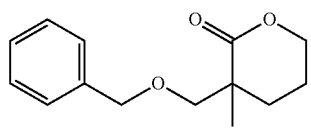 [SMILES: CC1(COCc2ccccc2)CCCOC1=O]

δ-Valerolactone (5.23 g, 52.2 mmol) was dissolved in a mixture of THF (120 mL) and HMPA (9.2 mL) under an atmosphere of argon. The reaction mixture was cooled to −78° C. and stirred for 10 min. A solution of lithium diisopropylamide, 2.0 M in THF (28.7 mL, 57.5 mmol) was added dropwise over 5 min. The reaction was stirred at −78° C. for 30 min and then neat MeI (3.3 mL, 52.8 mmol) was added to the reaction over 5 min. The mixture was stirred at −78° C. for 30 min then removed from the cooling bath and allowed to warm to 0° C. and stirred for 30 min (note: the mixture gradually became yellow during this time). The mixture was re-cooled to −78° C. and stirred for 10 min, and then an additional amount of lithium diisopropylamide, 2.0 M in THF (28.7 mL, 57.5 mmol) was added over 5 min. The reaction was stirred at −78° C. for 30 min, then neat benzyl chloromethyl ether (70%; 10.5 mL, 52.8 mmol) was added over 5 min. The mixture was left to warm to room temperature and stirred for 16h. The solvent was then removed under vacuum and the residue was partitioned between saturated ammonium chloride (200 mL) and EtOAc (200 mL). The aqueous layer was extracted with EtOAc (2×100 mL) and the combined organic layers were washed with brine (2×100 mL), dried (Na$_2$SO$_4$), filtered, and concentrated under vacuum (19 g). The residue was dry-loaded onto silica gel and purified by column chromatography on silica gel (120 g cartridge) using EtOAc/hexanes as eluent to give the product contaminated with an impurity (6.9 g). The residue was re-purified by column chromatography on silica gel using DCM/hexanes (0:1 to 4:1) as eluent to give the product (73a) (1.76 g) as a liquid. $^1$H-NMR (300 MHz, CDCl$_3$): δ 7.29-7.37 (m, 5H), 4.61 (dd, J=21.0, 12.3 Hz, 2H), 4.32-4.38 (m, 2H), 3.26-3.81 (dd, J=15.8, 8.1 Hz, 2H), 2.21-2.30 (m, 1H), 1.87-1.94 (m, 2H), 1.59-1.66 (m, 1H), 1.23 (s, 3H).

Step 2: Synthesis of 3-(hydroxymethyl)-3-methyltetrahydro-2H-pyran-2-one (73b)

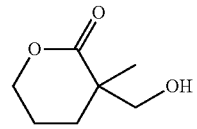

3-((Benzyloxy)methyl)-3-methyltetrahydro-2H-pyran-2-one (73a) (0.52 g, 2.2 mmol) was dissolved in 2-propanol (25 mL) and the solution was degassed and back-flushed with argon. (Note: do not use MeOH as solvent, as it may ring-open the lactone during hydrogenation). Palladium on carbon, 10% (0.26 g, 0.2 mmol), was added to the mixture and the system was sealed. The reaction was degassed and back-flushed with hydrogen (3 times) and stirred under an atmosphere of hydrogen for 2 h. The suspension was filtered through a pad of Celite®, and the filter cake washed with fresh 2-propanol (2×50 mL). The filtrate was concentrated under vacuum, and the product (73b) was used without further purification. $^1$H-NMR (300 MHz, CDCl$_3$): δ 4.27-4.45 (m, 2H), 3.67 (d, J=11.4 Hz, 1H), 3.52 (d, J=11.1 Hz, 1H), 1.84-2.03 (m, 2H), 1.58-1.64 (m, 1H), 1.29 (s, 3H).

Step 3: Synthesis of (3-methyl-2-oxotetrahydro-2H-pyran-3-yl)methyl sulfochloridate (73)

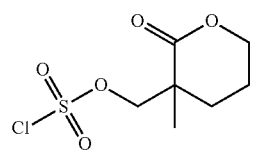

A solution of 3-(hydroxymethyl)-3-methyltetrahydro-2H-pyran-2-one (73b) (0.32 g, 2.2 mmol) and pyridine (0.21 mL, 2.6 mmol) in Et$_2$O (10 mL) was cooled to −78° C. under an atmosphere of argon. Neat sulfuryl chloride (0.21 mL, 2.6 mmol) was added dropwise to the above solution via a syringe. The mixture was stirred at −78° C. for 10 min, then the flask was warmed to room temperature and stirred for 1 h (monitored by TLC EtOAc/hexanes, 3:7). A precipitate formed to give a thick suspension. The suspension was filtered through a 0.45 μM Teflon® filter, and the filter cake rinsed with fresh Et$_2$O (2×5 mL). An aliquot (0.5 mL) was taken and concentrated, and an NMR was obtained for the mixture. The remaining solution containing the product (73) was used directly in the next step. $^1$H-NMR (300 MHz, CDCl$_3$): δ 4.87 (d, J=9.3 Hz, 1H), 4.25-4.50 (m, 2H), 4.32 (d, J=8.7 Hz, 1H), 2.00-2.20 (m, 2H), 1.75-2.00 (m, 2H), 1.39 (s, 3H).

Example 74

Synthesis of 2-(3-((chlorosulfonyl)oxy)-2,2-dimethylpropyl)phenyl acetate (74)

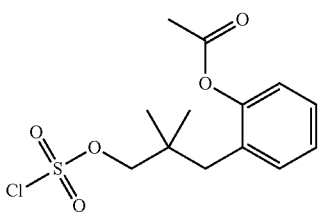 [SMILES: CC(=O)Oc1ccccc1CC(C)(C)COS(=O)(=O)Cl]

Step 1: Synthesis of ethyl 3-(2-methoxyphenyl)-2,2-dimethylpropanoate (74a)

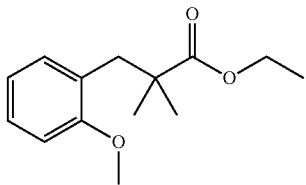 [SMILES: CCOC(=O)C(C)(C)Cc1ccccc1OC]

A stirred solution of lithium diisopropylamide, 2.0 M in THF (26.6 mL, 53.2 mmol) was diluted with THF (100 mL) was cooled to −78° C. under an atmosphere of argon, and stirred for 5 min. Neat ethyl isobutyrate (6.68 mL, 49.7 mmol) was added dropwise over 15 min, and the mixture allowed to stir at −78° C. for 1 h. A solution of 1-(bromomethyl)-2-methoxybenzene (prepared according to *J. Am. Chem. Soc.* 2013, 135, 11951) (12.0 g, 59.7 mmol) in THF (100 mL) was added dropwise over 30 min. The mixture was allowed to warm to room temperature and stirred for 20 h. The reaction was quenched with brine (100 mL) and extracted with Et$_2$O (4×100 mL). The combined organic layers were dried (MgSO$_4$), filtered, and concentrated under vacuum. The crude residue was purified by column chromatography on silica gel (120 g column) using EtOAc/hexanes (0:1 to 5:95) as eluent to give the product (74a) as a liquid (8.06 g, 68%). $^1$H-NMR (300 MHz, CDCl$_3$): δ 7.18 (dt, J=1.8, 8.1 Hz, 1H), 7.06 (dd, J=1.5, 8.1 Hz, 1H), 6.82-6.87 (m, 2H), 4.12 (q, J=6.9 Hz, 2H), 3.77 (s, 3H), 2.92 (s, 2H), 1.26 (t, J=6.9 Hz, 3H), 1.15 (s, 6H).

Step 2: Synthesis of 3,3-dimethylchroman-2-one (74b)

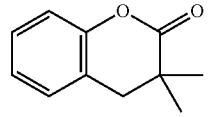

Ethyl 3-(2-methoxyphenyl)-2,2-dimethylpropanoate (74a) (8.1 g, 34.2 mmol) was dissolved in DCM (200 mL) and cooled to 0° C. under an atmosphere of argon. A solution of BBr$_3$ (3.6 mL, 37.7 mmol) in DCM (100 mL) was added dropwise to the cold solution. The mixture was warmed to room temperature and stirred overnight (a solid formed during the reaction). The colored suspension was cooled in an ice water bath and water (150 mL) was added to the mixture. The organic and aqueous layers were separated, and the aqueous layer was extracted with DCM (3×75 mL). The combined organic layers were dried (MgSO$_4$; note: the solution became darker), filtered, and concentrated under vacuum to give the product (74b) (4.85 g, 80%) as an oil. This material was used without further purification. $^1$H-NMR (300 MHz, CDCl$_3$): δ 7.01-7.25 (m, 3H), 2.85 (s, 2H), 1.29 (s, 6H).

Step 3: Synthesis of 2-(3-hydroxy-2,2-dimethylpropyl)phenol (74c)

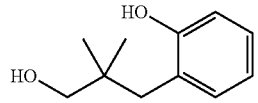

LiAlH$_4$ (1.94 g, 51.1 mmol) was suspended in Et$_2$O (52.5 mL) under an atmosphere of argon and the mixture was cooled to 0° C. in an ice water bath. A solution of 3,3-dimethylchroman-2-one (74b) (4.85 g, 27.5 mmol) in Et$_2$O (50 mL) and added dropwise to the suspension over 30 min. The mixture was warmed to room temperature and stirred for 20 h. The mixture was cooled in an ice water bath and water (2 mL), 15% aqueous sodium hydroxide (2 mL), and water (6 mL), were sequentially added by slow addition. The mixture was warmed to room temperature and stirred for 15 min. Anhydrous MgSO$_4$ was added to the suspension and the mixture stirred for 15 min. The mixture was filtered, and the filter cake washed with Et$_2$O (3×50 mL). The filtrate was concentrated under vacuum to give the product (74c) (4.34 g, 88%) as a solid. This material was used without further purification. $^1$H-NMR (300 MHz, CDCl$_3$): δ 7.15 (dt, J=8.1, 1.5 Hz, 1H), 7.04 (dd, J=7.5, 1.8 Hz, 1H), 6.82-7.01 (m, 2H), 3.22 (s, 2H), 2.61 (s, 2H), 0.98 (s, 6H).

Step 4: Synthesis of 2-(3-((tert-butyldimethylsilyl)oxy)-2,2-dimethylpropyl)phenol (74d)

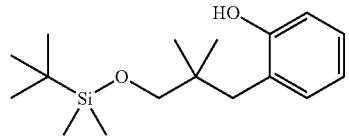 [SMILES: CC(C)(CO[Si](C)(C)C(C)(C)C)Cc1ccccc1O]

A solution of 2-(3-hydroxy-2,2-dimethylpropyl)phenol (74c) (4.0 g, 22.2 mmol) and imidazole (3.8 g, 56.0 mmol) was dissolved in DMF (50 mL) and tert-butyldimethylsilyl chloride (4.0 g, 26.6 mmol) was added to the solution and stirred for 2 h. The solvent was removed under high vacuum and the residue was purified by column chromatography on silica gel (40 g cartridge) with hexanes (5:95 to 2:3) as eluent to give the product (74d) as an oil (7.34 g, >100%). The compound was approximately 90% pure and was used directly in the next step without further purification. $^1$H-NMR (300 MHz, CDCl$_3$): δ 7.11 (dt, J=7.5, 1.8 Hz, 1H), 7.10 (dd, J=7.5, 1.8 Hz, 1H), 6.90 (dd, J=8.1, 1.5 Hz, 1H), 6.79 (dt, J=6.9, 0.9 Hz, 1H), 3.17 (s, 2H), 2.57 (s, 2H), 0.97 (s, 9H), 0.92 (s, 6H), 0.13 (s, 6H).

Step 5: Synthesis of 2-(3-((tert-butyldimethylsilyl)oxy)-2,2-dimethylpropyl)phenyl acetate (74e)

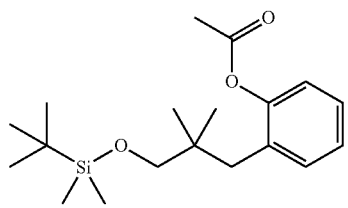 [SMILES: CC(=O)Oc1ccccc1CC(C)(C)CO[Si](C)(C)C(C)(C)C]

A solution of 2-(3-((tert-butyldimethylsilyl)oxy)-2,2-dimethylpropyl)phenol (74d) (ca. 90% purity; 2.5 g, 7.6 mmol) and Et$_3$N (2.3 g, 22.9 mmol) in THF (90 mL) was cooled to 0° C. in an ice bath under an atmosphere of argon. Acetyl chloride (0.65 mL, 9.2 mmol) was added dropwise to the mixture, and after complete addition the ice bath was removed. The reaction was allowed to warm to room temperature and stirred for 2 h. The suspension was filtered and the solid washed with fresh THF (2×20 mL). The filtrate was concentrated under vacuum and the residue dry-loaded onto silica gel, then purified by column chromatography on silica gel (40 g cartridge) using 0-8% EtOAc/hexanes (0:1 to 8:92) as eluent to give the product (74e) (2.16 g, 84%) as an oil. $^1$H-NMR (300 MHz, CDCl$_3$): δ 7.11-7.27 (m, 3H), 7.04 (d, J=7.5 Hz, 1H), 3.25 (s, 2H), 2.51 (s, 2H), 2.30 (s, 3H), 0.93 (s, 9H), 0.81 (s, 6H), 0.06 (s, 6H).

Step 6: Synthesis of 2-(3-hydroxy-2,2-dimethylpropyl)phenyl acetate and 3-(2-hydroxyphenyl)-2,2-dimethylpropyl acetate (74f)

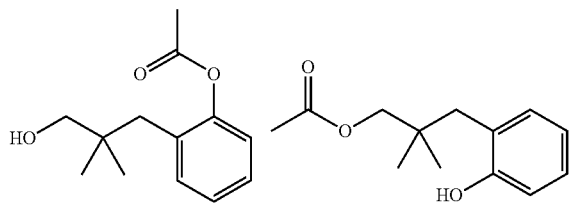

Pyridine hydrofluoride (70%, 1.3 mL, 10.4 mmol) was added to a stirred solution of 2-(3-((tert-butyldimethylsilyl)oxy)-2,2-dimethylpropyl)phenyl acetate (74e) (0.70 g, 2.1 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL), washed with brine (3×75 mL), dried (Na$_2$SO$_4$), filtered, and concentrated under vacuum to give a mixture of the desired alcohol and 3-(2-hydroxyphenyl)-2,2-dimethylpropyl acetate in a 65:35. NMR analysis showed the presence of both esters of the product (74f). This material was used directly in the next step without further purification. $^1$H-NMR (300 MHz, CDCl$_3$) of desired product: δ 6.8-7.26 (m, 4H), 3.79 (s, 2H), 3.27 (s, 2H), 2.62 (s, 2H), 2.53 (s, 2H), 2.33 (s, 3H), 2.13 (s, 3H), 0.974 (s, 6H), 0.90 (s, 6H).

Step 7: Synthesis of 2-(3-((chlorosulfonyl)oxy)-2,2-dimethylpropyl)phenyl acetate (74)

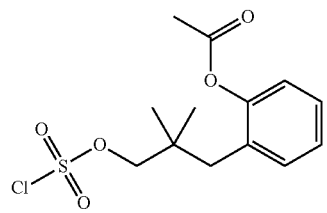 [SMILES: CC(=O)Oc1ccccc1CC(C)(C)COS(=O)(=O)Cl]

A solution of sulfuryl chloride (172 μL, 2.1 mmol) in Et$_2$O (6.8 mL) was cooled to −78° C. under an atmosphere of argon. A solution of 2-(3-hydroxy-2,2-dimethylpropyl)phenyl acetate (74f) (0.43 g, 1.9 mmol) and pyridine (172 μL, 2.1 mmol) in Et$_2$O (2.0 mL) was added dropwise to the sulfuryl chloride solution via cannula. The mixture was stirred at −78° C. for 10 min, then the flask was warmed to room temperature and stirred for 1.5 h (monitored by TLC 30% EtOAc/hexanes). The suspension was filtered through a 0.45 μm PTFE syringe filter, and the syringe filter was rinsed with fresh Et$_2$O (10 mL) to provide the product (74). The filtrate was used immediately in the next step without further purification. The yield was assumed to be quantitative.

Example 75

Synthesis of 2-(3-((chlorosulfonyl)oxy)-2,2-dimethylpropyl)phenyl pivalate (75)

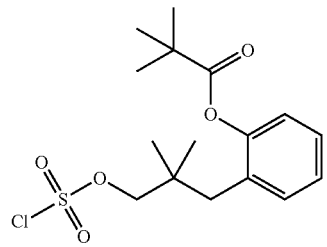 [SMILES: CC(C)(COS(=O)(=O)Cl)Cc1ccccc1OC(=O)C(C)(C)C]

Step 1: Synthesis of 2-(3-((tert-butyldimethylsilyl)oxy)-2,2-dimethylpropyl)phenyl pivalate (75a)

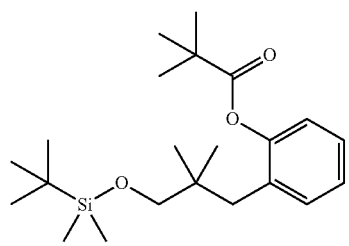 [SMILES: CC(C)(CO[Si](C)(C)C(C)(C)C)Cc1ccccc1OC(=O)C(C)(C)C]

2-(3-((tert-Butyldimethylsilyl)oxy)-2,2-dimethylpropyl) phenol (0.9 g, 3.1 mmol) and N,N-4-dimethylaminopyridine (0.93 g, 7.6 mmol) were dissolved in THF (50 mL) under an atmosphere of argon. Trimethylacetyl chloride (0.45 mL, 3.7 mmol) was added dropwise to the mixture at room temperature to immediately form a white solid, and the addition was continued until a suspension was formed. The reaction was stirred at room temperature for 2 h, and then filtered and the filter cake washed with THF (10 mL). The filtrate was dry-loaded on to silica gel (15 g) and purified by column chromatography on silica gel using EtOAc/hexanes (0:1 to 6:94) as eluent to give the product (75a) contaminated with ca. 3% of starting material by NMR analysis. This material was used without further purification. $^1$H-NMR (300 MHz, CDCl$_3$): δ 7.27 (dd, J=7.2, 2.1 Hz, 1H), 7.21 (dt, J=7.5, 1.8 Hz, 1H), 7.15 (dt, J=7.8, 1.8 Hz, 1H), 6.97 (dd, J=8.1, 1.8 Hz, 1H), 3.25 (s, 2H), 2.49 (s, 2H), 1.38 (s, 9H), 0.92 (s, 9H), 0.82 (s, 6H), 0.05 (s 6H).

Step 2: Synthesis of 2-(3-hydroxy-2,2-dimethylpropyl)phenyl pivalate (75b)

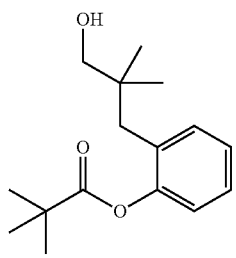 [SMILES: CC(C)(CO)Cc1ccccc1OC(=O)C(C)(C)C]

Pyridine hydrofluoride (70%, 1.3 mL, 10.4 mmol) was added to a stirred solution of 2-(3-((tert-butyldimethylsilyl)oxy)-2,2-dimethylpropyl)phenyl pivalate (75a) (0.70 g, 1.8 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL) and washed with brine (3×75 mL), dried (Na$_2$SO$_4$), filtered, and concentrated under vacuum to give the desired product (75b) as an oil. This material was used directly in the next step without further purification. $^1$H-NMR (300 MHz, CDCl$_3$): δ 7.12-7.26 (m, 3H), 6.98 (m, 1H), 3.31 (s, 2H), 2.51 (s, 2H), 1.39 (s, 9H), 0.89 (s, 9H).

Step 3: Synthesis of 2-(3-((chlorosulfonyl)oxy)-2,2-dimethylpropyl)phenyl pivalate (75)

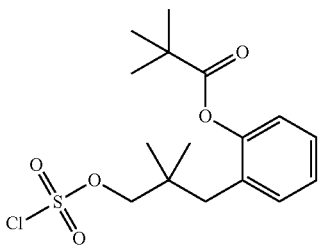 [SMILES: CC(C)(COS(=O)(=O)Cl)Cc1ccccc1OC(=O)C(C)(C)C]

A solution of sulfuryl chloride (173 µL, 2.1 mmol) in Et$_2$O (7.5 mL) was cooled to −78° C. under an argon atmosphere.

A solution of 2-(3-hydroxy-2,2-dimethylpropyl)phenyl pivalate (75b) (0.47 g, 1.8 mmol) and pyridine (173 µL, 2.1 mmol) in Et$_2$O (2.2 mL) was added dropwise to the sulfuryl chloride solution via cannula. The mixture was stirred at −78° C. for 10 min, and then the flask was warmed to room temperature and stirred for 1.5 h (monitored by TLC 30% EtOAc/hexanes). The suspension was filtered through a 0.45-µm PTFE syringe filter, and the syringe filter was rinsed with fresh Et$_2$O to provide the product (75). The filtrate was used immediately in the next step without further purification. The yield was assumed to be quantitative.

Example 76

Synthesis of S-(4-((chlorosulfonyl)oxy)-3,3-dimethylbutyl) ethanethioate (73)

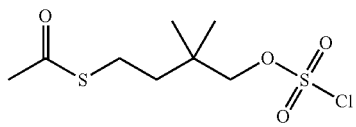

A solution of freshly distilled sulfuryl chloride (271 µL, 3.7 mmol) in Et$_2$O (5 mL) was cooled to −78° C. under an atmosphere of argon. A solution of S-(4-hydroxy-3,3-dimethylbutyl) ethanethioate (prepared according to *Chem. Commun.* 2011, 47, 2038) (500 mg, 2.8 mmol) and pyridine (267 µL, 3.3 mmol) in Et$_2$O (3 mL) was added dropwise to the sulfuryl chloride solution over the course of 5 min. The flask was rinsed with diethyl ether (2×5 mL) and the rinse was also added to the reaction mixture. The mixture was stirred at −78° C. for 1 h and allowed to warm to room temperature and stirred at room temperature for another 20 min. The precipitate was filtered (quickly) and the filter cake rinsed with Et$_2$O (12 mL). The filtrate was concentrated under vacuum at room temperature to afford the title compound (76) as an oil which was used immediately for the next step without further purification.

Example 77

Synthesis of S-(5-((chlorosulfonyl)oxy)-4,4-dimethylpentyl) ethanethioate (77)

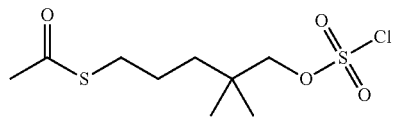 [SMILES: CC(=O)SCCCC(C)(C)COS(=O)(=O)Cl]

Step 1: Synthesis of 5-bromo-2,2-dimethylpentan-1-ol (74a)

Br⟋⟍⟋⟍OH

DCM (18 mL) was added to LiBH$_4$ (0.66 g, 30.4 mmol) followed by dropwise addition of anhydrous MeOH (1.2 ml, 30.4 mmol) over 20 min under an atmosphere of argon. After the H₂ effervescence had ceased, a solution of ethyl 5-bromo-2,2-dimethylpentanoate (prepared according to PCT Application Publication No. 2011046771) (4.5 g, 19.0 mmol) in DCM (10 mL) was added dropwise over 20 min. The reaction mixture was heated to reflux for 16 h, cooled to room temperature, and carefully hydrolyzed with a saturated NH₄Cl solution (30 mL). The suspension was extracted with DCM (3×50 mL). The combined organic layers were washed with 1N HCl (26 mL) and brine (40 mL), dried, and concentrated under vacuum to give the product (77a) (3.61 g, 97%) as an oil. ¹H-NMR (300 MHz, CDCl₃): δ 3.39 (t, J=6.9 Hz, 2H), 3.24 (s, 2H), 1.90-1.76 (m, 2H), 1.48 (br. s, 1H), 1.41-1.36 (m, 2H), 0.88 (s, 6H).

Step 2: Synthesis of S-(5-hydroxy-4,4-dimethylpentyl) ethanethioate (77b)

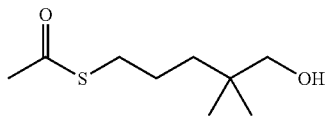

A solution of 5-bromo-2,2-dimethylpentan-1-ol (77a) (2.0 g, 10.3 mmol) and potassium thioacetate (2.34 g, 20.5 mmol) in acetone (22 mL) was stirred under an inert atmosphere at room temperature for 23 h. After removing the solvents under vacuum at room temperature, the residue was purified by column chromatography on silica gel column using EtOAc/hexanes (0:1 to 2:3) as eluent to give the product (77b) (1.2 g, 61%) as an oil. ¹H-NMR (300 MHz, CDCl₃): δ 3.31 (s, 2H), 2.85 (t, J=7.8 Hz, 2H), 2.32 (s, 3H), 1.62-1.48 (m, 2H), 1.32-1.21 (m, 2H), 0.86 (s, 6H).

Step 3: Synthesis of S-(5-((chlorosulfonyl)oxy)-4,4-dimethylpentyl) ethanethioate (77)

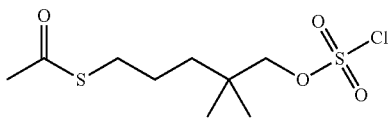 [SMILES: CC(=O)SCCCC(C)(C)COS(=O)(=O)Cl]

A solution of freshly distilled sulfuryl chloride (379 μL, 5.2 mmol) in Et₂O (8 mL) was cooled to −78° C. under an atmosphere of argon. A solution of S-(5-hydroxy-4,4-dimethylpentyl) ethanethioate (77b) (700 mg, 3.6 mmol) and pyridine (374 μL, 4.6 mmol) in Et₂O (4 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with Et₂O (10 mL). The filtrate was concentrated under vacuum at room temperature to afford the title compound (77) as an oil which was used immediately for the next step without further purification.

Example 78

Synthesis of S-(3-((chlorosulfonyl)oxy)-2,2-dimethylpropyl) ethanethioate (78)

Step 1: Synthesis of S-(3-hydroxy-2,2-dimethylpropyl) ethanethioate (78a)

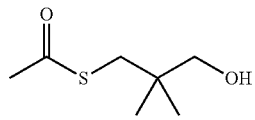

Potassium thioacetate (4.1 g, 35.8 mmol) was dissolved in DMF (20 mL) under an atmosphere of argon. 3-Hydroxy-2,2-dimethylpropyl 4-methylbenzenesulfonate (prepared according to PCT Application Publication No. 2012165648) (4.2 g, 16.3 mmol) was added, and the mixture was stirred at 80° C. for 2.5 h. After cooling, brine (100 mL) was added, and the mixture was extracted with Et₂O (3×100 mL). The combined organic layers were washed with brine (5×50 mL), dried (Na₂SO₄), filtered, and concentrated under vacuum (residual DMF was removed by high vacuum). The residue was purified by column chromatography on silica gel using EtOAc/hexanes (0:1 to 15:85) as eluent to provide the product (78a) (1.06 g, 40%) as an oil. ¹H-NMR (300 MHz, CDCl₃): δ 3.23 (br. s, 2H), 2.89 (s, 2H), 2.62 (br. s, 1H), 2.37 (s, 3H), 0.94 (s, 6H).

Step 2: Synthesis of S-(3-((chlorosulfonyl)oxy)-2,2-dimethylpropyl) ethanethioate (78)

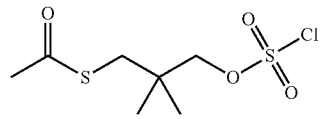

A solution of freshly distilled sulfuryl chloride (283 μL, 3.9 mmol) in Et₂O (4 mL) was cooled to −78° C. under an argon atmosphere. A solution of S-(3-hydroxy-2,2-dimethylpropyl) ethanethioate (78a) (520 mg, 3.1 mmol) and pyridine (327 μL, 4.0 mmol) in Et₂O (6 mL) was added dropwise to the sulfuryl chloride solution over the course of 5 min. The mixture was stirred at −78° C. for 1 h, then allowed to warm to room temperature. The precipitate was filtered (quickly) and the filter cake rinsed with Et₂O (10 mL). The filtrate was concentrated under vacuum at room temperature to afford the title compound (78) as an oil which was used immediately for the next step without further purification.

Example 79

Synthesis of 3-((chlorosulfonyl)oxy)-2,2-dimethylpropyl 2,6-dimethylbenzoate (79)

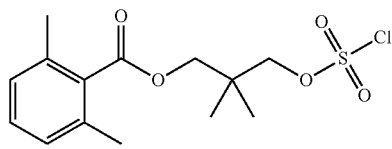 [SMILES: Cc1cccc(C)c1C(=O)OCC(C)(C)COS(=O)(=O)Cl]

Step 1: Synthesis of 3-hydroxy-2,2-dimethylpropyl 2,6-dimethylbenzoate (79a)

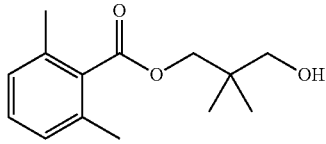 [SMILES: Cc1cccc(C)c1C(=O)OCC(C)(C)CO]

To a stirred solution of 2,2-dimethylpropane-1,3-diol (2.5 g, 24.3 mmol) in DCM (60 mL) at ca. 0° C. (ice bath) under an atmosphere of argon, was added 2,6-dimethylbenzoyl chloride (1.2 mL, 8.1 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of $NaHCO_3$ and brine, dried ($MgSO_4$), filtered and concentrated under vacuum. The residue was purified by column chromatography on silica gel using EtOAc/hexanes (1:9 to 2:3) as eluent to give the product (79a) (1.5 g, 78%) as an oil. $^1$H-NMR (300 MHz, $CDCl_3$): δ 7.21 (m, 1H), 7.04 (m, 2H), 4.18 (s, 2H), 3.41 (s, 2H), 2.32 (s, 6H), 2.20 (br. s, 1H), 0.99 (s, 6H).

Step 2: Synthesis of 3-((chlorosulfonyl)oxy)-2,2-dimethylpropyl 2,6-dimethylbenzoate (79)

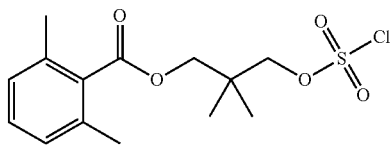 [SMILES: Cc1cccc(C)c1C(=O)OCC(C)(C)COS(=O)(=O)Cl]

A solution of freshly distilled sulfuryl chloride (0.25 mL, 3.9 mmol) in $Et_2O$ (6 mL) was cooled to −78° C. under an argon atmosphere. A solution of 3-hydroxy-2,2-dimethylpropyl 2,6-dimethylbenzoate (79a) (500 mg, 2.1 mmol) and pyridine (0.26 mL, 3.3 mmol) in $Et_2O$ (6 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with $Et_2O$ (12 mL). The filtrate was concentrated under vacuum at room temperature to afford the title compound (79) as an oil, which was used immediately in the next step without further purification.

Example 80

Synthesis of 3-((chlorosulfonyl)oxy)-2,2-dimethylpropyl (3r,5r,7r)-adamantane-1-carboxylate (80)

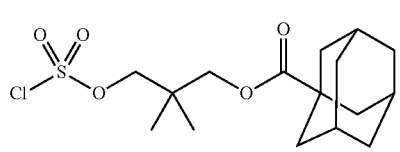 [SMILES: CC(C)(COC(=O)C12CC3CC(CC(C3)C1)C2)COS(=O)(=O)Cl]

Step 1: Synthesis of 3-hydroxy-2,2-dimethylpropyl (3r,5r,7r)-adamantane-1-carboxylate (80a)

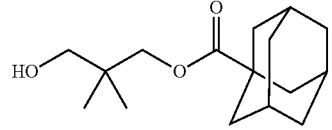 [SMILES: CC(C)(CO)COC(=O)C12CC3CC(CC(C3)C1)C2]

To a stirred solution of 2,2-dimethylpropane-1,3-diol (2.5 g, 24.3 mmol) in DCM (60 mL) at ca. 0° C. (ice bath) under an argon atmosphere, was added 1-adamantane-carbonyl chloride (1.36 g, 6.9 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of $NaHCO_3$ and brine, dried ($MgSO_4$), filtered, and concentrated under vacuum to give the product (80a) (1.82 g, 100%) as an oil. $^1$H-NMR (300 MHz, $CDCl_3$): δ 3.91 (s, 2H), 3.25 (s, 2H), 2.01 (br. s, 3H), 1.89 (br. s, 6H), 1.71 (br. s, 7H), 0.91 (s, 6H).

Step 2: Synthesis of 3-((chlorosulfonyl)oxy)-2,2-dimethylpropyl (3r,5r,7r)-adamantane-1-carboxylate (80)

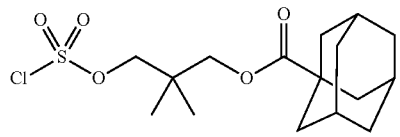

A solution of freshly distilled sulfuryl chloride (266 μL, 3.3 mmol) in $Et_2O$ (4 mL) was cooled to −78° C. under an argon atmosphere. A solution of 3-hydroxy-2,2-dimethylpropyl-adamantane-1-carboxylate (80a) (600 mg, 2.2 mmol) and pyridine (0.28 mL, 3.5 mmol) in $Et_2O$ (4 mL) was added dropwise to the sulfuryl chloride solution over the course of 5 min. The flask was rinsed with $Et_2O$ (5 mL), and the rinse was also added to the reaction mixture. The mixture was stirred at −78° C. for 1 h, and then allowed to warm to room temperature. The precipitate was filtered (quickly) and the filter cake rinsed with $Et_2O$ (12 mL). The filtrate was concentrated under vacuum at room temperature to afford the title compound (80) as an oil, which was used immediately in the next step without further purification.

Example 81

Synthesis of diethyl 2-(((chlorosulfonyl)oxy)methyl)-2-methylmalonate (81)

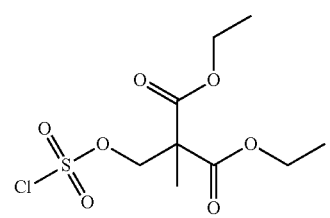 [SMILES: CCOC(=O)C(C)(COS(=O)(=O)Cl)C(=O)OCC]

Step 1: Synthesis of diethyl 2-(hydroxymethyl)-2-methylmalonate (81a)

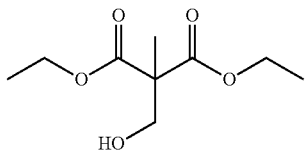

To a suspension of paraformaldehyde (1.3 g, 43.3 mmol) and K$_2$CO$_3$ (11 g, 79 mmol) in EtOH (150 mL) was added diethyl 2-methylmalonate (4.5 mL, 26.3 mmol). The mixture was stirred at room temperature for 17 h, then filtered through a pad of Celite®, and the filter cake washed with EtOH (2×30 mL). The filtrate was concentrated under vacuum and the residue was purified by column chromatography on silica gel using EtOAc/hexanes (0:1 to 3:2) as eluent to afford the product (81a) (4.0 g, 74%) as an oil. $^1$H-NMR (300 MHz, CDCl$_3$): δ 4.22 (q, J=6.9 Hz, 4H), 3.83 (d, J=6.9 Hz, 2H), 2.90 (t, J=7.8 Hz, 1H), 1.42 (s, 3H), 1.26 (t, J=6.9 Hz, 6H).

Step 2: Synthesis of diethyl 2-(((chlorosulfonyl)oxy)methyl)-2-methylmalonate (81)

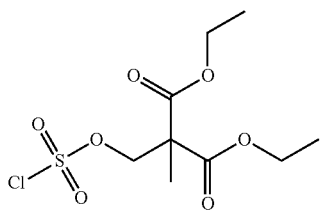 [SMILES: CCOC(=O)C(C)(COS(=O)(=O)Cl)C(=O)OCC]

A solution of freshly distilled sulfuryl chloride (248 μL, 3.0 mmol) in Et$_2$O (8 mL) was cooled to −78° C. under an atmosphere of argon. A solution of diethyl 2-(hydroxymethyl)-2-methylmalonate (81a) (500 mg, 2.4 mmol) and pyridine (0.26 mL, 3.2 mmol) in Et$_2$O (4 mL) was added dropwise to the sulfuryl chloride solution over the course of 5 min. The flask was rinsed with Et$_2$O (5 mL), and the rinse was also added to the reaction mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (81) as an oil which was used immediately in the next step without further purification.

Example 82

Synthesis of propyl 3-((chlorosulfonyl)oxy)-2,2-dimethylpropanoate (82)

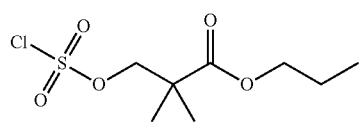

Step 1: Synthesis of propyl 3-hydroxy-2,2-dimethylpropanoate (82a)

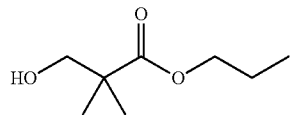

A mixture of 3-hydroxy-2,2-dimethylpropanoic acid (1.15 g, 9.7 mmol) was charged and 1-propanol (15 mL) and conc. H$_2$SO$_4$ (70 μL, 1.3 mmol) in a 20 mL-microwave vial was stirred at room temperature and then heated in a microwave at 80° C. for 2 h and stirred at room temperature overnight. When the desired product was identified by TLC (EtOAc/hexanes; 3:7) the mixture was concentrated under vacuum (40° C.) and diluted with EtOAc (80 mL) and H$_2$O (30 mL). The organic layer was washed with H$_2$O (twice), and brine, then dried (Na$_2$SO$_4$), filtered, and concentrated to give the product (82a) (1.18 g, 76%) as an oil. The material was used next step directly without purification. $^1$H-NMR (300 MHz, CDCl$_3$): δ 4.07 (t, J=6.6 Hz, 2H), 3.55 (s, 2H), 2.42 (br. s, 1H), 1.70-1.61 (m, 2H), 1.19 (s, 6H), 0.95 (t, J=7.5 Hz, 3H).

Step 2: Synthesis of propyl 3-((chlorosulfonyl)oxy)-2,2-dimethylpropanoate (82)

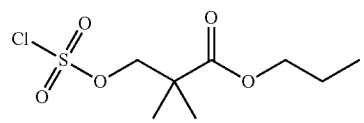

A solution of freshly distilled sulfuryl chloride (194 μL, 2.7 mmol) in Et$_2$O (1.0 mL) was cooled to −78° C. under an atmosphere of argon. A solution of propyl 3-hydroxy-2,2-dimethylpropanoate (82a) (0.42 g, 2.6 mmol) and pyridine (215 μL, 2.7 mmol) in Et$_2$O was added dropwise to the sulfuryl chloride solution over the course of 5 min. The flask was rinsed with Et$_2$O (3×1 mL), and the rinse was added to the reaction mixture. The mixture was stirred at −78° C. for 5 min and then allowed to warm to room temperature and stirred for 1 h. The mixture was filtered and the filtrate was concentrated under vacuum to afford the title compound (82) (0.56 g, 83%) as an oil, which was used immediately in the next step without further purification. $^1$H-NMR (300 MHz, CDCl$_3$): δ 4.50 (s, 2H), 4.10 (t, J=6.6 Hz, 2H), 1.72-1.64 (m, 2H), 1.32 (s, 6H), 0.95 (t, J=7.2 Hz, 3H).

Example 83

Synthesis of butyl 3-((chlorosulfonyl)oxy)-2,2-dimethylpropanoate (83)

Step 1: Synthesis of butyl 3-hydroxy-2,2-dimethylpropanoate (83a)

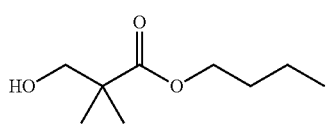

A mixture of 3-hydroxy-2,2-dimethylpropanoic acid (1.15 g, 9.7 mmol) was charged and 1-butanol (15 mL) and conc. H$_2$SO$_4$ (70 µL, 1.3 mmol) in a 20 mL-microwave vial was stirred at room temperature then heated in a microwave at 80° C. for 2 h, then stirred at room temperature overnight. When the desired product was identified by TLC (EtOAc/hexanes; 3:7) the mixture was concentrated under vacuum (40° C.; co-evaporated with toluene×3) and diluted with EtOAc (80 mL) and H$_2$O (30 mL). The organic layer was washed with H$_2$O (twice), and brine, then dried (Na$_2$SO$_4$), filtered and concentrated to give the product (83a) (1.24 g, 81%) as an oil. The material was used next step directly without purification. $^1$H-NMR (300 MHz, CDCl$_3$): δ 4.11 (t, J=6.5 Hz, 2H), 3.55 (s, 2H), 2.42 (br. s, 1H), 1.65-1.58 (m, 2H), 1.43-1.35 (m, 2H), 1.19 (s, 6H), 0.94 (t, J=7.5 Hz, 3H).

Step 2: Synthesis of butyl 3-((chlorosulfonyl)oxy)-2,2-dimethylpropanoate (83)

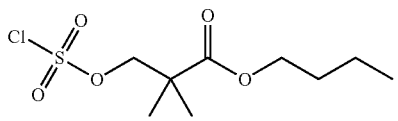 [SMILES: CCCCOC(=O)C(C)(C)COS(=O)(=O)Cl]

A solution of freshly distilled sulfuryl chloride (198 µL, 2.7 mmol) in Et$_2$O (1.0 mL) was cooled to −78° C. under an atmosphere of argon. A solution of propyl 3-hydroxy-2,2-dimethylpropanoate (83a) (0.47 g, 2.7 mmol) and pyridine (219 µL, 2.7 mmol) in Et$_2$O was added dropwise to the sulfuryl chloride solution over the course of 5 min. The flask was rinsed with Et$_2$O (3×1 mL), which was added to the reaction mixture. The mixture was stirred at −78° C. for 5 min and then allowed to warm to room temperature and stirred for 1 h. The mixture was filtered, and the filtrate was concentrated under vacuum to afford the title compound (83) (0.52 g, 72%) as an oil, which was used immediately in the next step without further purification. $^1$H-NMR (300 MHz, CDCl$_3$): δ 4.50 (s, 2H), 4.14 (t, J=6.8 Hz, 2H), 1.66-1.59 (m, 2H), 1.43-1.35 (m, 2H), 1.32 (s, 6H), 0.94 (t, J=7.4 Hz, 3H).

Example 84

Synthesis of 4-((chlorosulfonyl)oxy)-3,3-dimethylbutyl pivalate (84)

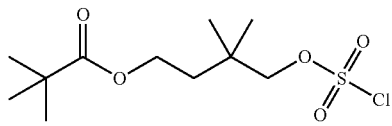 [SMILES: CC(C)(CCOC(=O)C(C)(C)C)COS(=O)(=O)Cl]

Step 1: Synthesis of 4-hydroxy-3,3-dimethylbutyl pivalate (84a)

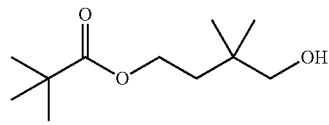

To a stirred solution of 2,2-dimethylbutane-1,4-diol (47a) (0.86 g, 7.3 mmol) in DCM (9 mL) at ca. 0° C. (ice bath) under an argon atmosphere, was added trimethylacetyl chloride (0.89 mL, 7.3 mmol), Et$_3$N (1.17 mL, 14.5 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$ and brine, then dried (Na$_2$SO$_4$), and concentrated under vacuum. The residue was purified by column chromatography on silica gel using EtOAc/hexanes (0:1 to 3:7) as eluent to give the desired product (84a) (0.42 g, 28%). $^1$H-NMR (300 MHz, CDCl$_3$): δ 4.13 (t, J=7.1 Hz, 2H), 3.35 (s, 2H), 1.61 (q, J=6.9 Hz, 2H), 1.19 (s, 9H), 0.93 (s, 6H).

Step 2: Synthesis of 4-((chlorosulfonyl)oxy)-3,3-dimethylbutyl pivalate (84)

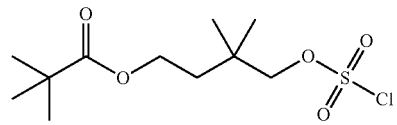 [SMILES: CC(C)(CCOC(=O)C(C)(C)C)COS(=O)(=O)Cl]

A solution of freshly distilled sulfuryl chloride (153 µL, 2.1 mmol) in Et$_2$O (4.5 mL) was cooled to −78° C. under an argon atmosphere. A solution of 4-hydroxy-3,3-dimethylbutyl pivalate (84a) (0.42 g, 2.1 mmol) and pyridine (203 µL, 2.5 mmol) in Et$_2$O (3 mL) was added dropwise to the sulfuryl chloride solution over the course of 60 min. The mixture was allowed to warm to room temperature and stirred for 30 min. The mixture was filtered, and the filtrate was concentrated under vacuum to afford the title compound (84) as an oil, which was used immediately in the next step without further purification. $^1$H-NMR (300 MHz, CDCl$_3$): δ 4.23 (s, 2H), 4.13 (t, J=6.8 Hz, 2H), 1.71 (t, J=6.6 Hz, 2H), 1.19 (s, 9H), 1.08 (s, 6H).

Example 85

Synthesis of ethyl 2-(((chlorosulfonyl)oxy)methyl)-2-ethylbutanoate (85)

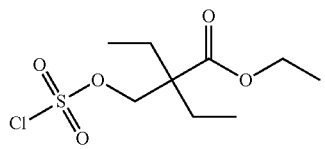 [SMILES: CCOC(=O)C(CC)(CC)COS(=O)(=O)Cl]

A solution of freshly distilled sulfuryl chloride (126 µL, 1.7 mmol) in Et$_2$O (3.2 mL) was cooled to −78° C. under an argon atmosphere. A solution of ethyl 2-ethyl-2-(hydroxymethyl)butanoate (ex-enamine) (0.30 g, 1.7 mmol) and pyridine (153 µL, 1.9 mmol) in Et$_2$O (2.1 mL) was added dropwise to the sulfuryl chloride solution over the course of 60 min. The mixture was allowed to warm to room temperature and stirred for 30 min. The mixture was re-cooled to −78° C. and sulfuryl chloride (20 µL) was added, and the reaction allowed to warm to room temperature and stirred for a further 30 min. Et$_2$O (5 mL) was added and the mixture stirred for 5 min, then filtered, and the filtrate was concentrated under vacuum to afford the title compound (85), which was used immediately in the next step without further purification. $^1$H-NMR (300 MHz, CDCl$_3$): δ 4.62 (s, 2H), 4.21 (q, J=7.3 Hz, 2H), 1.78-1.58 (m, 4H), 1.28 (t, J=7.1 Hz, 3H), 0.88 (t, J=7.7 Hz, 6H).

Example 86

Synthesis of 4-((chlorosulfonyl)oxy)-3,3-dimethylbutyl 2,6-dimethylbenzoate (86)

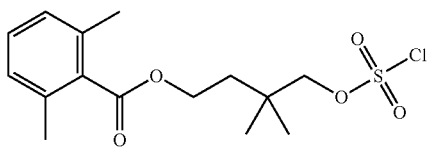 [SMILES: Cc1cccc(C)c1C(=O)OCCC(C)(C)COS(=O)(=O)Cl]

Step 1: Synthesis of 4-hydroxy-3,3-dimethylbutyl 2,6-dimethylbenzoate (86a)

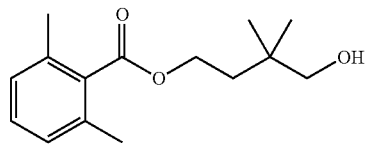 [SMILES: Cc1cccc(C)c1C(=O)OCCC(C)(C)CO]

To a stirred solution of 2,2-dimethylbutane-1,4-diol (47a) (0.84 g, 7.1 mmol) in DCM (9 mL) at ca. 0° C. (ice bath) under an argon atmosphere, was added 2,6-dimethylbenzoyl chloride (1.0 g, 5.9 mmol), pyridine (0.96 mL, 11.9 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$, and then dried (Na$_2$SO$_4$), and concentrated under vacuum. The residue was purified by column chromatography on silica gel using EtOAc/hexanes (0:1 to 3:7) as eluent to give the desired product (86a) (0.42 g, 28%). $^1$H-NMR (300 MHz, CDCl$_3$): δ 7.18 (t, J=7.6 Hz, 1H), 7.04-7.01 (m, 2H), 4.41 (t, J=7.6 Hz, 2H), 3.37 (s, 2H), 2.31 (s, 6H), 1.76 (t, J=7.5 Hz, 2H), 0.97 (s, 6H).

Step 2: Synthesis of 4-((chlorosulfonyl)oxy)-3,3-dimethylbutyl 2,6-dimethylbenzoate (86)

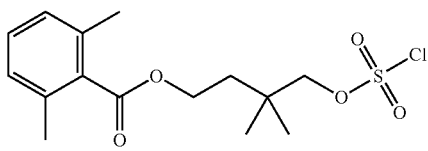 [SMILES: Cc1cccc(C)c1C(=O)OCCC(C)(C)COS(=O)(=O)Cl]

A solution of freshly distilled sulfuryl chloride (122 μL, 1.7 mmol) in Et$_2$O (1.0 mL) was cooled to −78° C. under an atmosphere of argon. A solution of 4-hydroxy-3,3-dimethylbutyl 2,6-dimethylbenzoate (86a) (0.42 g, 1.7 mmol) and pyridine (136 μL, 1.7 mmol) in Et$_2$O (1.5 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (86) as an oil, which was used immediately in the next step without further purification (not pure). $^1$H-NMR (300 MHz, CDCl$_3$): δ 7.19 (t, J=7.7 Hz, 1H), 7.03 (d, J=7.5 Hz, 2H), 4.41 (t, J=7.4 Hz, 2H), 4.23 (s, 2H), 2.31 (s, 6H), 1.84 (t, J=6.9 Hz, 2H), 1.11 (s, 6H).

Example 87

Synthesis of 4-((chlorosulfonyl)oxy)-3,3-dimethylbutyl adamantane-1-carboxylate (87)

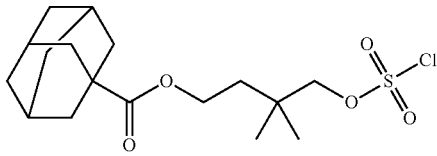 [SMILES: CC(C)(CCOC(=O)C12CC3CC(CC(C3)C1)C2)COS(=O)(=O)Cl]

Step 1: Synthesis of 4-hydroxy-3,3-dimethylbutyl adamantane-1-carboxylate (87a)

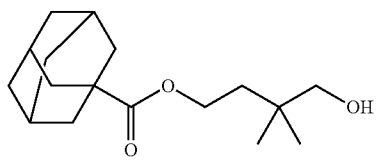 [SMILES: CC(C)(CO)CCOC(=O)C12CC3CC(CC(C3)C1)C2]

To a stirred solution of 2,2-dimethylbutane-1,4-diol (45a) (0.72 g, 6.1 mmol) in DCM (20 mL) at ca. 0° C. (ice bath) under an atmosphere of argon, was added 1-adamantanecarbonyl chloride (1.1 g, 10.1 mmol), pyridine (0.82 mL, 10.1 mmol), and N,N-4-dimethylaminopyridine (0.03 g, 0.3 mmol). The reaction mixture was allowed to gradually warm to room temperature and the mixture was stirred overnight. The mixture was quenched by the addition of 1N HCl. The organic and aqueous layers were partitioned, and the aqueous layer was extracted with DCM (twice). The combined organic layers were washed with saturated NaHCO$_3$ and brine, and then dried (MgSO$_4$), and concentrated under vacuum. The residue was purified by column chromatography on silica gel using EtOAc/hexanes (0:1 to 1:1) as eluent to give the desired product (87a) (0.49 g, 35%). $^1$H-NMR (300 MHz, CDCl$_3$): δ 4.14-4.09 (m, 2H), 3.34 (s, 2H), 2.00 (m, 3H), 1.90-1.86 (m, 6H), 1.75-1.59 (m, 6H), 1.59 (t, J=7.1 Hz, 2H), 0.92 (s, 6H).

Step 2: Synthesis of 4-((chlorosulfonyl)oxy)-3,3-dimethylbutyl adamantane-1-carboxylate (87)

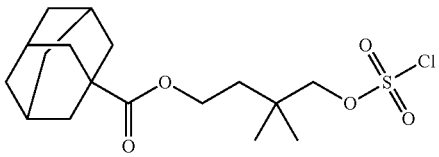 [SMILES: CC(C)(CCOC(=O)C12CC3CC(CC(C3)C1)C2)COS(=O)(=O)Cl]

A solution of freshly distilled sulfuryl chloride (127 μL, 1.7 mmol) in Et$_2$O (1.2 mL) was cooled to −78° C. under an atmosphere of argon. A solution of 4-hydroxy-3,3-dimethylbutyl adamantane-1-carboxylate (87a) (0.48 g, 1.7 mmol) and pyridine (141 μL, 1.7 mmol) in Et$_2$O (1.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (87) as an oil, which was used immediately in the next step without further purification (not pure). $^1$H-NMR (300 MHz, CDCl$_3$): δ 4.25 (s, 2H), 4.13 (t, J=6.8 Hz, 2H), 2.01 (m, 3H), 1.90-1.85 (m, 6H), 1.73-1.69 (m, 8H), 1.08 (s, 6H).

Example 88

Synthesis of 4-((chlorosulfonyl)oxy)-3,3-dimethylbutyl 2,6-dimethoxybenzoate (88)

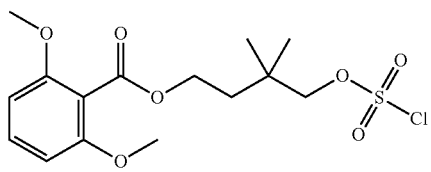 [SMILES: COc1cccc(OC)c1C(=O)OCCC(C)(C)COS(=O)(=O)Cl]

Step 1: Synthesis of 4-hydroxy-3,3-dimethylbutyl 2,6-dimethoxybenzoate (88a)

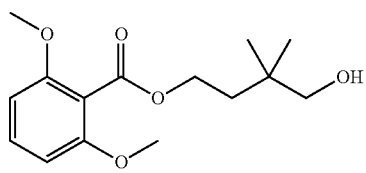 [SMILES: COc1cccc(OC)c1C(=O)OCCC(C)(C)CO]

To a stirred solution of 2,2-dimethylbutane-1,4-diol (47a) (1.85 g, 15.7 mmol) in DCM (28 mL) at ca. 0° C. (ice bath) under an atmosphere of argon, was added 2,6-dimethoxybenzoyl chloride (80%; 3.93 g, 15.7 mmol), Et$_3$N (2.5 mL, 31.3 mmol), and N,N-4-dimethylaminopyridine (catalytic amount). The reaction mixture was allowed to gradually warm to room temperature and the mixture was stirred overnight. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 2:3) as eluent to give the desired product (88a) (ca. 80% purity; 0.92 g). $^1$H-NMR (300 MHz, CDCl$_3$): δ 7.29-7.26 (m, 1H), 6.57-6.53 (m, 3H), 4.43-4.39 (m, 2H), 3.83 (s, 6H), 3.36 (s, 2H), 1.74 (t, J=6.5 Hz, 2H), 0.95 (s, 6H).

Step 2: Synthesis of 4-((chlorosulfonyl)oxy)-3,3-dimethylbutyl 2,6-dimethoxybenzoate (88)

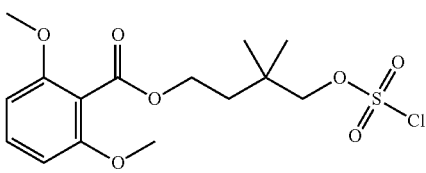 [SMILES: COc1cccc(OC)c1C(=O)OCCC(C)(C)COS(=O)(=O)Cl]

A solution of freshly distilled sulfuryl chloride (0.2 mL, 2.7 mmol) in Et$_2$O (1.9 mL) was cooled to −78° C. under an argon atmosphere. A solution of 4-hydroxy-3,3-dimethylbutyl 2,6-dimethoxybenzoate (88a) (ca. 80% purity; 0.97 g, 2.7 mmol) and pyridine (222 μL, 2.7 mmol) in Et$_2$O (2.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (88) as an oil, which was used immediately in the next step without further purification (not pure).

Example 89

Synthesis of 5-((chlorosulfonyl)oxy)-4,4-dimethylpentyl benzoate (89)

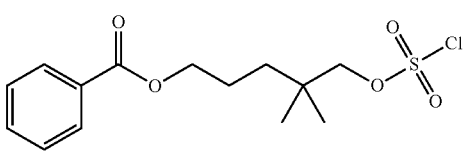 [SMILES: CC(C)(CCCOC(=O)c1ccccc1)COS(=O)(=O)Cl]

Step 1: Synthesis of 5-hydroxy-4,4-dimethylpentyl benzoate (89a)

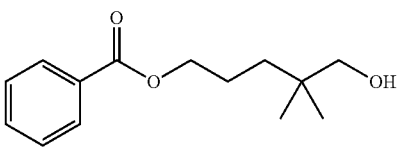 [SMILES: CC(C)(CO)CCCOC(=O)c1ccccc1]

To a stirred solution of 2,2-dimethylpentane-1,5-diol (*J. Org. Chem.* 2010, 75, 1892-1897; PCT International Publication No. WO 2002092606) (1.55 g, 11.7 mmol) in DCM (20 mL) at ca. 0° C. (ice bath) under an argon atmosphere, was added benzoyl chloride (1.5 mL, 12.9 mmol). The reaction mixture was stirred at room temperature for 2.5 h and concentrated under vacuum. EtOAc was added to the residue and the mixture was stirred. The filtrate was concentrated under the residue purified by column chromatography on silica gel using EtOAc/hexanes (0:1 to 1:4) as eluent to give the product (89a) (1.38 g, 50%) as an oil. $^1$H-NMR (300 MHz, CDCl$_3$): δ 8.04 (d, J=6.9 Hz, 2H), 7.56 (t, J=7.5 Hz, 1H), 7.44 (t, J=7.5 Hz, 2H), 4.31 (t, J=6.8 Hz, 2H), 3.36 (s, 2H), 1.81-1.71 (m, 2H), 1.42-1.36 (m, 2H), 0.92 (s, 6H).

Step 2: Synthesis of 5-((chlorosulfonyl)oxy)-4,4-dimethylpentyl benzoate (89)

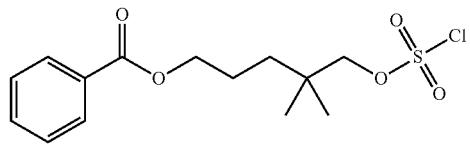 [SMILES: CC(C)(CCCOC(=O)c1ccccc1)COS(=O)(=O)Cl]

A solution of freshly distilled sulfuryl chloride (0.2 mL, 2.7 mmol) in Et$_2$O (1.9 mL) was cooled to −78° C. under an argon atmosphere. A solution of 4-hydroxy-3,3-dimethylpentyl benzoate (89a) (0.76 g, 3.2 mmol) and pyridine (218 μL, 2.7 mmol) in Et$_2$O (2.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (89) as an oil, which was used immediately in the next step without further purification (not pure). $^1$H-NMR (300 MHz, CDCl$_3$): δ 8.04 (d, J=7.5 Hz, 2H), 7.57-7.55 (m, 1H), 7.48-7.33 (m, 1H), 4.35-4.29 (m, 2H), 4.23 (s, 2H), 1.81-1.74 (m, 2H), 1.53-1.21 (m, 2H), 1.06 (s, 6H).

Example 90

Synthesis of 5-((chlorosulfonyl)oxy)-4,4-dimethylpentyl 2,6-dimethoxybenzoate (90)

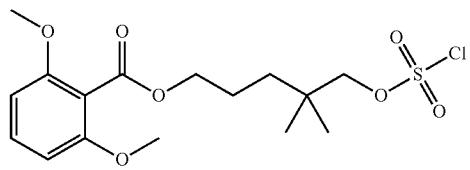 [SMILES: COc1cccc(OC)c1C(=O)OCCCC(C)(C)COS(=O)(=O)Cl]

Step 1: Synthesis of 5-hydroxy-4,4-dimethylpentyl 2,6-dimethoxybenzoate (90a)

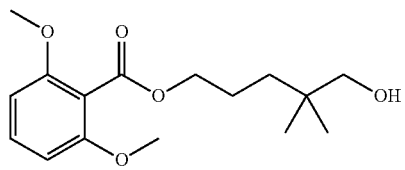 [SMILES: COc1cccc(OC)c1C(=O)OCCCC(C)(C)CO]

To a stirred solution of 2,2-dimethylpentane-1,5-diol (1.5 g, 11.3 mmol) in pyridine (8.3 mL) at 0° C. under an argon atmosphere was added 2,6-dimethoxybenzoyl chloride (80%; 1.4 g, 5.6 mmol) in one portion. The reaction mixture was allowed to warm to room temperature and for 3 h. The reaction mixture was concentrated to dryness and EtOAc was added. The mixture was filtered and the filtrate was concentrated under vacuum. The residue was purified by column chromatography on silica gel using EtOAc/hexanes (0:1 to 3:7) as eluent to give the product (90a) (0.65 g, 39%) as an oil. $^1$H-NMR (300 MHz, CDCl$_3$): δ 7.31-7.26 (m, 2H), 6.55 (d, J=8.1 Hz, 2H), 4.33 (t, J=6.2 Hz, 2H), 3.82 (s, 6H), 3.33 (s, 2H), 1.77-1.67 (m, 2H), 1.41-1.35 (m, 2H), 0.92 (s, 6H).

Step 2: Synthesis of 5-((chlorosulfonyl)oxy)-4,4-dimethylpentyl 2,6-dimethoxybenzoate (90)

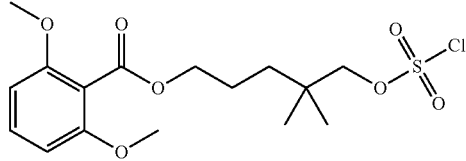 [SMILES: COc1cccc(OC)c1C(=O)OCCCC(C)(C)COS(=O)(=O)Cl]

A solution of freshly distilled sulfuryl chloride (0.16 mL, 2.2 mmol) in Et$_2$O was cooled to −78° C. under an atmosphere of argon. A solution of 5-hydroxy-4,4-dimethylpentyl 2,6-dimethoxybenzoate (90a) (0.65 g, 2.2 mmol) and pyridine (177 μL, 2.2 mmol) in Et$_2$O was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (90) as an oil, which was used immediately in the next step without further purification (not pure). $^1$H-NMR (300 MHz, CDCl$_3$): δ 7.32-7.26 (m, 1H), 6.56 (d, J=8.7 Hz, 2H), 4.34 (t, J=6.2 Hz, 2H), 4.21 (s, 2H), 3.81 (s, 6H), 1.77-1.71 (m, 2H), 1.52-1.46 (m, 2H), 1.03 (s, 6H).

Example 91

Synthesis of 5-((chlorosulfonyl)oxy)-4,4-dimethylpentyl 2,6-dimethylbenzoate (91)

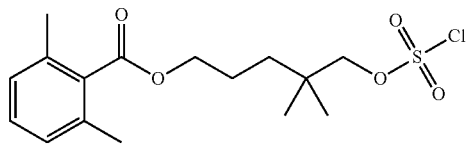 [SMILES: Cc1cccc(C)c1C(=O)OCCCC(C)(C)COS(=O)(=O)Cl]

Step 1: Synthesis of 5-hydroxy-3,3-dimethylpentyl 2,6-dimethylbenzoate (91a)

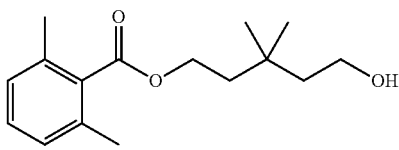 [SMILES: Cc1cccc(C)c1C(=O)OCCC(C)(C)CCO]

To a stirred solution of 2,2-dimethylpentane-1,5-diol (1.1 g, 8.3 mmol) in pyridine (8.3 mL) at 0° C. under an argon atmosphere was added 2,6-dimethylbenzoyl chloride in one portion. The reaction mixture was allowed to warm to room temperature for 3 h. The reaction was concentrated to dryness and EtOAc was added. The mixture was filtered and the filtrate was concentrated under vacuum. The residue was purified by column chromatography on silica gel using EtOAc/hexanes (0:1 to 1:4) as eluent to give the product (91a) (0.44 g, 25%) as an oil. $^1$H-NMR (300 MHz, CDCl$_3$): δ 7.18 (t, J=7.7 Hz, 1H), 7.03 (d, J=7.5 Hz, 2H), 4.32 (t, J=6.3 Hz, 2H), 3.34 (s, 2H), 2.32 (s, 6H), 1.78-1.68 (m, 2H), 1.40-1.34 (m, 2H), 0.90 (s, 6H).

Step 2: Synthesis of
5-((chlorosulfonyl)oxy)-4,4-dimethylpentyl
2,6-dimethylbenzoate (91)

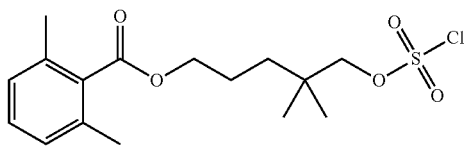 [SMILES: Cc1cccc(C)c1C(=O)OCCCC(C)(C)COS(=O)(=O)Cl]

A solution of freshly distilled sulfuryl chloride (122 μL, 1.7 mmol) in Et$_2$O was cooled to −78° C. under an atmosphere of argon. A solution of 5-hydroxy-4,4-dimethylpentyl 2,6-dimethylbenzoate (91a) (0.44 g, 1.7 mmol) and pyridine (135 μL, 1.7 mmol) in Et$_2$O was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (91), which was used immediately in the next step without further purification. $^1$H-NMR (300 MHz, CDCl$_3$): δ 7.19 (t, J=7.5 Hz, 1H), 7.03 (d, J=7.5 Hz, 2H), 4.33 (t, J=6.2 Hz, 2H), 4.20 (s, 2H), 2.32 (s, 6H), 1.81-1.71 (m, 2H), 1.51-1.45 (m, 2H), 1.04 (s, 6H).

Example 92

Synthesis of
4-((chlorosulfonyl)oxy)-3,3-dimethylbutyl
2-methylbenzoate (92)

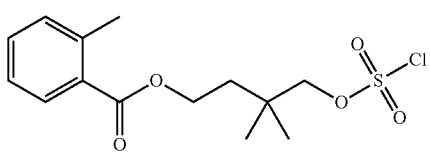 [SMILES: Cc1ccccc1C(=O)OCCC(C)(C)COS(=O)(=O)Cl]

Step 1: Synthesis of 4-hydroxy-3,3-dimethylbutyl
2-methylbenzoate (92a)

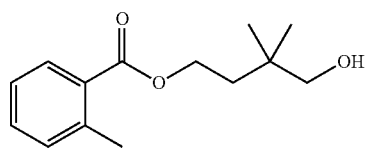 [SMILES: Cc1ccccc1C(=O)OCCC(C)(C)CO]

To a stirred solution of 2,2-dimethylbutane-1,4-diol (45a) (0.80 g, 6.8 mmol) in pyridine (5 mL) at ca. 0° C. (ice bath) under an argon atmosphere, was added toluoyl chloride (0.89 mL, 6.8 mmol) dropwise. The reaction mixture was allowed to gradually warm to room temperature and the mixture was stirred for 4 h. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 3:7) as eluent to give the desired product (92a) (0.7 g, 44%). $^1$H-NMR (300 MHz, CDCl$_3$): δ 7.88 (d, J=8.4 Hz, 1H), 7.40 (t, J=7.1 Hz, 1H), 7.26-7.24 (m, 2H), 4.38 (t, J=7.3 Hz, 2H), 3.41 (s, 3H), 2.60 (s, 3H), 1.78 (t, J=7.5 Hz, 2H), 0.98 (s, 6H).

Step 2: Synthesis of
4-((chlorosulfonyl)oxy)-3,3-dimethylbutyl
2-methylbenzoate (92)

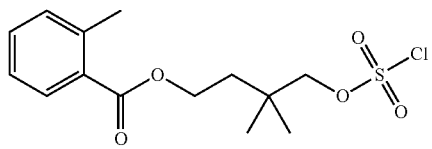 [SMILES: Cc1ccccc1C(=O)OCCC(C)(C)COS(=O)(=O)Cl]

A solution of freshly distilled sulfuryl chloride (96 μL, 1.3 mmol) in Et$_2$O (0.8 mL) was cooled to −78° C. under an atmosphere of argon. A solution of 4-hydroxy-3,3-dimethylbutyl 2-methylbenzoate (92a) (0.31 g, 1.3 mmol) and pyridine (106 μL, 1.3 mmol) in Et$_2$O (1.1 mL) was added dropwise to the sulfuryl chloride solution over the course of 15 min. The flask was rinsed with Et$_2$O (2×20 mL), which was added to the reaction mixture. The mixture was stirred at −78° C. for 10 min then allowed to warm to room temperature and stirred for 30 min. The mixture was filtered, and the product (92) was used immediately in the next step without further purification. $^1$H-NMR (300 MHz, CDCl$_3$): δ 7.89 (d, J=8.1 Hz, 1H), 7.41-7.39 (m, 1H), 7.26-7.25 (m, 2H), 4.41-4.35 (m, 2H), 4.28 (s, 2H), 2.61 (s, 3H), 1.87 (t, J=7.2 Hz, 2H), 1.13 (s, 6H).

Example 93

Synthesis of 4-((chlorosulfonyl)oxy)-2,2,3,3-tetramethylbutyl 3-chloro-2,6-dimethoxybenzoate (93)

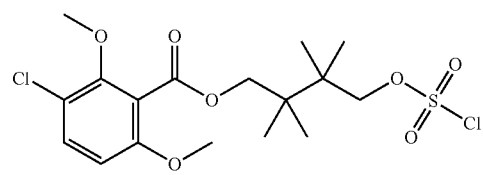 [SMILES: COc1ccc(Cl)c(OC)c1C(=O)OCC(C)(C)C(C)(C)COS(=O)(=O)Cl]

Step 1: Synthesis of
4-hydroxy-2,2,3,3-tetramethylbutyl
2,6-dimethoxybenzoate (93a)

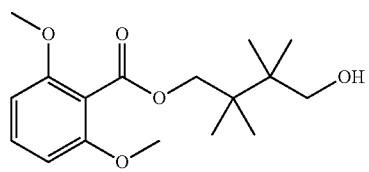 [SMILES: COc1cccc(OC)c1C(=O)OCC(C)(C)C(C)(C)CO]

To a stirred solution of 2,2,3,3-tetramethylbutane-1,4-diol (67a) (0.7 g, 4.8 mmol) in DCM (20 mL) at 0° C. under an atmosphere of argon was added 2,6-dimethoxybenzoyl chloride (80%; 0.55 g, 2.2 mmol), pyridine (0.36 mL, 4.4 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (93a) as an oil. $^1$H-NMR (300 MHz, CDCl$_3$): δ 7.29 (t, J=8.4 Hz, 1H), 6.56 (d, J=8.1 Hz, 2H), 4.24 (s, 2H), 3.81 (s, 6H), 3.49 (s, 2H), 0.98 (s, 6H), 0.92 (s, 6H).

Step 2: Synthesis of 4-((chlorosulfonyl)oxy)-2,2,3,3-tetramethylbutyl 3-chloro-2,6-dimethoxybenzoate (93)

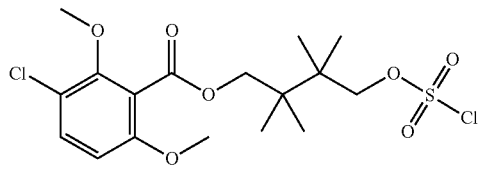 [SMILES: COc1ccc(Cl)c(OC)c1C(=O)OCC(C)(C)C(C)(C)COS(=O)(=O)Cl]

Pyridine (0.15 mL, 1.8 mmol) was added to a stirred mixture of 4-hydroxy-2,2,3,3-tetramethylbutyl propionate (93a) (0.30 g, 1.5 mmol) and Et$_2$O (10 mL) under an atmosphere of argon. The solution was cooled to −78° C. and sulfuryl chloride (0.15 mL, 1.8 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the title compound (93) as an oil, that was used directly in the next step without further purification (yield assumed quantitative).

Example 94

Synthesis of 2-(((chlorosulfonyl)oxy)methyl)-2-methylpropane-1,3-diyl dibenzoate (94)

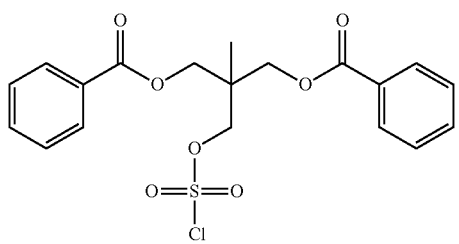 [SMILES: CC(COC(=O)c1ccccc1)(COC(=O)c1ccccc1)COS(=O)(=O)Cl]

Step 1: Synthesis of 2-(hydroxymethyl)-2-methylpropane-1,3-diyl dibenzoate (91a)

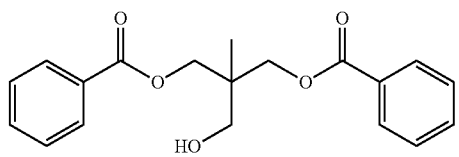 [SMILES: CC(CO)(COC(=O)c1ccccc1)COC(=O)c1ccccc1]

Benzoyl chloride (2.46 mL, 20.0 mmol) was added dropwise to a mixture of 2-(hydroxymethyl)-2-methylpropane-1,3-diol (1.2 g, 10.0 mmol), pyridine (2.02 mL, 25.0 mmol), and N,N-4-dimethylaminopyridine (0.06 g, 0.4 mmol) in DCM (30 mL) at room temperature. After stirring at room temperature overnight, the organic phase was washed with 1 M HCl, water, and brine, dried (MgSO$_4$), and concentrated under vacuum. The residue was purified by column chromatography on silica gel using EtOAc/hexanes (0:1 to 2:3) as eluent to give the product (94a) (1.3 g, 40%) as an oil. $^1$H-NMR (300 MHz, CDCl$_3$): δ 8.06-8.02 (m, 4H), 7.62-7.56 (m, 2H), 7.49-7.42 (m, 4H), 4.39 (s, 2H), 4.38 (s, 2H), 3.59 (s, 2H), 1.16 (s, 3H).

Step 2: Synthesis of 2-(((chlorosulfonyl)oxy)methyl)-2-methylpropane-1,3-diyl dibenzoate (94)

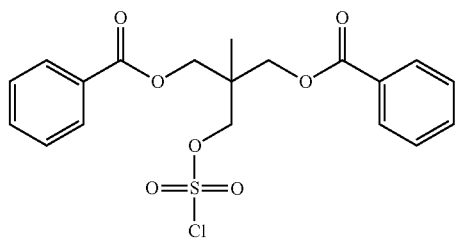 [SMILES: CC(COC(=O)c1ccccc1)(COC(=O)c1ccccc1)COS(=O)(=O)Cl]

A solution of freshly distilled sulfuryl chloride (0.3 mL, 3.7 mmol) in Et$_2$O (5 mL) was cooled to −78° C. under an atmosphere of argon. A solution of 2-(hydroxymethyl)-2-methylpropane-1,3-diyl dibenzoate (94a) (800 mg, 2.4 mmol) and pyridine (0.32 mL, 3.9 mmol) in Et$_2$O (5 mL) was added dropwise to the sulfuryl chloride solution over the course of 5 min. The flask was rinsed with Et$_2$O (3 mL), which was also added to the mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (94) as an oil which was used immediately in the next step without further purification.

Example 95

Synthesis of 2-(((chlorosulfonyl)oxy)methyl)-2-methylpropane-1,3-diyl diacetate (95)

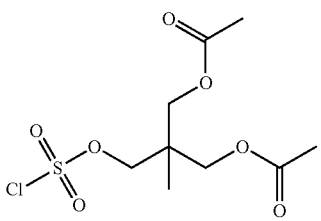 [SMILES: CC(=O)OCC(C)(COC(C)=O)COS(=O)(=O)Cl]

Step 1: Synthesis of 2-(hydroxymethyl)-2-methylpropane-1,3-diyl diacetate (95a)

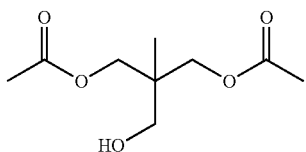

Acetic anhydride (3.46 mL, 36.6 mmol) was added dropwise to a mixture of 2-(hydroxymethyl)-2-methylpropane-1,3-diol (2.2 g, 18.0 mmol), pyridine (12 mL, 25.0 mmol), and N,N-4-dimethylaminopyridine (0.05 g) at room temperature. After stirring at room temperature overnight, the mixture was concentrated under vacuum. The mixture was suspended in EtOAc (100 mL), and $H_2O$ (20 mL) was slowly added at 0° C. The aqueous and organic layers were partitioned, and the organic layer was washed with and brine, dried ($Na_2SO_4$), then concentrated under vacuum. The residue was purified by column chromatography on silica gel using EtOAc/hexanes (0:1 to 3:2) as eluent to give the product (95a) (1.0 g, 26%). $^1$H-NMR (300 MHz, $CDCl_3$): δ 4.02 (s, 4H), 3.41 (s, 2H), 2.08 (s, 6H), 0.96 (s, 3H).

Step 2: Synthesis of 2-(((chlorosulfonyl)oxy)methyl)-2-methylpropane-1,3-diyl diacetate (95)

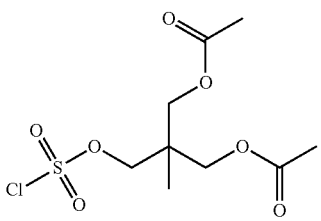 [SMILES: CC(=O)OCC(C)(COC(C)=O)COS(=O)(=O)Cl]

A solution of freshly distilled sulfuryl chloride (0.33 mL, 4.0 mmol) in $Et_2O$ (4 mL) was cooled to −78° C. under an atmosphere of argon. A solution of 2-(hydroxymethyl)-2-methylpropane-1,3-diyl diacetate (95a) (550 mg, 2.7 mmol) and pyridine (0.35 mL, 4.3 mmol) in $Et_2O$ (4 mL) was added dropwise to the sulfuryl chloride solution over the course of 5 min. The flask was rinsed with $Et_2O$ (5 mL), which was also added to the mixture. The mixture was stirred at −78° C. for 1 h, then allowed to warm to room temperature. The precipitate was filtered (quickly) and the filter cake rinsed with $Et_2O$ (12 mL). The filtrate was concentrated under vacuum at room temperature to afford the title compound (95) as an oil which was used immediately for the next step without further purification.

Example 96

Synthesis of 5-((chlorosulfonyl)oxy)-2,2,4,4-tetramethylpentyl 2,6-dimethoxybenzoate (96)

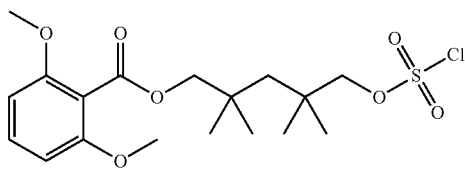 [SMILES: COc1cccc(OC)c1C(=O)OCC(C)(C)CC(C)(C)COS(=O)(=O)Cl]

Step 1: Synthesis of 5-hydroxy-2,2,4,4-tetramethylpentyl 2,6-dimethoxybenzoate (96a)

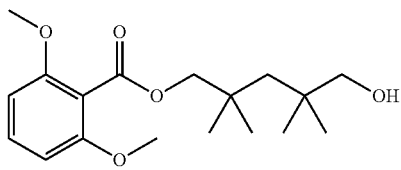 [SMILES: COc1cccc(OC)c1C(=O)OCC(C)(C)CC(C)(C)CO]

To a stirred solution of 2,2,4,4-tetramethylpentane-1,5-diol (64c) (0.64 g, 4.0 mmol) and pyridine (0.32 mL, 4.0 mmol) in DCM (27 mL) was added 2,6-dimethoxybenzoyl chloride (80%; 1.0 g, 4.0 mmol) in DCM (10 mL) dropwise over the course of 30 min at 0° C. (ice bath) under an atmosphere of argon. The reaction mixture was allowed to warm to room temperature and stirred overnight. The mixture was diluted with $H_2O$ (30 mL), and the layers were separated. The aqueous layer was extracted with DCM (2×30 mL), and the combined organic layers were washed with brine (30 mL), dried ($Na_2SO_4$), and concentrated under vacuum. The residue was purified by column chromatography on silica gel using EtOAc/hexanes (0:1 to 2:98) as eluent to give the product (96a) (927 mg, 71%) as an oil. The compound was contaminated, presumably with the diacylated byproduct. The material was used in the next step without further purification.

Step 2: Synthesis of 5-((chlorosulfonyl)oxy)-2,2,4,4-tetramethylpentyl 2,6-dimethoxybenzoate (96)

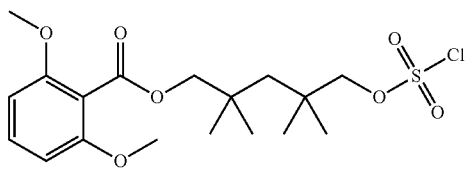 [SMILES: COc1cccc(OC)c1C(=O)OCC(C)(C)CC(C)(C)COS(=O)(=O)Cl]

A solution of sulfuryl chloride (0.21 mL, 2.8 mmol) in $Et_2O$ (13 mL) was cooled to −78° C. under an argon atmosphere. A solution of 5-hydroxy-2,2,4,4-tetramethyl-pentyl 2,6-dimethoxybenzoate (96a) (921 mg, 2.8 mmol) and pyridine (0.23 mL, 2.8 mmol) in Et₂O (13 mL) was added dropwise to the sulfuryl chloride solution over the course of 10 min. The mixture was stirred at −78° C. for 5 h. The mixture was filtered and the filtrate stored to give a solution of the product (96) in Et₂O (ca. 20 mL). The yield was assumed to be quantitative. This mixture was used in the next step without further purification.

Example 97

Synthesis of R/S-ethyl 3-((chlorosulfonyl)oxy)-2,2-dimethylbutanoate (97)

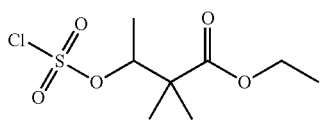

A solution of freshly distilled sulfuryl chloride (148 µL, 2.0 mmol) in Et₂O (0.2 mL) was cooled to −78° C. under an argon atmosphere. A solution of ethyl 3-hydroxy-2,2-dimethylbutanoate (prepared according to *J. Med. Chem.* 1987, 30, 366-374 and *Ad. Synth. Catal.* 2009, 351, 3128-3132) (324 mg, 2.0 mmol) and pyridine (164 µL, 2.0 mmol) in Et₂O (0.2 mL) was added dropwise to the sulfuryl chloride solution over the course of 15 min. The flask was rinsed with Et₂O (2×20 mL), which was added to the reaction mixture. The mixture was stirred at −78° C. for 30 min. The mixture was filtered and the product (97a) was used directly in the next step with an assumed quantitative yield. ¹H-NMR (300 MHz, CDCl₃): δ 5.34-5.29 (m, 1H), 4.22-4.14 (m, 2H), 1.55-1.52 (m, 3H), 1.35-1.08 (m, 9H).

Example 98

Synthesis of (3,5,5-trimethyl-2-oxotetrahydrofuran-3-yl)methyl sulfochloridate (98)

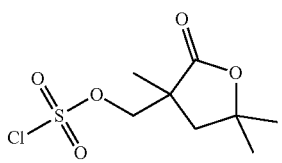

Step 1: Synthesis of 3,5,5-trimethyldihydrofuran-2(3H)-one (98a)

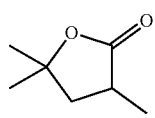

5,5-Dimethyldihydrofuran-2(3H)-one (4.7 g, 41.2 mmol) was dissolved in THF (94 mL) and the mixture was cooled to −78° C. under an atmosphere of argon. A solution of lithium diisopropylamide, 2.0 M solution in THF (22.6 mL, 45.2 mmol) was added dropwise over 10 min. The reaction was stirred at −78° C. for 2 h, and then neat MeI (2.6 mL, 41.6 mmol) was added to the reaction over 5 min. The reaction was stirred at −78° C. for 45 min, and then the mixture was allowed to warm to room temperature and stirred for 16 h. The reaction was quenched with saturated NH₄Cl (25 mL) and the mixture concentrated to remove THF. The aqueous residue was diluted with H₂O to dissolve solid and then extracted with ethyl acetate (3×40 mL). The combined organic layer was concentrated under vacuum, and the residue was purified by column chromatography on silica gel using EtOAc/hexanes (0:1 to 2:3) as eluent to provide a liquid which solidified on standing. This solid was purified further via Kugelrohr distillation to give the product (98a) (3.2 g) as an oil. ¹H-NMR (300 MHz, CDCl₃): δ 2.78-2.87 (m, 1H), 2.33 (dd, J=9.3, 12.3 Hz, 1H), 1.71 (t, J=12.3 Hz, 1H), 1.45 (s, 3H), 1.38 (s, 3H), 1.29 (d, J=6.9 Hz, 3H).

Step 2: Synthesis of 3-((benzyloxy)methyl)-3,5,5-trimethyldihydrofuran-2(3H)-one (98b)

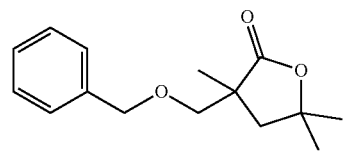 [SMILES: CC1(C)CC(C)(COCc2ccccc2)C(=O)O1]

3,5,5-Trimethyldihydrofuran-2(3H)-one (98a) (3.2 g, 25.0 mmol) was dissolved in THF (60 mL) and the mixture was cooled to −78° C. under an atmosphere of argon. A solution of lithium diisopropylamide, 2.0 M in THF (13.7 mL, 27.5 mmol) was added dropwise over 10 min. The mixture was stirred at −78° C. for 30 min, then neat benzyl chloromethyl ether (90%; 4.2 mL, 27.5 mmol) was added over 5 min. The mixture was allowed to warm to room temperature and was stirred for 16 h. Saturated NH₄Cl (10 mL) and H₂O (10 mL) was added and the solvent was removed under vacuum. The residue was extracted with EtOAc (2×75 mL) and the combined organic layers were washed with brine (2×75 mL), dried (Na₂SO₄), filtered and concentrated under vacuum (5.8 g). The residue was purified by column chromatography on silica gel using EtOAc/hexanes (0:1 to 2:3) as eluent to give the product (2.27 g) and impure fractions (1.35 g). The impure fractions were re-purified by column chromatography on silica gel using EtOAc/hexanes (0:1 to 1:4) as eluent to give additional pure product (98b) (1.39 g). The product (3.66 g) was an oil. ¹H-NMR (300 MHz, CDCl₃): δ 7.28-7.34 (m, 5H), 4.62 (dd, J=11.7, 35.1 Hz, 2H), 3.61 (d, J=11.7 Hz, 1H), 3.32 (d, J=11.7 Hz, 1H), 2.48 (d, J=12.9 Hz, 1H), 1.89 (d, J=12.9 Hz, 1H), 1.45 (d, J=6.9 Hz, 6H), 1.26 (s, 3H).

Step 3: Synthesis of 3-(hydroxymethyl)-3,5,5-trimethyldihydrofuran-2(3H)-one (98c)

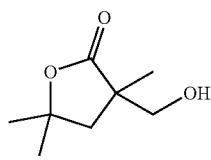

3-((Benzyloxy)methyl)-3,5,5-trimethyldihydrofuran-2 (3H)-one (98b) (1.8 g, 7.2 mmol) was dissolved in 2-propanol (60 mL) and the solution was degassed with argon. Solid 10.0% palladium on carbon (0.31 g, 0.3 mmol) was added to the flask. The flask was sealed and vacuum degassed, and then back flushed with hydrogen (3 times). The reaction was stirred for 6 h. The suspension was filtered through Celite® and the filter cake washed with 2-propanol (15 mL). The filtrate was concentrated under vacuum to provide the product (98c) as a crude oil. $^1$H-NMR (300 MHz, CDCl$_3$): δ 3.75 (dd, J=6.9, 11.1 Hz, 1H), 3.51 (dd, J=5.7, 11.1 Hz, 1H), 2.33 (d, J=12.9 Hz, 1H), 2.23 (t, J=6 Hz, 1H), 1.94 (d, J=12.9 Hz, 1H), 1.48 (d, J=6.9 Hz, 6H), 1.32 (s, 3H).

Step 4: Synthesis of (3,5,5-trimethyl-2-oxotetrahydrofuran-3-yl)methyl sulfochloridate (98)

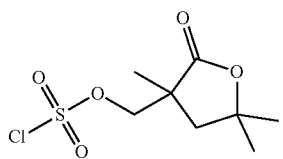

A solution of 3-(hydroxymethyl)-3,5,5-trimethyldihydrofuran-2(3H)-one (98c) (0.50 g, 3.2 mmol) and pyridine (0.28 mL, 3.5 mmol) in Et$_2$O (10 mL) was cooled to −78° C. under an atmosphere of argon. Neat sulfuryl chloride (0.28 mL, 3.5 mmol) was added dropwise to the above solution via syringe. The mixture was stirred at −78° C. for 10 min, then the flask was warmed to room temperature and stirred for 1 h (monitored by TLC 30% EA/hexanes). A precipitate formed to give a thick suspension. The suspension was filtered through a 0.45-μM Teflon® filter and the filter cake rinsed with fresh Et$_2$O (2×5 mL). An aliquot (0.5 mL) was taken and concentrated and an NMR was obtained for the mixture. The remaining solution containing the product (98) was used directly in the next step. $^1$H-NMR (300 MHz, CDCl$_3$): δ 4.60 (d, J=9.3 Hz, 1H), 4.36 (d, J=9.3 Hz, 1H), 2.37 (d, J=14.1 Hz, 1H), 2.09 (d, J=13.5 Hz, 1H), 1.51 (d, J=8.4 Hz, 6H), 1.44 (s, 3H).

Example 99

Aztreonam Release from Prodrug

U.S. application Ser. No. 15/934,497, filed on Mar. 23, 2018, and due to issue as U.S. Pat. No. 10,085,999, discloses derivatives of the β-lactamase inhibitor, avibactam, having promoieties similar to those disclosed herein. Several of the avibactam derivatives exhibited oral bioavailability of the parent drug, avibactam, following oral administration to rats, dogs, and monkeys. Based on these results, it can be expected that the derivatives of aztreonam disclosed herein, including the compounds of Formula (1)-(4) will adhere to the same release mechanism and will exhibit oral bioavailability of the parent drug, aztreonam.

Example 100

Oral Bioavailability

A pharmacokinetic (PK) study can be performed in three male Sprague-Dawley (SD) rats following intravenous (IV) and oral (PO) administration of aztreonam at 2 mg/kg and test compounds at 10 mg/kg, respectively and aztreonam measured in plasma.

Aztreonam is dissolved in phosphate buffered saline (PBS) (pH 7.5) at 0.4 mg/mL for intravenous (IV) injection. Compounds for oral administration are formulated in 10% ethanol/40% polyethylene glycol (PEG) 400/50% water for injection (WFI) (pH 6.5) at 1 mg/mL. The dosing volumes are 5 mL/kg for IV and 10 mL/kg for PO. All aspects of this work including housing, experimentation, and animal disposal are performed in general accordance with the "Guide for the Care and Use of Laboratory Animals: Eighth Edition" (National Academies Press, Washington, D.C., 2011); and Suckow et al., Ed. The Laboratory Rat. 2nd Edition. Academic Press. New York. 2005. Animals have access to standard lab diet and autoclaved tap water ad libitum.

Blood aliquots (300 μL to 400 μL) are collected from jugular vein-catheterized rats into tubes coated with lithium heparin at various times. The tubes are mixed gently and kept on ice and then centrifuged at 2,500 rpm for 15 min at 4° C., within 1 h after collection. For animals in the control groups, blood is collected by cardiac puncture and the plasma is harvested and kept frozen at −70° C. until further analysis. Beaudoin et al., Bioanalytical method validation for the simultaneous determination of ceftazidime and aztreonam in rat plasma. Bioanalysis. 2016 8:111-22.

Plasma samples are processed using acetonitrile precipitation and analyzed by LC-MS/MS. A plasma calibration curve is generated with aliquots of drug-free plasma are spiked with the test substance at the specified concentration levels. The spiked plasma samples are processed together with the unknown plasma samples using the same procedure. The processed plasma samples can be stored at −70° C. until receiving LC-MS/MS analysis, at which time peak areas are recorded, and the concentrations of the test substance in the unknown plasma samples are determined using the respective calibration curve. The reportable linear range of the assay is determined, along with the lower limit of quantitation (LLQ). Plots of plasma concentration of compound versus time are constructed. The pharmacokinetic parameters of compound after IV and PO dosing (AUC$_{last}$, AUC$_{INF}$, T$_{1/2}$, T$_{max}$, and C$_{max}$) are obtained from the non-compartmental analysis (NCA) of the plasma data using WinNonlin. WinNonlin® Certara L.P. Pharsight, St. Louis, Mo.

Example 101

Minimum Inhibitory Concentration

Minimum inhibitor concentration (MIC) values of the monobactam antibiotics are determined by broth microdilution susceptibility testing conducted in accordance with guidelines from the Clinical and Laboratory Standards Institute (Clinical and Laboratory Standards Institute (CLSI). Methods for Dilution Antimicrobial Susceptibility Tests for Bacteria That Grow Aerobically; Approved Standard-Tenth Edition. CLSI document M07-A10. CLSI, 950 West Valley Road, Suite 2500, Wayne, Pa. 19087-1898 USA, 2015; CLSI, Performance Standards for Antimicrobial Susceptibility Testing: Twenty-Sixth Informational Supplement. CLSI document M100-S26. CLSI, 950 West Valley Road, Suite 2500, Wayne, Pa. 19087 USA, 2016) against a panel of gram-negative bacterial strains. Compounds are stored as dry powder and stored at −20° C. prior to testing. These compounds and comparative antibiotics are solubilized in the appropriate solvent on the day of the assay. All antibiotics are tested using a concentration, for example, within a range from 0.001 µg/mL to 64 µg/mL. Antibiotics are tested at a constant concentration of, for example, 4 µg/mL. Isolates are streaked onto appropriate media and incubated overnight at 35° C. The MIC values are determined using cation-adjusted Mueller Hinton broth (MHBII; BD, Sparks, Md.) in accordance with CLSI guidelines in 96-well format plates. MICs are recorded after 18 h incubation at 35° C. The MIC is read and recorded as the lowest concentration of antibiotic that inhibits visible growth of the organism.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:
1. A compound of Formula (1):

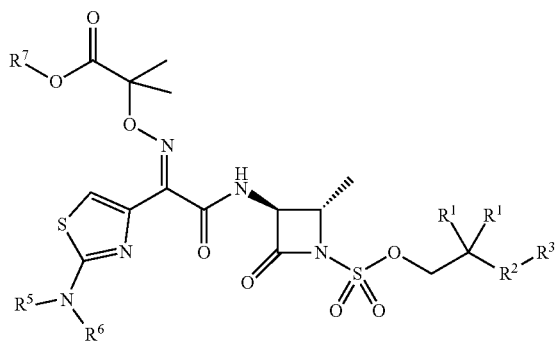

(1)

wherein,
each $R^1$ is independently selected from $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; or a pharmaceutically acceptable salt thereof.

2. The compound of claim 1, wherein each substituent is independently selected from —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R is independently selected from hydrogen and $C_{1-6}$ alkyl.

3. The compound of claim 1, wherein each of $R^5$, $R_6$, and $R^7$ is hydrogen.

4. The compound of claim 1, wherein,
each of $R^5$ and $R^6$ is hydrogen; and
$R^7$ is selected from hydrogen, $C_{1-6}$ alkyl, $C_{1-6}$ heteroalkyl, and 4-(yl-methyl)-5-methyl-1,3-dioxol-2-one.

5. The compound of claim 1, wherein each $R^1$ is independently $C_{1-6}$ alkyl, or each $R^1$ together with the geminal carbon atom to which each $R^1$ is bonded form a $C_{3-6}$ cycloalkyl ring or a substituted $C_{3-6}$ cycloalkyl ring.

6. The compound of claim 1, wherein $R^2$ is selected from a single bond, $C_{1-6}$ alkyl, $C_{1-2}$ alkanediyl, and substituted $C_{1-2}$ alkanediyl.

7. The compound of claim 1, wherein $R^3$ is selected from —O—C(O)—$R^4$, —C(O)—O—$R^4$, —S—C(O)—$R^4$, —C(O)—S—$R^4$, —S—S—$R^4$, —NH—$R^4$, and —CH(—NH$_2$)(—$R^4$); where $R^4$ is defined as for Formula (1), or each $R^4$ can be selected from hydrogen and $C_{1-8}$ alkyl.

8. The compound of claim 1, wherein $R^3$ is —C(O)—O—$R^4$, and $R^4$ is selected from hydrogen and $C_{1-8}$ alkyl.

9. The compound of claim 1, wherein $R^3$ is —C(O)—O—$R^{4'}$ wherein $R^4$ is selected from $C_{1-8}$ alkyl, $C_{1}$s heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

10. The compound of claim 1, wherein,
$R^2$ is a single bond;
$R^3$ is $C_{1-3}$ alkyl;
each $R^1$ together with the carbon atom to which each $R^1$ is bonded form a $C_{4-6}$ heterocycloalkyl ring or a substituted $C_{4-6}$ heterocycloalkyl ring
each of $R^5$ and $R^6$ is hydrogen; and
$R^7$ is selected from hydrogen, $C_{1-6}$ alkyl, $C_{1-6}$ heteroalkyl, and 4-(yl-methyl)-5-methyl-1,3-dioxol-2-one.

11. The compound of claim 1, wherein,
each $R^1$ is methyl;
$R^2$ is selected from a single bond, methanediyl, ethanediyl, —CH(—OH)—, —CH(—O—C(O)—CH$_2$CH$_3$)—, and 1,2-benzene-diyl;
$R^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$), wherein R$^4$ is selected from C$_1$s alkyl, C$_{1-8}$ heteroalkyl, C$_{7-9}$ arylalkyl, and C$_{5-7}$ heterocycloalkyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

12. The compound of claim 1, wherein,
each $R^1$ is methyl;
$R^2$ is selected from a single bond, methanediyl, ethanediyl, —CH(—OH)—, —CH(—O—C(O)—CH$_2$CH$_3$)—, and 1,2-benzene-diyl;
$R^3$ is selected from —C(O)—O—R$^4$, wherein R$^4$ is selected from C$_{1-8}$ alkyl, C$_{1-8}$ heteroalkyl, C$_{7-9}$ arylalkyl, and C$_{5-7}$ heterocycloalkyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

13. The compound of claim 1, wherein,
each $R^1$ is methyl;
$R^2$ is selected from a single bond, methanediyl, ethanediyl, —CH(—OH)—, —CH(—O—C(O)—CH$_2$CH$_3$)—, and 1,2-benzene-diyl;
$R^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$), wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

14. The compound of claim 1, wherein,
each $R^1$ is methyl;
$R^2$ is selected from a single bond, methanediyl, ethanediyl, —CH(—OH)—, —CH(—O—C(O)—CH$_2$CH$_3$)—, and 1,2-benzene-diyl;
$R^3$ is selected from —C(O)—O—R$^4$, wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

15. The compound of claim 1, wherein,
each $R^1$ is independently C$_{1-3}$ alkyl;
each $R^2$ is a single bond; and
each of $R^5$, $R^6$, and $R^7$ is hydrogen.

16. The compound of claim 1, wherein,
each $R^1$ is methyl;
$R^2$ is a single bond;
$R^3$ is —C(O)—O—R$^4$, wherein R$^4$ is selected from C$_{1-10}$ alkyl, C$_{1-10}$ heteroalkyl, C$_{7-10}$ alkylarene, and C$_{5-10}$ heteroalkylcycloalkyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

17. The compound of claim 1, wherein,
each $R^1$ can be selected from C$_{1-6}$ alkyl;
$R^4$ can be selected from C$_{1-6}$ alkyl, C$_{1-6}$ heteroalkyl, C$_{5-6}$ cycloalkyl, and C$_{5-6}$ heterocycloalkyl;
each of $R^5$ and $R^6$ is hydrogen; and
$R^7$ is selected from hydrogen, C$_{1-6}$ alkyl, C$_{1-6}$ heteroalkyl, and 4-(yl-methyl)-5-methyl-1,3-dioxol-2-one.

18. The compound of claim 1, wherein the compound is selected from:
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-3-oxo-3-propoxypropoxy)sulfonyl)-2-methyl-4-oxoazetidin-3-yl)amino)-2-oxoethylidene)amino)oxy)-2-methylpropanoic acid;
methyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
ethyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
propyl 3-((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
a pharmaceutically acceptable salt of any of the foregoing; and
a combination of any of the foregoing.

19. A pharmaceutical composition comprising the compound of claim 1 and a pharmaceutically acceptable vehicle.

20. The pharmaceutical composition of claim 19, wherein the pharmaceutical composition comprises an oral dosage formulation.

21. A method of treating a bacterial infection in a patient having a bacterial infection comprising administering to a patient in need of such treatment a therapeutically effective amount of the compound of claim 1.

22. The method of claim 19, wherein administering comprises orally administering.

23. The method of claim 19, further comprising administering a therapeutically effective amount of a β-lactamase inhibitor to the patient.

24. The method of claim 21, wherein the bacterial infection is capable of being treated by co-administering a therapeutically effective amount of aztreonam and a β-lactamase inhibitor.

25. A method of treating a bacterial infection in a patient having a bacterial infection comprising administering to a patient in need of such treatment a therapeutically effective amount of the pharmaceutical composition of claim 19.

26. The method of claim 25, wherein administering comprises orally administering.

27. The method of claim 25, further comprising administering a β-lactamase inhibitor to the patient.

* * * * *

UNITED STATES PATENT AND TRADEMARK OFFICE
CERTIFICATE OF CORRECTION

PATENT NO. : 10,280,161 B2
APPLICATION NO. : 16/148788
DATED : May 7, 2019
INVENTOR(S) : Eric M. Gordon et al.

Page 1 of 1

It is certified that error appears in the above-identified patent and that said Letters Patent is hereby corrected as shown below:

Column 186, Claim 3, Line 33, that reads "$R^5$, $R_6$" should read -- $R^5$, $R^6$ --

Column 186, Claim 9, Line 54, that reads "$C_{1-s}$" should read -- $C_{1-8}$ --

Column 187, Claim 11, Line 9, that reads "$C_{1-s}$" should read -- $C_{1-8}$ --

Signed and Sealed this
First Day of October, 2019

Andrei Iancu
*Director of the United States Patent and Trademark Office*